(12) United States Patent
Ricci

(10) Patent No.: US 10,534,819 B2
(45) Date of Patent: Jan. 14, 2020

(54) VEHICLE INTRUDER ALERT DETECTION AND INDICATION

(71) Applicant: IP Optimum Limited, Dublin (IE)

(72) Inventor: Christopher P. Ricci, Saratoga, CA (US)

(73) Assignee: IP Optimum Limited, Dublin (IE)

( * ) Notice: Subject to any disclaimer, the term of this patent is extended or adjusted under 35 U.S.C. 154(b) by 346 days.

(21) Appl. No.: 15/269,434

(22) Filed: Sep. 19, 2016

(65) Prior Publication Data

US 2017/0066406 A1    Mar. 9, 2017

Related U.S. Application Data

(63) Continuation of application No. 14/253,099, filed on Apr. 15, 2014, now abandoned, and a continuation of
(Continued)

(51) Int. Cl.
*H04W 48/04*        (2009.01)
*G06F 16/951*       (2019.01)
(Continued)

(52) U.S. Cl.
CPC .......... *G06F 16/951* (2019.01); *A61B 5/0077* (2013.01); *A61B 5/4809* (2013.01); *A61B 5/6808* (2013.01); *A61B 5/742* (2013.01); *A61B 5/7405* (2013.01); *A61B 7/04* (2013.01); *B60C 1/00* (2013.01); *B60H 1/00742* (2013.01); *B60K 35/00* (2013.01); *B60N 2/0244* (2013.01); *B60Q 9/00* (2013.01); *B60R 25/00* (2013.01); *B60R 25/01* (2013.01); *B60R 25/102* (2013.01); *B60R 25/1004* (2013.01); *B60R 25/20* (2013.01); *B60R 25/25* (2013.01); *B60W 50/085* (2013.01);
(Continued)

(58) Field of Classification Search
CPC ..................................................... B60W 40/08
See application file for complete search history.

(56) References Cited

U.S. PATENT DOCUMENTS 6,373,148 B1 *  4/2002  Daiss ..................... B60K 28/02
                                              307/10.1
6,480,224 B1   11/2002  Brown
(Continued)

FOREIGN PATENT DOCUMENTS

EP      1211141 A2    6/2002
WO    2010045554 A1    4/2010

OTHER PUBLICATIONS

"Subcommittee on Aviation Hearing on the Use of Biometrics to Improve Aviation Security", 2004 (Year: 2004).*
(Continued)

*Primary Examiner* — Dennis W Ruhl

(57) ABSTRACT

Methods and systems for a detecting an intruder near or within a vehicle are disclosed. Specifically, a method to detect and identify a person near or within a vehicle as an authorized or an unauthorized user is provided. In the event an unauthorized user is detected within a vehicle, the system may take a number of actions. In one embodiment, the actions comprise providing notice to one or more authorized users of the vehicle, disabling the vehicle, notifying emergency personnel or police, and emitting a visual or audio alarm.

20 Claims, 45 Drawing Sheets

Related U.S. Application Data application No. 14/253,351, filed on Apr. 15, 2014, now abandoned, and a continuation of application No. 14/253,423, filed on Apr. 15, 2014, now abandoned, and a continuation of application No. 14/958,371, filed on Dec. 3, 2015, now abandoned, which is a continuation of application No. 14/253,388, filed on Apr. 15, 2014, now abandoned.

(60) Provisional application No. 61/811,981, filed on Apr. 15, 2013, provisional application No. 61/865,954, filed on Aug. 14, 2013, provisional application No. 61/870,698, filed on Aug. 27, 2013, provisional application No. 61/891,217, filed on Oct. 15, 2013, provisional application No. 61/904,205, filed on Nov. 14, 2013, provisional application No. 61/924,572, filed on Jan. 7, 2014, provisional application No. 61/926,749, filed on Jan. 13, 2014.

(51) Int. Cl.

| | | |
|---|---|---|
| *H04W 36/34* | (2009.01) | |
| *H04W 36/00* | (2009.01) | |
| *H04N 21/2225* | (2011.01) | |
| *H04N 21/239* | (2011.01) | |
| *H04N 21/226* | (2011.01) | |
| *H04N 21/4363* | (2011.01) | |
| *H04N 21/436* | (2011.01) | |
| *H04N 21/258* | (2011.01) | |
| *H04N 21/454* | (2011.01) | |
| *H04N 21/6408* | (2011.01) | |
| *H04N 21/643* | (2011.01) | |
| *H04W 84/18* | (2009.01) | |
| *H04W 4/21* | (2018.01) | |
| *H04W 4/60* | (2018.01) | |
| *H04W 76/11* | (2018.01) | |
| *G06F 16/25* | (2019.01) | |
| *G06F 16/182* | (2019.01) | |
| *G06F 16/583* | (2019.01) | |
| *G06F 16/2457* | (2019.01) | |
| *H04W 4/48* | (2018.01) | |
| *B60R 25/10* | (2013.01) | |
| *G06F 21/31* | (2013.01) | |
| *G06F 21/32* | (2013.01) | |
| *H04L 29/08* | (2006.01) | |
| *G06Q 30/00* | (2012.01) | |
| *G08G 1/0967* | (2006.01) | |
| *H04W 12/08* | (2009.01) | |
| *G08B 13/196* | (2006.01) | |
| *G08B 21/06* | (2006.01) | |
| *G08B 29/18* | (2006.01) | |
| *G06Q 10/00* | (2012.01) | |
| *G06K 9/00* | (2006.01) | |
| *B60W 50/08* | (2012.01) | |
| *B60W 50/10* | (2012.01) | |
| *B60W 50/14* | (2012.01) | |
| *G06F 3/01* | (2006.01) | |
| *G08B 25/01* | (2006.01) | |
| *H04W 4/12* | (2009.01) | |
| *G05D 23/19* | (2006.01) | |
| *G06F 3/0481* | (2013.01) | |
| *G06F 3/0484* | (2013.01) | |
| *G06F 21/00* | (2013.01) | |
| *G06Q 10/02* | (2012.01) | |
| *G06Q 30/02* | (2012.01) | |
| *G06Q 30/06* | (2012.01) | |
| *G06Q 50/30* | (2012.01) | |
| *G08B 21/02* | (2006.01) | |
| *B60R 25/00* | (2013.01) | |
| *G07C 5/02* | (2006.01) | |
| *G01C 21/36* | (2006.01) | |
| *B60R 25/01* | (2013.01) | |
| *B60K 35/00* | (2006.01) | |
| *G08G 1/01* | (2006.01) | |
| *B60C 1/00* | (2006.01) | |
| *G06F 3/06* | (2006.01) | |
| *A61B 5/00* | (2006.01) | |
| *A61B 7/04* | (2006.01) | |
| *B60Q 9/00* | (2006.01) | |
| *H04W 76/19* | (2018.01) | |
| *G05D 1/00* | (2006.01) | |
| *G08G 1/07* | (2006.01) | |
| *H04L 29/06* | (2006.01) | |
| *G05D 1/02* | (2006.01) | |
| *G08G 1/0968* | (2006.01) | |
| *G08G 1/16* | (2006.01) | |
| *H04W 4/70* | (2018.01) | |
| *H04W 4/80* | (2018.01) | |
| *B60R 25/20* | (2013.01) | |
| *G01S 19/42* | (2010.01) | |
| *B60H 1/00* | (2006.01) | |
| *B60N 2/02* | (2006.01) | |
| *B60R 25/102* | (2013.01) | |
| *B60R 25/25* | (2013.01) | |
| *G06F 9/451* | (2018.01) | |
| *G06F 3/0488* | (2013.01) | |
| *G09G 5/37* | (2006.01) | |
| *H04L 12/58* | (2006.01) | |
| *H04W 4/021* | (2018.01) | |
| *G01C 21/34* | (2006.01) | |
| *G06F 3/0482* | (2013.01) | |
| *G08G 1/00* | (2006.01) | |
| *G08B 21/18* | (2006.01) | |
| *H04W 4/40* | (2018.01) | |
| *H04W 4/30* | (2018.01) | |
| *B60Q 1/52* | (2006.01) | |
| *H04N 7/18* | (2006.01) | |
| *H04W 12/06* | (2009.01) | |
| *B60W 50/00* | (2006.01) | |
| *H04W 12/00* | (2009.01) | |
| *H04W 84/00* | (2009.01) | |
| *B60R 11/04* | (2006.01) | |
| *G02B 27/00* | (2006.01) | |

(52) U.S. Cl.
CPC ............ *B60W 50/10* (2013.01); *B60W 50/14* (2013.01); *G01C 21/3484* (2013.01); *G01C 21/365* (2013.01); *G01C 21/3667* (2013.01); *G01C 21/3691* (2013.01); *G01C 21/3697* (2013.01); *G01S 19/42* (2013.01); *G05D 1/0016* (2013.01); *G05D 1/0276* (2013.01); *G05D 23/1917* (2013.01); *G06F 3/013* (2013.01); *G06F 3/017* (2013.01); *G06F 3/0481* (2013.01); *G06F 3/0482* (2013.01); *G06F 3/04842* (2013.01); *G06F 3/04886* (2013.01); *G06F 3/0622* (2013.01); *G06F 3/0637* (2013.01); *G06F 3/0673* (2013.01); *G06F 9/451* (2018.02); *G06F 16/183* (2019.01); *G06F 16/24575* (2019.01); *G06F 16/25* (2019.01); *G06F 16/252* (2019.01); *G06F 16/583* (2019.01); *G06F 21/00* (2013.01); *G06F 21/31* (2013.01); *G06F*

21/32 (2013.01); *G06K 9/00255* (2013.01); *G06K 9/00268* (2013.01); *G06K 9/00288* (2013.01); *G06K 9/00335* (2013.01); *G06K 9/00355* (2013.01); *G06K 9/00832* (2013.01); *G06K 9/00838* (2013.01); *G06Q 10/00* (2013.01); *G06Q 10/02* (2013.01); *G06Q 10/20* (2013.01); *G06Q 30/00* (2013.01); *G06Q 30/012* (2013.01); *G06Q 30/0265* (2013.01); *G06Q 30/0266* (2013.01); *G06Q 30/0633* (2013.01); *G06Q 30/0639* (2013.01); *G06Q 30/0641* (2013.01); *G06Q 30/0645* (2013.01); *G06Q 50/30* (2013.01); *G07C 5/02* (2013.01); *G08B 13/19647* (2013.01); *G08B 21/0205* (2013.01); *G08B 21/06* (2013.01); *G08B 21/18* (2013.01); *G08B 25/016* (2013.01); *G08B 29/188* (2013.01); *G08G 1/01* (2013.01); *G08G 1/07* (2013.01); *G08G 1/0968* (2013.01); *G08G 1/096725* (2013.01); *G08G 1/096741* (2013.01); *G08G 1/096775* (2013.01); *G08G 1/096805* (2013.01); *G08G 1/096811* (2013.01); *G08G 1/096844* (2013.01); *G08G 1/164* (2013.01); *G08G 1/207* (2013.01); *G09G 5/37* (2013.01); *H04L 51/02* (2013.01); *H04L 63/0236* (2013.01); *H04L 63/0428* (2013.01); *H04L 63/102* (2013.01); *H04L 67/10* (2013.01); *H04L 67/12* (2013.01); *H04L 67/26* (2013.01); *H04L 67/306* (2013.01); *H04N 21/2225* (2013.01); *H04N 21/2265* (2013.01); *H04N 21/2393* (2013.01); *H04N 21/25816* (2013.01); *H04N 21/43615* (2013.01); *H04N 21/43637* (2013.01); *H04N 21/454* (2013.01); *H04N 21/6408* (2013.01); *H04N 21/64322* (2013.01); *H04W 4/021* (2013.01); *H04W 4/12* (2013.01); *H04W 4/21* (2018.02); *H04W 4/30* (2018.02); *H04W 4/40* (2018.02); *H04W 4/48* (2018.02); *H04W 4/60* (2018.02); *H04W 4/70* (2018.02); *H04W 4/80* (2018.02); *H04W 12/08* (2013.01); *H04W 36/0005* (2013.01); *H04W 36/34* (2013.01); *H04W 48/04* (2013.01); *H04W 76/11* (2018.02); *H04W 76/19* (2018.02); *H04W 84/18* (2013.01); *H05K 999/00* (2013.01); *H05K 999/99* (2013.01); *A61B 2503/04* (2013.01); *B60K 2370/11* (2019.05); *B60K 2370/146* (2019.05); *B60K 2370/15* (2019.05); *B60K 2370/193* (2019.05); *B60K 2370/52* (2019.05); *B60Q 1/52* (2013.01); *B60R 11/04* (2013.01); *B60R 25/2081* (2013.01); *B60R 25/257* (2013.01); *B60W 2050/0067* (2013.01); *B60W 2050/0085* (2013.01); *G01C 21/362* (2013.01); *G02B 27/0093* (2013.01); *G05D 1/021* (2013.01); *G06F 3/0488* (2013.01); *G06F 2203/04803* (2013.01); *G06K 9/00221* (2013.01); *G06K 2009/00939* (2013.01); *G09G 2380/10* (2013.01); *H04L 67/34* (2013.01); *H04N 7/181* (2013.01); *H04W 12/00508* (2019.01); *H04W 12/06* (2013.01); *H04W 84/005* (2013.01)

(56) References Cited

U.S. PATENT DOCUMENTS

| | | | | |
|---|---|---|---|---|
| 2002/0097145 | A1* | 7/2002 | Tumey | B60R 25/04 340/426.28 |
| 2003/0222758 | A1* | 12/2003 | Willats | B60R 25/04 340/5.72 |
| 2004/0217850 | A1 | 11/2004 | Perttunen et al. | |
| 2006/0036358 | A1 | 2/2006 | Hale et al. | |
| 2006/0082434 | A1* | 4/2006 | Brey | B60R 25/04 340/5.6 |
| 2006/0217864 | A1* | 9/2006 | Johnson | B60N 2/002 701/45 |
| 2006/0287865 | A1 | 12/2006 | Cross et al. | |
| 2007/0241861 | A1* | 10/2007 | Venkatanna | G06F 21/32 340/5.52 |
| 2010/0087987 | A1* | 4/2010 | Huang | B60W 40/08 701/36 |
| 2014/0200737 | A1* | 7/2014 | Lortz | B60R 25/25 701/1 |

OTHER PUBLICATIONS

European Office Action, EP Application No. 14766878.4, PCT/US20141/034108, dated Dec. 15, 2016.

* cited by examiner

Tap

Long Press

Drag

Flick

Pinch

Spread

VEHICLE INTRUDER ALERT DETECTION AND INDICATION

CROSS REFERENCE TO RELATED APPLICATIONS

The present application is a continuation of and claims priority to U.S. Patent Application Ser. Nos.: (1) Ser. No. 14/253,099, filed Apr. 15, 2014, entitled "Vehicle Intruder Alert Detection and Indication"; (2) Ser. No. 14/253,351, filed Apr. 15, 2014, entitled "Vehicle Maintenance and Warranty Compliance Detection"; (3) Ser. No. 14/253,423, filed Apr. 14, 2015, entitled "Vehicle Diagnostics and Roadside Assistance"; and (4) Ser. No. 14/958,371, filed Dec. 3, 2015, which is a continuation of and claims priority to U.S. patent application Ser. No. 14/253,388 filed Apr. 14, 2015, now abandoned, entitled "Automatic Vehicle Diagnostic Detection and Communication." Each of the foregoing applications claims the benefits of and priority, under 35 U.S.C. § 119(e), to U.S. Provisional Application Ser. No. 61/811,981, filed on Apr. 15, 2013, entitled "Functional Specification for a Next Generation Automobile"; 61/865,954, filed on Aug. 14, 2013, entitled "Gesture Control of Vehicle Features"; 61/870,698, filed on Aug. 27, 2013, entitled "Gesture Control and User Profiles Associated with Vehicle Features"; 61/891,217, filed on Oct. 15, 2013, entitled "Gesture Control and User Profiles Associated with Vehicle Features"; 61/904,205, filed on Nov. 14, 2013, entitled "Gesture Control and User Profiles Associated with Vehicle Features"; 61/924,572, filed on Jan. 7, 2014, entitled "Gesture Control and User Profiles Associated with Vehicle Features"; and 61/926,749, filed on Jan. 13, 2014, entitled "Method and System for Providing Infotainment in a Vehicle." The entire disclosures of the applications listed above are hereby incorporated by reference, in their entirety, for all that they teach and for all purposes.

This application is also related to U.S. patent application Ser. No. 13/420,236, filed on Mar. 14, 2012, entitled, "Configurable Vehicle Console"; Ser. No. 13/420,240, filed on Mar. 14, 2012, entitled "Removable, Configurable Vehicle Console"; Ser. No. 13/462,593, filed on May 2, 2012, entitled "Configurable Dash Display"; Ser. No. 13/462,596, filed on May 2, 2012, entitled "Configurable Heads-Up Dash Display"; Ser. No. 13/679,459, filed on Nov. 16, 2012, entitled "Vehicle Comprising Multi-Operating System"; Ser. No. 13/679,234, filed on Nov. 16, 2012, entitled "Gesture Recognition for On-Board Display"; Ser. No. 13/679,412, filed on Nov. 16, 2012, entitled "Vehicle Application Store for Console"; Ser. No. 13/679,857, filed on Nov. 16, 2012, entitled "Sharing Applications/Media Between Car and Phone (Hydroid)"; Ser. No. 13/679,878, filed on Nov. 16, 2012, entitled "In-Cloud Connection for Car Multimedia"; Ser. No. 13/679,875, filed on Nov. 16, 2012, entitled "Music Streaming"; Ser. No. 13/679,676, filed on Nov. 16, 2012, entitled "Control of Device Features Based on Vehicle State"; Ser. No. 13/678,673, filed on Nov. 16, 2012, entitled "Insurance Tracking"; Ser. No. 13/678,691, filed on Nov. 16, 2012, entitled "Law Breaking/Behavior Sensor"; Ser. No. 13/678,699, filed on Nov. 16, 2012, entitled "Etiquette Suggestion"; Ser. No. 13/678,710, filed on Nov. 16, 2012, entitled "Parking Space Finder Based on Parking Meter Data"; Ser. No. 13/678,722, filed on Nov. 16, 2012, entitled "Parking Meter Expired Alert"; Ser. No. 13/678,726, filed on Nov. 16, 2012, entitled "Object Sensing (Pedestrian Avoidance/Accident Avoidance)"; Ser. No. 13/678,735, filed on Nov. 16, 2012, entitled "Proximity Warning Relative to Other Cars"; Ser. No. 13/678,745, filed on Nov. 16, 2012, entitled "Street Side Sensors"; Ser. No. 13/678,753, filed on Nov. 16, 2012, entitled "Car Location"; Ser. No. 13/679,441, filed on Nov. 16, 2012, entitled "Universal Bus in the Car"; Ser. No. 13/679,864, filed on Nov. 16, 2012, entitled "Mobile Hot Spot/Router/Application Share Site or Network"; Ser. No. 13/679,815, filed on Nov. 16, 2012, entitled "Universal Console Chassis for the Car"; Ser. No. 13/679,476, filed on Nov. 16, 2012, entitled "Vehicle Middleware"; Ser. No. 13/679,306, filed on Nov. 16, 2012, entitled "Method and System for Vehicle Data Collection Regarding Traffic"; Ser. No. 13/679,369, filed on Nov. 16, 2012, entitled "Method and System for Vehicle Data Collection"; Ser. No. 13/679,680, filed on Nov. 16, 2012, entitled "Communications Based on Vehicle Diagnostics and Indications"; Ser. No. 13/679,443, filed on Nov. 16, 2012, entitled "Method and System for Maintaining and Reporting Vehicle Occupant Information"; Ser. No. 13/678,762, filed on Nov. 16, 2012, entitled "Behavioral Tracking and Vehicle Applications"; Ser. No. 13/679,292, filed Nov. 16, 2012, entitled "Branding of Electrically Propelled Vehicles Via the Generation of Specific Operating Output"; Ser. No. 13/679,400, filed Nov. 16, 2012, entitled "Vehicle Climate Control"; Ser. No. 13/840,240, filed on Mar. 15, 2013, entitled "Improvements to Controller Area Network Bus"; Ser. No. 13/678,773, filed on Nov. 16, 2012, entitled "Location Information Exchange Between Vehicle and Device"; Ser. No. 13/679,887, filed on Nov. 16, 2012, entitled "In Car Communication Between Devices"; Ser. No. 13/679,842, filed on Nov. 16, 2012, entitled "Configurable Hardware Unit for Car Systems"; Ser. No. 13/679,204, filed on Nov. 16, 2012, entitled "Feature Recognition for Configuring a Vehicle Console and Associated Devices"; Ser. No. 13/679,350, filed on Nov. 16, 2012, entitled "Configurable Vehicle Console"; Ser. No. 13/679,358, filed on Nov. 16, 2012, entitled "Configurable Dash Display"; Ser. No. 13/679,363, filed on Nov. 16, 2012, entitled "Configurable Heads-Up Dash Display"; and Ser. No. 13/679,368, filed on Nov. 16, 2012, entitled "Removable, Configurable Vehicle Console". The entire disclosures of the applications listed above are hereby incorporated by reference, in their entirety, for all that they teach and for all purposes.

BACKGROUND

Whether using private, commercial, or public transport, the movement of people and/or cargo has become a major industry. In today's interconnected world, daily travel is essential to engaging in commerce. Commuting to and from work can account for a significant portion of a traveler's day. As a result, vehicle manufacturers have begun to focus on making this commute, and other journeys, more enjoyable.

Currently, vehicle manufacturers attempt to entice travelers to use a specific conveyance based on any number of features. Most of these features focus on vehicle safety or efficiency. From the addition of safety-restraints, air-bags, and warning systems to more efficient engines, motors, and designs, the vehicle industry has worked to appease the supposed needs of the traveler. Recently, however, vehicle manufactures have shifted their focus to user and passenger comfort as a primary concern. Making an individual more comfortable while traveling instills confidence and pleasure in using a given vehicle, increasing an individual's preference for a given manufacturer and/or vehicle type.

One way to instill comfort in a vehicle is to create an environment within the vehicle similar to that of an individual's home. Integrating features in a vehicle that are associated with comfort found in an individual's home can ease a traveler's transition from home to vehicle. Several manufacturers have added comfort features in vehicles such as the following: leather seats, adaptive and/or personal climate control systems, music and media players, ergonomic controls, and, in some cases, Internet connectivity. However, because these manufacturers have added features to a conveyance, they have built comfort around a vehicle and failed to build a vehicle around comfort.

SUMMARY

There is a need for a vehicle ecosystem, which can integrate both physical and mental comforts, while seamlessly communicating with current electronic devices to result in a totally intuitive and immersive user experience. These and other needs are addressed by the various aspects, embodiments, and/or configurations of the present disclosure. Also, while the disclosure is presented in terms of exemplary and optional embodiments, it should be appreciated that individual aspects of the disclosure can be separately claimed.

Embodiments include a method, comprising: receiving sensor data; determining, from the sensor data, if a user is in contact with a vehicle; determining if a user in contact with the vehicle is an unauthorized user; and taking an action if a user in contact with the vehicle is an unauthorized user. Aspects of the above method include wherein receiving sensor data comprises receiving sensor data from one or more vehicle sensors. Aspects of the above method include further comprising comparing the sensor data to stored authorized user profile data. Aspects of the above method include wherein the taking action comprises providing an alert. Aspects of the above method include wherein the user is not an unauthorized user if one or more characteristics of the authorized user profile data match one or more characteristics of the user in contact with the vehicle. Aspects of the above method include wherein the one or more vehicle sensors comprise an image sensor and a seat weight sensor. Aspects of the above method include wherein the providing an alert comprises a visual alert, an audio alert, emergency responder alert, and alert to one or more authorized users. Aspects of the above method include wherein determining if a user in contact with the vehicle is an unauthorized user comprises comparing biometric data of the user in contact with the vehicle with biometric data of authorized users. Aspects of the above method include wherein the one or more vehicle sensors comprises at least one image sensor. Aspects of the above method include wherein determining if a user in contact with the vehicle is an unauthorized user comprises identifying facial features of the user in contact with the vehicle by the at least one image sensor and comparing the identified facial features with facial features of authorized users. Aspects of the above method include wherein the taking action comprises disabling the vehicle. Aspects of the above method include wherein the alert is sent in real-time. Aspects of the above method include further comprising recording sensor data associated with the user in contact with the vehicle.

Embodiments include a non-transitory computer readable medium having instructions stored thereon that, when executed by a processor, perform operations comprising the above methods. Embodiments include a device, means, and/or system configured to perform the above methods.

Embodiments include an intruder alert system for a vehicle comprising a vehicle control system configured to: receive sensor data; determine, from the sensor data, if a user is in contact with a vehicle; determine if a user in contact with the vehicle is an unauthorized user; and take an action if a user in contact with the vehicle is an unauthorized user. Aspects of the above system include wherein the vehicle control system is further configured to determine if a user in contact with the vehicle is an unauthorized user comprising comparing biometric data of the user in contact with the vehicle with biometric data of authorized users.

Embodiments include a method comprising: receiving sensor data from one or more vehicle sensors; determining, from the sensor data, if vehicle damage has occurred; and taking action if vehicle damage occurs. Aspects of the above method include further comprising comparing the sensor data to vehicle damage threshold data. Aspects of the above method include wherein vehicle damage occurs if one or more vehicle damage thresholds are exceeded. Aspects of the above method include wherein the vehicle damage threshold data is stored in authorized user profile data. Aspects of the above method include wherein the one or more vehicle sensors comprise an image sensor, a motion sensor, a vibration sensor and a force sensor. Aspects of the above method include wherein the taking action comprises providing an alert. Aspects of the above method include wherein the providing an alert comprises a visual alert, an audio alert, emergency responder alert, and alert to one or more authorized users. Aspects of the above method include further comprising providing a notice in real-time. Aspects of the above method include further comprising identifying at least one of the location of the damage and the degree of the damage. Aspects of the above method include wherein both the location of the damage and the degree of the damage are identified and both are communicated to a third party. Aspects of the above method include wherein the taking action comprises guiding one or more vehicle sensors to sense an area surrounding the vehicle damage. Aspects of the above method include wherein the one or more vehicle sensor comprise a sensor located within a body frame of the vehicle. Aspects of the above method include further comprising recording sensor data associated with vehicle damage.

Embodiments include a non-transitory computer readable medium having instructions stored thereon that, when executed by a processor, perform operations comprising the above methods. Embodiments include a device, means, and/or system configured to perform the above methods.

Embodiments include a vehicle damage incident detection system comprising a vehicle control system configured to: a vehicle control system configured to: receive sensor data from one or more vehicle sensors; determine, from the sensor data, if vehicle damage has occurred; and take action if vehicle damage occurs. Aspects of the above system include wherein the vehicle control system is further configured to compare the sensor data to vehicle damage threshold data.

Embodiments include a method comprising: receiving sensor data from one or more vehicle sensors; identifying, from the sensor data, an identity of a user of a vehicle; determining, from the sensor data, if a user is not in compliance with a user vehicle operating term; and taking action if the user is not in compliance with a user vehicle operating term. Aspects of the above method include wherein the user vehicle operating term is at least one of a maintenance standard, a warranty requirement and a user operating restriction. Aspects of the above method include further comprising comparing the sensor data to at least one of vehicle maintenance standards, vehicle warranty requirements and user profile operating restrictions. Aspects of the above method include wherein the user is not in compliance with a user vehicle operating term if the comparison results in one or more characteristics of vehicle maintenance standards, vehicle warranty requirements and user profile operating restrictions not satisfied. Aspects of the above method include wherein the taking action comprises noticing a third party if the user is not in compliance with a user vehicle operating term. Aspects of the above method include wherein the third party is at least one of an insurance provider, warranty provider, authorized monitor and user. Aspects of the above method include further comprising updating a user profile database regarding the user vehicle not in compliance. Aspects of the above method include wherein the one or more vehicle sensors include an odometer, a tachometer, an oil level meter and an image sensor. Aspects of the above method include wherein the taking action comprises providing an alert. Aspects of the above method include wherein the providing an alert comprises a visual alert, an audio alert, emergency responder alert, and alert to an authorized monitor. Aspects of the above method include further comprising identifying the one or more characteristics of vehicle maintenance standards, vehicle warranty requirements and user profile operating restrictions not satisfied. Aspects of the above method include wherein the taking action comprises noticing a third party if the user is not in compliance with a user vehicle operating term. Aspects of the above method include further comprising receiving a query from a warranty provider if a user is not in compliance with a vehicle warranty requirement.

Embodiments include a non-transitory computer readable medium having instructions stored thereon that, when executed by a processor, perform operations comprising the above methods. Embodiments include a device, means, and/or system configured to perform the above methods.

Embodiments include a vehicle maintenance and warranty compliance detection system comprising a vehicle control system configured to: receive sensor data from one or more vehicle sensors; identify, from the sensor data, an identity of a user of a vehicle; determine, from the sensor data, if a user is not in compliance with a user vehicle operating term; and take action if the user is not in compliance with a user vehicle operating term. Aspects of the above system include wherein the user vehicle operating term is at least one of a maintenance standard, a warranty requirement and a user operating restriction.

Embodiments include a method comprising: receiving occupant health sensor data for one or more vehicle occupants; determining, from occupant health sensor data for the one or more vehicle occupants, if one or more vehicle occupants are in need of medical attention; and taking action if one or more vehicle occupants are in need of medical attention. Aspects of the above method include further comprising comparing the occupant health sensor data to baseline health threshold data for the one or more vehicle occupants. Aspects of the above method include wherein one or more vehicle occupants are in need of medical attention if a baseline health threshold is exceeded. Aspects of the above method include wherein the health sensor data senses user parameters comprising body temperature, blood pressure, pulse rate, respiratory rate, and other vital signs. Aspects of the above method include wherein the baseline health threshold data comprises body temperature, blood pressure, pulse rate, respiratory rate, and associated vital signs. Aspects of the above method include wherein the taking action comprises providing an alert. Aspects of the above method include wherein the providing an alert comprises a visual alert, an audio alert, emergency responder alert, and alert to one or more authorized users. Aspects of the above method include further comprising receiving vehicle sensor data from one or more vehicle sensors and determining, from the vehicle sensor data, if vehicle damage has occurred. Aspects of the above method include further comprising identifying at least one of the location of the damage and the degree of the damage. Aspects of the above method include wherein both the location of the damage and the degree of the damage are identified and both are communicated to a third party. Aspects of the above method include wherein the taking action comprises guiding one or more vehicle sensors to sense an area surrounding the vehicle damage. Aspects of the above method include further comprising recording sensor data associated with the vehicle damage. Aspects of the above method include further comprising receiving vehicle sensor data from one or more vehicle sensors and determining, from the vehicle sensor data, if vehicle damage has occurred.

Embodiments include a non-transitory computer readable medium having instructions stored thereon that, when executed by a processor, perform operations comprising the above methods. Embodiments include a device, means, and/or system configured to perform the above methods.

Embodiments include an automatic communication of damage and health of users in detected vehicle incidents damage incident detection system comprising a vehicle control system configured to: receive vehicle sensor data from one or more vehicle sensors; determine, from the vehicle sensor data, if vehicle damage has occurred; receive occupant health sensor data for one or more vehicle occupants; determine, from occupant health sensor data for the one or more vehicle occupants, if one or more vehicle occupants are in need of medical attention; and take action if one or more vehicle occupants are in need of medical attention. Aspects of the above system include wherein the health sensor data senses user parameters comprising body temperature, blood pressure, pulse rate, respiratory rate, and other vital signs.

Embodiments include a method comprising: receiving sensor data from one or more vehicle sensors; determining vehicle health state of one or more subsystems of a vehicle; determining an overall vehicle health status; and taking action regarding the vehicle health status. Aspects of the above method include further comprising comparing the sensor data to subsystem specification data. Aspects of the above method include wherein the subsystem specification data is stored in a maintenance database. Aspects of the above method include wherein the one or more subsystems of a vehicle is unhealthy if the comparison results in one or more characteristics of subsystem specification data not satisfied. Aspects of the above method include wherein if one or more subsystems of a vehicle is unhealthy, the vehicle is unhealthy. Aspects of the above method include further comprising noticing a third party if the vehicle is in an unhealthy status. Aspects of the above method include wherein the third party is at least one of an original equipment manufacturer (OEM), a maintenance provider, a regulatory monitor and a user. Aspects of the above method include further comprising updating a fleet-wide OEM performance database if one or more subsystems are unhealthy. Aspects of the above method include wherein the taking action comprises providing an alert. Aspects of the above method include further comprising receiving a query from a third-party as to the health state of one or more subsystems of the vehicle. Aspects of the above method include further comprising diagnosing the unhealthy subsystem. Aspects of the above method include further comprising noticing a third party if the vehicle is in an unhealthy status. Aspects of the above method include where the one or more vehicle sensors include an odometer, a tachometer, an oil level meter and an image sensor.

Embodiments include a non-transitory computer readable medium having instructions stored thereon that, when executed by a processor, perform operations comprising the above methods. Embodiments include a device, means, and/or system configured to perform the above methods.

Embodiments include a vehicle diagnostic detection and communication system comprising a vehicle control system configured to: receive sensor data from one or more vehicle sensors; determine vehicle health state of one or more subsystems of a vehicle; determine an overall vehicle health status; and take action regarding the vehicle health status. Aspects of the above system include the vehicle control system further configured to compare the sensor data to subsystem specification data, wherein the one or more subsystems of a vehicle is unhealthy if the comparison results in one or more characteristics of subsystem specification data not satisfied.

Embodiments include a method comprising receiving sensor data from one or more vehicle sensors comprising a vehicle skin sensor; calibrating a vehicle skin baseline condition; determining, from the sensor data as against the vehicle skin baseline condition, if a vehicle skin event has occurred; and taking action if a vehicle skin event occurs. Aspects of the above method include further comprising comparing the sensor data to vehicle skin event threshold data. Aspects of the above method include wherein vehicle skin damage occurs if one or more vehicle skin events exceed one or more skin damage thresholds. Aspects of the above method include wherein the vehicle skin damage threshold data is stored in authorized user profile data. Aspects of the above method include wherein the vehicle skin sensor is disposed on or within a portion of an exterior surface of the vehicle. Aspects of the above method include wherein the taking action comprises providing an alert. Aspects of the above method include wherein the providing an alert comprises a visual alert, an audio alert, emergency responder alert, and alert to one or more authorized users. Aspects of the above method include wherein the taking action comprises providing a notice, the notice comprising identification of a location of vehicle skin damage, wherein vehicle skin damage occurs if one or more vehicle skin events exceed one or more skin damage thresholds. Aspects of the above method include wherein both the location of the vehicle skin damage and the degree of the vehicle skin damage are identified and both are communicated to a third party. Aspects of the above method include wherein the taking action comprises guiding one or more vehicle sensors to sense an area surrounding the vehicle skin event. Aspects of the above method include further comprising recording sensor data associated with the vehicle skin damage. Aspects of the above method include wherein the vehicle skin sensor comprises an electrical resistivity sensor, a magnetic field sensor, an image sensor, an RF sensor, a vibration sensor and a frequency sensor. Aspects of the above method include wherein the calibrating a vehicle skin baseline condition comprises a frequency response of at least a portion of the vehicle skin.

Embodiments include a non-transitory computer readable medium having instructions stored thereon that, when executed by a processor, perform operations comprising the above methods. Embodiments include a device, means, and/or system configured to perform the above methods.

Embodiments include a vehicle skin event detection system comprising a vehicle control system configured to: receive sensor data from one or more vehicle sensors comprising a vehicle skin sensor; calibrate a vehicle skin baseline condition; determine, from the sensor data as against the vehicle skin baseline condition, if a vehicle skin event has occurred; and take action if a vehicle skin event occurs. Aspects of the above system include wherein the vehicle skin sensor is disposed on or within a portion of an exterior surface of the vehicle.

Embodiments include a method comprising: receiving sensor data from one or more vehicle sensors; determining vehicle health state of one or more subsystems of a vehicle; determining an overall vehicle health status; and noticing a user if vehicle is unhealthy; seeking authorization from the user to take action if vehicle is unhealthy; and taking action regarding the vehicle health status. Aspects of the above method include further comprising comparing the sensor data to subsystem specification data. Aspects of the above method include wherein the one or more subsystems of a vehicle is unhealthy if the comparison results in one or more characteristics of subsystem specification data not satisfied. Aspects of the above method include wherein if one or more subsystems of a vehicle is unhealthy, the vehicle is unhealthy. Aspects of the above method include further comprising noticing a third party if the vehicle is in an unhealthy status. Aspects of the above method include wherein the third party is at least one of an original a maintenance provider, an emergency agency and a user. Aspects of the above method include wherein the taking action comprises providing an alert. Aspects of the above method include further comprising diagnosing the unhealthy subsystem. Aspects of the above method include wherein the one or more vehicle sensors include an odometer, a tachometer, an oil level meter and an image sensor. Aspects of the above method include further comprising receiving occupant health sensor data for one or more vehicle occupants and determining, from occupant health sensor data for the one or more vehicle occupants, if one or more vehicle occupants are in need of medical attention. Aspects of the above method include further comprising comparing the occupant health sensor data to baseline health threshold data for the one or more vehicle occupants. Aspects of the above method include wherein the health sensor data senses user parameters comprise body temperature, blood pressure, pulse rate, respiratory rate, and other vital signs. Aspects of the above method include further comprising taking action if one or more vehicle occupants are in need of medical attention.

Embodiments include a non-transitory computer readable medium having instructions stored thereon that, when executed by a processor, perform operations comprising the above methods. Embodiments include a device, means, and/or system configured to perform the above methods.

Embodiments include a vehicle diagnostics and roadside assistance system comprising a vehicle control system configured to: receive sensor data from one or more vehicle sensors; determine vehicle health state of one or more subsystems of a vehicle; determine an overall vehicle health status; and notice a user if vehicle is unhealthy; seek authorization from the user to take action if vehicle is unhealthy; and take action regarding the vehicle health status. Aspects of the above system include the vehicle control system further configured to compare the sensor data to subsystem specification data, wherein the one or more subsystems of a vehicle is unhealthy if the comparison results in one or more characteristics of subsystem specification data not satisfied.

The present disclosure can provide a number of advantages depending on the particular aspect, embodiment, and/or configuration. For example, a method and system for detecting an intruder near or within a vehicle increases safety of drivers of vehicles and serves as a deterrent to theft and vandalism. A method and system to detect, identify and communicate vehicle damage streamlines the vehicle repair and insurance claim process. A method and system to monitor the compliance of a user with vehicle maintenance and operating requirements and vehicle warranty terms increases the timely and effective care of a vehicle thereby providing safer vehicle operations. A method and system to monitor the health of occupants and detect and identify any occupants experiencing a medical anomaly provides for healthier drivers and more effective emergency care. A method and system to monitor the health of vehicle systems and subsystems and diagnose detected anomalies enables a vehicle fleet-wide performance database to enable identification and analysis of systemic fleet-wide data. A method and system to monitor the exterior surface of skin of a vehicle enables detection and identification of damage to the vehicle exterior surface. And a method and system for vehicle diagnostics and roadside assistance allows safer and more confident vehicle operations.

These and other advantages will be apparent from the disclosure.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refer to any process or operation done without material human input when the process or operation is performed. However, a process or operation can be automatic, even though performance of the process or operation uses material or immaterial human input, if the input is received before the performance of the process or operation. Human input is deemed to be material if such input influences how the process or operation will be performed. Human input that consents to the performance of the process or operation is not deemed to be "material."

The term "automotive navigation system" can refer to a satellite navigation system designed for use in vehicles. It typically uses a GPS navigation device to acquire position data to locate the user on a road in the unit's map database. Using the road database, the unit can give directions to other locations along roads also in its database. Dead reckoning using distance data from sensors attached to the drivetrain, a gyroscope and an accelerometer can be used for greater reliability, as GPS signal loss and/or multipath can occur due to urban canyons or tunnels.

The term "bus" and variations thereof, as used herein, can refer to a subsystem that transfers information and/or data between various components. A bus generally refers to the collection communication hardware interface, interconnects, bus architecture, standard, and/or protocol defining the communication scheme for a communication system and/or communication network. A bus may also refer to a part of a communication hardware that interfaces the communication hardware with the interconnects that connect to other components of the corresponding communication network. The bus may be for a wired network, such as a physical bus, or wireless network, such as part of an antenna or hardware that couples the communication hardware with the antenna. A bus architecture supports a defined format in which information and/or data is arranged when sent and received through a communication network. A protocol may define the format and rules of communication of a bus architecture.

The terms "communication device," "smartphone," and "mobile device," and variations thereof, as used herein, can be used interchangeably and may include any type of device capable of communicating with one or more of another device and/or across a communications network, via a communications protocol, and the like. Exemplary communication devices may include but are not limited to smartphones, handheld computers, laptops, netbooks, notebook computers, subnotebooks, tablet computers, scanners, portable gaming devices, phones, pagers, GPS modules, portable music players, and other Internet-enabled and/or network-connected devices.

A "communication modality" can refer to any protocol- or standard defined or specific communication session or interaction, such as Voice-Over-Internet-Protocol ("VoIP), cellular communications (e.g., IS-95, 1G, 2G, 3G, 3.5G, 4G, 4G/IMT-Advanced standards, 3GPP, WIMAX™, GSM, CDMA, CDMA2000, EDGE, 1xEVDO, iDEN, GPRS, HSPDA, TDMA, UMA, UMTS, ITU-R, and 5G), Bluetooth™, text or instant messaging (e.g., AIM, Blauk, eBuddy, Gadu-Gadu, IBM Lotus Sametime, ICQ, iMessage, IMVU, Lync, MXit, Paltalk, Skype, Tencent QQ, Windows Live Messenger™ or MSN Messenger™, Wireclub, Xfire, and Yahoo! Messenger™), email, Twitter (e.g., tweeting), Digital Service Protocol (DSP), and the like.

The term "communication system" or "communication network" and variations thereof, as used herein, can refer to a collection of communication components capable of one or more of transmission, relay, interconnect, control, or otherwise manipulate information or data from at least one transmitter to at least one receiver. As such, the communication may include a range of systems supporting point-to-point or broadcasting of the information or data. A communication system may refer to the collection individual communication hardware as well as the interconnects associated with and connecting the individual communication hardware. Communication hardware may refer to dedicated communication hardware or may refer a processor coupled with a communication means (i.e., an antenna) and running software capable of using the communication means to send and/or receive a signal within the communication system. Interconnect refers some type of wired or wireless communication link that connects various components, such as communication hardware, within a communication system. A communication network may refer to a specific setup of a communication system with the collection of individual communication hardware and interconnects having some definable network topography. A communication network may include wired and/or wireless network having a pre-set to an ad hoc network structure.

The term "computer-readable medium," as used herein refers to any tangible storage and/or transmission medium that participates in providing instructions to a processor for execution. Such a medium may take many forms, including but not limited to, non-volatile media, volatile media, and transmission media. Non-volatile media includes, for example, non-volatile random access memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a compact disc read only memory (CD-ROM), any other optical medium, punch cards, paper tape, any other physical medium with patterns of holes, a random access memory (RAM), a programmable read only memory (PROM), and erasable programmable read only memory EPROM, a FLASH-EPROM, a solid state medium like a memory card, any other memory chip or cartridge, a carrier wave as described hereinafter, or any other medium from which a computer can read. A digital file attachment to an e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. It should be noted that any computer readable medium that is not a signal transmission may be considered non-transitory.

The terms dash and dashboard and variations thereof, as used herein, may be used interchangeably and can be any panel and/or area of a vehicle disposed adjacent to an operator, user, and/or passenger. Dashboards may include, but are not limited to, one or more control panel(s), instrument housing(s), head unit(s), indicator(s), gauge(s), meter(s), light(s), audio equipment, computer(s), screen(s), display(s), HUD unit(s), and graphical user interface(s).

The term "module" as used herein refers to any known or later developed hardware, software, firmware, artificial intelligence, fuzzy logic, or combination of hardware and software that is capable of performing the functionality associated with that element.

The term "desktop" refers to a metaphor used to portray systems. A desktop is generally considered a "surface" that may include pictures, called icons, widgets, folders, etc. that can activate and/or show applications, windows, cabinets, files, folders, documents, and other graphical items. The icons are generally selectable to initiate a task through user interface interaction to allow a user to execute applications and/or conduct other operations.

The term "display" refers to a portion of a physical screen used to display the output of a computer to a user.

The term "displayed image" refers to an image produced on the display. A typical displayed image is a window or desktop. The displayed image may occupy all or a portion of the display.

The term "display orientation" refers to the way in which a rectangular display is oriented for viewing. The two most common types of display orientations are portrait and landscape. In landscape mode, the display is oriented such that the width of the display is greater than the height of the display (such as a 4:3 ratio, which is 4 units wide and 3 units tall, or a 16:9 ratio, which is 16 units wide and 9 units tall). Stated differently, the longer dimension of the display is oriented substantially horizontal in landscape mode while the shorter dimension of the display is oriented substantially vertical. In the portrait mode, by contrast, the display is oriented such that the width of the display is less than the height of the display. Stated differently, the shorter dimension of the display is oriented substantially horizontal in the portrait mode while the longer dimension of the display is oriented substantially vertical. A multi-screen display can have one composite display that encompasses all the screens. The composite display can have different display characteristics based on the various orientations of the device.

The term "electronic address" can refer to any contactable address, including a telephone number, instant message handle, e-mail address, Uniform Resource Locator ("URL"), Global Universal Identifier ("GUID"), Universal Resource Identifier ("URI"), Address of Record ("AOR"), electronic alias in a database, etc., combinations thereof.

The term "gesture" refers to a user action that expresses an intended idea, action, meaning, result, and/or outcome. The user action can include manipulating a device (e.g., opening or closing a device, changing a device orientation, moving a trackball or wheel, etc.), movement of a body part in relation to the device, movement of an implement or tool in relation to the device, audio inputs, etc. A gesture may be made on a device (such as on the screen) or with the device to interact with the device.

The term "gesture capture" refers to a sense or otherwise a detection of an instance and/or type of user gesture. The gesture capture can be received by sensors in three-dimensional space. Further, the gesture capture can occur in one or more areas of a screen, for example, on a touch-sensitive display or a gesture capture region. A gesture region can be on the display, where it may be referred to as a touch sensitive display, or off the display, where it may be referred to as a gesture capture area.

The terms "infotainment" and "infotainment system" may be used interchangeably and can refer to the hardware/software products, data, content, information, and/or systems, which can be built into or added to vehicles to enhance driver and/or passenger experience. Infotainment may provide media and/or multimedia content. An example is information-based media content or programming that also includes entertainment content.

A "multi-screen application" refers to an application that is capable of producing one or more windows that may simultaneously occupy one or more screens. A multi-screen application commonly can operate in single-screen mode in which one or more windows of the application are displayed only on one screen or in multi-screen mode in which one or more windows are displayed simultaneously on multiple screens.

A "single-screen application" refers to an application that is capable of producing one or more windows that may occupy only a single screen at a time.

The terms "online community," "e-community," or "virtual community" can mean a group of people that interact via a computer network, for social, professional, educational, and/or other purposes. The interaction can use a variety of media formats, including wikis, blogs, chat rooms, Internet forums, instant messaging, email, and other forms of electronic media. Many media formats may be used in social software separately and/or in combination, including text-based chat rooms and forums that use voice, video text or avatars.

The term "satellite positioning system receiver" can refer to a wireless receiver or transceiver to receive and/or send location signals from and/or to a satellite positioning system (SPS), such as the Global Positioning System ("GPS") (US), GLONASS (Russia), Galileo positioning system (EU), Compass navigation system (China), and Regional Navigational Satellite System (India).

The term "social network service" may include a service provider that builds online communities of people, who share interests and/or activities, or who are interested in exploring the interests and/or activities of others. Social network services can be network-based and may provide a variety of ways for users to interact, such as e-mail and instant messaging services.

The term "social network" can refer to a network-based social network.

The term "screen," "touch screen," "touchscreen," or "touch-sensitive display" refers to a physical structure that enables the user to interact with the computer by touching areas on the screen and provides information to a user through a display. The touch screen may sense user contact in a number of different ways, such as by a change in an electrical parameter (e.g., resistance or capacitance), acoustic wave variations, infrared radiation proximity detection, light variation detection, and the like. In a resistive touch screen, for example, normally separated conductive and resistive metallic layers in the screen pass an electrical current. When a user touches the screen, the two layers make contact in the contacted location, whereby a change in electrical field is noted and the coordinates of the contacted location calculated. In a capacitive touch screen, a capacitive layer stores electrical charge, which is discharged to the user upon contact with the touch screen, causing a decrease in the charge of the capacitive layer. The decrease is measured, and the contacted location coordinates determined. In a surface acoustic wave touch screen, an acoustic wave is transmitted through the screen, and the acoustic wave is disturbed by user contact. A receiving transducer detects the user contact instance and determines the contacted location coordinates.

The term "window" refers to a, typically rectangular, displayed image on at least part of a display that contains or provides content different from the rest of the screen. The window may obscure the desktop. The dimensions and orientation of the window may be configurable either by another module or by a user. When the window is expanded, the window can occupy substantially all of the display space on a screen or screens.

The terms "determine," "calculate," and "compute," and variations thereof, as used herein, are used interchangeably and include any type of methodology, process, mathematical operation, or technique.

It shall be understood that the term "means," as used herein, shall be given its broadest possible interpretation in accordance with 35 U.S.C., Section 112, Paragraph 6 or other applicable law. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The terms "vehicle," "car," "automobile," and variations thereof may be used interchangeably herein and can refer to a device or structure for transporting animate and/or inanimate or tangible objects (e.g., persons and/or things), such as a self-propelled conveyance. A vehicle as used herein can include any conveyance or model of a conveyance, where the conveyance was originally designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

The term "profile," as used herein, can refer to any data structure, data store, and/or database that includes one or more items of information associated with a vehicle, a vehicle system, a device (e.g., a mobile device, laptop, mobile phone, etc.), or a person.

The term "in communication with," as used herein, refers to any coupling, connection, or interaction using electrical signals to exchange information or data, using any system, hardware, software, protocol, or format, regardless of whether the exchange occurs wirelessly or over a wired connection.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible utilizing, alone or in combination, one or more of the features set forth above or described in detail below.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference letter or label.

DETAILED DESCRIPTION

Presented herein are embodiments of systems, devices, processes, data structures, user interfaces, etc. The embodiments may relate to an automobile and/or an automobile environment. The automobile environment can include systems associated with the automobile and devices or other systems in communication with the automobile and/or automobile systems. Furthermore, the systems can relate to communications systems and/or devices and may be capable of communicating with other devices and/or to an individual or group of individuals. Further, the systems can receive user input in unique ways. The overall design and functionality of the systems provide for an enhanced user experience making the automobile more useful and more efficient. As described herein, the automobile systems may be electrical, mechanical, electro-mechanical, software-based, and/or combinations thereof.

Figure 1:
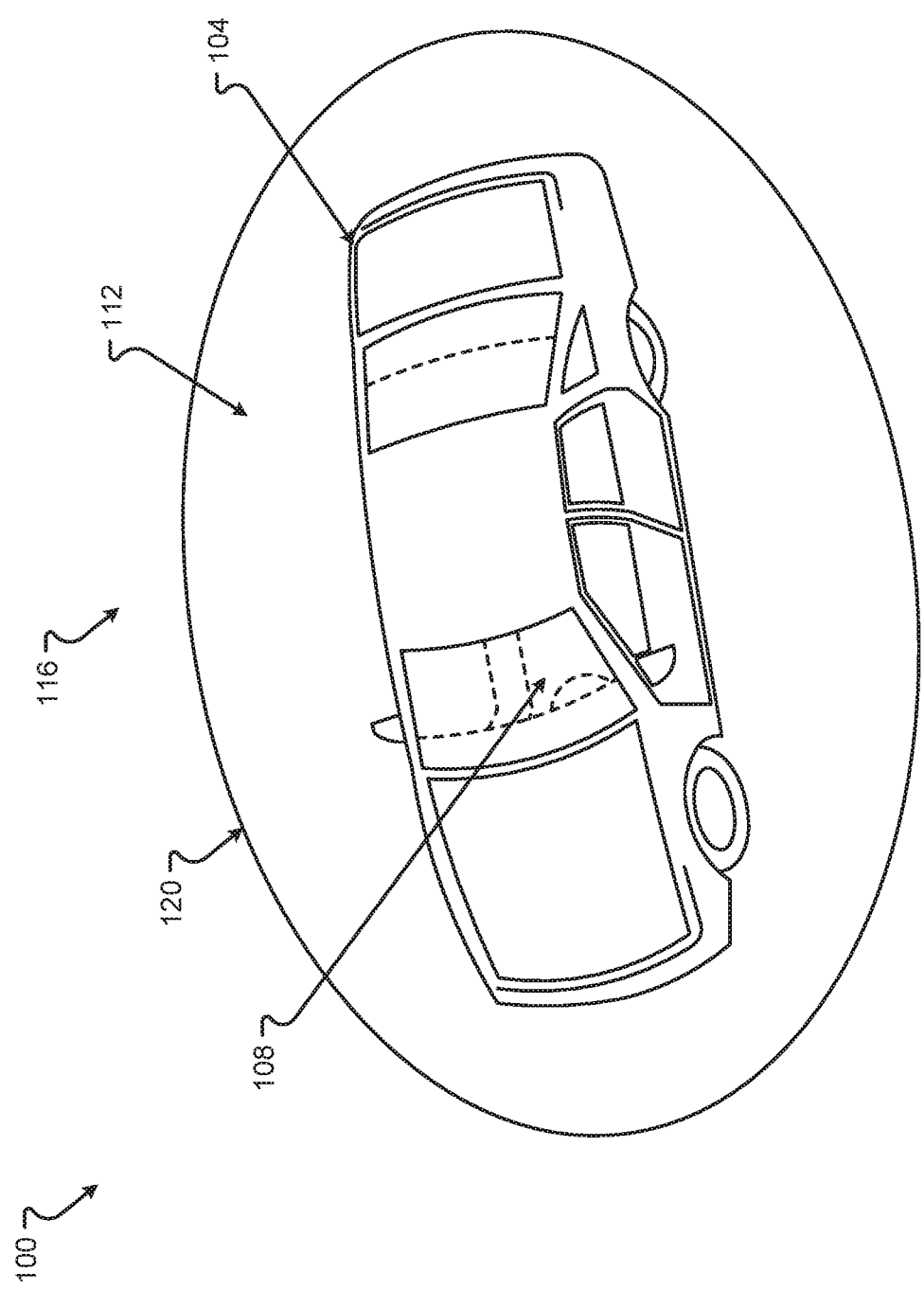
FIG. 1 depicts an embodiment of a vehicle operating environment.

A vehicle environment 100 that may contain a vehicle ecosystem is shown in FIG. 1. The vehicle environment 100 can contain areas associated with a vehicle or conveyance 104. The vehicle 104 is shown as a car but can be any type of conveyance. The environment 100 can include at least three zones. A first zone 108 may be inside a vehicle 104. The zone 108 includes any interior space, trunk space, engine compartment, or other associated space within or associated with the vehicle 104. The interior zone 108 can be defined by one or more techniques, for example, geo-fencing.

A second zone 112 may be delineated by line 120. The zone 112 is created by a range of one or more sensors associated with the vehicle 104. Thus, the area 112 is exemplary of the range of those sensors and what can be detected by those sensors associated with the vehicle 104. Although sensor range is shown as a fixed and continuous oval, the sensor range may be dynamic and/or discontinuous. For example, a ranging sensor (e.g., radar, lidar, ladar, etc.) may provide a variable range depending on output power, signal characteristics, or environmental conditions (e.g., rain, fog, clear, etc.). The rest of the environment includes all space beyond the range of the sensors and is represented by space 116. Thus, the environment 100 may have an area 116 that includes all areas beyond the sensor range 112. The area 116 may include locations of travel that the vehicle 104 may proceed to in the future.

Figure 2:
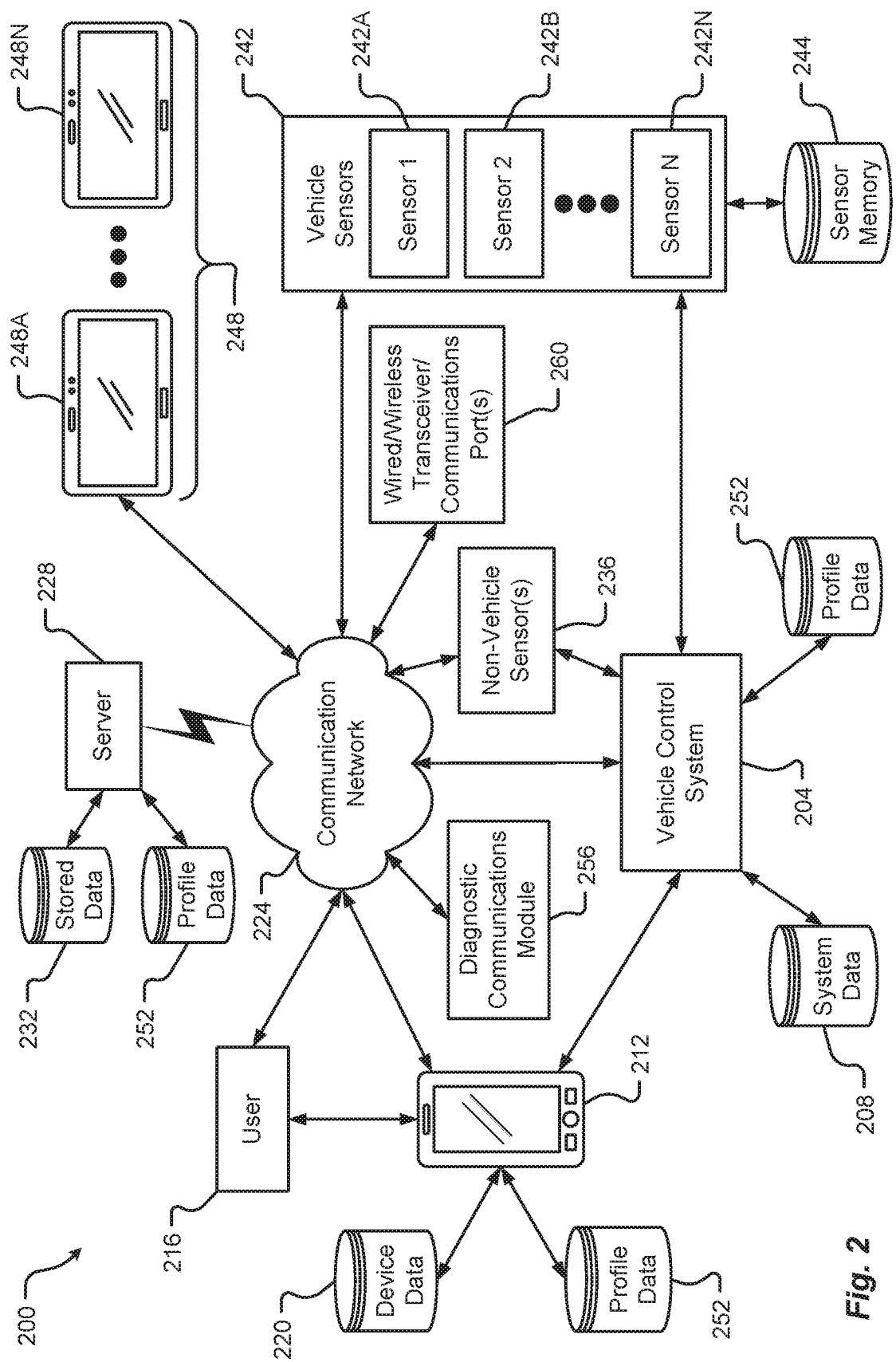
FIG. 2 is a block diagram of an embodiment of a vehicle system.

An embodiment of a vehicle system 200 is shown in FIG. 2. The vehicle system 200 may comprise hardware and/or software that conduct various operations for or with the vehicle 104. The operations can include, but are not limited to, providing information to the user 216, receiving input from the user 216, and controlling the functions or operation of the vehicle 104, etc. The vehicle system 200 can include a vehicle control system 204. The vehicle control system 204 can be any type of computing system operable to conduct the operations as described herein. An example of a vehicle control system may be as described in conjunction with FIG. 3.

The vehicle control system 204 may interact with a memory or storage system 208 that stores system data. System data 208 may be any type of data needed for the vehicle control system 204 to control effectively the vehicle 104. The system data 208 can represent any type of database or other storage system. Thus, the system data 208 can be a flat file data system, an object-oriented data system, or some other data system that may interface with the vehicle control system 204.

The vehicle control system 204 may communicate with a device or user interface 212, 248. The user interface 212, 248 may be operable to receive user input either through touch input, on one or more user interface buttons, via voice command, via one or more image sensors, or through a graphical user interface that may include a gesture capture region, as described in conjunction with the other figures provided herein. Further, the symbol 212, 248 can represent a device that is located or associated with the vehicle 104. The device 212, 248 can be a mobile device, including, but not limited to, a mobile telephone, a mobile computer, or other type of computing system or device that is either permanently located in or temporarily associated with, but not necessarily connected to, the vehicle 104. Thus, the vehicle control system 204 can interface with the device 212, 248 and leverage the device's computing capability to provide one or more of the features or functions as described herein.

The device or user interface 212, 248 can receive input or provide information to a user 216. The user 216 may thus interact with the vehicle control system 204 through the interface or device 212, 248. Further, the device 212, 248 may include or have access to device data 220 and/or profile data 252. The device data 220 can be any type of data that is used in conjunction with the device 212, 248 including, but not limited to, multimedia data, preferences data, device identification information, or other types of data. The profile data 252 can be any type of data associated with at least one user 216 including, but in no way limited to, bioinformatics, medical information, driving history, personal information (e.g., home physical address, business physical address, contact addresses, likes, dislikes, hobbies, size, weight, occupation, business contacts—including physical and/or electronic addresses, personal contacts—including physical and/or electronic addresses, family members, and personal information related thereto, etc.), other user characteristics, advertising information, user settings and feature preferences, travel information, associated vehicle preferences, communication preferences, historical information (e.g., including historical, current, and/or future travel destinations), Internet browsing history, or other types of data. In any event, the data may be stored as device data 220 and/or profile data 252 in a storage system similar to that described in conjunction with FIGS. 12A through 12D.

As an example, the profile data 252 may include one or more user profiles. User profiles may be generated based on data gathered from one or more of vehicle preferences (e.g., seat settings, HVAC settings, dash configurations, and the like), recorded settings, geographic location information (e.g., provided by a satellite positioning system (e.g., GPS), Wi-Fi hotspot, cell tower data, etc.), mobile device information (such as mobile device electronic addresses, Internet browsing history and content, application store selections, user settings and enabled and disabled features, and the like), private information (such as user information from a social network, user presence information, user business account, and the like), secure data, biometric information, audio information from on board microphones, video information from on board cameras, Internet browsing history and browsed content using an on board computer and/or the local area network enabled by the vehicle 104, geographic location information (e.g., a vendor storefront, roadway name, city name, etc.), and the like.

The profile data 252 may include one or more user accounts. User accounts may include access and permissions to one or more settings and/or feature preferences associated with the vehicle 104, communications, infotainment, content, etc. In one example, a user account may allow access to certain settings for a particular user, while another user account may deny access to the settings for another user, and vice versa. The access controlled by the user account may be based on at least one of a user account priority, role, permission, age, family status, a group priority (e.g., the user account priority of one or more users, etc.), a group age (e.g., the average age of users in the group, a minimum age of the users in the group, a maximum age of the users in the group, and/or combinations thereof, etc.).

For example, a user 216 may be allowed to purchase applications (e.g., software, etc.) for the vehicle 104 and/or a device associated with the vehicle 104 based on information associated with the user account. This user account information may include a preferred payment method, permissions, and/or other account information. As provided herein, the user account information may be part of the user profile and/or other data stored in the profile data 252.

As another example, an adult user (e.g., a user with an age of 18 years old and/or over, etc.) may be located in an area of a vehicle 104, such as a rear passenger area. Continuing this example a child user (e.g., a user with an age of 17 years old and/or less, etc.) may be located in the same, or close, area. In this example, the user account information in the profile data 252 associated with both the adult user and the child user may be used by the vehicle 104 in determining whether content is appropriate for the area given the age of the child user. For instance, a graphic movie containing violence (e.g., a movie associated with a mature rating, such as a Motion Picture Association of America (MPAA) rating of "R," "NC-17," etc.) may be suitable to present to a display device associated with the adult user but may not be acceptable to present to the display device if a 12-year old child user may see and/or hear the content of the movie.

The vehicle control system 204 may also communicate with or through a communication network 224. The communication network 224 can represent any type of wireless and/or wired communication system that may be included within the vehicle 104 or operable to communicate outside the vehicle 104. Thus, the communication network 224 can include a local area communication capability and a wide area communication capability. For example, the communication network 224 can include a Bluetooth® wireless system, an 802.11x (e.g., 802.11G/802.11N/802.11AC, or the like, wireless system), a CAN bus, an Ethernet network within the vehicle 104, or other types of communication networks that may function with or be associated with the vehicle 104. Further, the communication network 224 can also include wide area communication capabilities, including one or more of, but not limited to, a cellular communication capability, satellite telephone communication capability, a wireless wide area network communication capability, or other types of communication capabilities that allow for the vehicle control system 204 to communicate outside the vehicle 104.

The vehicle control system 204 may communicate through the communication network 224 to a server 228 that may be located in a facility that is not within physical proximity to the vehicle 104. Thus, the server 228 may represent a cloud computing system or cloud storage that allows the vehicle control system 204 to either gain access to further computing capabilities or to storage at a location outside of the vehicle 104. The server 228 can include a computer processor and memory and be similar to any computing system as understood to one skilled in the art.

Further, the server 228 may be associated with stored data 232. The stored data 232 may be stored in any system or by any method, as described in conjunction with system data 208, device data 220, and/or profile data 252. The stored data 232 can include information that may be associated with one or more users 216 or associated with one or more vehicles 104. The stored data 232, being stored in a cloud or in a distant facility, may be exchanged among vehicles 104 or may be used by a user 216 in different locations or with different vehicles 104. Additionally or alternatively, the server may be associated with profile data 252 as provided herein. It is anticipated that the profile data 252 may be accessed across the communication network 224 by one or more components of the system 200. Similar to the stored data 232, the profile data 252, being stored in a cloud or in a distant facility, may be exchanged among vehicles 104 or may be used by a user 216 in different locations or with different vehicles 104.

The vehicle control system 204 may also communicate with one or more sensors 236, 242, which are either associated with the vehicle 104 or communicate with the vehicle 104. Vehicle sensors 242 may include one or more sensors for providing information to the vehicle control system 204 that determine or provide information about the environment 100 in which the vehicle 104 is operating. Embodiments of these sensors may be as described in conjunction with FIGS. 6A-7B. Non-vehicle sensor 236 can be any type of sensor that is not currently associated with the vehicle 104. For example, non-vehicle sensor 236 can be sensors in a traffic system operated by a third party that provides data to the vehicle control system 204. Further, the non-vehicle sensor(s) 236 can be other types of sensors which provide information about the distant environment 116 or other information about the vehicle 104 or the environment 100. These non-vehicle sensors 236 may be operated by third parties but provide information to the vehicle control system 204. Examples of information provided by the sensors 236 and that may be used by the vehicle control system 204 may include weather tracking data, traffic data, user health tracking data, vehicle maintenance data, or other types of data, which may provide environmental or other data to the vehicle control system 204. The vehicle control system 204 may also perform signal processing of signals received from one or more sensors 236, 242. Such signal processing may include estimation of a measured parameter from a single sensor, such as multiple measurements of a range state parameter from the vehicle 104 to an obstacle, and/or the estimation, blending, or fusion of a measured state parameter from multiple sensors such as multiple radar sensors or a combination of a ladar/lidar range sensor and a radar sensor. Signal processing of such sensor signal measurements may comprise stochastic signal processing, adaptive signal processing, and/or other signal processing techniques known to those skilled in the art.

The various sensors 236, 242 may include one or more sensor memory 244. Embodiments of the sensor memory 244 may be configured to store data collected by the sensors 236, 242. For example, a temperature sensor may collect temperature data associated with a vehicle 104, user 216, and/or environment, over time. The temperature data may be collected incrementally, in response to a condition, or at specific time periods. In this example, as the temperature data is collected, it may be stored in the sensor memory 244. In some cases, the data may be stored along with an identification of the sensor and a collection time associated with the data. Among other things, this stored data may include multiple data points and may be used to track changes in sensor measurements over time. As can be appreciated, the sensor memory 244 can represent any type of database or other storage system.

The diagnostic communications module 256 may be configured to receive and transmit diagnostic signals and information associated with the vehicle 104. Examples of diagnostics signals and information may include, but is in no way limited to, vehicle system warnings, sensor data, vehicle component status, service information, component health, maintenance alerts, recall notifications, predictive analysis, and the like. Embodiments of the diagnostic communications module 256 may handle warning/error signals in a predetermined manner. The signals, for instance, can be presented to one or more of a third party, occupant, vehicle control system 204, and a service provider (e.g., manufacturer, repair facility, etc.).

Optionally, the diagnostic communications module 256 may be utilized by a third party (i.e., a party other than the user 216, etc.) in communicating vehicle diagnostic information. For instance, a manufacturer may send a signal to a vehicle 104 to determine a status associated with one or more components associated with the vehicle 104. In response to receiving the signal, the diagnostic communications module 256 may communicate with the vehicle control system 204 to initiate a diagnostic status check. Once the diagnostic status check is performed, the information may be sent via the diagnostic communications module 256 to the manufacturer. This example may be especially useful in determining whether a component recall should be issued based on the status check responses returned from a certain number of vehicles.

Wired/wireless transceiver/communications ports 260 may be included. The wired/wireless transceiver/communications ports 260 may be included to support communications over wired networks or links, for example with other communication devices, server devices, and/or peripheral devices. Examples of wired/wireless transceiver/communications ports 260 include Ethernet ports, Universal Serial Bus (USB) ports, Institute of Electrical and Electronics Engineers (IEEE) 1594, or other interface ports.

Figure 3:
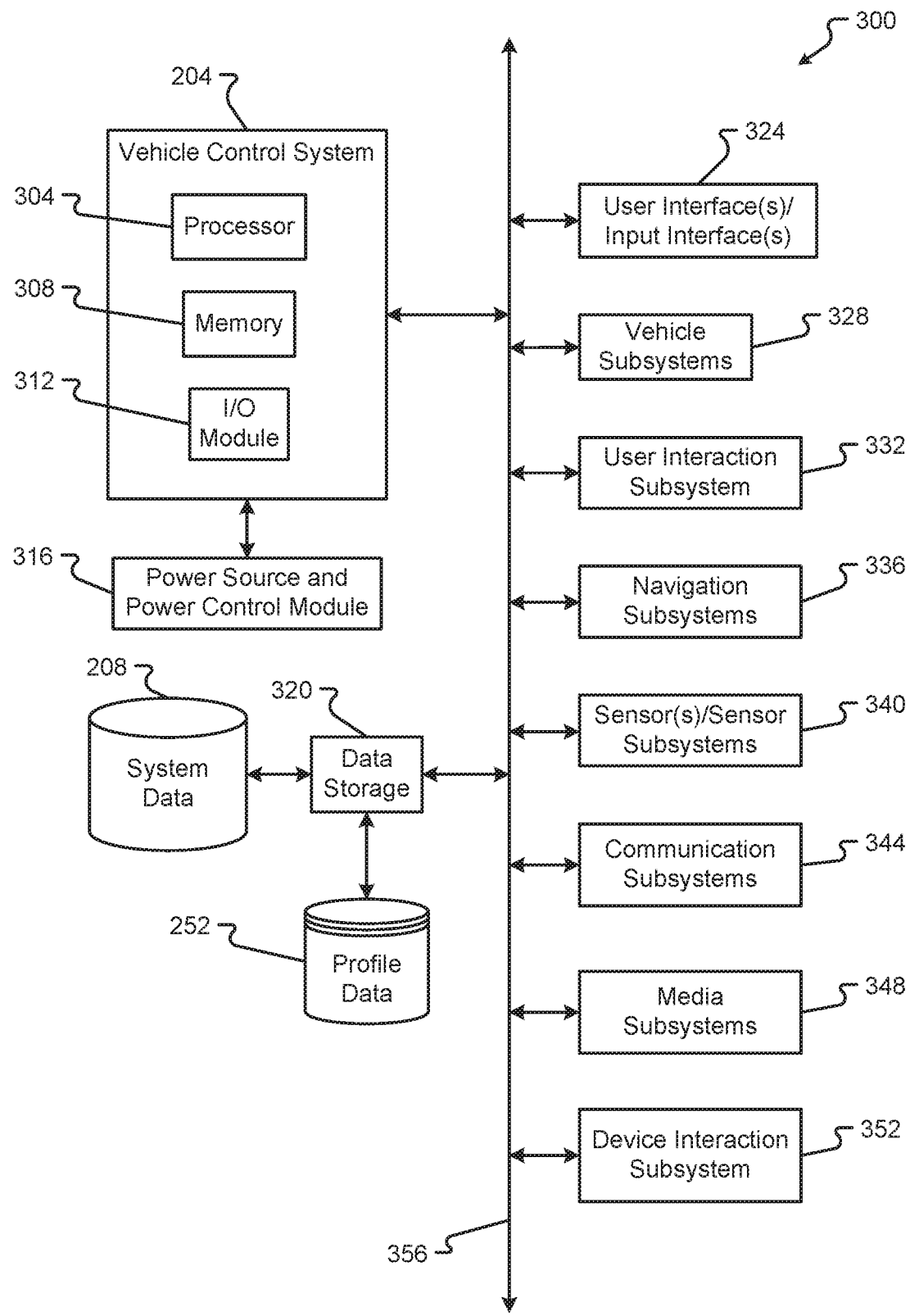
FIG. 3 is a block diagram of an embodiment of a vehicle control system environment.

An embodiment of a vehicle control environment 300 including a vehicle control system 204 may be as shown in FIG. 3. Beyond the vehicle control system 204, the vehicle control environment 300 can include one or more of, but is not limited to, a power source and/or power control module 316, a data storage module 320, user interface(s)/input interface(s) 324, vehicle subsystems 328, user interaction subsystems 332, Global Positioning System (GPS)/Navigation subsystems 336, sensor(s) and/or sensor subsystems 340, communication subsystems 344, media subsystems 348, and/or device interaction subsystems 352. The subsystems, modules, components, etc. 316-352 may include hardware, software, firmware, computer readable media, displays, input devices, output devices, etc. or combinations thereof. The system, subsystems, modules, components, etc. 204, 316-352 may communicate over a network or bus 356. This communication bus 356 may be bidirectional and perform data communications using any known or future-developed standard or protocol. An example of the communication bus 356 may be as described in conjunction with FIG. 4.

The vehicle control system 204 can include a processor 304, memory 308, and/or an input/output (I/O) module 312. Thus, the vehicle control system 204 may be a computer system, which can comprise hardware elements that may be electrically coupled. The hardware elements may include one or more central processing units (CPUs) 304; one or more components of the I/O module 312 including input devices (e.g., a mouse, a keyboard, etc.) and/or one or more output devices (e.g., a display device, a printer, etc.).

The processor 304 may comprise a general purpose programmable processor or controller for executing application programming or instructions. The processor 304 may, optionally, include multiple processor cores, and/or implement multiple virtual processors. Additionally or alternatively, the processor 304 may include multiple physical processors. As a particular example, the processor 304 may comprise a specially configured application specific integrated circuit (ASIC) or other integrated circuit, a digital signal processor, a controller, a hardwired electronic or logic circuit, a programmable logic device or gate array, a special purpose computer, or the like. The processor 304 generally functions to run programming code or instructions implementing various functions of the vehicle control system 204.

The input/output module 312 and associated ports may be included to support communications over wired or wireless networks or links, for example with other communication devices, server devices, and/or peripheral devices. Examples of an input/output module 312 include an Ethernet port, a Universal Serial Bus (USB) port, Institute of Electrical and Electronics Engineers (IEEE) 1594, or other interface.

The vehicle control system 204 may also include one or more storage devices 308. By way of example, storage devices 308 may be disk drives, optical storage devices, solid-state storage devices such as a random access memory ("RAM") and/or a read-only memory ("ROM"), which can be programmable, flash-updateable and/or the like. The vehicle control system 204 may additionally include a computer-readable storage media reader; a communications system (e.g., a modem, a network card (wireless or wired), an infrared communication device, etc.); and working memory 308, which may include RAM and ROM devices as described above. The vehicle control system 204 may also include a processing acceleration unit, which can include a digital signal processor (DSP), a special-purpose processor, and/or the like.

The computer-readable storage media reader can further be connected to a computer-readable storage medium, together (and, optionally, in combination with storage device(s)) comprehensively representing remote, local, fixed, and/or removable storage devices plus storage media for temporarily and/or more permanently containing computer-readable information. The communications system may permit data to be exchanged with an external or internal network and/or any other computer or device described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices, and/or other machine readable mediums for storing information.

Figure 10:
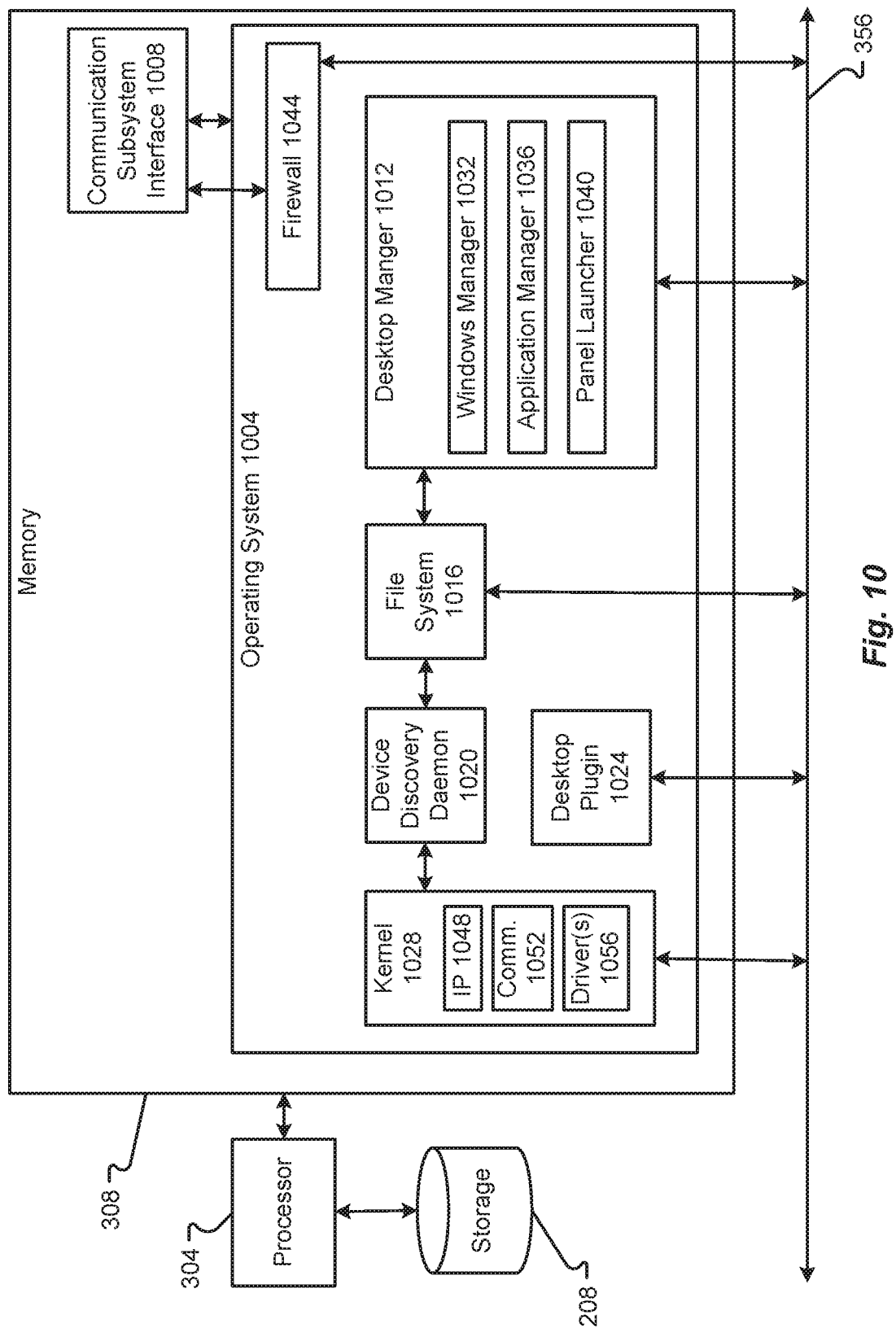
FIG. 10 is a block diagram of an embodiment of a software architecture for the vehicle control system.

The vehicle control system 204 may also comprise software elements including an operating system and/or other code, as described in conjunction with FIG. 10. It should be appreciated that alternates to the vehicle control system 204 may have numerous variations from that described herein. For example, customized hardware might also be used and/or particular elements might be implemented in hardware, software (including portable software, such as applets), or both. Further, connection to other computing devices such as network input/output devices may be employed.

The power source and/or power control module 316 can include any type of power source, including, but not limited to, batteries, alternating current sources (from connections to a building power system or power line), solar cell arrays, etc. One or more components or modules may also be included to control the power source or change the characteristics of the provided power signal. Such modules can include one or more of, but is not limited to, power regulators, power filters, alternating current (AC) to direct current (DC) converters, DC to AC converters, receptacles, wiring, other converters, etc. The power source and/or power control module 316 functions to provide the vehicle control system 204 and any other system with power.

The data storage 320 can include any module for storing, retrieving, and/or managing data in one or more data stores and/or databases. The database or data stores may reside on a storage medium local to (and/or resident in) the vehicle control system 204 or in the vehicle 104. Alternatively, some of the data storage capability may be remote from the vehicle control system 204 or automobile, and in communication (e.g., via a network) to the vehicle control system 204. The database or data stores may reside in a storage-area network ("SAN") familiar to those skilled in the art. Similarly, any necessary files for performing the functions attributed to the vehicle control system 204 may be stored locally on the respective vehicle control system 204 and/or remotely, as appropriate. The databases or data stores may be a relational database, and the data storage module 320 may be adapted to store, update, and retrieve data in response to specifically-formatted commands. The data storage module 320 may also perform data management functions for any flat file, object oriented, or other type of database or data store.

A first data store that may be part of the vehicle control environment 300 is a profile data store 252 for storing data about user profiles and data associated with the users. A system data store 208 can include data used by the vehicle control system 204 and/or one or more of the components 324-352 to facilitate the functionality described herein. The data stores 208 and/or 252 may be as described in conjunction with FIG. 1 and/or 12A-12D.

The user interface/input interfaces 324 may be as described herein for providing information or data and/or for receiving input or data from a user. Vehicle systems 328 can include any of the mechanical, electrical, electromechanical, computer, or other systems associated with the function of the vehicle 100. For example, vehicle systems 328 can include one or more of, but is not limited to, the steering system, the braking system, the engine and engine control systems, the electrical system, the suspension, the drive train, the cruise control system, the radio, the heating, ventilation, air conditioning (HVAC) system, the windows and/or doors, etc. These systems are well known in the art and will not be described further.

Examples of the other systems and subsystems 324-352 may be as described further herein. For example, the user interface(s)/input interface(s) 324 may be as described in FIGS. 2 and 8B; the vehicle subsystems 328 may be as described in FIG. 6a et. seq.; the user interaction subsystem 332 may be as described in conjunction with the user/device interaction subsystem 817 of FIG. 8B; the Navigation subsystem 336 may be as described in FIGS. 6A and 8C; the sensor(s)/sensor subsystem 340 may be as described in FIGS. 7A and 7B; the communication subsystem 344 may be as described in FIGS. 2, 4, 5B, 5C, and 9; the media subsystem 348 may be as described in FIG. 8A; and, the device interaction subsystem 352 may be as described in FIG. 2 and in conjunction with the user/device interaction subsystem 817 of FIG. 8B.

Figure 4:
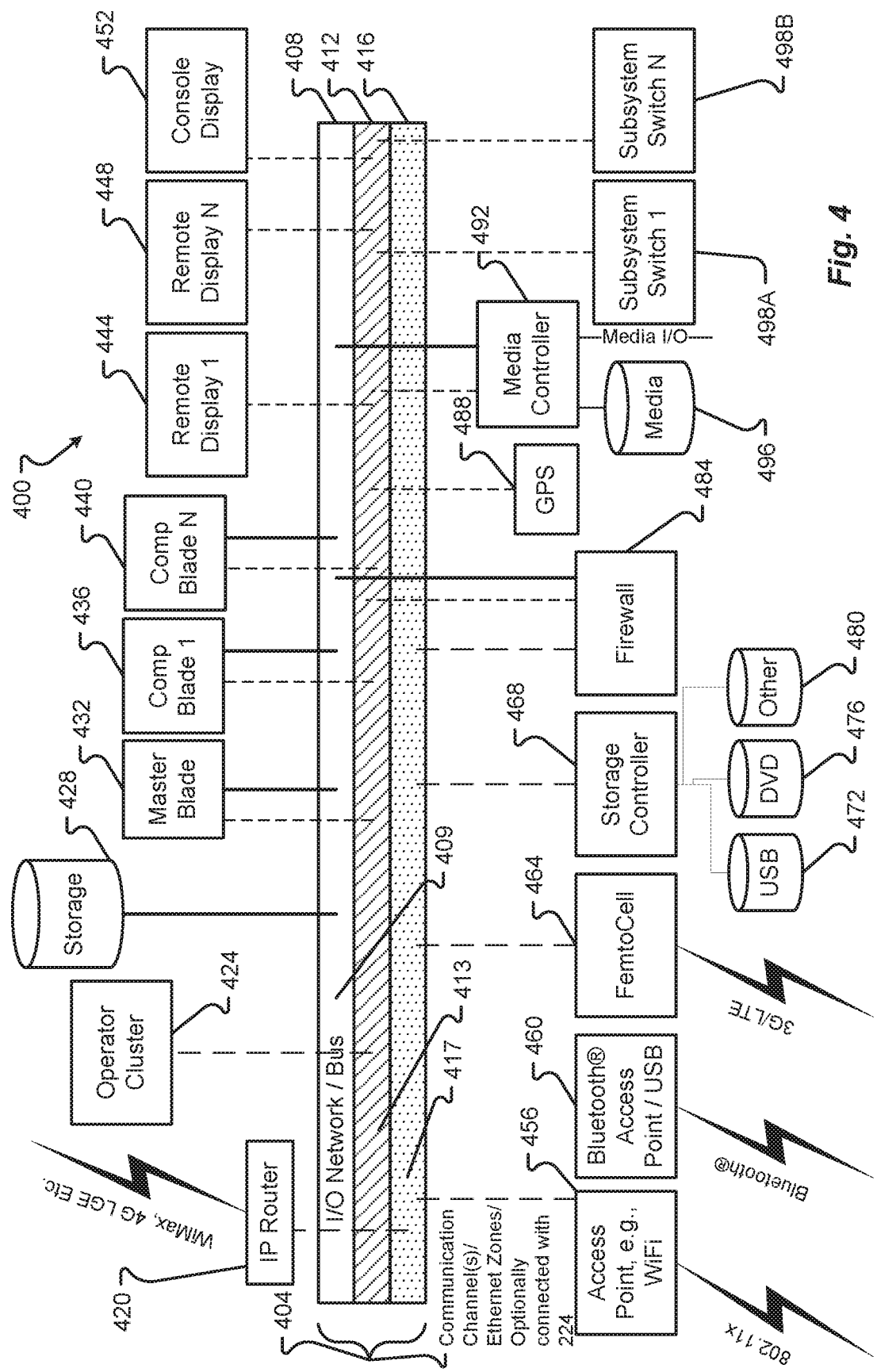
FIG. 4 is a block diagram of an embodiment of a vehicle communications subsystem.

FIG. 4 illustrates an optional communications channel architecture 400 and associated communications components. FIG. 4 illustrates some of the optional components that can be interconnected via the communication channels/zones 404. Communication channels/zones 404 can carry information on one or more of a wired and/or wireless communications link with, in the illustrated example, there being three communications channels/zones, 408, 412, and 416.

This optional environment 400 can also include an IP router 420, an operator cluster 424, one or more storage devices 428, one or more blades, such as master blade 432, and computational blades 436 and 440. Additionally, the communications channels/zones 404 can interconnect one or more displays, such as, remote display 1 444, remote display N 448, and console display 452. The communications channels/zones 404 also interconnect an access point 456, a Bluetooth® access point/USB hub 460, a Femtocell 464, a storage controller 468, that is connected to one or more of USB devices 472, DVDs 476, or other storage devices 480. To assist with managing communications within the communication channel, the environment 400 optionally includes a firewall 484 which will be discussed hereinafter in greater detail. Other components that could also share the communications channel/zones 404 include GPS 488, media controller 492, which is connected to one or more media sources 496, and one or more subsystems, such as subsystem switches 498.

Optionally, the communications channels/zones 404 can be viewed as an I/O network or bus where the communications channels are carried on the same physical media. Optionally, the communication channels 404 can be split amongst one or more physical media and/or combined with one or more wireless communications protocols. Optionally, the communications channels 404 can be based on wireless protocols with no physical media interconnecting the various elements described herein.

The environment 400 shown in FIG. 4 can include a collection of blade processors that are housed in a "crate." The crate can have a PC-style backplane connector 408 and a backplane Ethernet 408 that allows the various blades to communicate with one another using, for example, an Ethernet.

Various other functional elements illustrated in FIG. 4 can be integrated into this crate architecture with, as discussed hereinafter, various zones utilized for security. Optionally, as illustrated in FIG. 4, the backplane 404/408 can have two separate Ethernet zones that may or may not be on the same communications channel Optionally, the zones exist on a single communications channel on the I/O network/bus 408. Optionally, the zones are actually on different communications channels, e.g., 412, 416; however, the implementation is not restricted to any particular type of configuration. Rather, as illustrated in FIG. 4, there can be a red zone 417 and a green zone 413, and the I/O backplane on the network/bus 408 that enables standard I/O operations. This backplane or I/O network/bus 408 also optionally can provide power distribution to the various modules and blades illustrated in FIG. 4. The red and green Ethernet zones, 417 and 413 respectively, can be implemented as Ethernet switches, with one on each side of the firewall 484. Two Ethernets (untrusted and trusted) are not connected in accordance with an optional embodiment. Optionally, the connector geometry for the firewall can be different for the Ethernet zones than for the blades that are a part of the system.

The red zone 417 only needs to go from the modular connector to the input side of the backplane connector of the firewall 484. While FIG. 4 indicates that there are five external red zone connectors to the firewall 484, provisions can be made for any number of ports with the connections being made at the access point 456, the Bluetooth® access point (combo controller) 460, Femtocell 464, storage controller 468, and/or firewall 484. Optionally, the external port connections can be made through a manufacturer configurable modular connector panel, and one or more of the red zone Ethernet ports could be available through a customer supplied crate which allows, for example, wired Ethernet connections from a bring-your-own-device (BYOD) to the firewall 484.

The green zone 413 goes from the output side of the firewall 484 and generally defines the trusted Ethernet. The Ethernet on the backplane 408 essentially implements an Ethernet switch for the entire system, defining the Ethernet backbone of the vehicle 104. All other modules, e.g., blades, etc., can connect to a standard backplane bus and the trusted Ethernet. Some number of switch ports can be reserved to connect to an output modular connector panel to distribute the Ethernet throughout the vehicle 104, e.g., connecting such elements as the console display 452, remote displays 444, 448, GPS 488, etc. Optionally, only trusted components, either provided or approved by the manufacturer after testing, can be attached to the green zone 413, which is by definition in the trusted Ethernet environment.

Optionally, the environment 400, shown in FIG. 4, utilizes IPv6 over Ethernet connections wherever possible. Using, for example, the Broadcom single-twisted pair Ethernet technology, wiring harnesses are simplified and data transmission speeds are maximized. However, while the Broadcom single-twisted pair Ethernet technology can be used, in general, systems and methods can work comparably well with any type of well-known Ethernet technology or other comparable communications technology.

As illustrated in FIG. 4 the I/O network/bus 408 is a split-bus concept that contains three independent bus structures:

The red zone 417—the untrusted Ethernet environment. This zone 417 may be used to connect network devices and customer provided devices to the vehicle information system with these devices being on the untrusted side of the firewall 484.

The green zone 413—the trusted Ethernet environment, this zone 413 can be used to connect manufacturer certified devices such as GPS units, remote displays, subsystem switches, and the like, to the vehicle network 404. Manufacturer certified devices can be implemented by vendors that allow the vehicle software system to validate whether or not a device is certified to operate with the vehicle 100. Optionally, only certified devices are allowed to connect to the trusted side of the network.

The I/O bus 409—the I/O bus may be used to provide power and data transmission to bus-based devices such as the vehicle solid state drive, the media controller blade 492, the computational blades 436, 440, and the like.

As an example, the split-bus structure can have the following minimum configuration:

Two slots for the red zone Ethernet;
One slot for built-in LTE/WiMax access 420 from the car to other network resources such as the cloud/Internet;
One slot for user devices or bring-your-own device access, this slot can implement, for example, WiFi, Bluetooth®, and/or USB connectivity 456, which can be provided in, for example, the customer crate;
One slot for combined red zone and green zone Ethernet, this slot can be reserved for the firewall controller;
Two slots for computational blades. Here the two computation blades are illustratively as shown the optional master blade and the multimedia blade or controller 492 which can be provided as standard equipment; and
The expansion controller that allows the I/O bus to be extended and provides additional Ethernet switch ports for one or more of the red or green zones, which may require that the basic green zone Ethernet switch implementation will support additional ports beyond the initial three that are needed for the basic exemplary system.

It should be possible to build 8 or 16 or more Ethernet switches that allow for the expansion with existing component(s) in a straight-forward manner.

The red zone 417 can be implemented as an 8-port Ethernet switch that has three actual bus ports within the crate with the remaining five ports being available on the customer crate. The crate implements red zone slots for the firewall controller 484, the combo controller which includes WiFi, Bluetooth®, USB hub (456, 460) and the IP router 420.

The firewall controller 484 can have a dedicated slot that bridges the red zone 417, green zone 413, and uses the I/O bus for power connections. In accordance with an optional low cost implementation, the firewall 484 can be implemented by a dummy module that simply bridges the red zone 417 and the green zone 413 without necessarily providing any firewall functionality. The combo controller 460 that includes the WiFi, Bluetooth®, and USB hub can be provided for consumer device connections. This controller can also implement the IPv6 (un-routable) protocol to insure that all information is packetized for transmission via IP over the Ethernet in the I/O network/bus 408.

The combo controller 460 with the USB hub can have ports in the customer crate. The combo controller 460 can implement USB discovery functions and packetizes the information for transmission via IP over Ethernet. The combo controller 460 can also facilitate installation of the correct USB driver for the discovered device, such as a BYOD from the user. The combo controller 460 and USB hub can then map the USB address to a "local" IPv6 address for interaction with one or more of the computational blades which is generally going to be the media controller 492.

The IP router 420 can implement Internet access through a manufacturer provided service. This service can allow, for example, a manufacturer to offer value-added services to be integrated into the vehicle information systems. The existence of the manufacturer provided Internet access can also allow the "e-Call" function and other vehicle data recorder functions to be implemented. IP router 420 also allows, for example, WiMax, 4G LTE, and other connections to the Internet through a service provider that can be, for example, contracted by the manufacturer. Internally, the IP router 420 can allow cellular handset connections to the Internet through a Femtocell 464 that is part of the IP router implementation. The IP router 420, with the Femtocell 464, can also allow a cone of silence functionality to be implemented. The IP router 420 can be an optional component for a vehicle provided by, for example, the manufacturer, a dealer, or installed by a user. In the absence of the IP router 420, it is possible to connect a consumer handheld device to the I/O network/bus 408 using, for example, either WiFi or Bluetooth® 456, 460. While functionality may be somewhat reduced when using a handheld device instead of a built-in Ethernet connection, systems and methods of this invention can also work utilizing this consumer handheld device which then connects to the Internet via, for example, WiMax, 4G, 4G LTE, or the like.

Figure 5A:
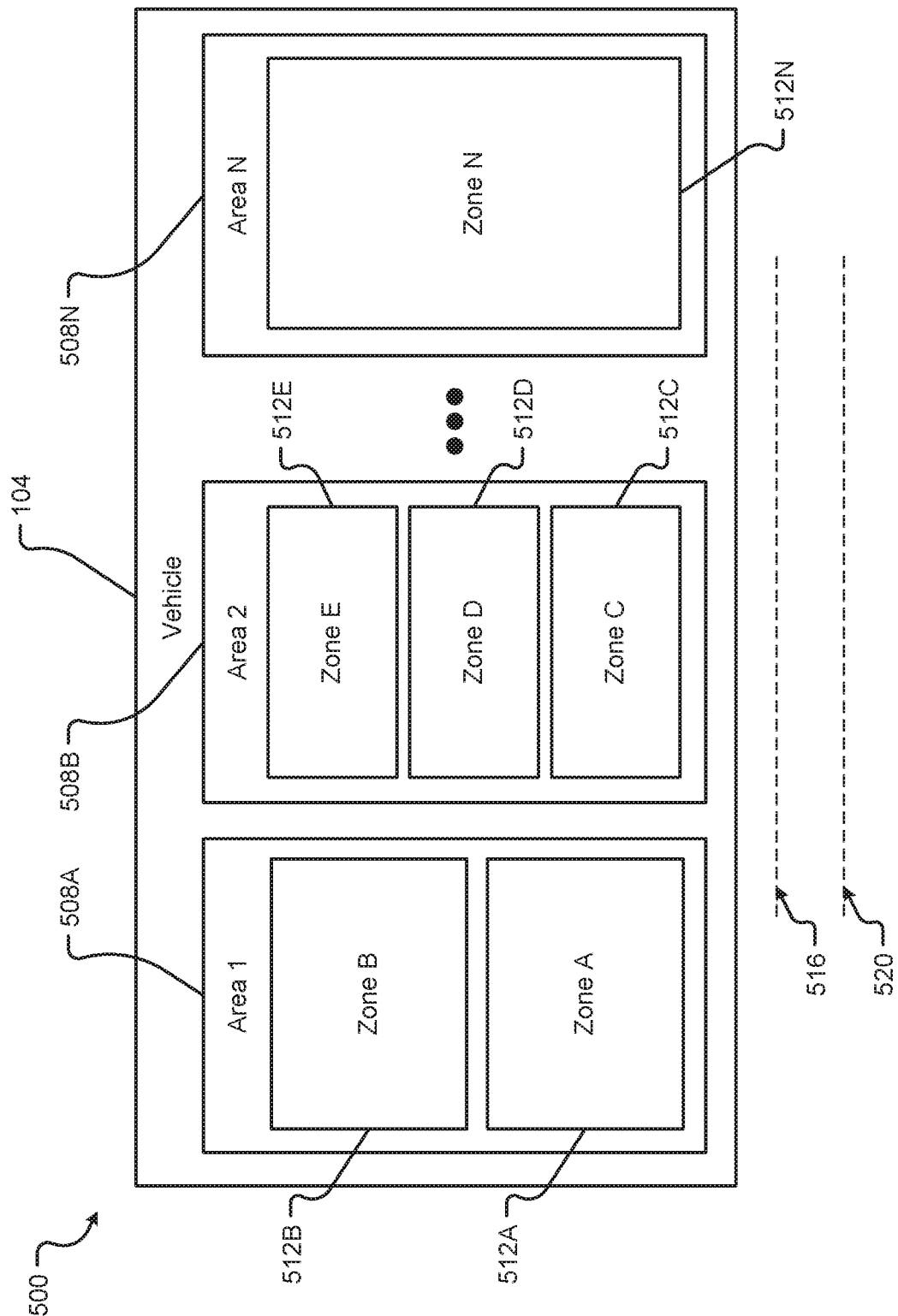
FIG. 5A is a first block diagram of an embodiment of a vehicle interior environment separated into areas and/or zones.
Figure 5B:
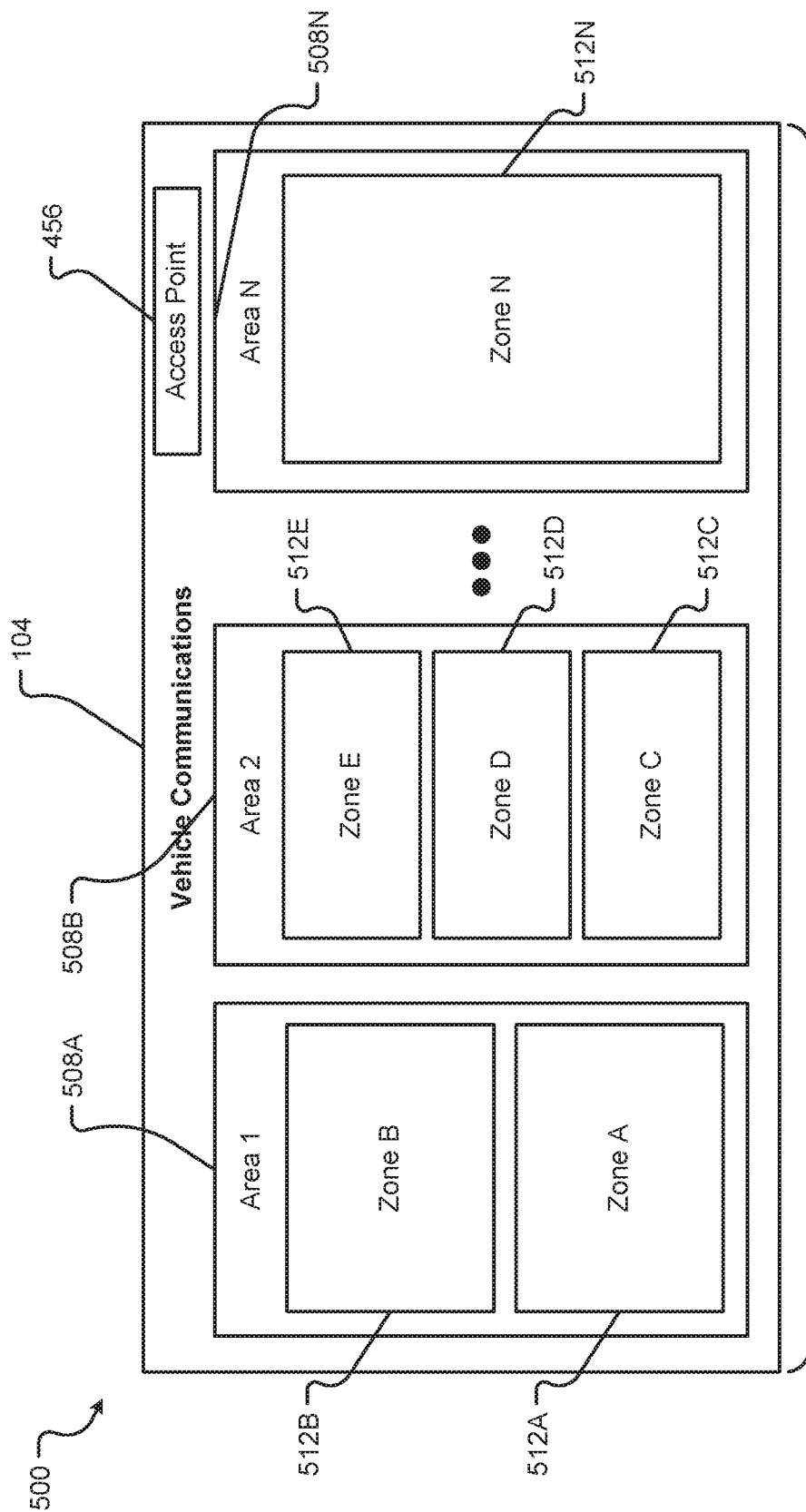
FIG. 5B is a second block diagram of an embodiment of a vehicle interior environment separated into areas and/or zones.
Figure 5C:
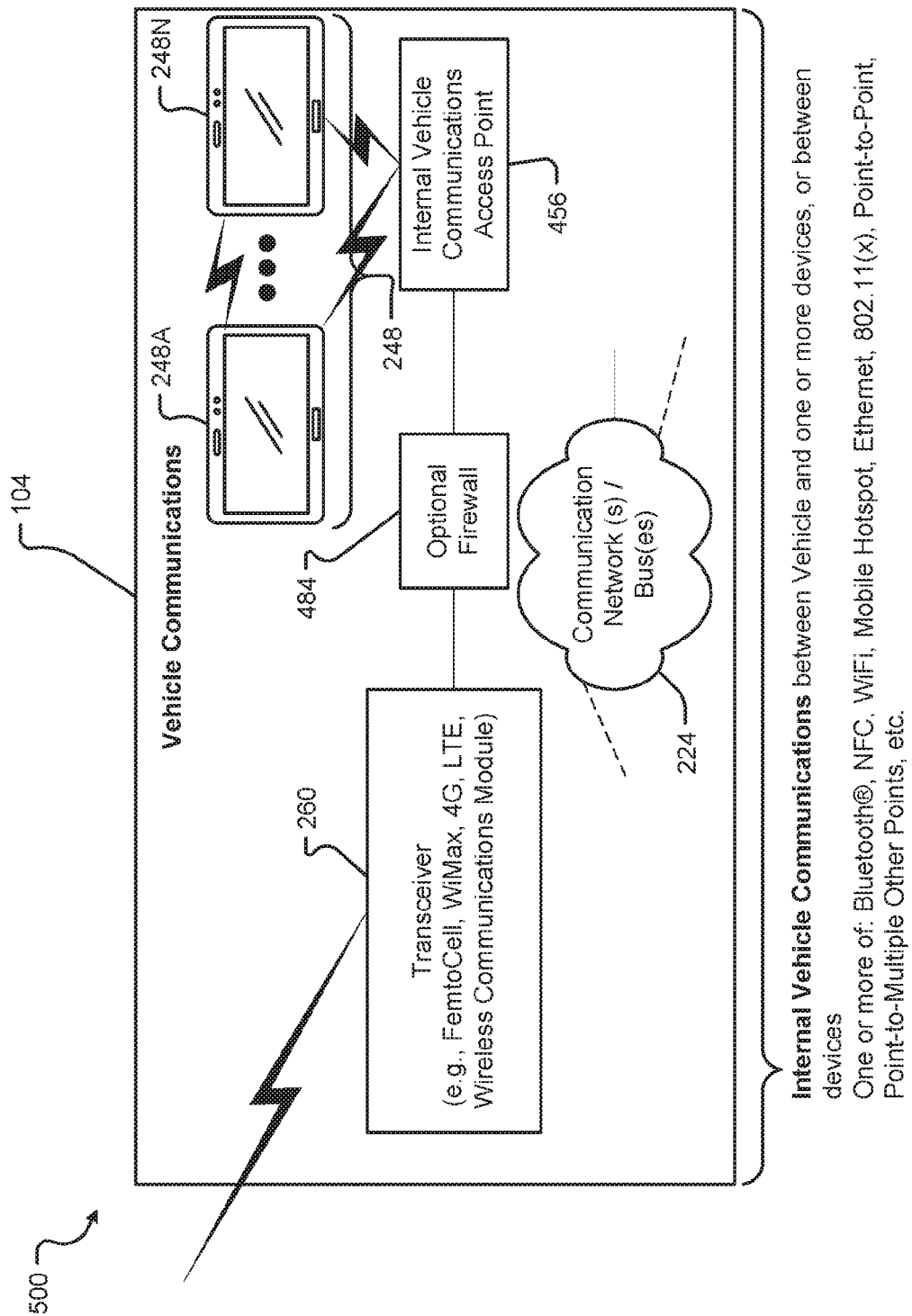
FIG. 5C is a third block diagram of an embodiment of a vehicle interior environment separated into areas and/or zones.

FIGS. 5A-5C show configurations of a vehicle 104. In general, a vehicle 104 may provide functionality based at least partially on one or more areas, zones, and distances, associated with the vehicle 104. Non-limiting examples of this functionality are provided herein below.

An arrangement or configuration for sensors within a vehicle 104 is as shown in FIG. 5A. The sensor arrangement 500 can include one or more areas 508 within the vehicle. An area can be a larger part of the environment inside or outside of the vehicle 104. Thus, area one 508A may include the area within the trunk space or engine space of the vehicle 104 and/or the front passenger compartment. Area two 508B may include a portion of the interior space 108 (e.g., a passenger compartment, etc.) of the vehicle 104. The area N, 508N, may include the trunk space or rear compartment area, when included within the vehicle 104. The interior space 108 may also be divided into other areas. Thus, one area may be associated with the front passenger's and driver's seats, a second area may be associated with the middle passengers' seats, and a third area may be associated with a rear passenger's seat. Each area 508 may include one or more sensors that are positioned or operate to provide environmental information about that area 508.

Each area 508 may be further separated into one or more zones 512 within the area 508. For example, area 1 508A may be separated into zone A 512A, and zone B 512B. Each zone 512 may be associated with a particular portion of the interior occupied by a passenger. For example, zone A 512A may be associated with a driver. Zone B 512B, may be associated with a front passenger. Each zone 512 may include one or more sensors that are positioned or configured to collect information about the environment or ecosystem associated with that zone or person.

A passenger area 508B may include more than two zones as described in conjunction with area 508A. For example, area 508B may include three zones, 512C, 512D, and 512E. These three separate zones 512C, 512D, and 512E may be associated with three passenger seats typically found in the rear passenger area of a vehicle 104. An area 508N and may include a single zone 512N as there may be no separate passenger areas but may include a single trunk area within the vehicle 104. The number of zones 512 is unlimited within the areas as the areas are also unlimited inside the vehicle 104. Further, it should be noted that there may be one or areas 508 or zones 512 that may be located outside the vehicle 104 that may have a specific set of sensors associated therewith.

Optionally, each area/access point 508, 456, 516, 520, and/or zone 512, associated with a vehicle 104, may comprise one or more sensors to determine a presence of a user 216 and/or device 212, 248 in and/or adjacent to each area 508, 456, 516, 520, and/or zone 512. The sensors may include vehicle sensors 242 and/or non-vehicle sensors 236 as described herein. It is anticipated that the sensors may be configured to communicate with a vehicle control system 204 and/or the diagnostic communications module 256. Additionally or alternatively, the sensors may communicate with a device 212, 248. The communication of sensors with the vehicle 104 may initiate and/or terminate the control of device 212, 248 features. For example, a vehicle operator may be located in a second outside area 520 associated with a vehicle 104. As the operator approaches the first outside area 516, associated with the vehicle 104, the vehicle control system 204 may determine to control features associated with one or more device 212, 248 and diagnostic communications module 256.

Optionally, the location of the device 212, 248 relative to the vehicle 104 may determine vehicle functionality and/or features to be provided and/or restricted to a user 216. By way of example, a device 212, 248 associated with a user 216 may be located at a second outside area 520 from the vehicle 104. In this case, and based at least partially on the distance of the device 212, 248 from the vehicle 104 (e.g., provided by detecting the device 212, 248 at or beyond the second outside area 520) the vehicle 104 may lock one or more features (e.g., ignition access, vehicle access, communications ability, etc.) associated with the vehicle 104. Optionally, the vehicle 104 may provide an alert based on the distance of the device 212, 248 from the vehicle 104. Continuing the example above, once the device 212, 248 reaches the first outside area 516 of the vehicle 104 at least one of the vehicle features may be unlocked. For instance, by reaching the first outside area 516, the vehicle 104 may unlock a door of the vehicle 104. In some cases, when the device is detected to be inside the vehicle 104, the various sensors 236, 242 may determine that the user 216 is in an area 508 and/or zone 512. As is further described herein, features of the vehicle 104, device 212, 248, and/or other components may be controlled based on rules stored in a memory.

FIG. 5B illustrates optional internal vehicle communications between one or more of the vehicle and one or more devices or between devices. Various communications can occur utilizing one or more Bluetooth®, NFC, WiFi, mobile hot spot, point-to-point communications, point-to-multipoint other point communications, an ad hoc network, or in general any known communications protocol over any known communications media or media-types.

Optionally, various types of internal vehicle communications can be facilitated using an access point 456 that utilizes one or more of Bluetooth®, NFC, WiFi, wireless Ethernet, mobile hot spot technology, or the like. Upon being connected with, and optionally authenticated to the access point 456, the connected device is able to communicate with one or more of the vehicle and one or more other devices that are connected to the access point 456. The type of connection to the access point 456 can be based on, for example, the zone 512, in which the device is located.

The user may identify their zone 512 in conjunction with an authentication procedure to the access point 456. For example, a driver in zone A 512A, upon authenticating to the access point 456, can cause the access point 456 to send a query to the device asking the device user in which zone 512 they are located. As discussed hereinafter, the zone 512 the user device is located in may have an impact on the type of communications, available bandwidth, the types of other devices or vehicle systems or subsystems the device could communicate with, and the like. As a brief introduction, internal communications with zone A 512A may be given preferential treatment over those communications originating from area 2 508B, which could have in itself, preferential treatment over communications originating within area N 508N.

Moreover, the device in zone A 512A can include profile information that governs the other devices that are allowed to connect to the access point 456 and what those devices have access to, how they can communicate, how much bandwidth they are allocated, and the like. While, optionally, the device associated with zone A 512A will be considered the "master" controller of the profile that governs the internal vehicle communications, it should be appreciated that this was arbitrarily chosen since it is assumed that there will always be a driver in a car that is present in zone A 512A. However, it should be appreciated the driver in zone A 512A, for example, may not have a communications device in which case a device associated with one of the other areas or zones, such as zone B 512B, area 2 508B, or area N 508N could also be associated with or control this master profile.

Optionally, various devices located within the various zones 512 can connect using, for example, ports provided by access point 456 or Bluetooth® access point/USB hub 460 as illustrated in FIG. 4. Similarly, the device(s) could connect utilizing the Femtocell 464 and optionally be directly connected via, for example, a standard Ethernet port.

As discussed, each one of the areas, area 1 508A, area 2 508B, and area N 508N, can each have associated therewith a profile that governs, for example, how many and what types of devices can connect from that area 508, bandwidth allocated to that area 508, the types of media or content available to device(s) within that area 508, the interconnection of devices within that area 508 or between areas 508, or, in general, can control any aspect of communication of an associated device with any one or more other associated devices/vehicle systems within the vehicle 104.

Optionally, area 2 508B devices can be provided with full access to multimedia and infotainment available within the vehicle 104, however, devices in area 2 508B may be restricted from any access to vehicle functions. Only devices in area 1 508A may be able to access vehicle control functions such as when "parents" are located in area 1 508A and the children are located in area 2 508B. Optionally, devices found in zone E 512E of area 2 508B may be able to access limited vehicle control functionality such as climate control within area 2. Similarly, devices in area N 508N may be able to control climate features within zone N 512N.

As will be appreciated, profiles can be established that allow management of communications within each of the areas 508, and further optionally within each of the zones 512. The profile can be granular in nature controlling not only what type of devices can connect within each zone 512, but how those devices can communicate with other devices and/or the vehicle and types of information that can be communicated.

To assist with identifying a location of a device within a zone 512, a number of different techniques can be utilized. One optional technique involves one or more of the vehicle sensors detecting the presence of an individual within one of the zones 512. Upon detection of an individual in a zone 512, communications subsystems 344 and the access point 456 can cooperate to not only associate the device within the zone 512 with the access point 456 but to also determine the location of the device within an area, and optionally within a zone 512. Once the device is established within a zone 512, a profile associated with the vehicle 104 can store information identifying that device and/or a person and optionally associating it with a particular zone 512 as a default. As discussed, there can be a master profile optionally associated with the device in zone A 512A, this master profile can govern communications with the communications subsystems 340 and where communications within vehicle 104 are to occur.

Some optional profiles are illustrated below where the Master Profile governs other device connectivity:

Master Profile:

| Area 1 508A | Area 2 508B | Area N 508N | Other |
|---|---|---|---|
| All Communications | Allow Access to Infotainment | No Access | Master Profile acts as Firewall and Router |
| All Vehicle Controls | Allow Area 2 Climate Control | | |

Secondary Profile (e.g., device in Zone B 512B, Area 1 508A)

| Area 1 508A | Area 2 508B | Area N 508N | Other |
|---|---|---|---|
| All Communications | Allow Access to Infotainment | Allow Access to Infotainment | Master Profile acts as Firewall and Router |
| All Vehicle Controls | Allow Area 2 Climate Control | Allow Area 2 Climate Control | |

Secondary Profile, Option 2

| Area 1 508A | Area 2 508B | Area N 508N | Other |
|---|---|---|---|
| All Communications | Allow Access to Infotainment, Internet | Allow Access to Infotainment | |
| All Vehicle Controls Except Driver-centric Controls | Allow Area 2 Climate Control | Allow Area 2 Climate Control | |

Some optional profiles are illustrated below where the Area/Zone governs device connectivity: Area 2 508B Profile:

| Area 1 508A | Area 2 508B | Area N 508N | Other |
|---|---|---|---|
| No Communications with Area 1 Devices | Allow Access to Infotainment, Allow Access to Other Area 2 or Zone N Devices, Internet | | |
| No Vehicle Controls | Allow Area 2 Climate Control | | |

Area N 508N Profile:

| Area 1 508A | Area 2 508B | Area N 508N | Other |
|---|---|---|---|
| Communications with Area 1, Zone B Device | | Allow Access to Infotainment, Allow Access to Other Area N or Zone N Devices | |
| No Vehicle Controls | | Allow Area N Climate Control | |
| Media Sharing with Area 1, Zone B and Vehicle | Allow Access to Infotainment, Allow Access to Other Area 2 or Zone N Devices, Internet and Femtocell | | |
| No Vehicle Controls | | | |

Area 2 508B Profile:

Optionally, a user's device, such as a SmartPhone, can store in, for example a profile, with which zone 512 the user's device is associated. Then, assuming the user sits in the same zone 512 and area 508 as previously, the user's device can re-establish the same communications protocols with the access point 456 as were previously established.

In addition or in the alternative, the areas 508 and zones 512 can have associated therewith restrictions as to which one or more other user's devices with which users' devices can connect. For example, a first user's device can connect with any other user device in area 2 508B or area N 508N, however is restricted from connecting with a user device in area 1 508A, zone A 512A. However, the first user device may be able to communicate with another user's device that is located in area 1 508A, zone B 512B. These communications can include any type of standard communications such as sharing content, exchanging messages, forwarding or sharing multimedia or infotainment, or in general can include any communications that would ordinarily be available between two devices and/or the vehicle and vehicle systems. As discussed, there may be restrictions on the type of communications that can be sent to the device in area 1 508A, zone A 512A. For example, the user's device in area 1 508A, zone A 512A may be restricted from receiving one or more of text messages, multimedia, infotainment, or in general anything that can be envisioned as a potential distraction to the driver. Moreover, it should be appreciated that the communications between the various devices and the various zones 512 need not necessarily occur with the assistance of access point 456, but the communications could also occur directly between the device(s).

FIG. 5C outlines optional internal vehicle communications between one or more of the vehicle and one or more devices. More specifically, FIG. 5C illustrates an example of vehicle communications where the vehicle 104 is equipped with the necessary transceivers to provide a mobile hot spot functionality to any user device(s) therein, such as user devices 248A and 248N.

Optionally, and as discussed above, one or more user devices can connect to the access point 456. This access point 456 is equipped to handle communications routing to not only the communication network/buses 224 for intra-vehicle communications, but optionally can also communicate with, for example, the Internet or the cloud, in cooperation with transceiver 260. Optionally included is a firewall 484 that has the capability of not only blocking certain types of content, such as a malicious content, but can also operate to exclude certain type of communications from emanating from the vehicle 104 and transceiver 260. As will be appreciated, various profiles could be established in the firewall 484 that controls not only the type of communications that can be received at the vehicle 104, but the type of communications that can be sent from the vehicle 104.

The transceiver 260 can be any type of well-known wireless transceiver that communicates using a known communications protocol such as WiMax, 4G, 4G LTE, 3G, or the like. The user devices can communicate via, for example, WiFi link 248 with the access point 456, with the transceiver 260 providing Internet connectivity to the various user devices. As will be appreciated, there may need to be an account associated with transceiver 260 with a wireless carrier to provide data and/or voice connectivity to enable the user devices to communicate with the Internet. Typically, the account is established on a month-to-month basis with an associated fee but could also be performed based on the amount of data to be transmitted, received, or in any other manner.

Moreover, one or more of the user's devices and access point 456 can maintain profile information that governs how the user's devices are able to communicate with other devices, and optionally the Internet. Optionally, a profile can exist that only allows the user's devices to communicate with other user's devices and/or the vehicle, multimedia and/or the vehicle infotainment system, and may not be allowed access to the Internet via transceiver 260. The profile can stipulate that the user's device could connect to the Internet via transceiver 260 for a specified period of time and/or up to a certain amount of data usage. The user's device can have full access to the Internet via transceiver 260 with no limit on time or data usage which would reduce the data usage of the user's device since it is connected via WiFi to the access point 456, but however, would increase the data usage by transceiver 260, and therefore, shift the billing for that data usage to the transceiver 260 instead of the user's device. Still further, and as previously discussed, the various profiles may stipulate which user's device has priority for use of the bandwidth provided by the transceiver 260. For example, a user's device located area 1 508A, zone A 512A may be given preferential routing treatment of data above that of a user's device in zone N 512N. In this manner, for example, a driver would be given priority for Internet access above that of the passengers. This could become important, for example, when the driver is trying to obtain traffic or direction information or, for example, when the vehicle is performing a download to update various software features.

As will be appreciated, the optional firewall 484 can cooperate with the access point 456 and the various profiles that area 508 associated with the various devices within the vehicle 104 and can fully implement communications restrictions, control bandwidth limits, Internet accessibility, malicious software blocking, and the like. Moreover, the optional firewall 484 can be accessed by an administrator with one or more of these configuration settings edited through an administrator's control panel. For example, in a scenario where parents are always in area 1 508A, it may be appropriate to give all of the user's devices in area 1 508A full access to the Internet utilizing transceiver 260, however, while restricting access and/or bandwidth to any other user devices within the vehicle 104. As the user's device and profile would be known by the firewall 484, upon the user's device being associated with the access point 456, the firewall 484 and transceiver 260 can be configured to allow communications in accordance with the stored profile.

Figure 6A:
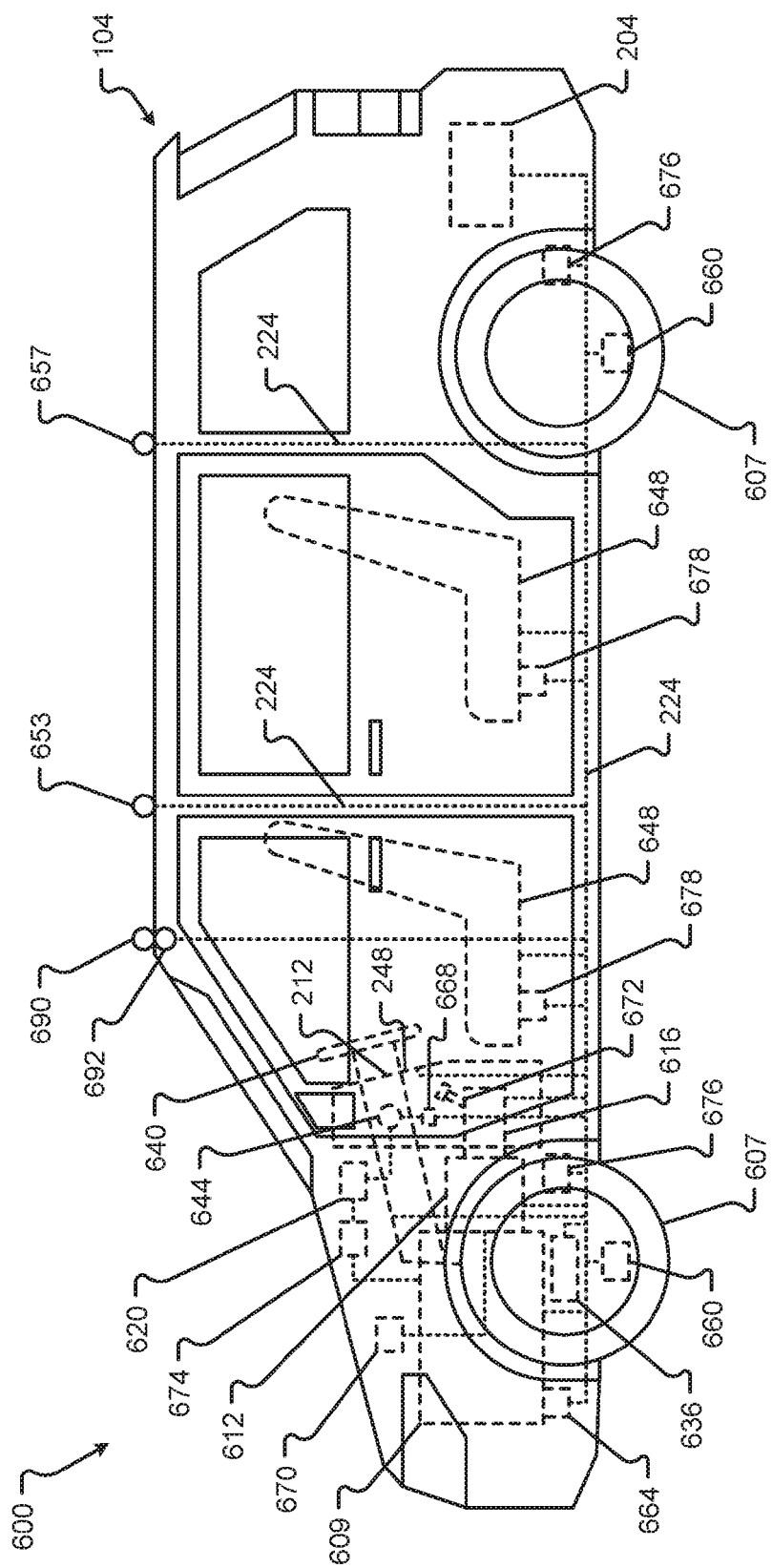
FIG. 6A depicts an embodiment of a sensor configuration for a vehicle.

A set of sensors or vehicle components 600 associated with the vehicle 104 may be as shown in FIG. 6A. The vehicle 104 can include, among many other components common to vehicles, wheels 607, a power source 609 (such as an engine, motor, or energy storage system (e.g., battery or capacitive energy storage system)), a manual or automatic transmission 612, a manual or automatic transmission gear controller 616, a power controller 620 (such as a throttle), a vehicle control system 204, the display device 212, a braking system 636, a steering wheel 640, a power source activation/deactivation switch 644 (e.g., an ignition), an occupant seating system 648, a wireless signal receiver 653 to receive wireless signals from signal sources such as roadside beacons and other electronic roadside devices, and a satellite positioning system receiver 657 (e.g., a Global Positioning System ("GPS") (US), GLONASS (Russia), Galileo positioning system (EU), Compass navigation system (China), and Regional Navigational Satellite System (India) receiver), driverless systems (e.g., cruise control systems, automatic steering systems, automatic braking systems, etc.).

The vehicle 104 can include a number of sensors in wireless or wired communication with the vehicle control system 204 and/or display device 212, 248 to collect sensed information regarding the vehicle state, configuration, and/or operation. Exemplary sensors may include one or more of, but are not limited to, wheel state sensor 660 to sense one or more of vehicle speed, acceleration, deceleration, wheel rotation, wheel speed (e.g., wheel revolutions-per-minute), wheel slip, and the like, a power source energy output sensor 664 to sense a power output of the power source 609 by measuring one or more of current engine speed (e.g., revolutions-per-minute), energy input and/or output (e.g., voltage, current, fuel consumption, and torque) (e.g., turbine speed sensor, input speed sensor, crankshaft position sensor, manifold absolute pressure sensor, mass flow sensor, and the like), and the like, a switch state sensor 668 to determine a current activation or deactivation state of the power source activation/deactivation switch 644, a transmission setting sensor 670 to determine a current setting of the transmission (e.g., gear selection or setting), a gear controller sensor 672 to determine a current setting of the gear controller 616, a power controller sensor 674 to determine a current setting of the power controller 620, a brake sensor 676 to determine a current state (braking or non-braking) of the braking system 636, a seating system sensor 678 to determine a seat setting and current weight of seated occupant, if any) in a selected seat of the seating system 648, exterior and interior sound receivers 690 and 692 (e.g., a microphone, sonar, and other type of acoustic-to-electric transducer or sensor) to receive and convert sound waves into an equivalent analog or digital signal. Examples of other sensors (not shown) that may be employed include safety system state sensors to determine a current state of a vehicular safety system (e.g., air bag setting (deployed or undeployed) and/or seat belt setting (engaged or not engaged)), light setting sensor (e.g., current headlight, emergency light, brake light, parking light, fog light, interior or passenger compartment light, and/or tail light state (on or off)), brake control (e.g., pedal) setting sensor, accelerator pedal setting or angle sensor, clutch pedal setting sensor, emergency brake pedal setting sensor, door setting (e.g., open, closed, locked or unlocked) sensor, engine temperature sensor, passenger compartment or cabin temperature sensor, window setting (open or closed) sensor, one or more interior-facing or exterior-facing cameras or other imaging sensors (which commonly convert an optical image into an electronic signal but may include other devices for detection objects such as an electromagnetic radiation emitter/receiver that emits electromagnetic radiation and receives electromagnetic waves reflected by the object) to sense objects, such as other vehicles and pedestrians and optionally determine the distance, trajectory and speed of such objects, in the vicinity or path of the vehicle, odometer reading sensor, trip mileage reading sensor, wind speed sensor, radar transmitter/receiver output, brake wear sensor, steering/torque sensor, oxygen sensor, ambient lighting sensor, vision system sensor, ranging sensor, parking sensor, heating, venting, and air conditioning (HVAC) sensor, water sensor, air-fuel ratio meter, blind spot monitor, hall effect sensor, microphone, radio frequency (RF) sensor, infrared (IR) sensor, vehicle control system sensors, wireless network sensor (e.g., Wi-Fi and/or Bluetooth® sensor), cellular data sensor, and other sensors either future-developed or known to those of skill in the vehicle art.

In the depicted vehicle embodiment, the various sensors can be in communication with the display device 212, 248 and vehicle control system 204 via signal carrier network 224. As noted, the signal carrier network 224 can be a network of signal conductors, a wireless network (e.g., a radio frequency, microwave, or infrared communication system using a communications protocol, such as Wi-Fi), or a combination thereof. The vehicle control system 204 may also provide signal processing of one or more sensors, sensor fusion of similar and/or dissimilar sensors, signal smoothing in the case of erroneous "wild point" signals, and/or sensor fault detection. For example, ranging measurements provided by one or more RF sensors may be combined with ranging measurements from one or more IR sensors to determine one fused estimate of vehicle range to an obstacle target.

The control system 204 may receive and read sensor signals, such as wheel and engine speed signals, as a digital input comprising, for example, a pulse width modulated (PWM) signal. The processor 304 can be configured, for example, to read each of the signals into a port configured as a counter or configured to generate an interrupt on receipt of a pulse, such that the processor 304 can determine, for example, the engine speed in revolutions per minute (RPM) and the speed of the vehicle in miles per hour (MPH) and/or kilometers per hour (KPH). One skilled in the art will recognize that the two signals can be received from existing sensors in a vehicle comprising a tachometer and a speedometer, respectively. Alternatively, the current engine speed and vehicle speed can be received in a communication packet as numeric values from a conventional dashboard subsystem comprising a tachometer and a speedometer. The transmission speed sensor signal can be similarly received as a digital input comprising a signal coupled to a counter or interrupt signal of the processor 304 or received as a value in a communication packet on a network or port interface from an existing subsystem of the vehicle 104. The ignition sensor signal can be configured as a digital input, wherein a HIGH value represents that the ignition is on and a LOW value represents that the ignition is OFF. Three bits of the port interface can be configured as a digital input to receive the gear shift position signal, representing eight possible gear shift positions. Alternatively, the gear shift position signal can be received in a communication packet as a numeric value on the port interface. The throttle position signal can be received as an analog input value, typically in the range 0-5 volts. Alternatively, the throttle position signal can be received in a communication packet as a numeric value on the port interface. The output of other sensors can be processed in a similar fashion.

Other sensors may be included and positioned in the interior space 108 of the vehicle 104. Generally, these interior sensors obtain data about the health of the driver and/or passenger(s), data about the safety of the driver and/or passenger(s), and/or data about the comfort of the driver and/or passenger(s). The health data sensors can include sensors in the steering wheel that can measure various health telemetry for the person (e.g., heart rate, temperature, blood pressure, blood presence, blood composition, etc.). Sensors in the seats may also provide for health telemetry (e.g., presence of liquid, weight, weight shifts, etc) Infrared sensors could detect a person's temperature; optical sensors can determine a person's position and whether the person has become unconscious. Other health sensors are possible and included herein.

Safety sensors can measure whether the person is acting safely. Optical sensors can determine a person's position and focus. If the person stops looking at the road ahead, the optical sensor can detect the lack of focus. Sensors in the seats may detect if a person is leaning forward or may be injured by a seat belt in a collision. Other sensors can detect that the driver has at least one hand on a steering wheel. Other safety sensors are possible and contemplated as if included herein.

Comfort sensors can collect information about a person's comfort. Temperature sensors may detect a temperature of the interior cabin. Moisture sensors can determine a relative humidity. Audio sensors can detect loud sounds or other distractions. Audio sensors may also receive input from a person through voice data. Other comfort sensors are possible and contemplated as if included herein.

Figure 6B:
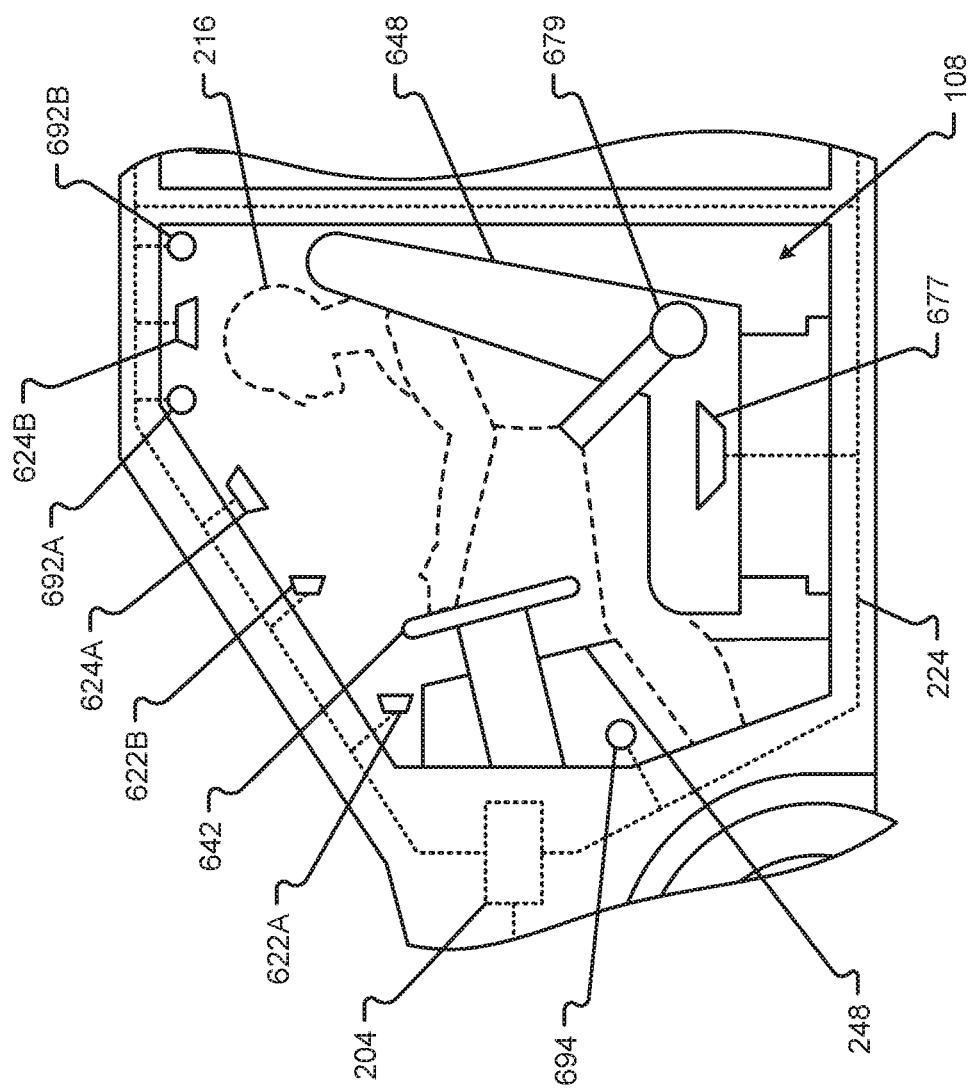
FIG. 6B depicts an embodiment of a sensor configuration for a zone of a vehicle.

FIG. 6B shows an interior sensor configuration for one or more zones 512 of a vehicle 104 optionally. Optionally, the areas 508 and/or zones 512 of a vehicle 104 may include sensors that are configured to collect information associated with the interior 108 of a vehicle 104. In particular, the various sensors may collect environmental information, user information, and safety information, to name a few. Embodiments of these sensors may be as described in conjunction with FIGS. 7A-8B.

Optionally, the sensors may include one or more of optical, or image, sensors 622A-B (e.g., cameras, etc.), motion sensors 624A-B (e.g., utilizing RF, IR, and/or other sound/image sensing, etc.), steering wheel user sensors 642 (e.g., heart rate, temperature, blood pressure, sweat, health, etc.), seat sensors 677 (e.g., weight, load cell, moisture, electrical, force transducer, etc.), safety restraint sensors 679 (e.g., seatbelt, airbag, load cell, force transducer, etc.), interior sound receivers 692A-B, environmental sensors 694 (e.g., temperature, humidity, air, oxygen, etc.), and the like.

The image sensors 622A-B may be used alone or in combination to identify objects, users 216, and/or other features, inside the vehicle 104. Optionally, a first image sensor 622A may be located in a different position within a vehicle 104 from a second image sensor 622B. When used in combination, the image sensors 622A-B may combine captured images to form, among other things, stereo and/or three-dimensional (3D) images. The stereo images can be recorded and/or used to determine depth associated with objects and/or users 216 in a vehicle 104. Optionally, the image sensors 622A-B used in combination may determine the complex geometry associated with identifying characteristics of a user 216. For instance, the image sensors 622A-B may be used to determine dimensions between various features of a user's face (e.g., the depth/distance from a user's nose to a user's cheeks, a linear distance between the center of a user's eyes, and more). These dimensions may be used to verify, record, and even modify characteristics that serve to identify a user 216. As can be appreciated, utilizing stereo images can allow for a user 216 to provide complex gestures in a 3D space of the vehicle 104. These gestures may be interpreted via one or more of the subsystems as disclosed herein. Optionally, the image sensors 622A-B may be used to determine movement associated with objects and/or users 216 within the vehicle 104. It should be appreciated that the number of image sensors used in a vehicle 104 may be increased to provide greater dimensional accuracy and/or views of a detected image in the vehicle 104.

The vehicle 104 may include one or more motion sensors 624A-B. These motion sensors 624A-B may detect motion and/or movement of objects inside the vehicle 104. Optionally, the motion sensors 624A-B may be used alone or in combination to detect movement. For example, a user 216 may be operating a vehicle 104 (e.g., while driving, etc.) when a passenger in the rear of the vehicle 104 unbuckles a safety belt and proceeds to move about the vehicle 104. In this example, the movement of the passenger could be detected by the motion sensors 624A-B. Optionally, the user 216 could be alerted of this movement by one or more of the devices 212, 248 in the vehicle 104. In another example, a passenger may attempt to reach for one of the vehicle control features (e.g., the steering wheel 640, the console, icons displayed on the head unit and/or device 212, 248, etc.). In this case, the movement (i.e., reaching) of the passenger may be detected by the motion sensors 624A-B. Optionally, the path, trajectory, anticipated path, and/or some other direction of movement/motion may be determined using the motion sensors 624A-B. In response to detecting the movement and/or the direction associated with the movement, the passenger may be prevented from interfacing with and/or accessing at least some of the vehicle control features (e.g., the features represented by icons may be hidden from a user interface, the features may be locked from use by the passenger, combinations thereof, etc.). As can be appreciated, the user 216 may be alerted of the movement/motion such that the user 216 can act to prevent the passenger from interfering with the vehicle 104 controls. Optionally, the number of motion sensors in a vehicle 104, or areas of a vehicle 104, may be increased to increase an accuracy associated with motion detected in the vehicle 104.

The interior sound receivers 692A-B may include, but are not limited to, microphones and other types of acoustic-to-electric transducers or sensors. Optionally, the interior sound receivers 692A-B may be configured to receive and convert sound waves into an equivalent analog or digital signal. The interior sound receivers 692A-B may serve to determine one or more locations associated with various sounds in the vehicle 104. The location of the sounds may be determined based on a comparison of volume levels, intensity, and the like, between sounds detected by two or more interior sound receivers 692A-B. For instance, a first interior sound receiver 692A may be located in a first area of the vehicle 104 and a second interior sound receiver 692B may be located in a second area of the vehicle 104. If a sound is detected at a first volume level by the first interior sound receiver 692A and a second, higher, volume level by the second interior sound receiver 692B in the second area of the vehicle 104, the sound may be determined to be closer to the second area of the vehicle 104. As can be appreciated, the number of sound receivers used in a vehicle 104 may be increased (e.g., more than two, etc.) to increase measurement accuracy surrounding sound detection and location, or source, of the sound (e.g., via triangulation, etc.).

Seat sensors 677 may be included in the vehicle 104. The seat sensors 677 may be associated with each seat and/or zone 512 in the vehicle 104. Optionally, the seat sensors 677 may provide health telemetry and/or identification via one or more of load cells, force transducers, weight sensors, moisture detection sensor, electrical conductivity/resistance sensor, and the like. For example, the seat sensors 677 may determine that a user 216 weighs 180 lbs. This value may be compared to user data stored in memory to determine whether a match exists between the detected weight and a user 216 associated with the vehicle 104. In another example, if the seat sensors 677 detect that a user 216 is fidgeting, or moving, in a seemingly uncontrollable manner, the system may determine that the user 216 has suffered a nervous and/or muscular system issue (e.g., seizure, etc.). The vehicle control system 204 may then cause the vehicle 104 to slow down and in addition or alternatively the automobile controller 8104 (described below) can safely take control of the vehicle 104 and bring the vehicle 104 to a stop in a safe location (e.g., out of traffic, off a freeway, etc).

Health telemetry and other data may be collected via the steering wheel user sensors 642. Optionally, the steering wheel user sensors 642 may collect heart rate, temperature, blood pressure, and the like, associated with a user 216 via at least one contact disposed on or about the steering wheel 640.

The safety restraint sensors 679 may be employed to determine a state associated with one or more safety restraint devices in a vehicle 104. The state associated with one or more safety restraint devices may serve to indicate a force observed at the safety restraint device, a state of activity (e.g., retracted, extended, various ranges of extension and/or retraction, deployment, buckled, unbuckled, etc.), damage to the safety restraint device, and more.

Environmental sensors 694, including one or more of temperature, humidity, air, oxygen, carbon monoxide, smoke, and other environmental condition sensors may be used in a vehicle 104. These environmental sensors 694 may be used to collect data relating to the safety, comfort, and/or condition of the interior space 108 of the vehicle 104. Among other things, the data collected by the environmental sensors 694 may be used by the vehicle control system 204 to alter functions of a vehicle. The environment may correspond to an interior space 108 of a vehicle 104 and/or specific areas 508 and/or zones 512 of the vehicle 104. It should be appreciate that an environment may correspond to a user 216. For example, a low oxygen environment may be detected by the environmental sensors 694 and associated with a user 216 who is operating the vehicle 104 in a particular zone 512. In response to detecting the low oxygen environment, at least one of the subsystems of the vehicle 104, as provided herein, may alter the environment, especially in the particular zone 512, to increase the amount of oxygen in the zone 512. Additionally or alternatively, the environmental sensors 694 may be used to report conditions associated with a vehicle (e.g., fire detected, low oxygen, low humidity, high carbon monoxide, etc.). The conditions may be reported to a user 216 and/or a third party via at least one communications module as provided herein.

Among other things, the sensors as disclosed herein may communicate with each other, with devices 212, 248, and/or with the vehicle control system 204 via the signal carrier network 224. Additionally or alternatively, the sensors disclosed herein may serve to provide data relevant to more than one category of sensor information including, but not limited to, combinations of environmental information, user information, and safety information to name a few.

Figure 7A:
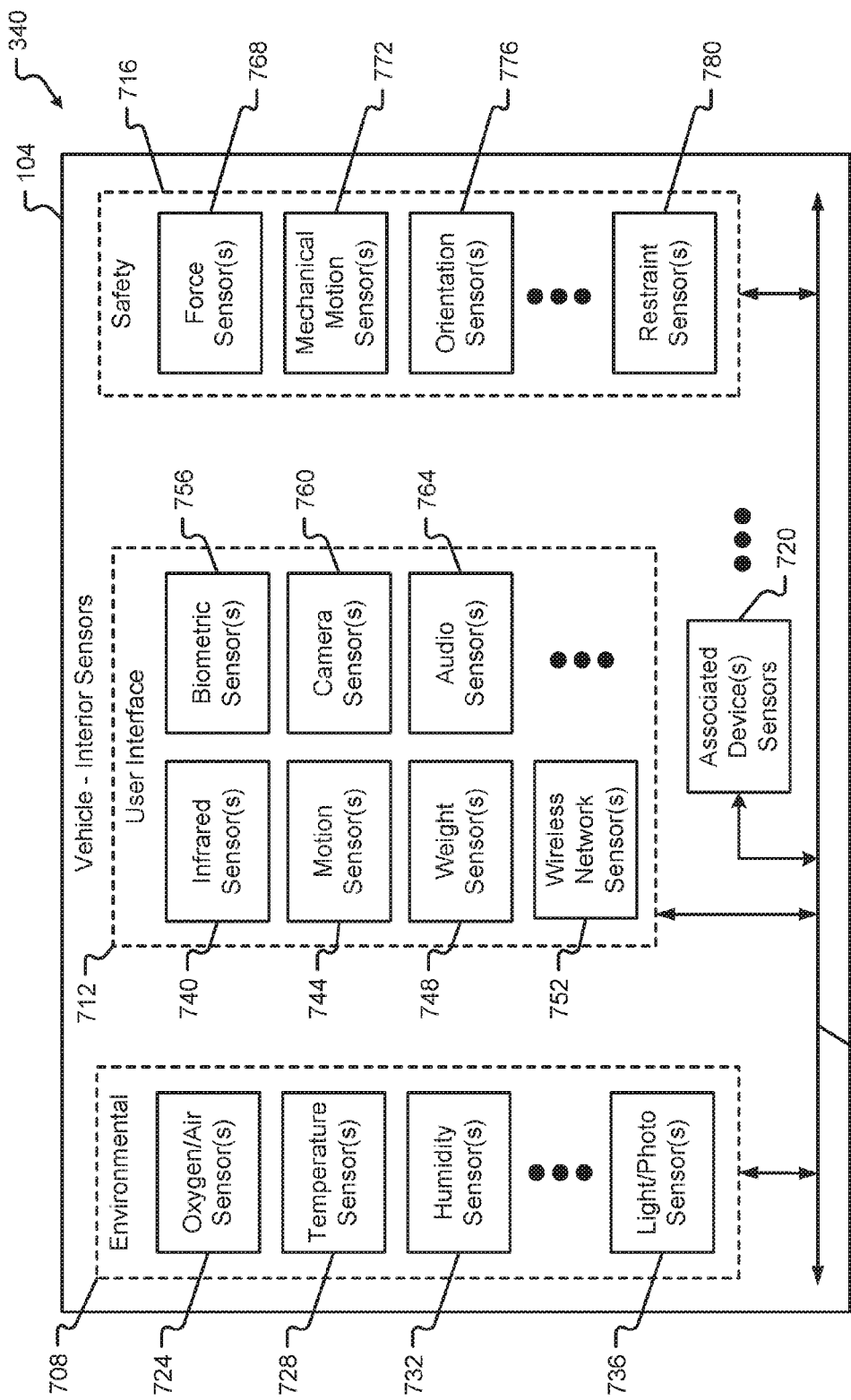
FIG. 7A is a block diagram of an embodiment of interior sensors for a vehicle.
Figure 7B:
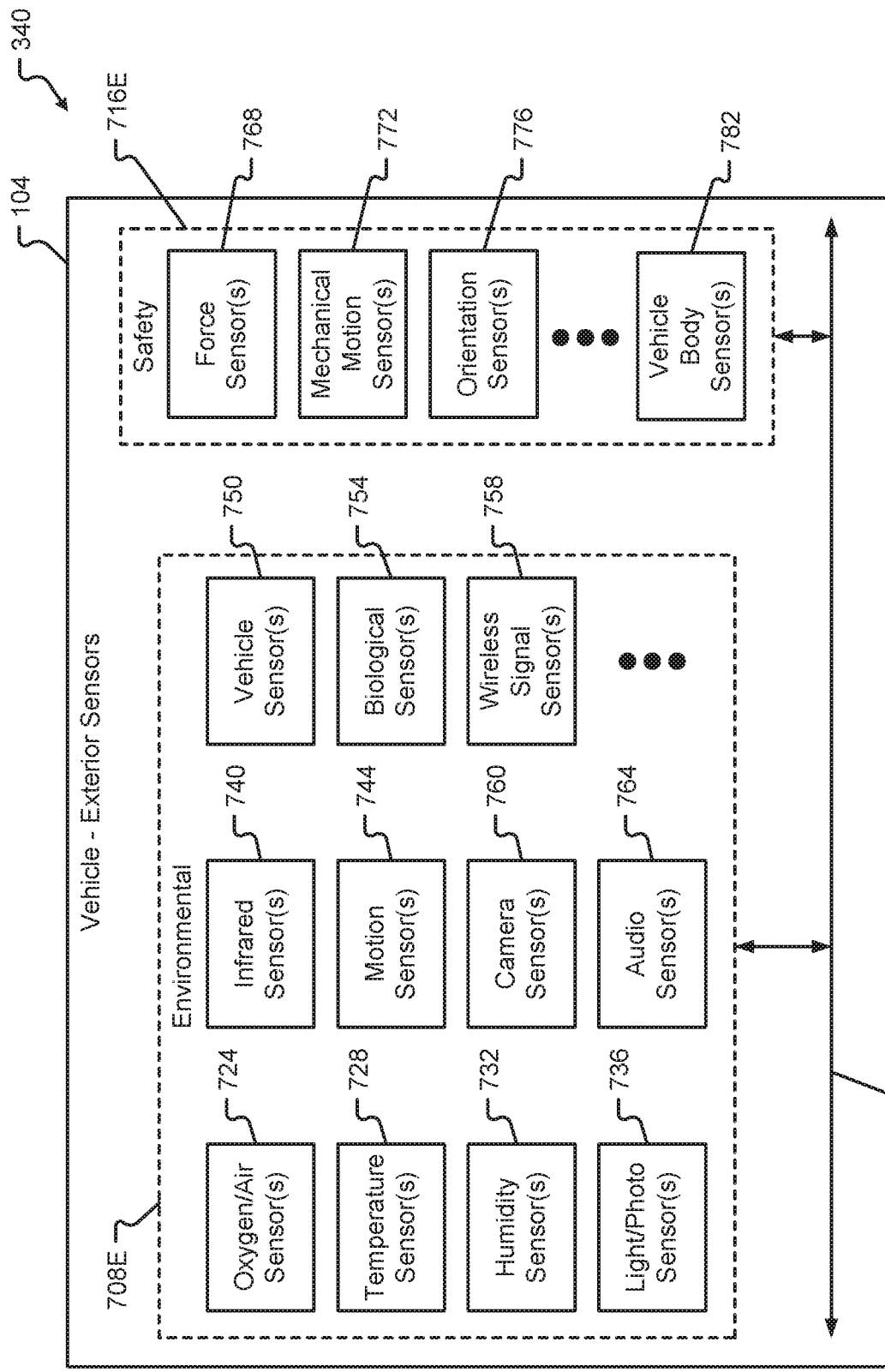
FIG. 7B is a block diagram of an embodiment of exterior sensors for a vehicle.

FIGS. 7A-7B show block diagrams of various sensors that may be associated with a vehicle 104. Although depicted as interior and exterior sensors, it should be appreciated that any of the one or more of the sensors shown may be used in both the interior space 108 and the exterior space of the vehicle 104. Moreover, sensors having the same symbol or name may include the same, or substantially the same, functionality as those sensors described elsewhere in the present disclosure. Further, although the various sensors are depicted in conjunction with specific groups (e.g., environmental 708, 708E, user interface 712, safety 716, 716E, etc.) the sensors should not be limited to the groups in which they appear. In other words, the sensors may be associated with other groups or combinations of groups and/or disassociated from one or more of the groups shown. The sensors as disclosed herein may communicate with each other, the devices 212, 248, and/or the vehicle control system 204 via one or more communications channel(s) 356.

FIG. 7A is a block diagram of an embodiment of interior sensors 340 for a vehicle 104 is provided. The interior sensors 340 may be arranged into one or more groups, based at least partially on the function of the interior sensors 340. The interior space 108 of a vehicle 104 may include an environmental group 708, a user interface group 712, and a safety group 716. Additionally or alternatively, there may be sensors associated with various devices inside the vehicle (e.g., devices 212, 248, smart phones, tablets, mobile computers, etc.)

The environmental group 708 may comprise sensors configured to collect data relating to the internal environment of a vehicle 104. It is anticipated that the environment of the vehicle 104 may be subdivided into areas 508 and zones 512 in an interior space 108 of a vehicle 104. In this case, each area 508 and/or zone 512 may include one or more of the environmental sensors. Examples of environmental sensors associated with the environmental group 708 may include, but are not limited to, oxygen/air sensors 724, temperature sensors 728, humidity sensors 732, light/photo sensors 736, and more. The oxygen/air sensors 724 may be configured to detect a quality of the air in the interior space 108 of the vehicle 104 (e.g., ratios and/or types of gasses comprising the air inside the vehicle 104, dangerous gas levels, safe gas levels, etc.). Temperature sensors 728 may be configured to detect temperature readings of one or more objects, users 216, and/or areas 508 of a vehicle 104. Humidity sensors 732 may detect an amount of water vapor present in the air inside the vehicle 104. The light/photo sensors 736 can detect an amount of light present in the vehicle 104. Further, the light/photo sensors 736 may be configured to detect various levels of light intensity associated with light in the vehicle 104.

The user interface group 712 may comprise sensors configured to collect data relating to one or more users 216 in a vehicle 104. As can be appreciated, the user interface group 712 may include sensors that are configured to collect data from users 216 in one or more areas 508 and zones 512 of the vehicle 104. For example, each area 508 and/or zone 512 of the vehicle 104 may include one or more of the sensors in the user interface group 712. Examples of user interface sensors associated with the user interface group 712 may include, but are not limited to, infrared sensors 740, motion sensors 744, weight sensors 748, wireless network sensors 752, biometric sensors 756, camera (or image) sensors 760, audio sensors 764, and more.

Infrared sensors 740 may be used to measure IR light irradiating from at least one surface, user 216, or other object in the vehicle 104. Among other things, the Infrared sensors 740 may be used to measure temperatures, form images (especially in low light conditions), identify users 216, and even detect motion in the vehicle 104.

The motion sensors 744 may be similar to the motion detectors 624A-B, as described in conjunction with FIG. 6B. Weight sensors 748 may be employed to collect data relating to objects and/or users 216 in various areas 508 of the vehicle 104. In some cases, the weight sensors 748 may be included in the seats and/or floor of a vehicle 104.

Optionally, the vehicle 104 may include a wireless network sensor 752. This sensor 752 may be configured to detect one or more wireless network(s) inside the vehicle 104. Examples of wireless networks may include, but are not limited to, wireless communications utilizing Bluetooth®, Wi-Fi™, ZigBee, IEEE 802.11, and other wireless technology standards. For example, a mobile hotspot may be detected inside the vehicle 104 via the wireless network sensor 752. In this case, the vehicle 104 may determine to utilize and/or share the mobile hotspot detected via/with one or more other devices 212, 248 and/or components associated with the vehicle 104.

Biometric sensors 756 may be employed to identify and/or record characteristics associated with a user 216. It is anticipated that biometric sensors 756 can include at least one of image sensors, IR sensors, fingerprint readers, weight sensors, load cells, force transducers, heart rate monitors, blood pressure monitors, and the like as provided herein.

The camera sensors 760 may be similar to image sensors 622A-B, as described in conjunction with FIG. 6B. Optionally, the camera sensors may record still images, video, and/or combinations thereof. The audio sensors 764 may be similar to the interior sound receivers 692A-B, as described in conjunction with FIGS. 6A-6B. The audio sensors may be configured to receive audio input from a user 216 of the vehicle 104. The audio input from a user 216 may correspond to voice commands, conversations detected in the vehicle 104, phone calls made in the vehicle 104, and/or other audible expressions made in the vehicle 104.

The safety group 716 may comprise sensors configured to collect data relating to the safety of a user 216 and/or one or more components of a vehicle 104. The vehicle 104 may be subdivided into areas 508 and/or zones 512 in an interior space 108 of a vehicle 104 where each area 508 and/or zone 512 may include one or more of the safety sensors provided herein. Examples of safety sensors associated with the safety group 716 may include, but are not limited to, force sensors 768, mechanical motion sensors 772, orientation sensors 776, restraint sensors 780, and more.

The force sensors 768 may include one or more sensors inside the vehicle 104 configured to detect a force observed in the vehicle 104. One example of a force sensor 768 may include a force transducer that converts measured forces (e.g., force, weight, pressure, etc.) into output signals.

Mechanical motion sensors 772 may correspond to encoders, accelerometers, damped masses, and the like. Optionally, the mechanical motion sensors 772 may be adapted to measure the force of gravity (i.e., G-force) as observed inside the vehicle 104. Measuring the G-force observed inside a vehicle 104 can provide valuable information related to a vehicle's acceleration, deceleration, collisions, and/or forces that may have been suffered by one or more users 216 in the vehicle 104. As can be appreciated, the mechanical motion sensors 772 can be located in an interior space 108 or an exterior of the vehicle 104.

Orientation sensors 776 can include accelerometers, gyroscopes, magnetic sensors, and the like that are configured to detect an orientation associated with the vehicle 104. Similar to the mechanical motion sensors 772, the orientation sensors 776 can be located in an interior space 108 or an exterior of the vehicle 104.

The restraint sensors 780 may be similar to the safety restraint sensors 679 as described in conjunction with FIGS. 6A-6B. These sensors 780 may correspond to sensors associated with one or more restraint devices and/or systems in a vehicle 104. Seatbelts and airbags are examples of restraint devices and/or systems. As can be appreciated, the restraint devices and/or systems may be associated with one or more sensors that are configured to detect a state of the device/system. The state may include extension, engagement, retraction, disengagement, deployment, and/or other electrical or mechanical conditions associated with the device/system.

The associated device sensors 720 can include any sensors that are associated with a device 212, 248 in the vehicle 104. As previously stated, typical devices 212, 248 may include smart phones, tablets, laptops, mobile computers, and the like. It is anticipated that the various sensors associated with these devices 212, 248 can be employed by the vehicle control system 204. For example, a typical smart phone can include, an image sensor, an IR sensor, audio sensor, gyroscope, accelerometer, wireless network sensor, fingerprint reader, and more. It is an aspect of the present disclosure that one or more of these associated device sensors 720 may be used by one or more subsystems of the vehicle system 200.

In FIG. 7B, a block diagram of an embodiment of exterior sensors 340 for a vehicle 104 is shown. The exterior sensors may include sensors that are identical, or substantially similar, to those previously disclosed in conjunction with the interior sensors of FIG. 7A. Optionally, the exterior sensors 340 may be configured to collect data relating to one or more conditions, objects, users 216, and other events that are external to the interior space 108 of the vehicle 104. For instance, the oxygen/air sensors 724 may measure a quality and/or composition of the air outside of a vehicle 104. As another example, the motion sensors 744 may detect motion outside of a vehicle 104.

The external environmental group 708E may comprise sensors configured to collect data relating to the external environment of a vehicle 104. In addition to including one or more of the sensors previously described, the external environmental group 708E may include additional sensors, such as, vehicle sensors 750, biological sensors, and wireless signal sensors 758. Vehicle sensors 750 can detect vehicles that are in an environment surrounding the vehicle 104. For example, the vehicle sensors 750 may detect vehicles in a first outside area 516, a second outside area 520, and/or combinations of the first and second outside areas 516, 520. Optionally, the vehicle sensors 750 may include one or more of RF sensors, IR sensors, image sensors, and the like to detect vehicles, people, hazards, etc. that are in an environment exterior to the vehicle 104. Additionally or alternatively, the vehicle sensors 750 can provide distance/directional information relating to a distance (e.g., distance from the vehicle 104 to the detected object) and/or a direction (e.g., direction of travel, etc.) associated with the detected object.

The biological sensors 754 may determine whether one or more biological entities (e.g., an animal, a person, a user 216, etc.) is in an external environment of the vehicle 104. Additionally or alternatively, the biological sensors 754 may provide distance information relating to a distance of the biological entity from the vehicle 104. Biological sensors 754 may include at least one of RF sensors, IR sensors, image sensors and the like that are configured to detect biological entities. For example, an IR sensor may be used to determine that an object, or biological entity, has a specific temperature, temperature pattern, or heat signature. Continuing this example, a comparison of the determined heat signature may be compared to known heat signatures associated with recognized biological entities (e.g., based on shape, locations of temperature, and combinations thereof, etc.) to determine whether the heat signature is associated with a biological entity or an inanimate, or non-biological, object.

The wireless signal sensors 758 may include one or more sensors configured to receive wireless signals from signal sources such as Wi-Fi™ hotspots, cell towers, roadside beacons, other electronic roadside devices, and satellite positioning systems. Optionally, the wireless signal sensors 758 may detect wireless signals from one or more of a mobile phone, mobile computer, keyless entry device, RFID device, near field communications (NFC) device, and the like.

The external safety group 716E may comprise sensors configured to collect data relating to the safety of a user 216 and/or one or more components of a vehicle 104. Examples of safety sensors associated with the external safety group 716E may include, but are not limited to, force sensors 768, mechanical motion sensors 772, orientation sensors 776, vehicle body sensors 782, and more. Optionally, the exterior safety sensors 716E may be configured to collect data relating to one or more conditions, objects, vehicle components, and other events that are external to the vehicle 104. For instance, the force sensors 768 in the external safety group 716E may detect and/or record force information associated with the outside of a vehicle 104. For instance, if an object strikes the exterior of the vehicle 104, the force sensors 768 from the exterior safety group 716E may determine a magnitude, location, and/or time associated with the strike.

The vehicle 104 may include a number of vehicle body sensors 782. The vehicle body sensors 782 may be configured to measure characteristics associated with the body (e.g., body panels, components, chassis, windows, etc.) of a vehicle 104. For example, two vehicle body sensors 782, including a first body sensor and a second body sensor, may be located at some distance apart. Continuing this example, the first body sensor may be configured to send an electrical signal across the body of the vehicle 104 to the second body sensor, or vice versa. Upon receiving the electrical signal from the first body sensor, the second body sensor may record a detected current, voltage, resistance, and/or combinations thereof associated with the received electrical signal. Values (e.g., current, voltage, resistance, etc.) for the sent and received electrical signal may be stored in a memory. These values can be compared to determine whether subsequent electrical signals sent and received between vehicle body sensors 782 deviate from the stored values. When the subsequent signal values deviate from the stored values, the difference may serve to indicate damage and/or loss of a body component. Additionally or alternatively, the deviation may indicate a problem with the vehicle body sensors 782. The vehicle body sensors 782 may communicate with each other, a vehicle control system 204, and/or systems of the vehicle system 200 via a communications channel 356. Although described using electrical signals, it should be appreciated that alternative embodiments of the vehicle body sensors 782 may use sound waves and/or light to perform a similar function.

Figure 8A:
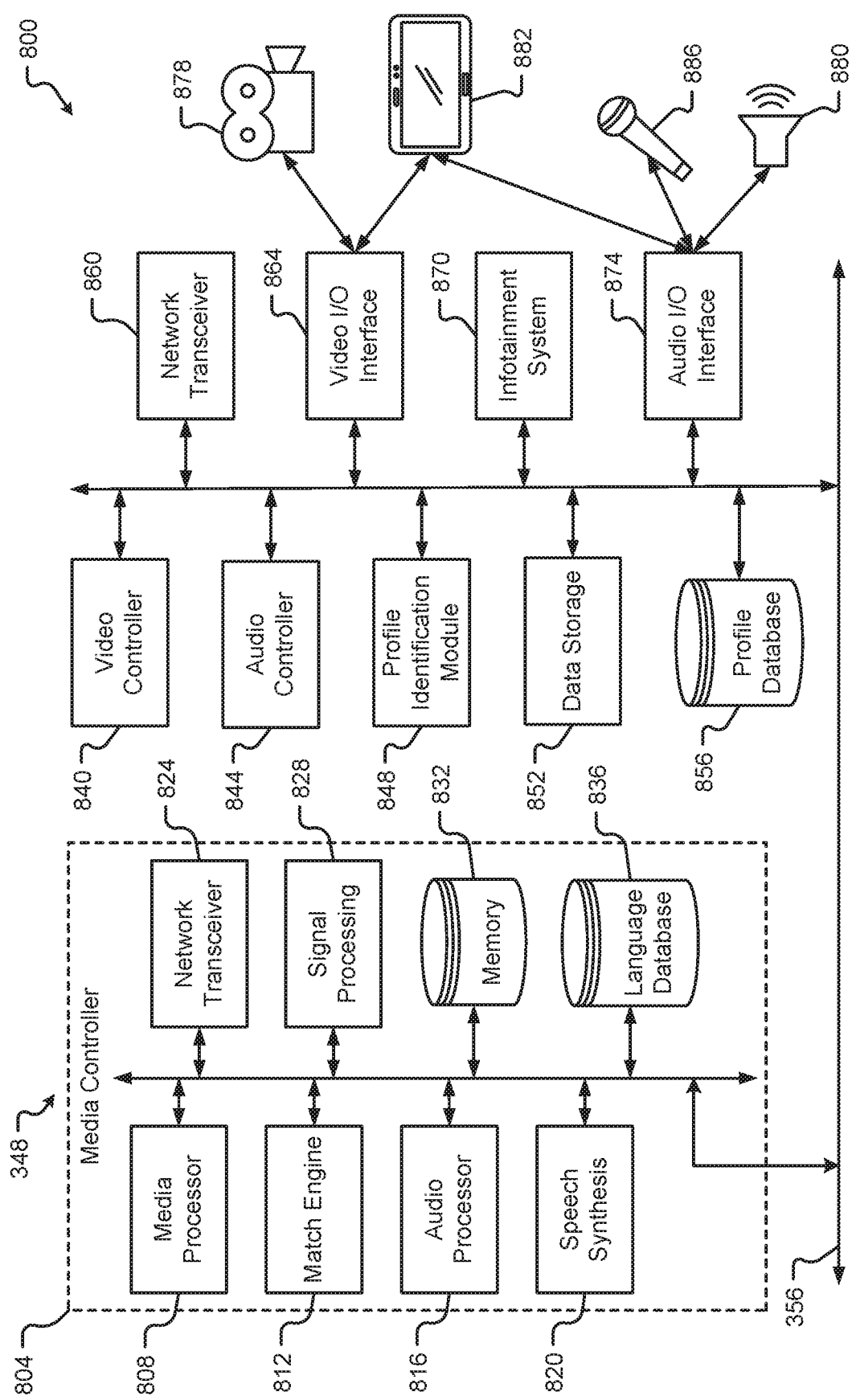
FIG. 8A is a block diagram of an embodiment of a media subsystem for a vehicle.

FIG. 8A is a block diagram of an embodiment of a media controller subsystem 348 for a vehicle 104. The media controller subsystem 348 may include, but is not limited to, a media controller 804, a media processor 808, a match engine 812, an audio processor 816, a speech synthesis module 820, a network transceiver 824, a signal processing module 828, memory 832, and a language database 836. Optionally, the media controller subsystem 348 may be configured as a dedicated blade that implements the media-related functionality of the system 200. Additionally or alternatively, the media controller subsystem 348 can provide voice input, voice output, library functions for multimedia, and display control for various areas 508 and/or zones 512 of the vehicle 104.

Optionally, the media controller subsystem 348 may include a local IP address (e.g., IPv4, IPv6, combinations thereof, etc.) and even a routable, global unicast address. The routable, global unicast address may allow for direct addressing of the media controller subsystem 348 for streaming data from Internet resources (e.g., cloud storage, user accounts, etc.). It is anticipated, that the media controller subsystem 348 can provide multimedia via at least one Internet connection, or wireless network communications module, associated with the vehicle 104. Moreover, the media controller subsystem 348 may be configured to service multiple independent clients simultaneously.

The media processor 808 may comprise a general purpose programmable processor or controller for executing application programming or instructions related to the media subsystem 348. The media processor 808 may include multiple processor cores, and/or implement multiple virtual processors. Optionally, the media processor 808 may include multiple physical processors. By way of example, the media processor 808 may comprise a specially configured application specific integrated circuit (ASIC) or other integrated circuit, a digital signal processor, a controller, a hardwired electronic or logic circuit, a programmable logic device or gate array, a special purpose computer, or the like. The media processor 808 generally functions to run programming code or instructions implementing various functions of the media controller 804.

The match engine 812 can receive input from one or more components of the vehicle system 800 and perform matching functions. Optionally, the match engine 812 may receive audio input provided via a microphone 886 of the system 800. The audio input may be provided to the media controller subsystem 348 where the audio input can be decoded and matched, via the match engine 812, to one or more functions available to the vehicle 104. Similar matching operations may be performed by the match engine 812 relating to video input received via one or more image sensors, cameras 878, and the like.

The media controller subsystem 348 may include a speech synthesis module 820 configured to provide audio output to one or more speakers 880, or audio output devices, associated with the vehicle 104. Optionally, the speech synthesis module 820 may be configured to provide audio output based at least partially on the matching functions performed by the match engine 812.

As can be appreciated, the coding/decoding, the analysis of audio input/output, and/or other operations associated with the match engine 812 and speech synthesis module 820, may be performed by the media processor 808 and/or a dedicated audio processor 816. The audio processor 816 may comprise a general purpose programmable processor or controller for executing application programming or instructions related to audio processing. Further, the audio processor 816 may be similar to the media processor 808 described herein.

The network transceiver 824 can include any device configured to transmit and receive analog and/or digital signals. Optionally, the media controller subsystem 348 may utilize a network transceiver 824 in one or more communication networks associated with the vehicle 104 to receive and transmit signals via the communications channel 356. Additionally or alternatively, the network transceiver 824 may accept requests from one or more devices 212, 248 to access the media controller subsystem 348. One example of the communication network is a local-area network (LAN). As can be appreciated, the functionality associated with the network transceiver 824 may be built into at least one other component of the vehicle 104 (e.g., a network interface card, communications module, etc.).

The signal processing module 828 may be configured to alter audio/multimedia signals received from one or more input sources (e.g., microphones 886, etc.) via the communications channel 356. Among other things, the signal processing module 828 may alter the signals received electrically, mathematically, combinations thereof, and the like.

The media controller 804 may also include memory 832 for use in connection with the execution of application programming or instructions by the media processor 808, and for the temporary or long term storage of program instructions and/or data. As examples, the memory 832 may comprise RAM, DRAM, SDRAM, or other solid state memory.

The language database 836 may include the data and/or libraries for one or more languages, as are used to provide the language functionality as provided herein. In one case, the language database 836 may be loaded on the media controller 804 at the point of manufacture. Optionally, the language database 836 can be modified, updated, and/or otherwise changed to alter the data stored therein. For instance, additional languages may be supported by adding the language data to the language database 836. In some cases, this addition of languages can be performed via accessing administrative functions on the media controller 804 and loading the new language modules via wired (e.g., USB, etc.) or wireless communication. In some cases, the administrative functions may be available via a vehicle console device 248, a user device 212, 248, and/or other mobile computing device that is authorized to access administrative functions (e.g., based at least partially on the device's address, identification, etc.).

One or more video controllers 840 may be provided for controlling the video operation of the devices 212, 248, 882 associated with the vehicle. Optionally, the video controller 840 may include a display controller for controlling the operation of touch sensitive screens, including input (touch sensing) and output (display) functions. Video data may include data received in a stream and unpacked by a processor and loaded into a display buffer. In this example, the processor and video controller 840 can optimize the display based on the characteristics of a screen of a display device 212, 248, 882. The functions of a touch screen controller may be incorporated into other components, such as a media processor 808 or display subsystem.

The audio controller 844 can provide control of the audio entertainment system (e.g., radio, subscription music service, multimedia entertainment, etc.), and other audio associated with the vehicle 104 (e.g., navigation systems, vehicle comfort systems, convenience systems, etc.). Optionally, the audio controller 844 may be configured to translate digital signals to analog signals and vice versa. As can be appreciated, the audio controller 844 may include device drivers that allow the audio controller 844 to communicate with other components of the system 800 (e.g., processors 816, 808, audio I/O 874, and the like).

The system 800 may include a profile identification module 848 to determine whether a user profile is associated with the vehicle 104. Among other things, the profile identification module 848 may receive requests from a user 216, or device 212, 228, 248, to access a profile stored in a profile database 856 or profile data 252. Additionally or alternatively, the profile identification module 848 may request profile information from a user 216 and/or a device 212, 228, 248, to access a profile stored in a profile database 856 or profile data 252. In any event, the profile identification module 848 may be configured to create, modify, retrieve, and/or store user profiles in the profile database 856 and/or profile data 252. The profile identification module 848 may include rules for profile identification, profile information retrieval, creation, modification, and/or control of components in the system 800.

By way of example, a user 216 may enter the vehicle 104 with a smart phone or other device 212. In response to determining that a user 216 is inside the vehicle 104, the profile identification module 848 may determine that a user profile is associated with the user's smart phone 212. As another example, the system 800 may receive information about a user 216 (e.g., from a camera 878, microphone 886, etc.), and, in response to receiving the user information, the profile identification module 848 may refer to the profile database 856 to determine whether the user information matches a user profile stored in the database 856. It is anticipated that the profile identification module 848 may communicate with the other components of the system to load one or more preferences, settings, and/or conditions based on the user profile. Further, the profile identification module 848 may be configured to control components of the system 800 based on user profile information.

Optionally, data storage 852 may be provided. Like the memory 832, the data storage 852 may comprise a solid state memory device or devices. Alternatively or in addition, the data storage 852 may comprise a hard disk drive or other random access memory. Similar to the data storage 852, the profile database 856 may comprise a solid state memory device or devices.

An input/output module 860 and associated ports may be included to support communications over wired networks or links, for example with other communication devices, server devices, and/or peripheral devices. Examples of an input/output module 860 include an Ethernet port, a Universal Serial Bus (USB) port, CAN Bus, Institute of Electrical and Electronics Engineers (IEEE) 1594, or other interface. Users may bring their own devices (e.g., Bring Your Own Device (BYOD), device 212, etc.) into the vehicle 104 for use with the various systems disclosed. Although most BYOD devices can connect to the vehicle systems (e.g., the media controller subsystem 348, etc.) via wireless communications protocols (e.g., Wi-Fi™, Bluetooth®, etc.) many devices may require a direct connection via USB, or similar. In any event, the input/output module 860 can provide the necessary connection of one or more devices to the vehicle systems described herein.

A video input/output interface 864 can be included to receive and transmit video signals between the various components in the system 800. Optionally, the video input/output interface 864 can operate with compressed and uncompressed video signals. The video input/output interface 864 can support high data rates associated with image capture devices. Additionally or alternatively, the video input/output interface 864 may convert analog video signals to digital signals.

The infotainment system 870 may include information media content and/or entertainment content, informational devices, entertainment devices, and the associated programming therefor. Optionally, the infotainment system 870 may be configured to handle the control of one or more components of the system 800 including, but in no way limited to, radio, streaming audio/video devices, audio devices 880, 882, 886, video devices 878, 882, travel devices (e.g., GPS, navigational systems, etc.), wireless communication devices, network devices, and the like. Further, the infotainment system 870 can provide the functionality associated with other infotainment features as provided herein.

An audio input/output interface 874 can be included to provide analog audio to an interconnected speaker 880 or other device, and to receive analog audio input from a connected microphone 886 or other device. As an example, the audio input/output interface 874 may comprise an associated amplifier and analog to digital converter. Alternatively or in addition, the devices 212, 248 can include integrated audio input/output devices 880, 886 and/or an audio jack for interconnecting an external speaker 880 or microphone 886. For example, an integrated speaker 880 and an integrated microphone 886 can be provided, to support near talk, voice commands, spoken information exchange, and/or speaker phone operations.

Among other things, the system 800 may include devices that are part of the vehicle 104 and/or part of a device 212, 248 that is associated with the vehicle 104. For instance, these devices may be configured to capture images, display images, capture sound, and present sound. Optionally, the system 800 may include at least one of image sensors/cameras 878, display devices 882, audio input devices/microphones 886, and audio output devices/speakers 880. The cameras 878 can be included for capturing still and/or video images. Alternatively or in addition, image sensors 878 can include a scanner or code reader. An image sensor/camera 878 can include or be associated with additional elements, such as a flash or other light source. In some cases, the display device 882 may include an audio input device and/or an audio output device in addition to providing video functions. For instance, the display device 882 may be a console, monitor, a tablet computing device, and/or some other mobile computing device.

Figure 8B:
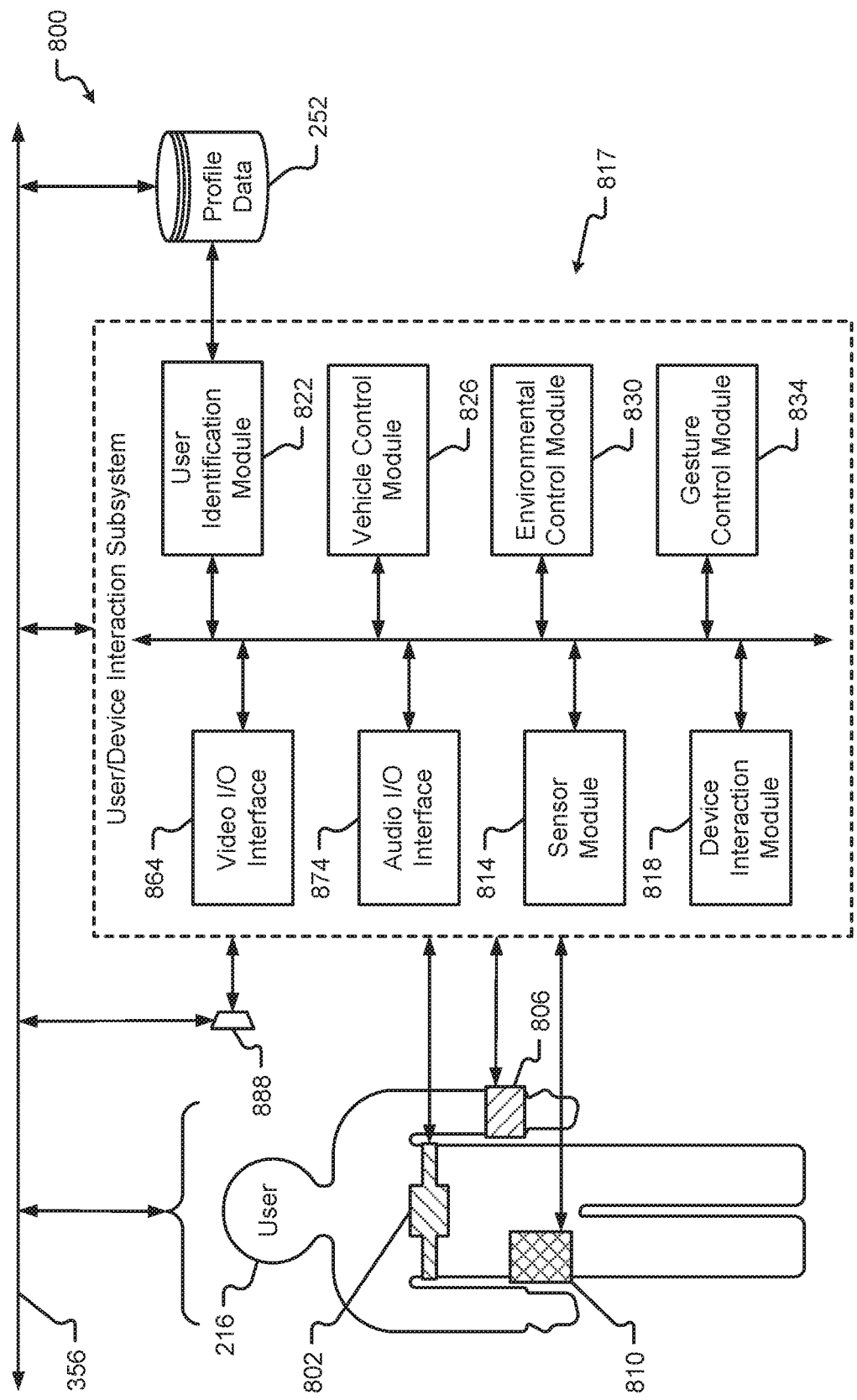
FIG. 8B is a block diagram of an embodiment of a user and device interaction subsystem for a vehicle.

FIG. 8B is a block diagram of an embodiment of a user/device interaction subsystem 817 in a vehicle system 800. The user/device interaction subsystem 817 may comprise hardware and/or software that conduct various operations for or with the vehicle 104. For instance, the user/device interaction subsystem 817 may include at least one user interaction subsystem 332 and device interaction subsystem 352 as previously described. These operations may include, but are not limited to, providing information to the user 216, receiving input from the user 216, and controlling the functions or operation of the vehicle 104, etc. Among other things, the user/device interaction subsystem 817 may include a computing system operable to conduct the operations as described herein.

Optionally, the user/device interaction subsystem 817 can include one or more of the components and modules provided herein. For instance, the user/device interaction subsystem 817 can include one or more of a video input/output interface 864, an audio input/output interface 874, a sensor module 814, a device interaction module 818, a user identification module 822, a vehicle control module 826, an environmental control module 830, and a gesture control module 834. The user/device interaction subsystem 817 may be in communication with other devices, modules, and components of the system 800 via the communications channel 356.

The user/device interaction subsystem 817 may be configured to receive input from a user 216 and/or device via one or more components of the system. By way of example, a user 216 may provide input to the user/device interaction subsystem 817 via wearable devices 802, 806, 810, video input (e.g., via at least one image sensor/camera 878, etc.) audio input (e.g., via the microphone, audio input source, etc.), gestures (e.g., via at least one image sensor 878, motion sensor 888, etc.), device input (e.g., via a device 212, 248 associated with the user, etc.), combinations thereof, and the like.

The wearable devices 802, 806, 810 can include heart rate monitors, blood pressure monitors, glucose monitors, pedometers, movement sensors, wearable computers, and the like. Examples of wearable computers may be worn by a user 216 and configured to measure user activity, determine energy spent based on the measured activity, track user sleep habits, determine user oxygen levels, monitor heart rate, provide alarm functions, and more. It is anticipated that the wearable devices 802, 806, 810 can communicate with the user/device interaction subsystem 817 via wireless communications channels or direct connection (e.g., where the device docks, or connects, with a USB port or similar interface of the vehicle 104).

A sensor module 814 may be configured to receive and/or interpret input provided by one or more sensors in the vehicle 104. In some cases, the sensors may be associated with one or more user devices (e.g., wearable devices 802, 806, 810, smart phones 212, mobile computing devices 212, 248, and the like). Optionally, the sensors may be associated with the vehicle 104, as described in conjunction with FIGS. 6A-7B.

The device interaction module 818 may communicate with the various devices as provided herein. Optionally, the device interaction module 818 can provide content, information, data, and/or media associated with the various subsystems of the vehicle system 800 to one or more devices 212, 248, 802, 806, 810, 882, etc. Additionally or alternatively, the device interaction module 818 may receive content, information, data, and/or media associated with the various devices provided herein.

The user identification module 822 may be configured to identify a user 216 associated with the vehicle 104. The identification may be based on user profile information that is stored in profile data 252. For instance, the user identification module 822 may receive characteristic information about a user 216 via a device, a camera, and/or some other input. The received characteristics may be compared to data stored in the profile data 252. Where the characteristics match, the user 216 is identified. As can be appreciated, where the characteristics do not match a user profile, the user identification module 822 may communicate with other subsystems in the vehicle 104 to obtain and/or record profile information about the user 216. This information may be stored in a memory and/or the profile data storage 252.

The vehicle control module 826 may be configured to control settings, features, and/or the functionality of a vehicle 104. In some cases, the vehicle control module 826 can communicate with the vehicle control system 204 to control critical functions (e.g., driving system controls, braking, accelerating, etc.) and/or noncritical functions (e.g., driving signals, indicator/hazard lights), mirror controls, window actuation, etc.) based at least partially on user/device input received by the user/device interaction subsystem 817.

The environmental control module 830 may be configured to control settings, features, and/or other conditions associated with the environment, especially the interior environment, of a vehicle 104. Optionally, the environmental control module 830 may communicate with the climate control system (e g changing cabin temperatures, fan speeds, air direction, etc.), oxygen and/or air quality control system (e.g., increase/decrease oxygen in the environment, etc.), interior lighting (e g, changing intensity of lighting, color of lighting, etc.), an occupant seating system 648 (e.g., adjusting seat position, firmness, height, etc.), steering wheel 640 (e.g., position adjustment, etc.), infotainment/entertainment system (e.g., adjust volume levels, display intensity adjustment, change content, etc.), and/or other systems associated with the vehicle environment. Additionally or alternatively, these systems can provide input, set-points, and/or responses, to the environmental control module 830. As can be appreciated, the environmental control module 830 may control the environment based at least partially on user/device input received by the user/device interaction subsystem 817.

The gesture control module 834 is configured to interpret gestures provided by a user 216 in the vehicle 104. Optionally, the gesture control module 834 may provide control signals to one or more of the vehicle systems 300 disclosed herein. For example, a user 216 may provide gestures to control the environment, critical and/or noncritical vehicle functions, the infotainment system, communications, networking, and more. Optionally, gestures may be provided by a user 216 and detected via one or more of the sensors as described in conjunction with FIGS. 6B-7A. As another example, one or more motion sensors 888 may receive gesture input from a user 216 and provide the gesture input to the gesture control module 834. Continuing this example, the gesture input is interpreted by the gesture control module 834. This interpretation may include comparing the gesture input to gestures stored in a memory. The gestures stored in memory may include one or more functions and/or controls mapped to specific gestures. When a match is determined between the detected gesture input and the stored gesture information, the gesture control module 834 can provide a control signal to any of the systems/subsystems as disclosed herein.

Figure 8C:
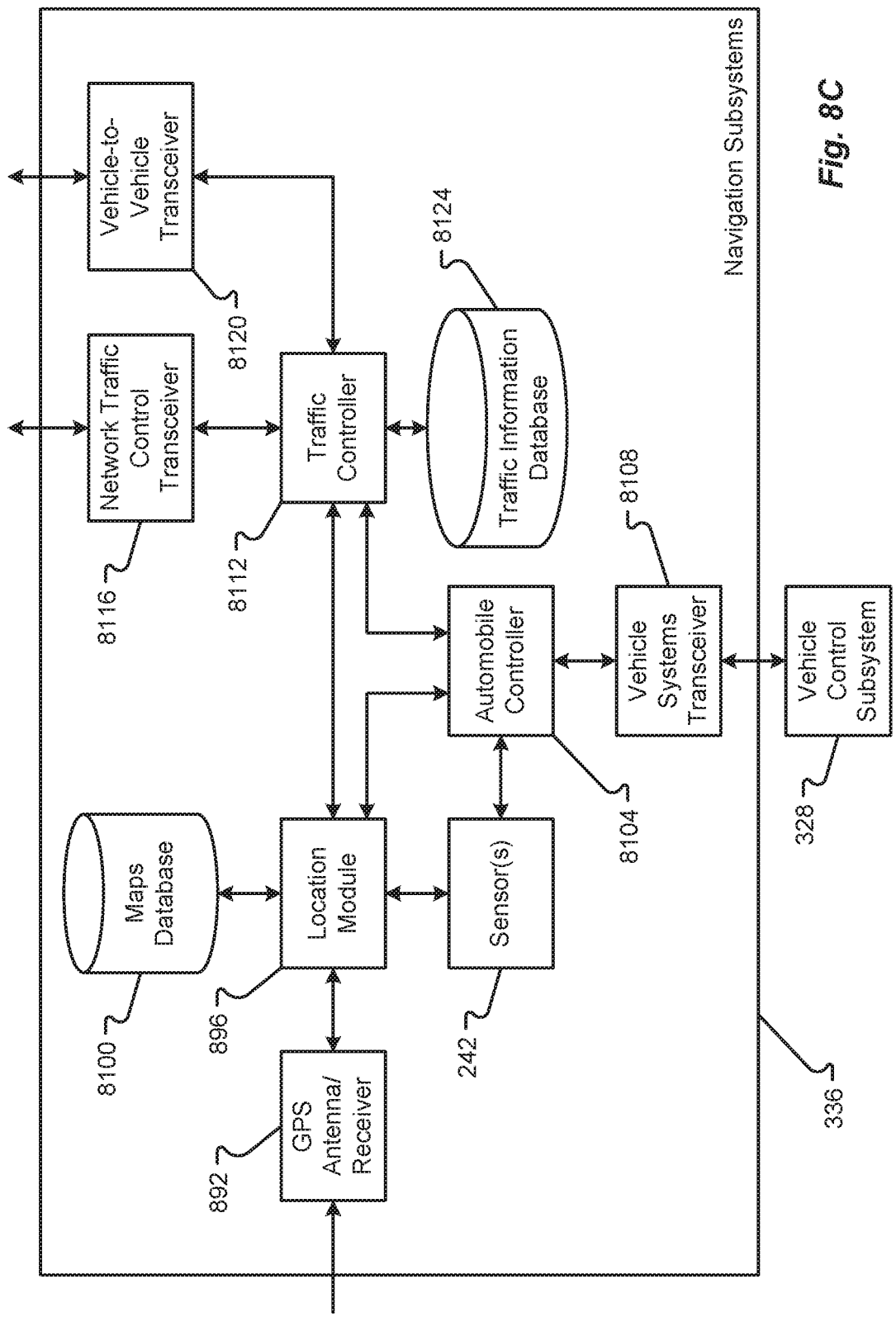
FIG. 8C is a block diagram of an embodiment of a Navigation subsystem for a vehicle.

FIG. 8C illustrates a GPS/Navigation subsystem(s) 336. The Navigation subsystem(s) 336 can be any present or future-built navigation system that may use location data, for example, from the Global Positioning System (GPS), to provide navigation information or control the vehicle 104. The Navigation subsystem(s) 336 can include several components or modules, such as, one or more of, but not limited to, a GPS Antenna/receiver 892, a location module 896, a maps database 8100, an automobile controller 8104, a vehicle systems transceiver 8108, a traffic controller 8112, a network traffic transceiver 8116, a vehicle-to-vehicle transceiver 8120, a traffic information database 8124, etc. Generally, the several components or modules 892-8124 may be hardware, software, firmware, computer readable media, or combinations thereof.

A GPS Antenna/receiver 892 can be any antenna, GPS puck, and/or receiver capable of receiving signals from a GPS satellite or other navigation system, as mentioned hereinbefore. The signals may be demodulated, converted, interpreted, etc. by the GPS Antenna/receiver 892 and provided to the location module 896. Thus, the GPS Antenna/receiver 892 may convert the time signals from the GPS system and provide a location (e.g., coordinates on a map) to the location module 896. Alternatively, the location module 896 can interpret the time signals into coordinates or other location information.

The location module 896 can be the controller of the satellite navigation system designed for use in automobiles. The location module 896 can acquire position data, as from the GPS Antenna/receiver 892, to locate the user or vehicle 104 on a road in the unit's map database 8100. Using the road database 8100, the location module 896 can give directions to other locations along roads also in the database 8100. When a GPS signal is not available, the location module 896 may apply dead reckoning to estimate distance data from sensors 242 including one or more of, but not limited to, a speed sensor attached to the drive train of the vehicle 104, a gyroscope, an accelerometer, etc. GPS signal loss and/or multipath can occur due to urban canyons, tunnels, and other obstructions. Additionally or alternatively, the location module 896 may use known locations of Wi-Fi hotspots, cell tower data, etc. to determine the position of the vehicle 104, such as by using time difference of arrival (TDOA) and/or frequency difference of arrival (FDOA) techniques.

The maps database 8100 can include any hardware and/or software to store information about maps, geographical information system information, location information, etc. The maps database 8100 can include any data definition or other structure to store the information. Generally, the maps database 8100 can include a road database that may include one or more vector maps of areas of interest. Street names, street numbers, house numbers, and other information can be encoded as geographic coordinates so that the user can find some desired destination by street address. Points of interest (waypoints) can also be stored with their geographic coordinates. For example, a point of interest may include speed cameras, fuel stations, public parking, and "parked here" (or "you parked here") information. The map database contents can be produced or updated by a server connected through a wireless system in communication with the Internet, even as the vehicle 104 is driven along existing streets, yielding an up-to-date map.

An automobile controller 8104 can be any hardware and/or software that can receive instructions from the location module 896 or the traffic controller 8112 and operate the vehicle 104. The automobile controller 8104 receives this information and data from the sensors 242 to operate the vehicle 104 without driver input. Thus, the automobile controller 8104 can drive the vehicle 104 along a route provided by the location module 896. The route may be adjusted by information sent from the traffic controller 8112. Discrete and real-time driving can occur with data from the sensors 242. To operate the vehicle 104, the automobile controller 8104 can communicate with a vehicle systems transceiver 8108.

The vehicle systems transceiver 8108 can be any present or future-developed device that can comprise a transmitter and/or a receiver, which may be combined and can share common circuitry or a single housing. The vehicle systems transceiver 8108 may communicate or instruct one or more of the vehicle control subsystems 328. For example, the vehicle systems transceiver 8108 may send steering commands, as received from the automobile controller 8104, to an electronic steering system, to adjust the steering of the vehicle 100 in real time. The automobile controller 8104 can determine the effect of the commands based on received sensor data 242 and can adjust the commands as need be. The vehicle systems transceiver 8108 can also communicate with the braking system, the engine and drive train to speed or slow the car, the signals (e.g., turn signals and brake lights), the headlights, the windshield wipers, etc. Any of these communications may occur over the components or function as described in conjunction with FIG. 4.

A traffic controller 8112 can be any hardware and/or software that can communicate with an automated traffic system and adjust the function of the vehicle 104 based on instructions from the automated traffic system. An automated traffic system is a system that manages the traffic in a given area. This automated traffic system can instruct cars to drive in certain lanes, instruct cars to raise or lower their speed, instruct a car to change their route of travel, instruct cars to communicate with other cars, etc. To perform these functions, the traffic controller 8112 may register the vehicle 104 with the automated traffic system and then provide other information including the route of travel. The automated traffic system can return registration information and any required instructions. The communications between the automated traffic system and the traffic controller 8112 may be received and sent through a network traffic transceiver 8116.

The network traffic transceiver 8116 can be any present or future-developed device that can comprise a transmitter and/or a receiver, which may be combined and can share common circuitry or a single housing. The network traffic transceiver 8116 may communicate with the automated traffic system using any known or future-developed, protocol, standard, frequency, bandwidth range, etc. The network traffic transceiver 8116 enables the sending of information between the traffic controller 8112 and the automated traffic system.

The traffic controller 8112 can also communicate with another vehicle, which may be in physical proximity (i.e., within range of a wireless signal), using the vehicle-to-vehicle transceiver 8120. As with the network traffic transceiver 8116, the vehicle-to-vehicle transceiver 8120 can be any present or future-developed device that can comprise a transmitter and/or a receiver, which may be combined and can share common circuitry or a single housing. Generally, the vehicle-to-vehicle transceiver 8120 enables communication between the vehicle 104 and any other vehicle. These communications allow the vehicle 104 to receive traffic or safety information, control or be controlled by another vehicle, establish an alternative communication path to communicate with the automated traffic system, establish a node including two or more vehicle that can function as a unit, etc. The vehicle-to-vehicle transceiver 8120 may communicate with the other vehicles using any known or future-developed, protocol standard, frequency, bandwidth range, etc.

The traffic controller 8112 can control functions of the automobile controller 8104 and communicate with the location module 896. The location module 896 can provide current location information and route information that the traffic controller 8112 may then provide to the automated traffic system. The traffic controller 8112 may receive route adjustments from the automated traffic system that are then sent to the location module 896 to change the route. Further, the traffic controller 8112 can also send driving instructions to the automobile controller 8104 to change the driving characteristics of the vehicle 104. For example, the traffic controller 8112 can instruct the automobile controller 8104 to accelerate or decelerate to a different speed, change lanes, or perform another driving maneuver. The traffic controller 8112 can also manage vehicle-to-vehicle communications and store information about the communications or other information in the traffic information database 8124.

The traffic information database 8124 can be any type of database, such as relational, hierarchical, object-oriented, and/or the like. The traffic information database 8124 may reside on a storage medium local to (and/or resident in) the vehicle control system 204 or in the vehicle 104. The traffic information database 8124 may be adapted to store, update, and retrieve information about communications with other vehicles or any active instructions from the automated traffic system. This information may be used by the traffic controller 8112 to instruct or adjust the performance of driving maneuvers.

Figure 9:
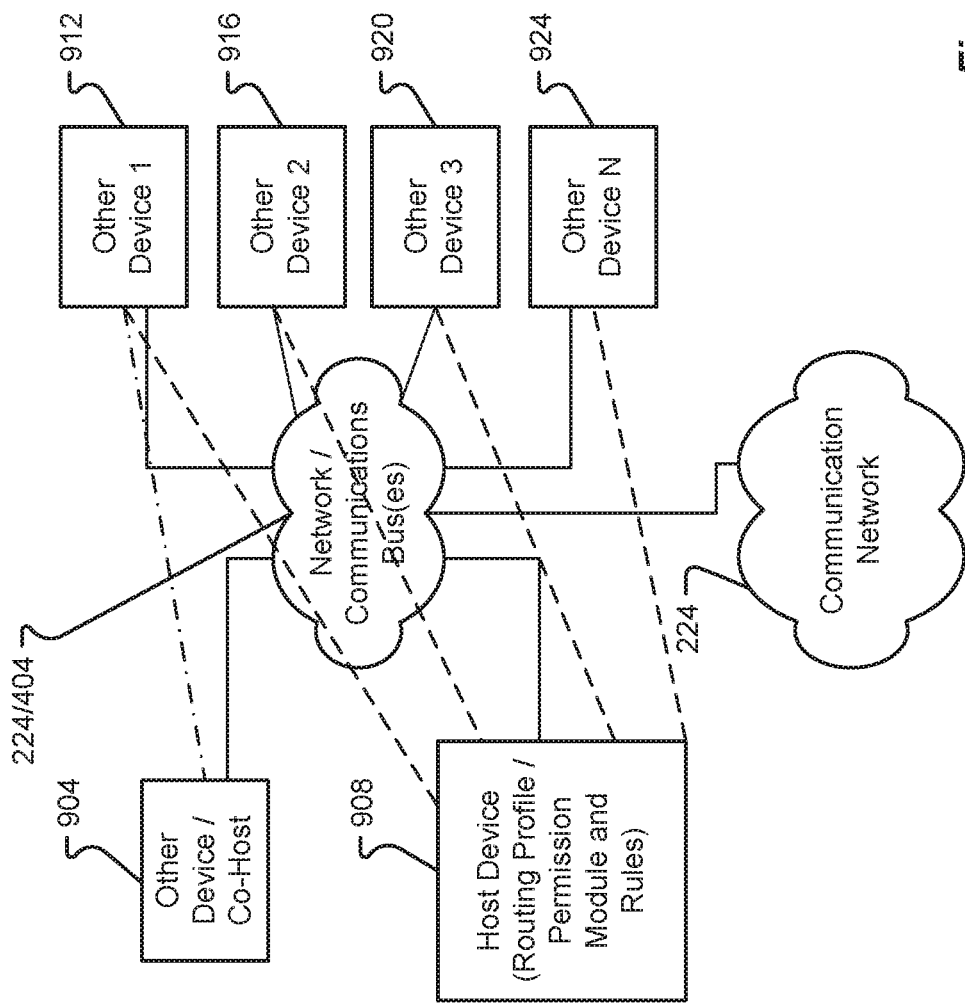
FIG. 9 is a block diagram of an embodiment of a communications subsystem for a vehicle.

FIG. 9 illustrates an optional communications architecture where, the host device 908 may include one more routing profiles, permission modules, and rules that control how communications within the vehicle 104 are to occur. This communications architecture can be used in conjunction with the routing tables, rules and permissions associated with access point 456 and optional firewall 484, or can be in lieu thereof. For example, the host device 908 acts as a mobile hot spot to one or more other devices within vehicle 104, such as, other device 1 912, other device 2 916, other device 3 920, and other device N 924. Optionally, one or more of the other devices 912 can communicate directly with the host device 908 which then provides Internet access to those devices 912 via the device 908. The host device 908 can act as a mobile hot spot for any one or more of the other devices 912, which may not need to communicate over the network/communications buses 224/404, but could instead connect directly to the host device 908 via, for example, NFC, Bluetooth®, WiFi, or the like. When the device 908 is acting as the host device, the device 908 can include one or more routing profiles, permissions, rules modules, and can also act as a firewall for the various inter and intra vehicle communications.

As will be appreciated, there could be alternative host devices, such as, host 904 which could also act as, for example, a co-host in association with device 908. Optionally, one or more of the routing profile, permission information, and rules could be shared between the co-host devices 904, 908, both of those devices being usable for Internet access for one or more of the other devices, 912-924. As will be appreciated, the other devices 912-924 need not necessarily connect to one or more of host device 908 and the other device 904 via a direct communications link, but could also interface with those devices 904, 908 utilizing the network/communications buses 224/404 associated with the vehicle 100. As previously discussed, one or more of the other devices can connect to the network/communications buses 224/404 utilizing the various networks and/or buses discussed herein which would therefore enable, for example, regulation of the various communications based on the Ethernet zone that the other device 912 is associated with.

An embodiment of one or more modules that may be associated with the vehicle control system 204 may be as shown in FIG. 10. The modules can include a communication subsystem interface 1008 in communication with an operating system 1004. The communications may pass through a firewall 1044. The firewall 1044 can be any software that can control the incoming and outgoing communications by analyzing the data packets and determining whether the packets should be allowed through the firewall, based on applied rule set. A firewall 1044 can establish a "barrier" between a trusted, secure internal network and another network (e.g., the Internet) that is not assumed to be secure and trusted.

In some situations, the firewall 1044 may establish security zones that are implemented by running system services and/or applications in restricted user groups and accounts. A set of configuration files and callbacks may then be linked to an IP table firewall. The IP table firewall can be configured to notify a custom filter application at any of the layers of the Ethernet packet. The different users/group rights to access the system may include: system users, which may have exclusive right over all device firewall rules and running software; a big-brother user, which may have access to on board device (OBD) control data and may be able to communicate with the vehicle subsystem 328 and may be able to alter the parameters in the vehicle control system 204; a dealer user, which can have rights to read OBD data for diagnostics and repairs; a dashboard user, which can have rights to launch dashboard applications and/or authenticate guest users and change their permissions to trusted/friend/family, and can read but cannot write into OBD diagnostic data; a world wide web (WWW) data user, which can have HTTP rights to respond to HTTP requests (the HTTP requests also can target different user data, but may be filtered by default user accounts); a guest user, which may have no rights; a family/friend user, which may have rights to play media from the media subsystem 348 and/or to stream media to the media subsystem 348.

The operating system 1004 can be a collection of software that manages computer hardware resources and provides common services for applications and other programs. The operating system 1004 may schedule time-sharing for efficient use of the system. For hardware functions, such as input, output, and memory allocation, the operating system 1004 can act as an intermediary between applications or programs and the computer hardware. Examples of operating systems that may be deployed as operating system 1004 include Android, BSD, iOS, Linux, OS X, QNX, Microsoft Windows, Windows Phone, IBM z/OS, etc.

The operating system 1004 can include one or more sub-modules. For example, a desktop manager 1012 can manage one or more graphical user interfaces (GUI) in a desktop environment. Desktop GUIs can help the user to easily access and edit files. A command-line interface (CLI) may be used if full control over the operating system (OS) 1004 is required. The desktop manager 1012 is described further hereinafter.

A kernel 1028 can be a computer program that manages input/output requests from software and translates them into data processing instructions for the processor 304 and other components of the vehicle control system 204. The kernel 1028 is the fundamental component of the operating system 1004 that can execute many of the functions associated with the OS 1004.

The kernel 1028 can include other software functions, including, but not limited to, driver(s) 1056, communication software 1052, and/or Internet Protocol software 1048. A driver 1056 can be any computer program that operates or controls a particular type of device that is attached to a vehicle control system 204. A driver 1056 can communicate with the device through the bus 356 or communications subsystem 1008 to which the hardware connects. When a calling program invokes a routine in the driver 1056, the driver 1056 may issue one or more commands to the device. Once the device sends data back to the driver 1056, the driver 1056 may invoke routines in the original calling program. Drivers can be hardware-dependent and operating-system-specific. Driver(s) 1056 can provide the interrupt handling required for any necessary asynchronous time-dependent hardware interface.

The IP module 1048 can conduct any IP addressing, which may include the assignment of IP addresses and associated parameters to host interfaces. The address space may include networks and sub-networks. The IP module 1048 can perform the designation of network or routing prefixes and may conduct IP routing, which transports packets across network boundaries. Thus, the IP module 1048 may perform all functions required for IP multicast operations.

The communications module 1052 may conduct all functions for communicating over other systems or using other protocols not serviced by the IP module 1048. Thus, the communications module 1052 can manage multicast operations over other busses or networks not serviced by the IP module 1048. Further, the communications module 1052 may perform or manage communications to one or more devices, systems, data stores, services, etc. that are in communication with the vehicle control system 204 or other subsystems through the firewall 1044. Thus, the communications module 1052 can conduct communications through the communication subsystem interface 1008.

A file system 1016 may be any data handling software that can control how data is stored and retrieved. The file system 1016 can separate the stored data into individual pieces, and giving each piece a name, can easily separate and identify the pieces of data. Each piece of data may be considered a "file". The file system 1016 can construct data structure and logic rules used to manage the information and the identifiers for the information. The structure and logic rules can be considered a "file system."

A device discovery daemon 1020 may be a computer program that runs as a background process that can discover new devices that connect with the network 356 or communication subsystem 1008 or devices that disconnect from the network 356 or communication subsystem 1008. The device discovery daemon 1020 can ping the network 356 (the local subnet) when the vehicle 104 starts, when a vehicle door opens or closes, or upon the occurrence of other events. Additionally or alternatively, the device discovery daemon 1020 may force Bluetooth®, USB, and/or wireless detection. For each device that responds to the ping, the device discovery daemon 1020 can populate the system data 208 with device information and capabilities, using any of one or more protocols, including one or more of, but not limited to, IPv6 Hop-by-Hop Option (HOPOPT), Internet Control Message Protocol (ICMP), Internet Group Management Protocol (IGMP), Gateway-to-Gateway Protocol (GGP), Internet Protocol (IP), Internet Stream Protocol (ST), Transmission Control Protocol (TCP), Exterior Gateway Protocol (EGP), CHAOS, User Datagram Protocol (UDP), etc.

For example, the device discovery daemon 1020 can determine device capabilities based on the opened ports the device exposes. If a camera exposes port 80, then the device discovery daemon 1020 can determine that the camera is using a Hypertext Transfer Protocol (HTTP). Alternatively, if a device is supporting Universal Plug and Play (UPnP), the system data 208 can include more information, for example, a camera control universal resource locator (URL), a camera zoom URL, etc. When a scan stops, the device discovery daemon 1020 can trigger a dashboard refresh to ensure the user interface reflects the new devices on the desktop.

A desktop manager 1012 may be a computer program that manages the user interface of the vehicle control system 204. The desktop environment may be designed to be customizable and allow the definition of the desktop configuration look-and-feel for a wide range of appliances or devices from computer desktops, mobile devices, computer tablets, etc. Launcher(s), panels, desktop areas, the desktop background, notifications, panes, etc., can be configured from a dashboard configuration file managed by the desktop manager 1012. The graphical elements in which the desktop manager 1012 controls can include launchers, the desktop, notification bars, etc.

The desktop may be an area of the display where the applications are running. The desktop can have a custom background. Further, the desktop may be divided into two or more areas. For example, the desktop may be divided into an upper half of a display and a lower half of the display. Each application can be configured to run in a portion of the desktop. Extended settings can be added to the desktop configuration file, such that, some objects may be displayed over the whole desktop or in custom size out of the context of the divided areas.

The notification bar may be a part of a bar display system, which may provide notifications by displaying, for example, icons and/or pop-up windows that may be associated with sound notifications. The notification mechanism can be designed for separate plug-ins, which run in separate processes and may subscribe to a system Intelligent Input Bus (IBUS)/D-BUS event service. The icons on the notifications bar can be accompanied with application short-cuts to associated applications, for example, a Bluetooth® manager, a USB manager, radio volume and or tone control, a security firewall, etc.

The desktop manager 1012 may include a windows manager 1032, an application launcher 1036, and/or a panel launcher 1040. Each of these components can control a different aspect of the user interface. The desktop manager 1012 can use a root window to create panels that can include functionality for one or more of, but not limited to: launching applications, managing applications, providing notifications, etc.

The windows manager 1032 may be software that controls the placement and appearance of windows within a graphical user interface presented to the user. Generally, the windows manager 1032 can provide the desktop environment used by the vehicle control system 204. The windows manager 1032 can communicate with the kernel 1028 to interface with the graphical system that provides the user interface(s) and supports the graphics hardware, pointing devices, keyboard, touch-sensitive screens, etc. The windows manager 1032 may be a tiling window manager (i.e., a window manager with an organization of the screen into mutually non-overlapping frames, as opposed to a coordinate-based stacking of overlapping objects (windows) that attempts to fully emulate the desktop metaphor). The windows manager 1032 may read and store configuration files, in the system data 208, which can control the position of the application windows at precise positions.

An application manager 1036 can control the function of any application over the lifetime of the process. The process or application can be launched from a panel launcher 1040 or from a remote console. The application manager 1036 can intercept the process name and may take appropriate action to manage that process. If the process is not running, the application manager 1036 can load the process and may bring the process to a foreground in a display. The application manager 1036 may also notify the windows manager 1032 to bring the associated window(s) to a top of a window stack for the display. When a process starts from a shell or a notification out of the context of the desktop, the application manager 1036 can scan files to match the process name with the entry name provided. When a match is found, the application manager 1036 can configure the process according to a settings file.

In some situations, the application manager 1036 may restrict an application as singleton (i.e., restricts the instantiation of a class to one object). If an application is already running and the application manager 1036 is asked to run the application again, the application manager 1036 can bring the running process to a foreground on a display. There can be a notification event exchange between the windows manager 1032 and the application manager 1036 for activating the appropriate window for the foreground process. Once an application is launched, the application may not be terminated or killed. The application can be sent to the background, except, possibly, for some applications (e.g., media player, Bluetooth®, notifications, etc.), which may be given a lowest process priority.

The panel launcher 1040 can be a widget configured to be placed along a portion of the display. The panel launcher 1040 may be built from desktop files from a desktop folder. The desktop folder location can be configured by a configuration file stored in system data 208. The panel launcher 1040 can allow for the launching or executing of applications or processes by receiving inputs from a user interface to launch programs.

A desktop plugin 1024 may be a software component that allows for customization of the desktop or software interface through the initiation of plug-in applications.

One or more gestures used to interface with the vehicle control system 204 may be as described in conjunction with FIG. 11A through 11K. FIGS. 11A through 11H depict various graphical representations of gesture inputs that may be recognized by the devices 212, 248. The gestures may be performed not only by a user's body part, such as a digit, but also by other devices, such as a stylus, that may be sensed by the contact sensing portion(s) of a screen associated with the device 212, 248. In general, gestures are interpreted differently, based on where the gestures are performed (either directly on a display or in a gesture capture region). For example, gestures in a display may be directed to a desktop or application, and gestures in a gesture capture region may be interpreted as for the system.

With reference to FIGS. 11A-11H, a first type of gesture, a touch gesture 1120, is substantially stationary on a portion (e.g., a screen, a display, etc.) of a device 212, 248 for a selected length of time. A circle 1128 represents a touch or other contact type received at particular location of a contact sensing portion of the screen. The circle 1128 may include a border 1132, the thickness of which indicates a length of time that the contact is held substantially stationary at the contact location. For instance, a tap 1120 (or short press) has a thinner border 1132A than the border 1132B for a long press 1124 (or for a normal press). The long press 1124 may involve a contact that remains substantially stationary on the screen for longer time period than that of a tap 1120. As will be appreciated, differently defined gestures may be registered depending upon the length of time that the touch remains stationary prior to contact cessation or movement on the screen.

Figure 11A:
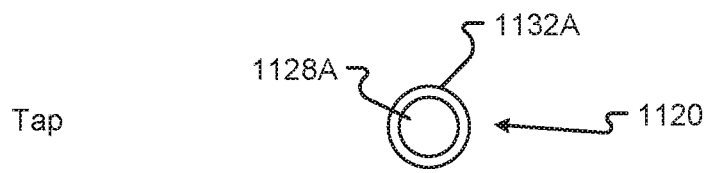
FIG. 11A is a graphical representation of an embodiment of a gesture that a user may perform to provide input to a vehicle control system.
Figure 11B:
FIG. 11B is a graphical representation of an embodiment of a gesture that a user may perform to provide input to a vehicle control system.
Figure 11C:
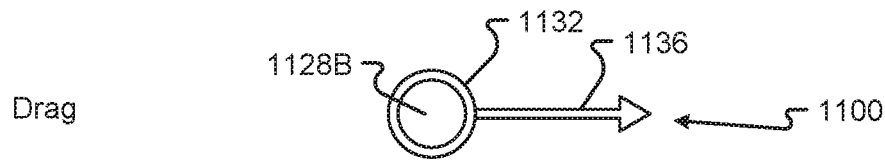
FIG. 11C is a graphical representation of an embodiment of a gesture that a user may perform to provide input to a vehicle control system.

With reference to FIG. 11C, a drag gesture 1100 on the screen is an initial contact (represented by circle 1128) with contact movement 1136 in a selected direction. The initial contact 1128 may remain stationary on the screen for a certain amount of time represented by the border 1132. The drag gesture typically requires the user to contact an icon, window, or other displayed image at a first location followed by movement of the contact in a drag direction to a new second location desired for the selected displayed image. The contact movement need not be in a straight line but have any path of movement so long as the contact is substantially continuous from the first to the second locations.

Figure 11D:
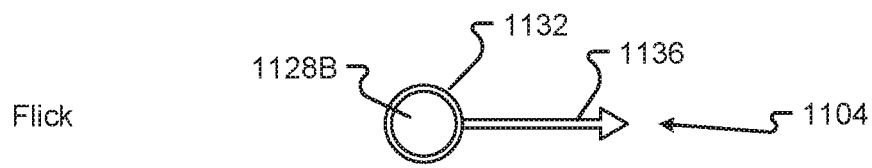
FIG. 11D is a graphical representation of an embodiment of a gesture that a user may perform to provide input to a vehicle control system.

With reference to FIG. 11D, a flick gesture 1104 on the screen is an initial contact (represented by circle 1128) with truncated contact movement 1136 (relative to a drag gesture) in a selected direction. A flick may have a higher exit velocity for the last movement in the gesture compared to the drag gesture. The flick gesture can, for instance, be a finger snap following initial contact. Compared to a drag gesture, a flick gesture generally does not require continual contact with the screen from the first location of a displayed image to a predetermined second location. The contacted displayed image is moved by the flick gesture in the direction of the flick gesture to the predetermined second location. Although both gestures commonly can move a displayed image from a first location to a second location, the temporal duration and distance of travel of the contact on the screen is generally less for a flick than for a drag gesture.

Figure 11E:
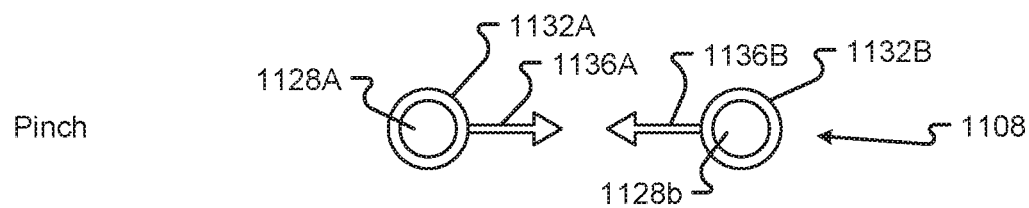
FIG. 11E is a graphical representation of an embodiment of a gesture that a user may perform to provide input to a vehicle control system.

With reference to FIG. 11E, a pinch gesture 1108 on the screen is depicted. The pinch gesture 1108 may be initiated by a first contact 1128A to the screen by, for example, a first digit and a second contact 1128B to the screen by, for example, a second digit. The first and second contacts 1128A,B may be detected by a common contact sensing portion of a common screen, by different contact sensing portions of a common screen, or by different contact sensing portions of different screens. The first contact 1128A is held for a first amount of time, as represented by the border 1132A, and the second contact 1128B is held for a second amount of time, as represented by the border 1132B. The first and second amounts of time are generally substantially the same, and the first and second contacts 1128A,B generally occur substantially simultaneously. The first and second contacts 1128A,B generally also include corresponding first and second contact movements 1136A,B, respectively. The first and second contact movements 1136A,B are generally in opposing directions. Stated another way, the first contact movement 1136A is towards the second contact 1136B, and the second contact movement 1136B is towards the first contact 1136A. More simply stated, the pinch gesture 1108 may be accomplished by a user's digits touching the screen in a pinching motion.

Figure 11F:
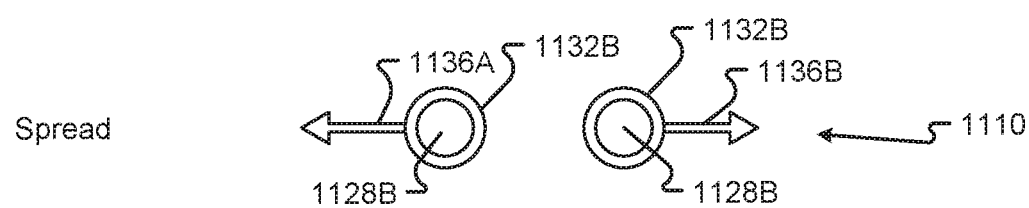
FIG. 11F is a graphical representation of an embodiment of a gesture that a user may perform to provide input to a vehicle control system.

With reference to FIG. 11F, a spread gesture 1110 on the screen is depicted. The spread gesture 1110 may be initiated by a first contact 1128A to the screen by, for example, a first digit, and a second contact 1128B to the screen by, for example, a second digit. The first and second contacts 1128A,B may be detected by a common contact sensing portion of a common screen, by different contact sensing portions of a common screen, or by different contact sensing portions of different screens. The first contact 1128A is held for a first amount of time, as represented by the border 1132A, and the second contact 1128B is held for a second amount of time, as represented by the border 1132B. The first and second amounts of time are generally substantially the same, and the first and second contacts 1128A,B generally occur substantially simultaneously. The first and second contacts 1128A,B generally also include corresponding first and second contact movements 1136A,B, respectively. The first and second contact movements 1136A,B are generally in an opposing direction. Stated another way, the first and second contact movements 1136A,B are away from the first and second contacts 1128A,B. More simply stated, the spread gesture 1110 may be accomplished by a user's digits touching the screen in a spreading motion.

Figure 11G:
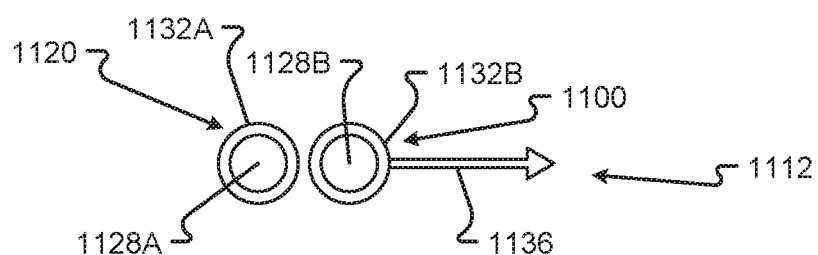
FIG. 11G is a graphical representation of an embodiment of a gesture that a user may perform to provide input to a vehicle control system.
Figure 11H:
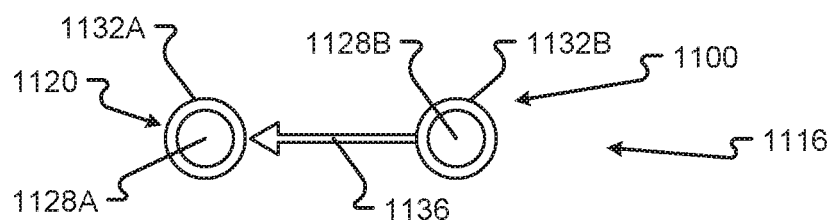
FIG. 11H is a graphical representation of an embodiment of a gesture that a user may perform to provide input to a vehicle control system.

The above gestures may be combined in any manner, such as those shown by FIGS. 11G and 11H, to produce a determined functional result. For example, in FIG. 11G a tap gesture 1120 is combined with a drag or flick gesture 1112 in a direction away from the tap gesture 1120. In FIG. 11H, a tap gesture 1120 is combined with a drag or flick gesture 1116 in a direction towards the tap gesture 1120.

The functional result of receiving a gesture can vary depending on a number of factors, including a state of the vehicle 104, display, or screen of a device, a context associated with the gesture, or sensed location of the gesture, etc. The state of the vehicle 104 commonly refers to one or more of a configuration of the vehicle 104, a display orientation, and user and other inputs received by the vehicle 104. Context commonly refers to one or more of the particular application(s) selected by the gesture and the portion(s) of the application currently executing, whether the application is a single- or multi-screen application, and whether the application is a multi-screen application displaying one or more windows. A sensed location of the gesture commonly refers to whether the sensed set(s) of gesture location coordinates are on a touch sensitive display or a gesture capture region of a device 212, 248, whether the sensed set(s) of gesture location coordinates are associated with a common or different display, or screen, or device 212, 248, and/or what portion of the gesture capture region contains the sensed set(s) of gesture location coordinates.

A tap, when received by a touch sensitive display of a device 212, 248, can be used, for instance, to select an icon to initiate or terminate execution of a corresponding application, to maximize or minimize a window, to reorder windows in a stack, and/or to provide user input such as by keyboard display or other displayed image. A drag, when received by a touch sensitive display of a device 212, 248, can be used, for instance, to relocate an icon or window to a desired location within a display, to reorder a stack on a display, or to span both displays (such that the selected window occupies a portion of each display simultaneously). A flick, when received by a touch sensitive display of a device 212, 248 or a gesture capture region, can be used to relocate a window from a first display to a second display or to span both displays (such that the selected window occupies a portion of each display simultaneously). Unlike the drag gesture, however, the flick gesture is generally not used to move the displayed image to a specific user-selected location but to a default location that is not configurable by the user.

The pinch gesture, when received by a touch sensitive display or a gesture capture region of a device 212, 248, can be used to minimize or otherwise increase the displayed area or size of a window (typically when received entirely by a common display), to switch windows displayed at the top of the stack on each display to the top of the stack of the other display (typically when received by different displays or screens), or to display an application manager (a "pop-up window" that displays the windows in the stack). The spread gesture, when received by a touch sensitive display or a gesture capture region of a device 212, 248, can be used to maximize or otherwise decrease the displayed area or size of a window, to switch windows displayed at the top of the stack on each display to the top of the stack of the other display (typically when received by different displays or screens), or to display an application manager (typically when received by an off-screen gesture capture region on the same or different screens).

The combined gestures of FIG. 11G, when received by a common display capture region in a common display or screen of a device 212, 248, can be used to hold a first window location constant for a display receiving the gesture while reordering a second window location to include a window in the display receiving the gesture. The combined gestures of FIG. 11H, when received by different display capture regions in a common display or screen of a device 212, 248 or in different displays or screens of one more devices 212, 248, can be used to hold a first window location for a display receiving the tap part of the gesture while reordering a second window location to include a window in the display receiving the flick or drag gesture. Although specific gestures and gesture capture regions in the preceding examples have been associated with corresponding sets of functional results, it is to be appreciated that these associations can be redefined in any manner to produce differing associations between gestures and/or gesture capture regions and/or functional results.

Figure 11I:
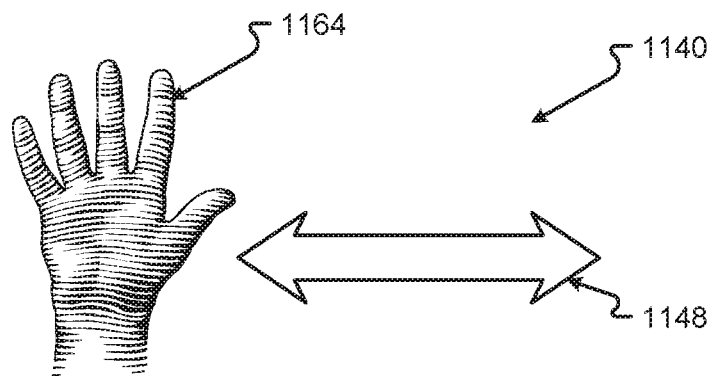
FIG. 11I is a graphical representation of an embodiment of a gesture that a user may perform to provide input to a vehicle control system.
Figure 11J:
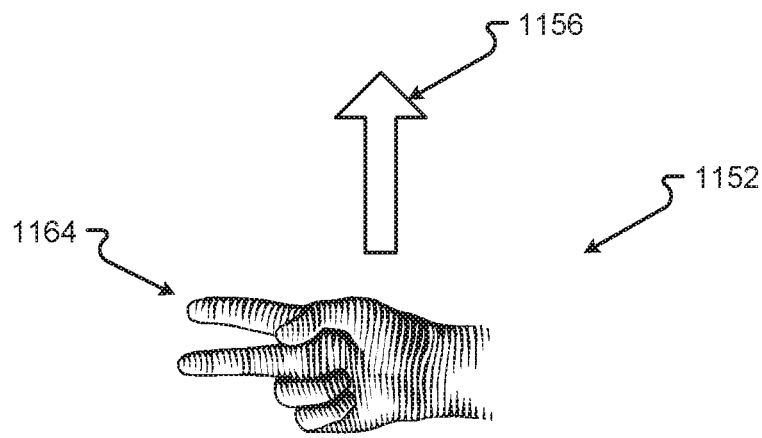
FIG. 11J is a graphical representation of an embodiment of a gesture that a user may perform to provide input to a vehicle control system.
Figure 11K:
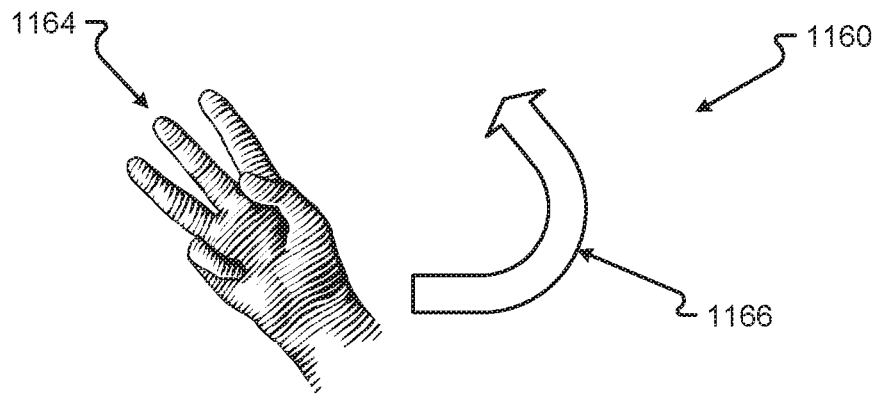
FIG. 11K is a graphical representation of an embodiment of a gesture that a user may perform to provide input to a vehicle control system.

Gestures that may be completed in three-dimensional space and not on a touch sensitive screen or gesture capture region of a device 212, 248 may be as shown in FIGS. 11I-11K. The gestures may be completed in an area where a sensor, such as an optical sensor, infrared sensor, or other type of sensor, may detect the gesture. For example, the gesture 1140 in FIG. 11I may be executed by a person when the person opens their hand 1164 and moves their hand in a back and forth direction 1148 as a gesture 1140 to complete some function with the vehicle 104. For example gesture 1140 may change the station of the radio in the vehicle 104. The sensors 242 may both determine the configuration of the hand 1164 and the vector of the movement. The vector and hand configuration can be interpreted to mean certain things to the vehicle control system 204 and produce different results.

In another example of a gesture 1152 in FIG. 11J, a user may configure their hand 1164 to extend two fingers and move the hand 1164 in an up and down operation 1156. This gesture 1152 may control the volume of the radio or some other function. For instance, this gesture 1152 may be configured to place the vehicle in a "valet" mode to, among other things, restrict access to certain features associated with the vehicle. Again, the sensors 242 may determine how the person has configured their hand 1164, and the vector of the movement. In another example of a gesture 1160 shown in FIG. 11K, a user may extend their middle three fingers at an angle that is substantially 45° for vertical from straight vertical and circle the hand in a counter-clockwise motion 1166. This gesture 1160 may cause the automobile to change the heat setting or do some other function. As can be understood by one skilled in the art, the configurations of the hand and the types of movement are variable. Thus, the user may configure the hand 1164 in any way imaginable and may also move that hand 1164 in any direction with any vector in three-dimensional space.

The gestures 1140, 1152, 1160, as shown in FIGS. 11I-11K, may occur in a predetermined volume of space within the vehicle 104. For example, a sensor may be configured to identify such gestures 1140, 1152, 1160 between the front passenger's and front driver's seats over a console area within the passenger compartment of the vehicle 104. The gestures 1140, 1152, 1160 may be made within area 1 508A between zones A 512A and B 512B. However, there may be other areas 508 where a user may use certain gestures, where sensors 242 may be able to determine a certain function is desired. Gestures that may be similar but used in different areas within the vehicle 104 may cause different functions to be performed. For example, the gesture 1140 in FIG. 11I, if used in zone E 512E, may change the heat provided in zone E 512E, but may change the station of a radio if used in zone A 512A and/or zone B 512B. Further, the gestures may be made with other body parts or, for example, different expressions of a person's face and may be used to control functions in the vehicle 104. Also, the user may use two hands in some circumstances or do other types of physical movements that can cause different reactions in the vehicle 104.

FIGS. 12A-12D show various embodiments of a data structure 1200 to store different settings. The data structure 1200 may include one or more of data files or data objects 1204, 1250, 1270, 1280. Thus, the data structure 1200 may represent different types of databases or data storage, for example, object-oriented data bases, flat file data structures, relational database, or other types of data storage arrangements. Embodiments of the data structure 1200 disclosed herein may be separate, combined, and/or distributed. As indicated in FIGS. 12A-12D, there may be more or fewer portions in the data structure 1200, as represented by ellipses 1244. Further, there may be more or fewer files in the data structure 1200, as represented by ellipses 1248.

Figure 12A:
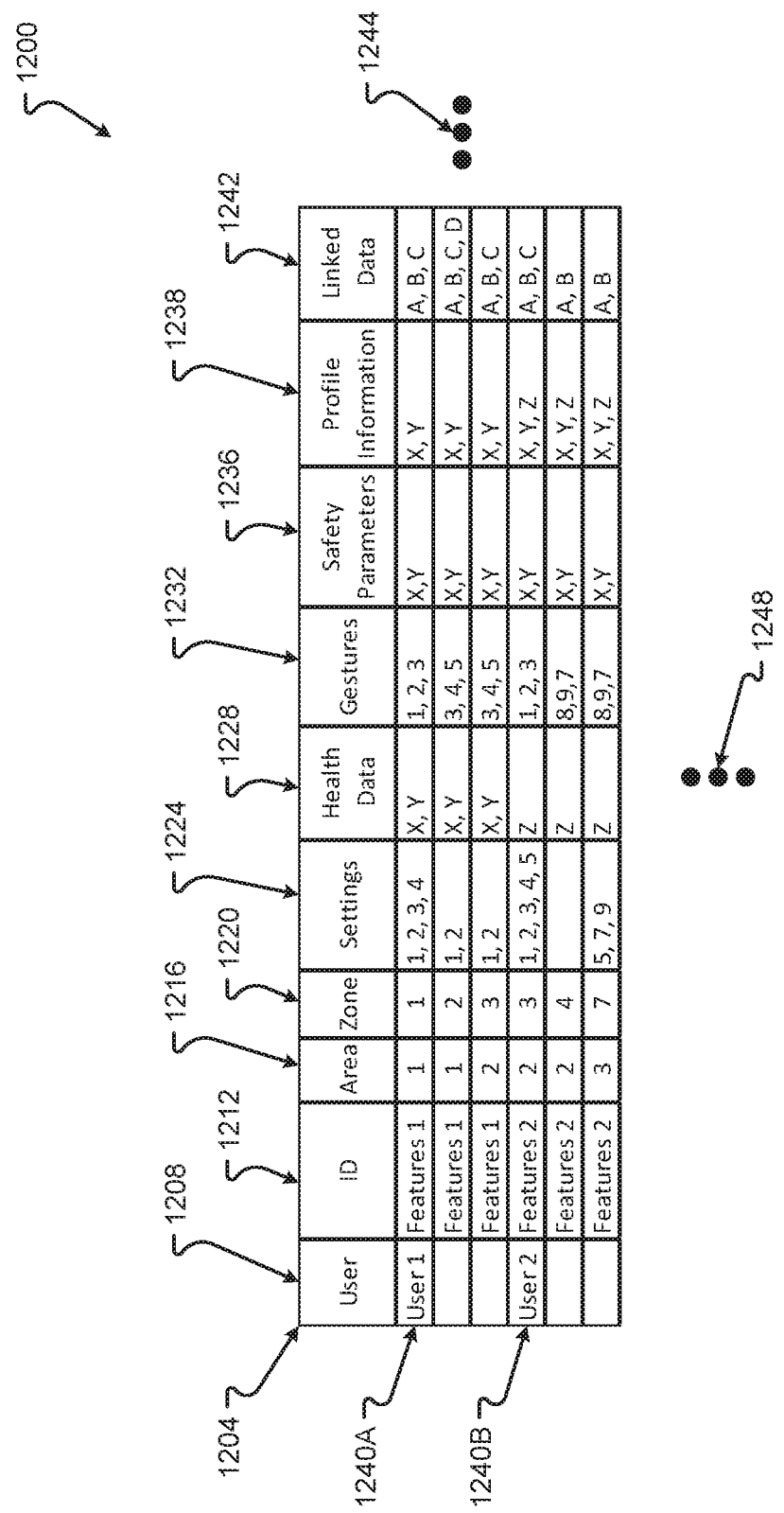
FIG. 12A is a diagram of an embodiment of a data structure for storing information about a user of a vehicle.

Referring to FIG. 12A, a first data structure is shown. The data file 1204 may include several portions 1208-1242 representing different types of data. Each of these types of data may be associated with a user, as shown in portion 1208.

There may be one or more user records 1240 and associated data stored within the data file 1204. As provided herein, the user can be any person that uses or rides within the vehicle or conveyance 104. The user may be identified in portion 1212. For the vehicle 104, the user may include a set of one or more features that may identify the user. These features may be the physical characteristics of the person that may be identified by facial recognition or some other type of system. In other situations, the user may provide a unique code to the vehicle control system 204 or provide some other type of data that allows the vehicle control system 204 to identify the user. The features or characteristics of the user are then stored in portion 1212.

Each user, identified in portion 1208, may have a different set of settings for each area 508 and/or each zone 512 within the vehicle 104. Thus, each set of settings may also be associated with a predetermined zone 512 or area 508. The zone 512 is stored in portion 1220, and the area 508 is stored in portion 1216.

One or more settings may be stored in portion 1224. These settings 1224 may be the configurations of different functions within the vehicle 104 that are specified by or for that user. For example, the settings 1224 may be the position of a seat, the position of a steering wheel, the position of accelerator and/or brake pedals, positions of mirrors, a heating/cooling setting, a radio setting, a cruise control setting, or some other type of setting associated with the vehicle 104. Further, in vehicles adapted to have a configurable console or a configurable dash or heads-up display, the settings 1224 may also provide for how that heads-up display, dash, or console are configured for this particular user.

Each setting 1224 may be associated with a different area 508 or zone 512. Thus, there may be more settings 1224 for when the user is the driver and in zone A 512A, 512A, of area 1, 508A. However, there may be similar settings 1224 among the different zones 512 or areas 508 as shown in portion 1224. For example, the heating or radio settings for the user may be similar in every zone 512.

The sensors 242 within the vehicle 104 may be able to either obtain or track health data in portion 1228. Health data 1228 may include any type of physical characteristic associated with the user. For example, a heart rate, a blood pressure, a temperature, or other types of heath data may be obtained and stored in portion 1228. The user may have this health data tracked over a period of time to allow for statistical analysis of the user's health while operating the vehicle 104. In this way, if some function of the user's health deviates from a norm (e.g., a baseline measurement, average measurements taken over time, and the like), the vehicle 104 may be able to determine there is a problem with the person and react to that data.

One or more gestures may be stored in portion 1232. Thus, the gestures used and described in conjunction FIG. 11A through 11K may be configurable. These gestures may be determined or created by the user and stored in portion 1132. A user may have different gestures for each zone 512 or area 508 within the vehicle. The gestures that do certain things while driving may do other things while in a different area 508 of the vehicle 104. Thus, the user may use a first set of gestures while driving and a second set while a passenger. Further, one or more users may share gestures as shown in portion 1232. Each driver may have a common set of gestures that they use in zone A 512A, 512A. Each of these gestures may be determined or captured and then stored with their characteristics (e.g., vector, position of gesture, etc.) in portion 1232.

One or more sets of safety parameters may be stored in portion 1236. Safety parameters 1236 may be common operating characteristics for this driver/passenger or for all drivers/passengers that if deviated from may determine there is a problem with the driver/passenger or the vehicle 104. For example, a certain route may be taken repeatedly and an average speed or mean speed may be determined. If the mean speed deviates by some number of standard deviations, a problem with the vehicle 104 or the user may be determined. In another example, the health characteristics or driving experience of the user may be determined. If the user drives in a certain position where their head occupies a certain portion of three-dimensional space within the vehicle 104, the vehicle control system 204 may determine that the safety parameter includes the users face or head being within this certain portion of the vehicle interior space. If the user's head deviates from that interior space for some amount of time, the vehicle control system 204 can determine that something is wrong with the driver and change the function or operation of the vehicle 104 to assist the driver. This may happen, for example, when a user falls asleep at the wheel. If the user's head droops and no longer occupies a certain three dimensional space, the vehicle control system 204 can determine that the driver has fallen asleep and may take control of the operation of the vehicle 204 and the automobile controller 8104 may steer the vehicle 204 to the side of the road. In other examples, if the user's reaction time is too slow or some other safety parameter is not nominal, the vehicle control system 204 may determine that the user is inebriated or having some other medical problem. The vehicle control system 204 may then assume control of the vehicle to ensure that the driver is safe.

Information corresponding to a user and/or a user profile may be stored in the profile information portion 1238. For example, the profile information 1238 may include data relating to at least one of current data, historical data, a user preference, user habit, user routine, observation, location data (e.g., programmed and/or requested destinations, locations of parking, routes traveled, average driving time, etc.), social media connections, contacts, brand recognition (e.g., determined via one or more sensors associated with the vehicle 104, a device 212, 248, etc.), audible recording data, text data, email data, political affiliation, preferred retail locations/sites (e.g., physical locations, web-based locations, etc.), recent purchases, behavior associated with the aforementioned data, and the like. The data in the profile information portion 1238 may be stored in one or more of the data structures 1200 provided herein. As can be appreciated, these one or more data structures may be stored in one or more memory locations. Examples of various memory locations are described in conjunction with FIG. 2.

One or more additional data fields may be stored in the linked data portion 1242 as data and/or locations of data. The linked data 1242 may include at least one of pointers, addresses, location identification, data source information, and other information corresponding to additional data associated with the data structure 1200. Optionally, the linked data portion 1242 may refer to data stored outside of a particular data structure 1200. For example, the linked data portion 1242 may include a link/locator to the external data. Continuing this example, the link/locator may be resolved (e.g., via one or more of the methods and/or systems provided herein, etc.) to access the data stored outside of the data structure 1200. Additionally or alternatively, the linked data portion 1242 may include information configured to link the data objects 1204 to other data files or data objects 1250, 1270, 1280. For instance, the data object 1204 relating to a user may be linked to at least one of a device data object 1250, a vehicle system data object 1270, and a vehicle data object 1280, to name a few.

Figure 12B:
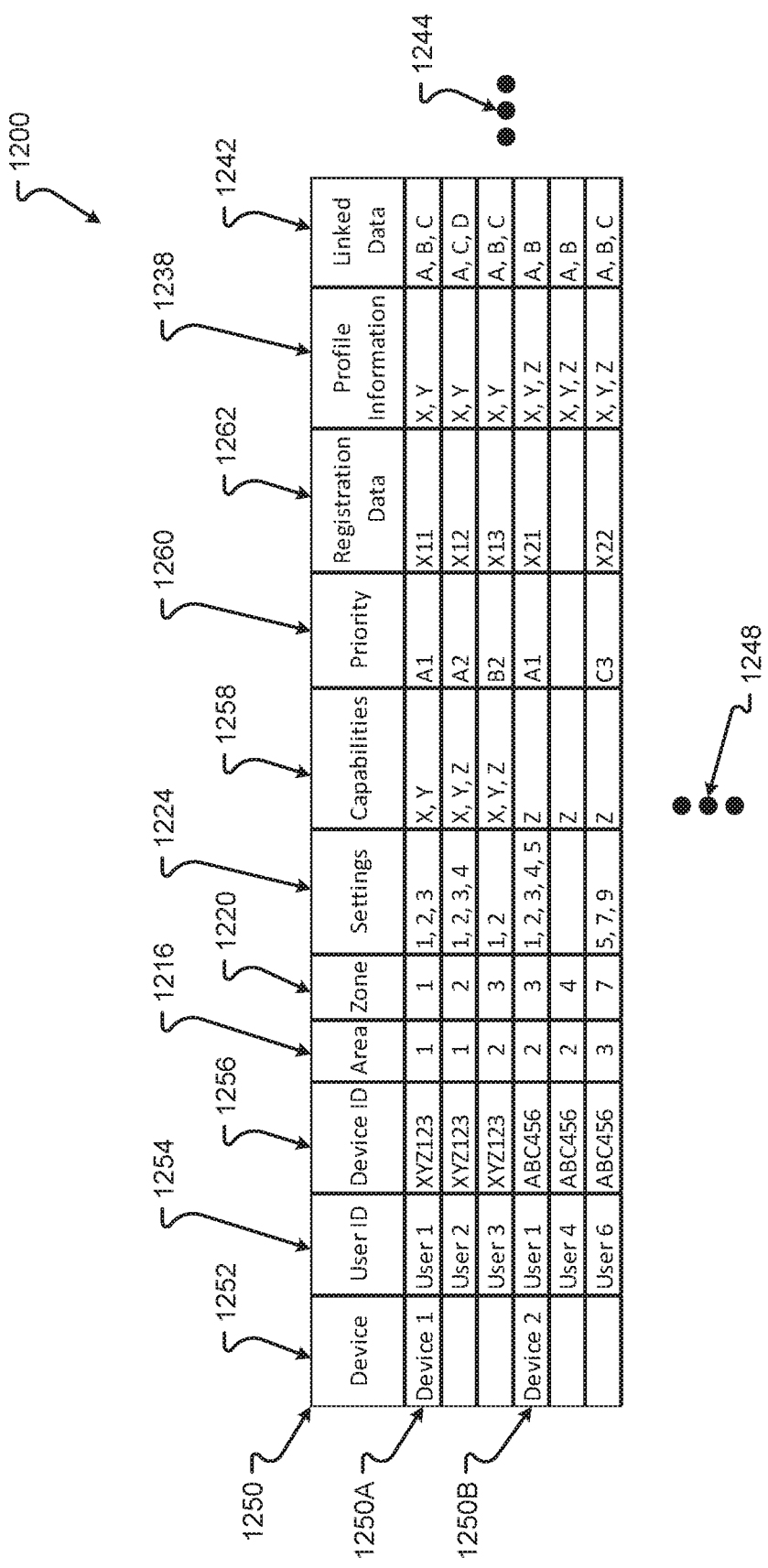
FIG. 12B is a diagram of an embodiment of a data structure for storing information about a device associated with or in a vehicle.

An embodiment of a data structure 1200 to store information associated with one or more devices is shown in FIG. 12B. The data file 1250 may include several portions 1216-1262 representing different types of data. Each of these types of data may be associated with a device, as shown in portion 1252.

There may be one or more device records 1250 and associated data stored within the data file 1250. As provided herein, the device may be any device that is associated with the vehicle 104. For example, a device may be associated with a vehicle 104 when that device is physically located within the interior space 108 of the vehicle 104. As another example, a device may be associated with a vehicle 104 when the device registers with the vehicle 104. Registration may include pairing the device with the vehicle 104 and/or one or more of the vehicle systems (e.g., as provided in FIG. 3). In some cases, the registration of a device with a vehicle 104 may be performed manually and/or automatically. An example of automatic registration may include detecting, via one or more of the vehicle systems, that a device is inside the vehicle 104. Upon detecting that the device is inside the vehicle 104, the vehicle system may identify the device and determine whether the device is or should be registered. Registration may be performed outside of a vehicle 104 via providing a unique code to the vehicle 104 and/or at least one of the vehicle systems.

The device may be identified in portion 1256. Among other things, the device identification may be based on the hardware associated with the device (e.g., Media Access Control (MAC) address, Burned-In Address (BIA), Ethernet Hardware Address (EHA), physical address, hardware address, and the like).

Optionally, a device may be associated with one or more users. For example, a tablet and/or graphical user interface (GUI) associated with the vehicle 104 may be used by multiple members of a family. For instance, the GUI may be located in a particular area 508 and/or zone 512 of the vehicle 104. Continuing this example, when a family member is located in the particular area 508 and/or zone 512, the device may include various settings, features, priorities, capabilities, and the like, based on an identification of the family member. The user may be identified in portion 1254. For the device, the user identification portion 1254 may include a set of one or more features that may identify a particular user. These features may be the physical characteristics of the person that may be identified by facial recognition, or some other type of system, associated with the device and/or the vehicle 104. Optionally, the user may provide a unique code to the device, or provide some other type of data, that allows the device to identify the user. The features or characteristics of the user are then stored in portion 1254.

Each device identified in the device identification portion 1256 may have a different set of settings for each area 508 and/or each zone 512, and/or each user of the device. Thus, each set of settings may also be associated with a predetermined zone 512, area 508, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a device is configured for a particular user. Each setting 1224 may be associated with a different area 508 or zone 512. Thus, there may be more restrictive settings 1224 (e.g., restricted multimedia, texting, limited access to device functions, and the like) for the device when the user is the driver and in zone A 512A, 512A, of area 1, 508A. However, when the user is in another zone 512 or area 508, for example, where the user is not operating a vehicle 104, the settings 1224 may provide unrestricted access to one or more features of the device (e.g., allowing texting, multimedia, etc.).

Optionally, the capabilities of a device may be stored in portion 1258. Examples of device capabilities may include, but are not limited to, a communications ability (e.g., via wireless network, EDGE, 3G, 4G, LTE, wired, Bluetooth®, Near Field Communications (NFC), Infrared (IR), etc.), hardware associated with the device (e.g., cameras, gyroscopes, accelerometers, touch interface, processor, memory, display, etc.), software (e.g., installed, available, revision, release date, etc.), firmware (e.g., type, revision, etc.), operating system, system status, and the like. Optionally, the various capabilities associated with a device may be controlled by one or more of the vehicle systems provided herein. Among other things, this control allows the vehicle 104 to leverage the power and features of various devices to collect, transmit, and/or receive data.

One or more priorities may be stored in portion 1260. The priority may correspond to a value, or combination of values, configured to determine how a device interacts with the vehicle 104 and/or its various systems. The priority may be based on a location of the device (e.g., as stored in portions 1216, 1220). A default priority can be associated with each area 508 and/or zone 512 of a vehicle 104. For example, the default priority associated with a device found in zone 1 512A of area 1 508A (e.g., a vehicle operator position) may be set higher than an (or the highest of any) alternative zone 512 or area 508 of the vehicle 104. Continuing this example, the vehicle 104 may determine that, although other devices are found in the vehicle, the device, having the highest priority, controls features associated with the vehicle 104. These features may include vehicle control features, critical and/or non-critical systems, communications, and the like. Additionally or alternatively, the priority may be based on a particular user associated with the device. Optionally, the priority may be used to determine which device will control a particular signal in the event of a conflict.

Registration data may be stored in portion 1262. As described above, when a particular device registers with a vehicle 104, data related to the registration may be stored in the registration data portion 1262. Such data may include, but is not limited to, registration information, registration codes, initial registration time, expiration of registration, registration timers, and the like. Optionally, one or more systems of the vehicle 104 may refer to the registration data portion 1262 to determine whether a device has been previously registered with the vehicle 104. As shown in FIG. 12B, User 4 of Device 2 has not been registered. In this case, the registration data field 1262, for this user, may be empty, contain a null value, or other information/indication that there is no current registration information associated with the user.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 12C:
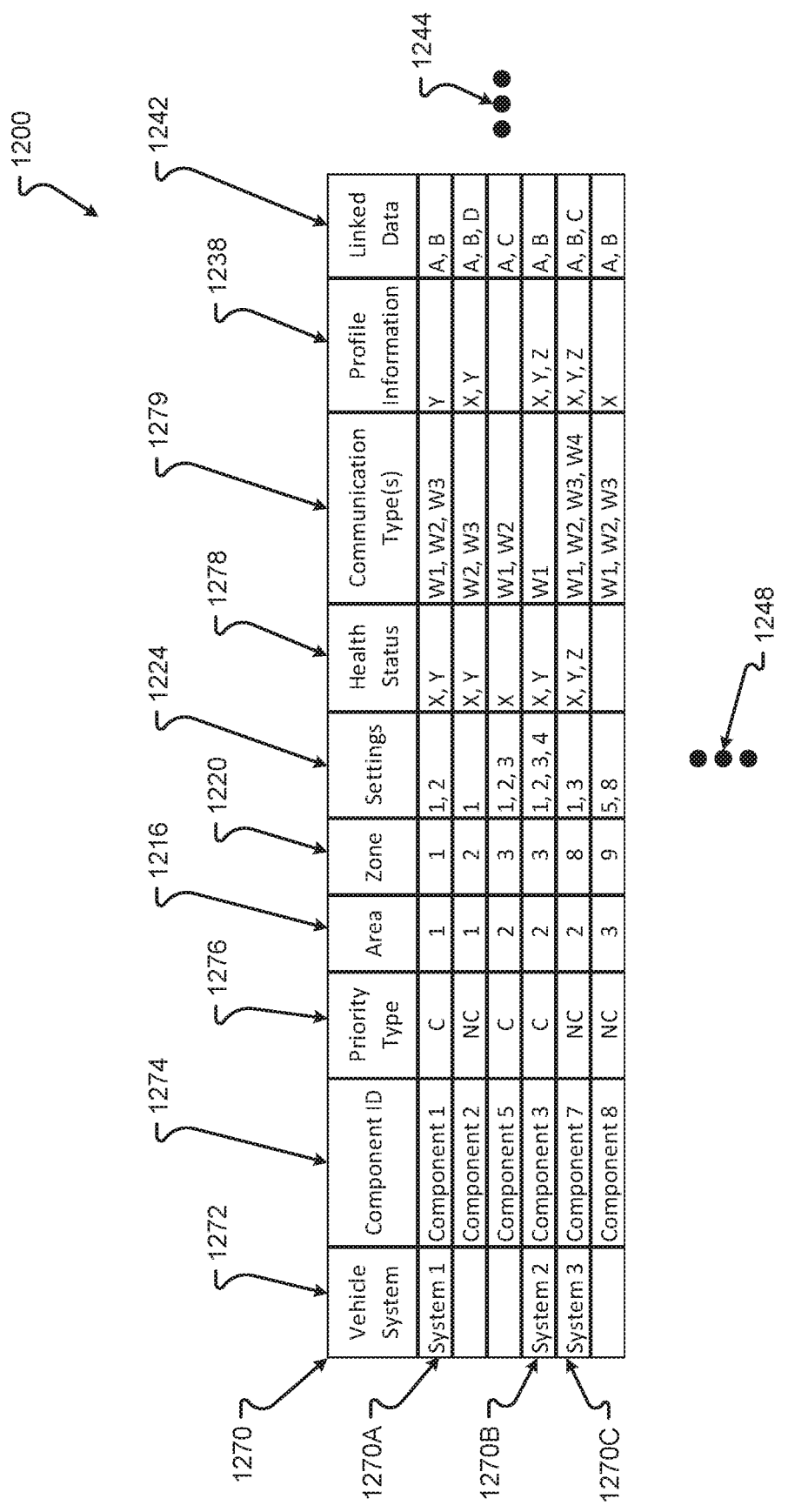
FIG. 12C is a diagram of an embodiment of a data structure for storing information about a system of a vehicle.

An embodiment of a data structure 1200 to store information associated with one or more vehicle systems is shown in FIG. 12C. The data file 1270 may include several portions 1216-1279 representing different types of data. Each of these types of data may be associated with a vehicle system, as shown in portion 1272.

There may be one or more system records 1270 and associated data stored within the data file 1270. As provided herein, the vehicle systems may be any system and/or subsystem that is associated with the vehicle 104. Examples of various systems are described in conjunction with FIG. 3 and other related figures (e.g., systems 324-352, etc.). One example of a system associated with the vehicle 104 is the vehicle control system 204. Other systems may include communications subsystems 344, vehicle subsystems 328, and media subsystems 348, to name a few. It should be appreciated that the various systems may be associated with the interior space 108 and/or the exterior of the vehicle 104.

Each system may include one or more components. The components may be identified in portion 1274. Identification of the one or more components may be based on hardware associated with the component. This identification may include hardware addresses similar to those described in conjunction with the devices of FIG. 12B. Additionally or alternatively, a component can be identified by one or more signals sent via the component. Such signals may include an Internet Protocol (IP), or similar, address as part of the signal. Optionally, the signal may identify the component sending the signal via one or more of a header, a footer, a payload, and/or an identifier associated with the signal (e.g., a packet of a signal, etc.).

Each system and/or component may include priority type information in portion 1276. Among other things, the priority type information stored in portion 1276 may be used by the various methods and systems provided herein to differentiate between critical and non-critical systems. Non-limiting examples of critical systems may correspond to those systems used to control the vehicle 104, such as, steering control, engine control, throttle control, braking control, and/or navigation informational control (e.g., speed measurement, fuel measurement, etc.) Non-critical systems may include other systems that are not directly related to the control of the vehicle 104. By way of example, non-critical systems may include media presentation, wireless communications, comfort settings systems (e.g., climate control, seat position, seat warmers, etc.), and the like. Although examples of critical and/or non-critical systems are provided above, it should be appreciated that the priority type of a system may change (e.g., from critical to non-critical, from non-critical to critical, etc.) depending on the scenario. For instance, although the interior climate control system may be classified as a non-critical system at a first point in time, it may be subsequently classified as a critical system when a temperature inside/outside of the vehicle 104 is measured at a dangerous level (e.g., sub-zero Fahrenheit, greater than 90-degrees Fahrenheit, etc.). As such, the priority type may be associated with temperature conditions, air quality, times of the day, condition of the vehicle 104, and the like.

Each system may be associated with a particular area 508 and/or zone 512 of a vehicle 104. Among other things, the location of a system may be used to assess a state of the system and/or provide how the system interacts with one or more users of the vehicle 104. As can be appreciated each system may have a different set of settings for each area 508 and/or each zone 512, and/or each user of the system. Thus, each set of settings may also be associated with a predetermined zone 512, area 508, system, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a system is configured for a particular user. Each setting 1224 may be associated with a different area 508 or zone 512. For instance, a climate control system may be associated with more than one area 508 and/or zone 512. As such, a first user seated in zone 1 512A of area 1 508A may store settings related to the climate control of that zone 512A that are different from other users and/or zones 512 of the vehicle 104. Optionally, the settings may not be dependent on a user. For instance, specific areas 508 and/or zones 512 of a vehicle 104 may include different, default, or the same settings based on the information stored in portion 1224.

The various systems and/or components may be able to obtain or track health status data of the systems and/or components in portion 1278. The health status 1278 may include any type of information related to a state of the systems. For instance, an operational condition, manufacturing date, update status, revision information, time in operation, fault status, state of damage detected, inaccurate data reporting, and other types of component/system health status data may be obtained and stored in portion 1278.

Each component and/or system may be configured to communicate with users, systems, servers, vehicles, third parties, and/or other endpoints via one or more communication type. At least one communication ability and/or type associated with a system may be stored in the communication type portion 1279. Optionally, the communication types contained in this portion 1279 may be ordered in a preferential order of communication types. For instance, a system may be configured to preferably communicate via a wired communication protocol over one or more wired communication channels (e.g., due to information transfer speeds, reliability, and the like). However, in this instance, if the one or more wired communication channels fail, the system may transfer information via an alternative communication protocol and channel (e.g., a wireless communication protocol and wireless communication channel, etc.). Among other things, the methods and systems provided herein may take advantage of the information stored in the communication type portion 1279 to open available communication channels in the event of a communication channel failure, listen on other ports for information transmitted from the systems, provide a reliability rating based on the number of redundant communication types for each component, and more. Optionally, a component or system may be restricted from communicating via a particular communication type (e.g., based on rules, traffic, critical/non-critical priority type, and the like). In this example, the component or system may be forced by the vehicle control system 204 to use an alternate communication type where available, cease communications, or store communications for later transfer.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 12D:
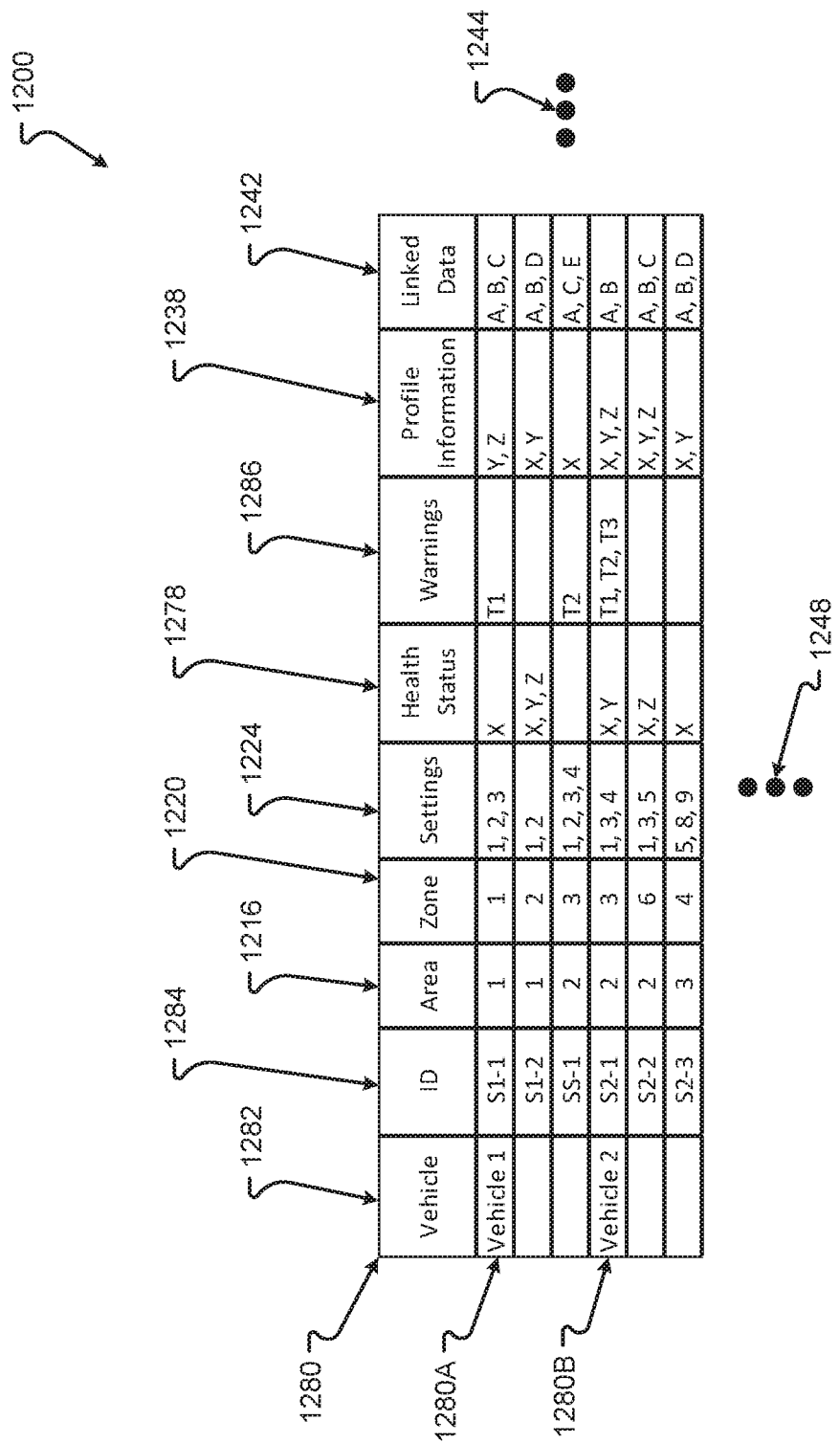
FIG. 12D is a diagram of an embodiment of a data structure for storing information about a vehicle.

Referring now to FIG. 12D, a data structure 1200 is shown optionally. The data file 1280 may include several portions 1216-1286 representing different types of data. Each of these types of data may be associated with a vehicle, as shown in portion 1282.

There may be one or more vehicle records 1280 and associated data stored within the data file 1282. As provided herein, the vehicle 104 can be any vehicle or conveyance 104 as provided herein. The vehicle 104 may be identified in portion 1282. Additionally or alternatively, the vehicle 104 may be identified by one or more systems and/or subsystems. The various systems of a vehicle 104 may be identified in portion 1284. For example, various features or characteristics of the vehicle 104 and/or its systems may be stored in portion 1284. Optionally, the vehicle 104 may be identified via a unique code or some other type of data that allows the vehicle 104 to be identified.

Each system may be associated with a particular area 508 and/or zone 512 of a vehicle 104. Among other things, the location of a system may be used to assess a state of the system and/or provide how the system interacts with one or more users of the vehicle 104. As can be appreciated each system may have a different set of settings for each area 508 and/or each zone 512, and/or each user of the system. Thus, each set of settings may also be associated with a predetermined zone 512, area 508, system, and/or user. The zone 512 is stored in portion 1220 and the area 508 is stored in portion 1216.

One or more settings may be stored in portion 1224. These settings 1224 may be similar and/or identical to those previously described. Further, the settings 1224 may also provide for how a vehicle and/or its systems are configured for one or more users. Each setting 1224 may be associated with a different area 508 or zone 512. Optionally, the settings may not be dependent on a particular user. For instance, specific areas 508 and/or zones 512 of a vehicle 104 may include different, default, or the same settings based on the information stored in portion 1224.

The various systems and/or components may be able to obtain or track health status data of the systems and/or components in portion 1278. The health status 1278 may include any type of information related to a state of the systems. For instance, an operational condition, manufacturing date, update status, revision information, time in operation, fault status, state of damage detected, inaccurate data reporting, and other types of component/system health status data may be obtained and stored in portion 1278.

One or more warnings may be stored in portion 1286. The warnings data 1286 may include warning generated by the vehicle 104, systems of the vehicle 104, manufacturer of the vehicle, federal agency, third party, and/or a user associated with the vehicle. For example, several components of the vehicle may provide health status information (e.g., stored in portion 1278) that, when considered together, may suggest that the vehicle 104 has suffered some type of damage and/or failure. Recognition of this damage and/or failure may be stored in the warnings data portion 1286. The data in portion 1286 may be communicated to one or more parties (e.g., a manufacturer, maintenance facility, user, etc.). In another example, a manufacturer may issue a recall notification for a specific vehicle 104, system of a vehicle 104, and/or a component of a vehicle 104. It is anticipated that the recall notification may be stored in the warning data field 1286. Continuing this example, the recall notification may then be communicated to the user of the vehicle 104 notifying the user of the recall issued by the manufacturer.

Additionally or alternatively, the data structure 1200 may include a profile information portion 1238 and/or a linked data portion 1242. Although the profile information portion 1238 and/or the linked data portion 1242 may include different information from that described above, it should be appreciated that the portions 1238, 1242 may be similar, or identical, to those as previously disclosed.

Figure 13:
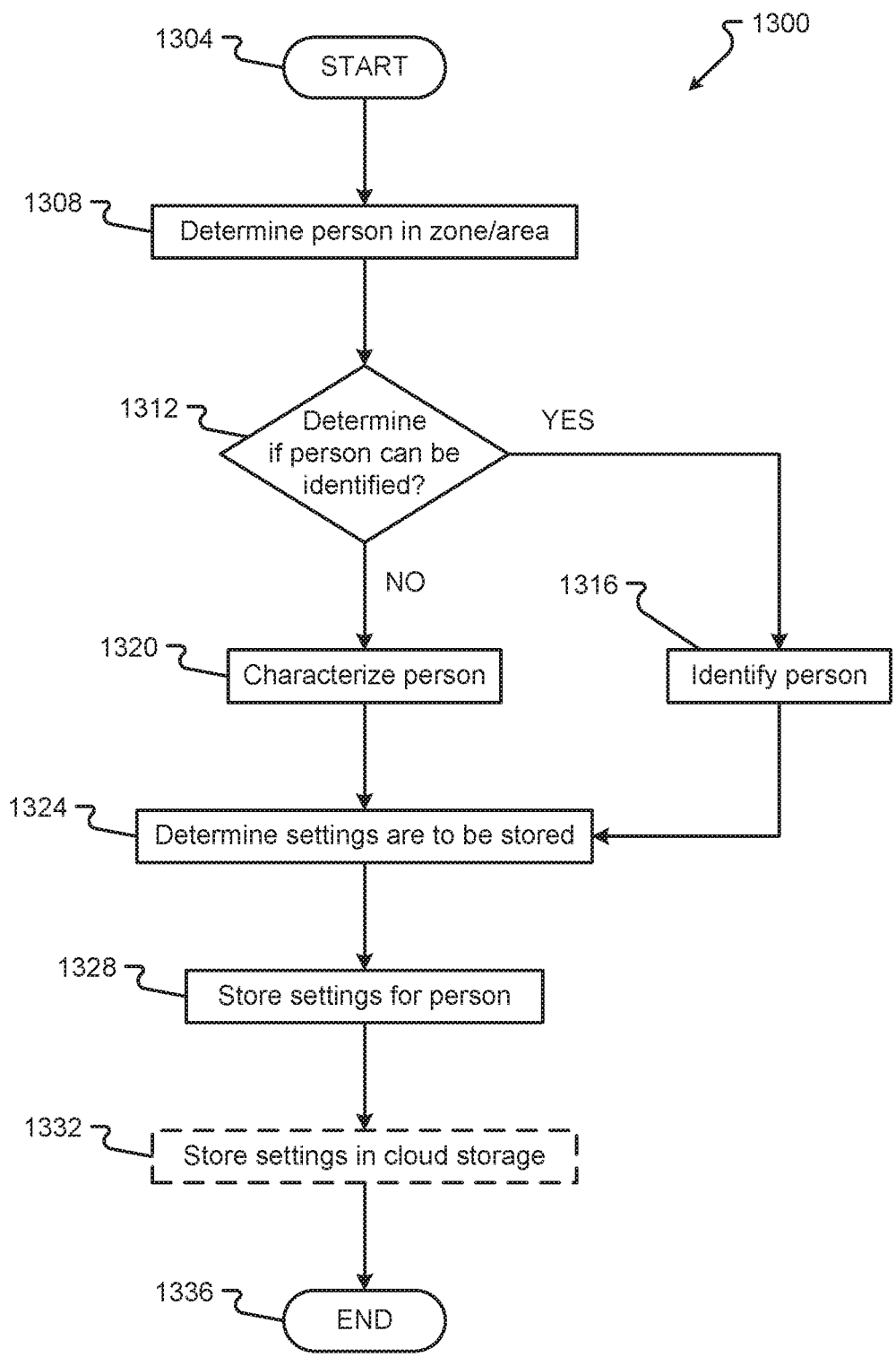
FIG. 13 is a flow or process diagram of a method for storing one or more settings associated with a user.

An embodiment of a method 1300 for storing settings for a user 216 associated with vehicle 104 is shown in FIG. 13. While a general order for the steps of the method 1300 is shown in FIG. 13, the method 1300 can include more or fewer steps or can arrange the order of the steps differently than those shown in FIG. 13. Generally, the method 1300 starts with a start operation 1304 and ends with an end operation 1336. The method 1300 can be executed as a set of computer-executable instructions executed by a computer system and encoded or stored on a computer readable medium. Hereinafter, the method 1300 shall be explained with reference to the systems, components, modules, software, data structures, user interfaces, etc. described in conjunction with FIGS. 1-12.

A person may enter the vehicle space 108. One or more sensors 242 may then identify that a person is sitting within the vehicle 104, in step 1308. For example, sensors 242 in a seat, may determine that some new amount of weight has been registered. The amount of weight may fall within predetermined parameters (e.g., over a threshold, in a specific range, etc.). This weight may then be determined to be a person by one or more optical or other sensors 242. The vehicle control system 204 may then determine that a person is in a certain zone 512 or area 508. For example, the sensors 242 may send signals to the vehicle controls system 204 that an event has occurred. This information may be sent to the vehicle control system processor 304 to determine the zone 512 and area 508 where the event occurred. Further, the vehicle control system 204 may then identify the person, in step 1312.

The vehicle control system 204 can receive the information from the sensors 242 and use that information to search the database 1200 that may be stored within the system data 208. The sensor data may be compared to ID characteristics 1212 to determine if the person has already been identified. The vehicle control system 204 may also send the characteristic data from the sensors to the communication network 224 to a server 228 to compare the sensor data to stored data 232 that may be stored in a cloud system. The person's features can be compared to stored features 1212 to determine if the person in the vehicle 104 can be identified.

If the person has been identified previously and their characteristics stored in portion 1212, the method 1300 proceeds YES to step 1316 where that person may be identified. In identifying a person, the information associated with that person 1240 may be retrieved and provided to the vehicle control system 204 for further action. If a person cannot be identified by finding their sensor characteristics in portion 1212, the method 1300 proceeds NO to step 1320. In step 1320, the vehicle control system 204, using an application, may create a new record in table 1200 for the user. This new record may store a user identifier and their characteristics 1212. It may also store the area 508 and zone 512 in data portions 1216 and 1220. The new record may then be capable of receiving new settings data for this particular user. In this way, the vehicle 104 can automatically identify or characterize a person so that settings may be established for the person in the vehicle 104.

The input module 312 may then determine if settings are to be stored, in step 1324. Settings might be any configuration of the vehicle 104 that may be associated with the user. The determination may be made after receiving a user input from the user. For example, the user may make a selection on a touch sensitive display indicating that settings currently made are to be stored. In other situations, a period of time may elapse after the user has made a configuration. After determining that the user is finished making changes to the settings, based on the length of the period of time since the setting was established, the vehicle control system 204 can save the setting. Thus, the vehicle control system 204 can make settings automatically based on reaching a steady state for settings for user.

The vehicle control system 204 may then store the settings for the person, in step 1328. The user interaction subsystem 332 can make a new entry for the user 1208 in data structure 1204. The new entry may be either a new user or a new settings listed in 1224. The settings may be stored based on the area 508 and zone 512. As explained previously, the settings can be any kind of configuration of the vehicle 104 that may be associated with the user in that area 508 and the zone 512.

The settings may also be stored in cloud storage, in step 1332. Thus, the vehicle control system 204 can send the new settings to the server 228 to be stored in storage 232. In this way, these new settings may be ported to other vehicles for the user. Further, the settings in storage system 232 may be retrieved, if local storage does not include the settings in storage system 208.

Additionally or alternatively, the settings may be stored in profile data 252. As provided herein, the profile data 252 may be associated with one or more devices 212, 248, servers 228, vehicle control systems 204, and the like. Optionally, the settings in profile data 252 may be retrieved in response to conditions. For instance, the settings may be retrieved from at least one source having the profile data if local storage does not include the settings in storage system 208. As another example, a user 216 may wish to transfer settings stored in profile data 252 to the system data 208. In any event, the retrieval and transfer of settings may be performed automatically via one or more devices 204, 212, 248, associated with the vehicle 104.

Figure 14:
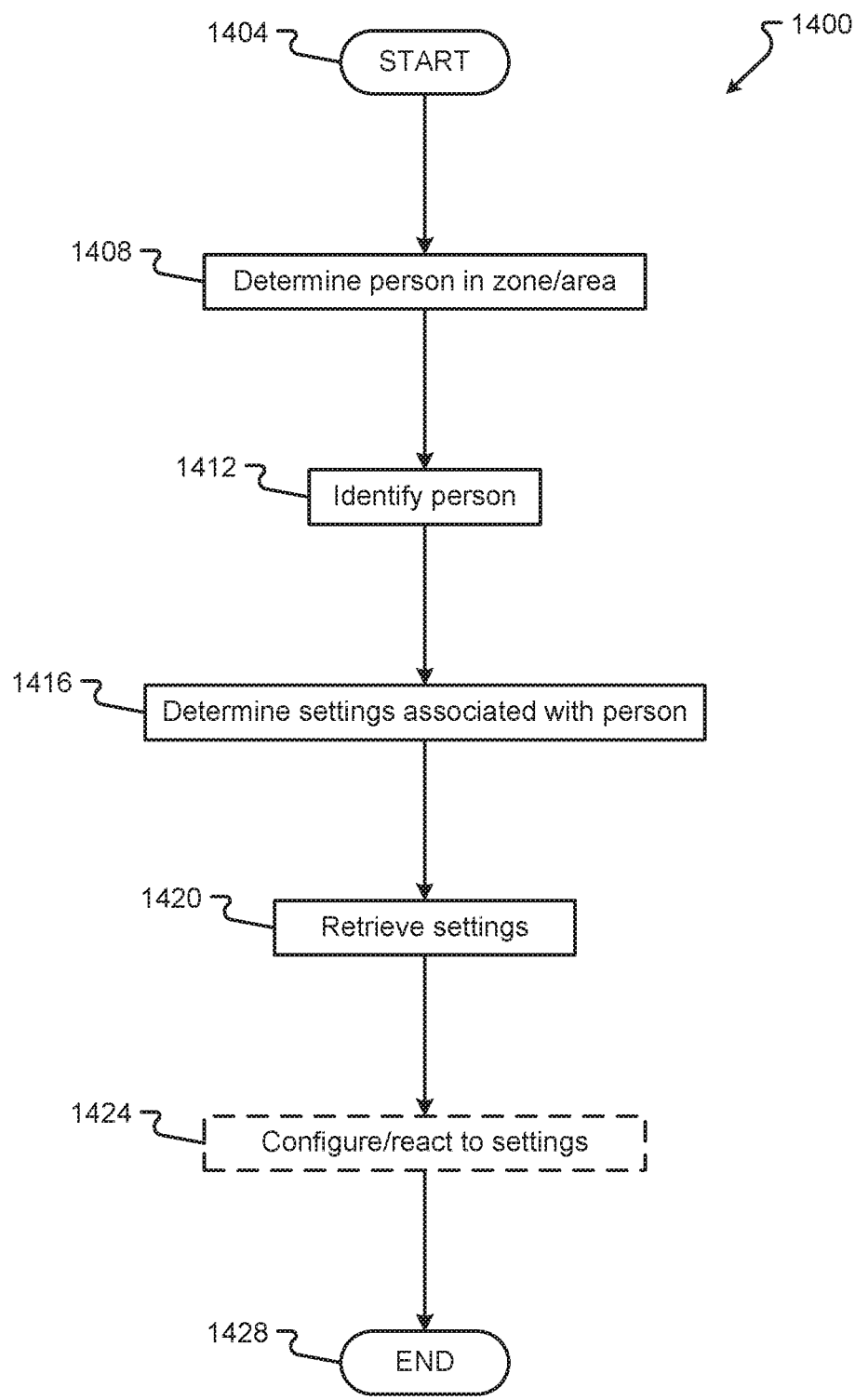
FIG. 14 is a flow or process diagram of a method for establishing one or more settings associated with a user.

An embodiment of a method 1400 to configure the vehicle 104 based on stored settings is shown in FIG. 14. A general order for the steps of the method 1400 is shown in FIG. 14. Generally, the method 1400 starts with a start operation 1404 and ends with an end operation 1428. The method 1400 can include more or fewer steps or can arrange the order of the steps differently than those shown in FIG. 14. The method 1400 can be executed as a set of computer-executable instructions executed by a computer system and encoded or stored on a computer readable medium. Hereinafter, the method 1400 shall be explained with reference to the systems, components, modules, software, data structures, user interfaces, etc. described in conjunction with FIGS. 1-13.

The vehicle control system 204 can determine if a person is in a zone 512 or area 508, in step 1408. This determination may be made by receiving data from one or more sensors 242. The vehicle 104 can use facial recognition, weight sensors, heat sensors, or other sensors to determine whether a person is occupying a certain zone 512.

Using the information from the sensors 242, the vehicle control system 204 can identify the person, in step 1412. The vehicle control system 204 can obtain characteristics for the user currently occupying the zone 512 and compare those characteristics to the identifying features in portion 1212 of data structure 1204. Thus, the settings in portion 1224 may be retrieved by identifying the correct zone 512, area 508, and characteristics for the user.

The vehicle control system 204 can first determine if there are settings associated with the identified person for that zone 512 and/or area 508, in step 1416. After identifying the user by matching characteristics with the features in portion 1212, the vehicle control system 204 can determine if there are settings for the user for the area 1216 and zone 1220 the user currently occupies. If there are settings, then the vehicle control system 204 can make the determination that there are settings in portion 1224, and the vehicle control system 204 may then read and retrieve those settings, in step 1420. The settings may be then used to configure or react to the presence of the user, in step 1424. Thus, these settings may be obtained to change the configuration of the vehicle 104, for example, how the position of the seats or mirrors are set, how the dash, console, or heads up display is configured, how the heat or cooling is configured, how the radio is configured, or how other different configurations are made.

Figure 15:
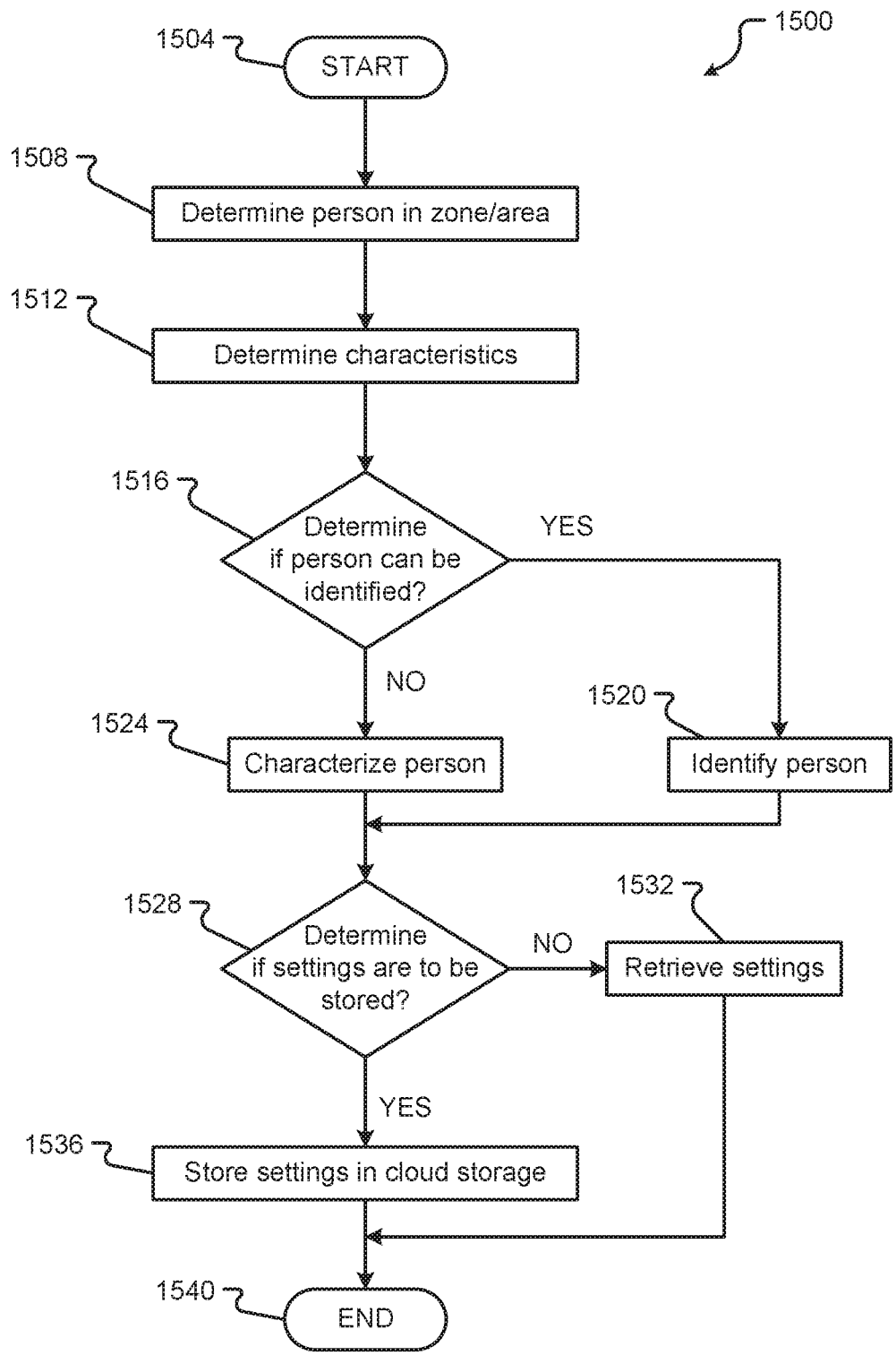
FIG. 15 is a flow or process diagram of a method for storing one or more settings associated with a user.

Embodiments of a method 1500 for storing settings in cloud storage are shown in FIG. 15. A general order for the steps of the method 1500 is shown in FIG. 15. Generally, the method 1500 starts with a start operation 1504 and ends with an end operation 1540. The method 1500 can include more or fewer steps or can arrange the order of the steps differently than those shown in FIG. 15. The method 1500 can be executed as a set of computer-executable instructions executed by a computer system and encoded or stored on a computer readable medium. Hereinafter, the method 1500 shall be explained with reference to the systems, components, modules, software, data structures, user interfaces, etc. described in conjunction with FIGS. 1-14.

The vehicle control system 204 can determine if a person is in a zone 512 or area 508, in step 1508. As explained previously, the vehicle control system 204 can receive vehicle sensor data from vehicle sensors 242 that show a person has occupied a zone 512 or an area 508 of the vehicle 104. Using the vehicle sensor data, the vehicle control system 204 can determine characteristics of the person, in step 1512. These characteristics are compared to the features in portion 1212 of the data structure 1204. From this comparison, the vehicle control system 204 can determine if the person is identified within the data structure 1204, in step 1516. If there is a comparison and the person can be identified, the method 1500 proceeds YES to step 1520. However, if the person cannot be identified, the method 1500 proceeds NO, to step 1524.

In step 1520, the person is identified in portion 1208 by the successful comparison of the characteristics and the features. It should be noted that there may be a degree of variability between the characteristics and the features in portion 1212. Thus, the comparison may not be an exact comparison but may use methods known in the art to make a statistically significant comparison between the characteristics received from the sensors 242 and the features stored in portion 1212. In step 1524, the characteristics received from sensors 242 are used to characterize the person. In this way, the received characteristics may be used as an ID, in portion 1212, for a new entry for a new user in portion 1208.

The user may make one or more settings for the vehicle 104. The vehicle control system 204 may determine if the settings are to be stored, in step 1528. If the settings are to be stored, the method 1500 proceeds YES to step 1536. If the settings are not to be stored or if there are no settings to be stored, the method 1500 proceeds NO to step 1532. In step 1532, the vehicle control system 204 can retrieve the settings in the portion 1224 of the data structure 1204. Retrieval of the settings may be as described in conjunction with FIG. 14. If settings are to be stored, the vehicle control system 204 can send those settings to server 228 to be stored in data storage 232, in step 1536. Data storage 232 acts as cloud storage that can be used to retrieve information on the settings from other vehicles or from other sources. Thus, the cloud storage 232 allows for permanent and more robust storage of user preferences for the settings of the vehicle 104.

Figure 16:
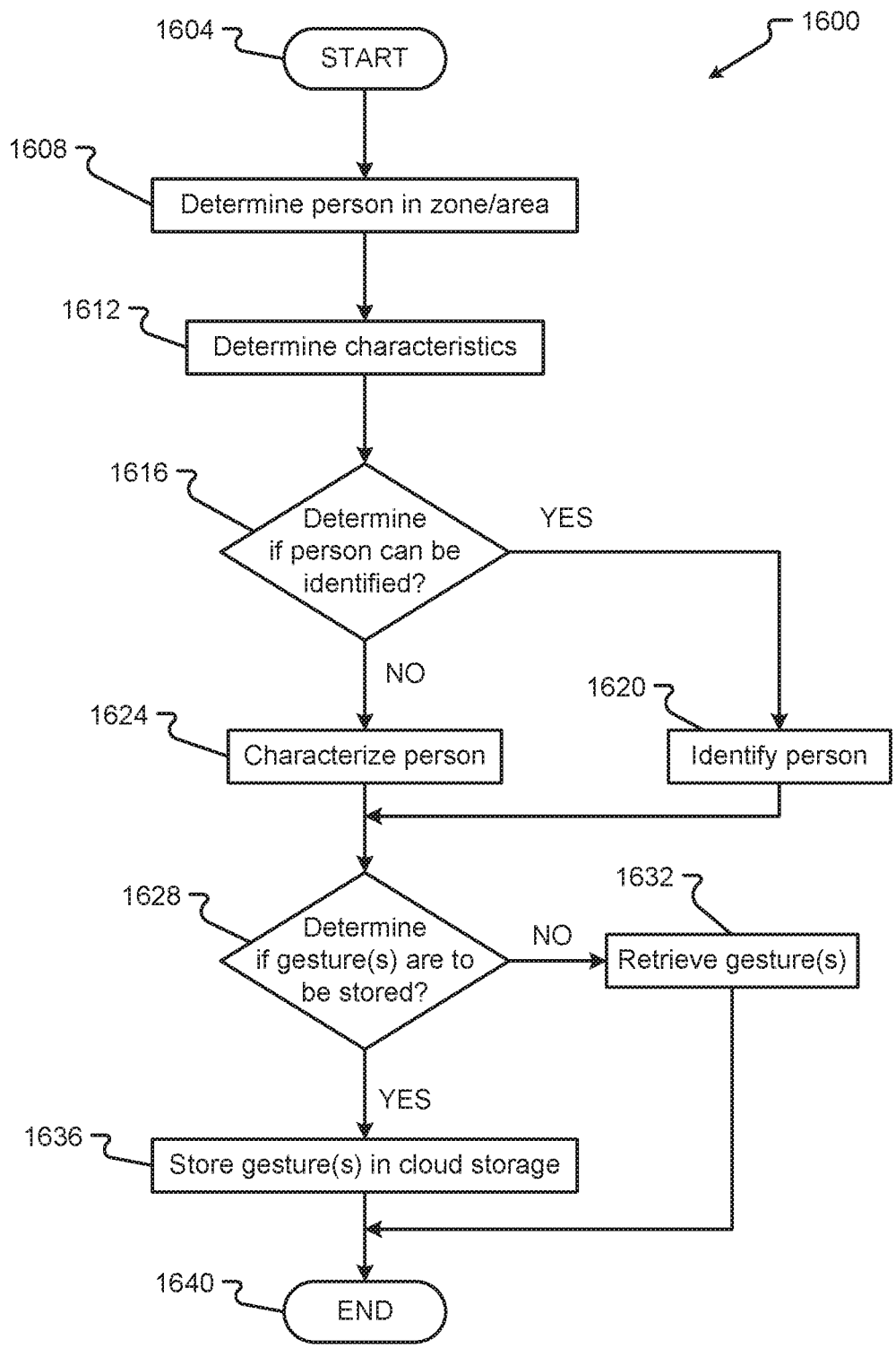
FIG. 16 is a flow or process diagram of a method for storing one or more gestures associated with a user.

An embodiment of a method 1600 for storing gestures associated with the user is shown in FIG. 16. A general order for the steps of the method 1600 is shown in FIG. 16. Generally, the method 1600 starts with a start operation 1604 and ends with an end operation 1640. The method 1600 can include more or fewer steps or can arrange the order of the steps differently than those shown in FIG. 16. The method 1600 can be executed as a set of computer-executable instructions executed by a computer system and encoded or stored on a computer readable medium. Hereinafter, the method 1600 shall be explained with reference to the systems, components, modules, software, data structures, user interfaces, etc. described in conjunction with FIGS. 1-15.

Vehicle control system 204 may receive sensor data from sensors 242 to determine a person is occupying a zone 512 in an area 508 of the vehicle 104, in step 1608. The sensor data may provide characteristics for the person, in step 1612. The vehicle control system 204 may then use the characteristics to determine if the person can be identified, in step 1616. The vehicle control system 204 may compare the characteristics to the features in portion 1212 for the people having been recognized and having data associated therewith. If a comparison is made between the characteristics and the features in portion 1212, the person can be identified, and the method 1600 proceeds YES to step 1620. If there is no comparison, the method 1600 may proceed NO to step 1624. In step 1620, the person may be identified by the vehicle control system 204. Thus, the person's features and associated data record 1240 may be determined and the user identified in portion 1208. If the person is not identified, the vehicle control system 204 can characterize the person in step 1624 by establishing a new record in data structure 1204 using the characteristics, received from the sensors 242, for the features in portion 1212.

Thereinafter, the vehicle control system 204 may determine if gestures are to be stored and associated with the user, in step 1628. The vehicle control system 204 may receive user input on a touch sensitive display or some other type of gesture capture region which acknowledges that the user wishes to store one or more gestures. Thus, the user may create their own gestures such as those described in conjunction with FIGS. 11A-11K. These gestures may then be characterized and stored in data structure 1204. If there are gestures to be stored, the method 1600 proceeds YES to step 1636. If gestures are not to be stored the method 1600 may proceed NO to step 1632.

In step 1632, the vehicle control system 204 can retrieve current gestures from portion 1232, which are associated with user 1240. These gestures may be used then to configure how the vehicle 104 will react if a gesture is received. If gestures are to be stored, the vehicle control system 204 may store characteristics, in step 1636, as received from sensor 242 or from one more user interface inputs. These characteristics may then be used to create the stored gestures 1232, in data structure 1204. The characteristics may include what the gesture looks like or appears and also what affect the gesture should have. This information may then be used to change the configuration or operation of the vehicle 104 based on the gesture if it is received at a later time.

Figure 17:
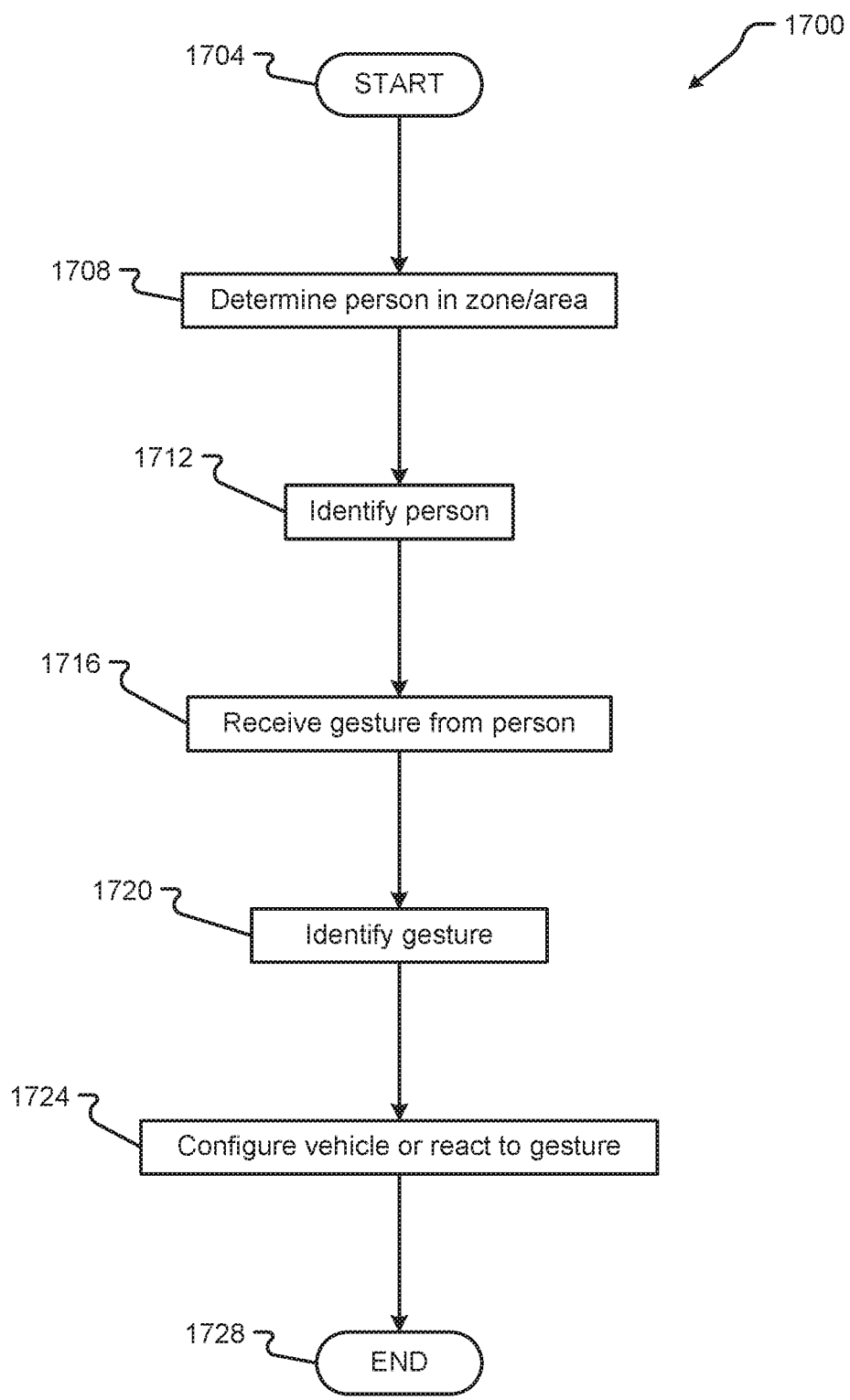
FIG. 17 is a flow or process diagram of a method for reacting to a gesture performed by a user.

An embodiment of a method 1700 for receiving a gesture and configuring the vehicle 104 based on the gesture may be as provided in FIG. 17. A general order for the steps of the method 1700 is shown in FIG. 17. Generally, the method 1700 starts with a start operation 1704 and ends with an end operation 1728. The method 1700 can include more or fewer steps or can arrange the order of the steps differently than those shown in FIG. 17. The method 1700 can be executed as a set of computer-executable instructions executed by a computer system and encoded or stored on a computer readable medium. Hereinafter, the method 1700 shall be explained with reference to the systems, components, modules, software, data structures, user interfaces, etc. described in conjunction with FIGS. 1-16.

A vehicle control system 204 can receive sensor data from vehicle sensors 242. The vehicle sensor data can be used by the vehicle control system 204 to determine that a person is in a zone 512 or area 508, in step 1708. The vehicle sensor data may then be used to compare against feature characteristics 1212 to identify a person, in step 1712. The vehicle control system 204 thereinafter may receive a gesture, in step 1716. The gesture may be perceived by vehicle sensors 242 or received in a gesture capture region. The gesture may be as described in conjunction with FIGS. 11A-11K. Upon receiving the gesture, the vehicle control system 204 can compare the gesture to gesture characteristics in portion 1232, in step 1720. The comparison may be made so that a statistically significant coorelation between the sensor data or gesture data and the gesture characteristic 1232 is made. Upon identifying the gesture, the vehicle control system 204 can configure the vehicle 104 and/or react to the gesture, in step 1724. The configuration or reaction to the gesture may be as prescribed in the gesture characteristic 1232.

Figure 18:
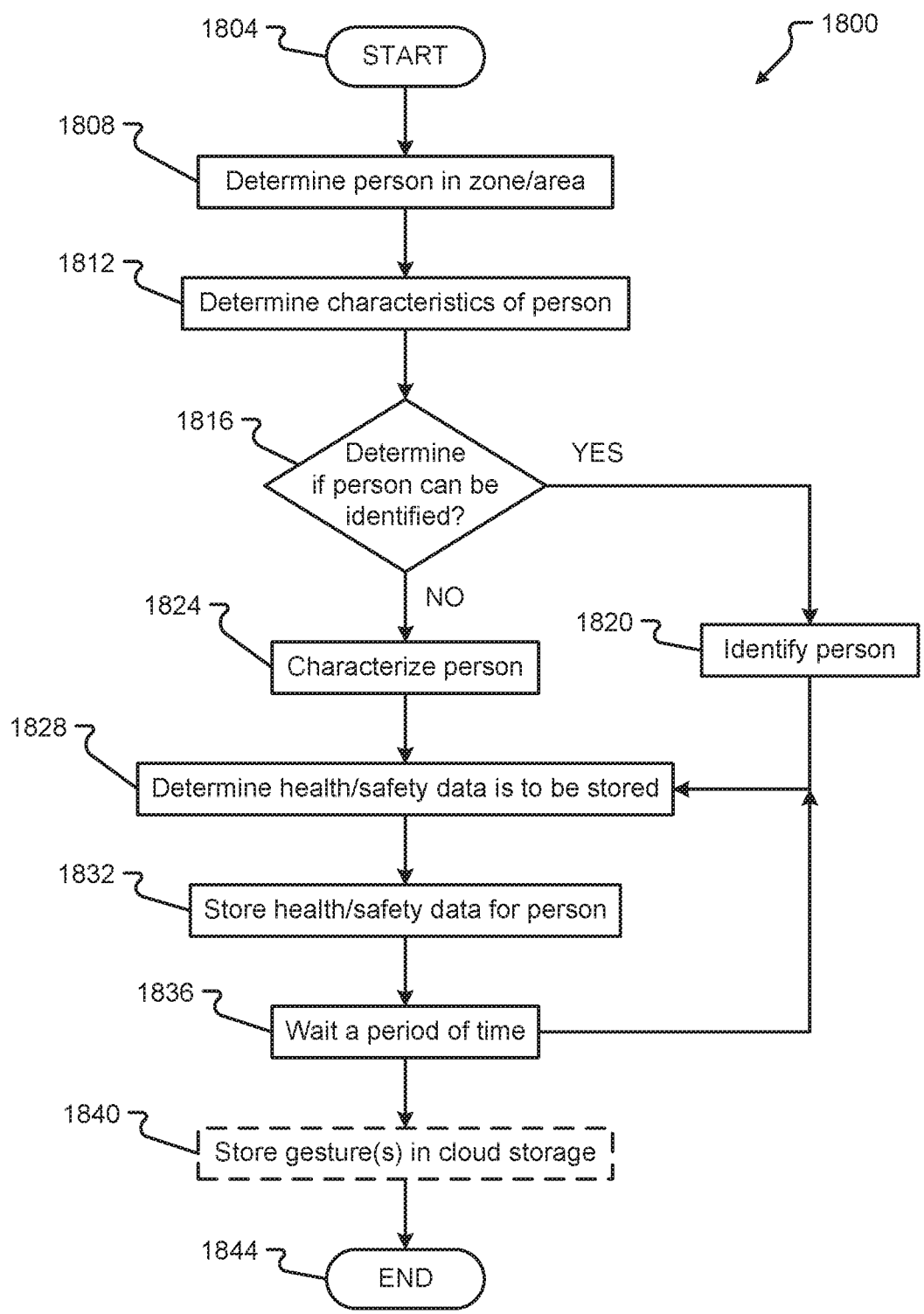
FIG. 18 is a flow or process diagram of a method for storing health data associated with a user.

An embodiment of a method 1800 for storing health data may be as shown in FIG. 18. A general order for the steps of the method 1800 is shown in FIG. 18. Generally, the method 1800 starts with a start operation 1804 and ends with an end operation 1844. The method 1800 can include more or fewer steps or can arrange the order of the steps differently than those shown in FIG. 18. The method 1800 can be executed as a set of computer-executable instructions executed by a computer system and encoded or stored on a computer readable medium. Hereinafter, the method 1800 shall be explained with reference to the systems, components, modules, software, data structures, user interfaces, etc. described in conjunction with FIGS. 1-17.

Vehicle control system 204 can receive sensor data from sensors 242. The sensor data may be used to determine that a person is in a zone 512 or area 508, in step 1808. The sensor data may then be used to determine characteristics of the person, in step 1812. From the characteristics, the vehicle control system 204 can determine if a person may be identified in data structure 1204, in step 1816. If it is determined that the person can be identified in step 1816, the method 1800 proceeds YES to step 1820. If the person cannot be identified, the method 1800 proceeds NO to step 1824. A person may be identified by matching the characteristics of a person from the sensor data to the features shown in portion 1212. If these comparisons are statistically significant, the person may be identified in portion 1208, in step 1820. However, if the person is not identified in portion 1208, the vehicle control system 204 can characterize the person using the vehicle sensor data, in step 1824. In this way, the vehicle control system 204 can create a new record for a new user in data structure 1204.

Thereinafter, the vehicle control system 204 may receive health and/or safety data from the vehicle sensors 242, in step 1828. The vehicle control system 204 can determine if the health or safety data is to be stored, in step 1832. The determination is made as to whether or not there is sufficient health data or safety parameters, in portion 1228 and 1236, to provide a reasonable baseline data pattern for the user 1240. If there is data to be received and stored, the vehicle control system 204 can store the data for the person in portions 1228 and 1236 of the data structure 1204, in step 1832.

The vehicle control system 204 may then wait a period of time, in step 1836. The period of time may be any amount of time from seconds to minutes to days. Thereinafter, the vehicle control system 204 can receive new data from vehicle sensors 242, in step 1828. Thus, the vehicle control system 204 can receive data periodically and update or continue to refine the health data and safety parameters in data structure 1204. Thereinafter, the vehicle control system 204 may optionally store the health and safety data in cloud storage 232 by sending it through the communication network 224 to the server 228, in step 1840.

Figure 19:
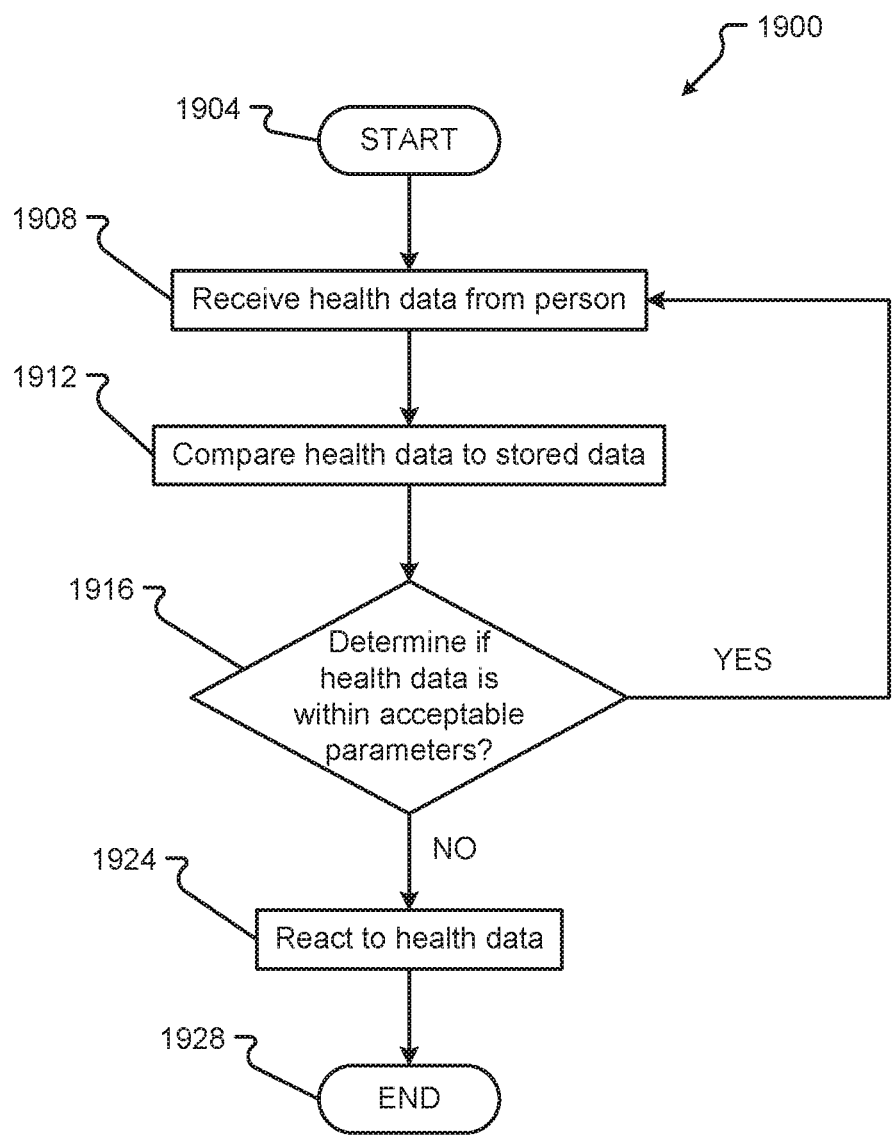
FIG. 19 is a flow or process diagram of a method for reacting to a gesture performed by a user.

An embodiment of a method 1900 for monitoring the health of a user may be as shown in FIG. 19. A general order for the steps of the method 1900 is shown in FIG. 19. Generally, the method 1900 starts with a start operation 1904 and ends with an end operation 1928. The method 1900 can include more or fewer steps or can arrange the order of the steps differently than those shown in FIG. 19. The method 1900 can be executed as a set of computer-executable instructions executed by a computer system and encoded or stored on a computer readable medium. Hereinafter, the method 1900 shall be explained with reference to the systems, components, modules, software, data structures, user interfaces, etc. described in conjunction with FIGS. 1-18.

The vehicle control system 204 can receive health data from sensors 242. The health data may be received in step 1908. The vehicle control system 204 may then compare the received health data to stored health parameters in portion 1228 or portion 1236, in step 1912. The comparison may check if there is statistically significant separation or disagreement between the received health data and the stored health data. Thus, the vehicle control system 204 can make a health comparison of the user based on a baseline of health data previously stored. A statistically significant comparison may include determining if there are any parameters more than three standard deviations from the average or norm, any parameter that is increasing or decreasing over a period of eight different measurements, a measurement that is more than two standard deviations from the norm more than three measurements consecutively, or other types of statistical comparisons.

If the vehicle control system 204 determines that measured health parameter does deviate from the norm, the vehicle control system 204 can determine whether the health data is within acceptable limits, in step 1916. If the health data is within acceptable limits, the method 1900 proceeds YES back to receiving new health data, in step 1908. In this way, the health data is periodically or continually monitored to ensure that the driver is in a healthy state and able to operate the vehicle. If the health data is not within acceptable parameters, the method 1900 may proceed NO to step 1924 where the vehicle control system 204 may react to the change in the health data. The reaction may include any measure to provide for the safety of the user, such as stopping the vehicle, beginning to drive the vehicle, driving the vehicle to a new location, such as a hospital, waking the driver with an alarm or other noise, or performing some other function that may help maintain the health or safety of the user.

The health data received may be a reaction from the driver. For example, the driver may call for help or ask the vehicle for assistance. For example, the driver or passenger may say that they are having a medical emergency and ask the car to perform some function to help. The function to help may include driving the person to a hospital or stopping the car and calling for emergency assistance.

A vehicle may provide methods and systems for a detecting an intruder near or within a vehicle. Specifically, a method to detect and identify a person near or within a vehicle as an authorized or an unauthorized user is provided. In the event an unauthorized user is detected within a vehicle, the system may take a number of actions. In one embodiment, the actions comprise notifying one or more authorized users of the vehicle, disabling the vehicle, notifying emergency personnel or police, and emitting a visual or audio alarm.

More specifically, a vehicle may detect and identify that an intruder is near a vehicle or has entered a vehicle. An action may then be taken, such as providing notice to one or more authorized users of the vehicle and disabling the vehicle.

Figure 20:
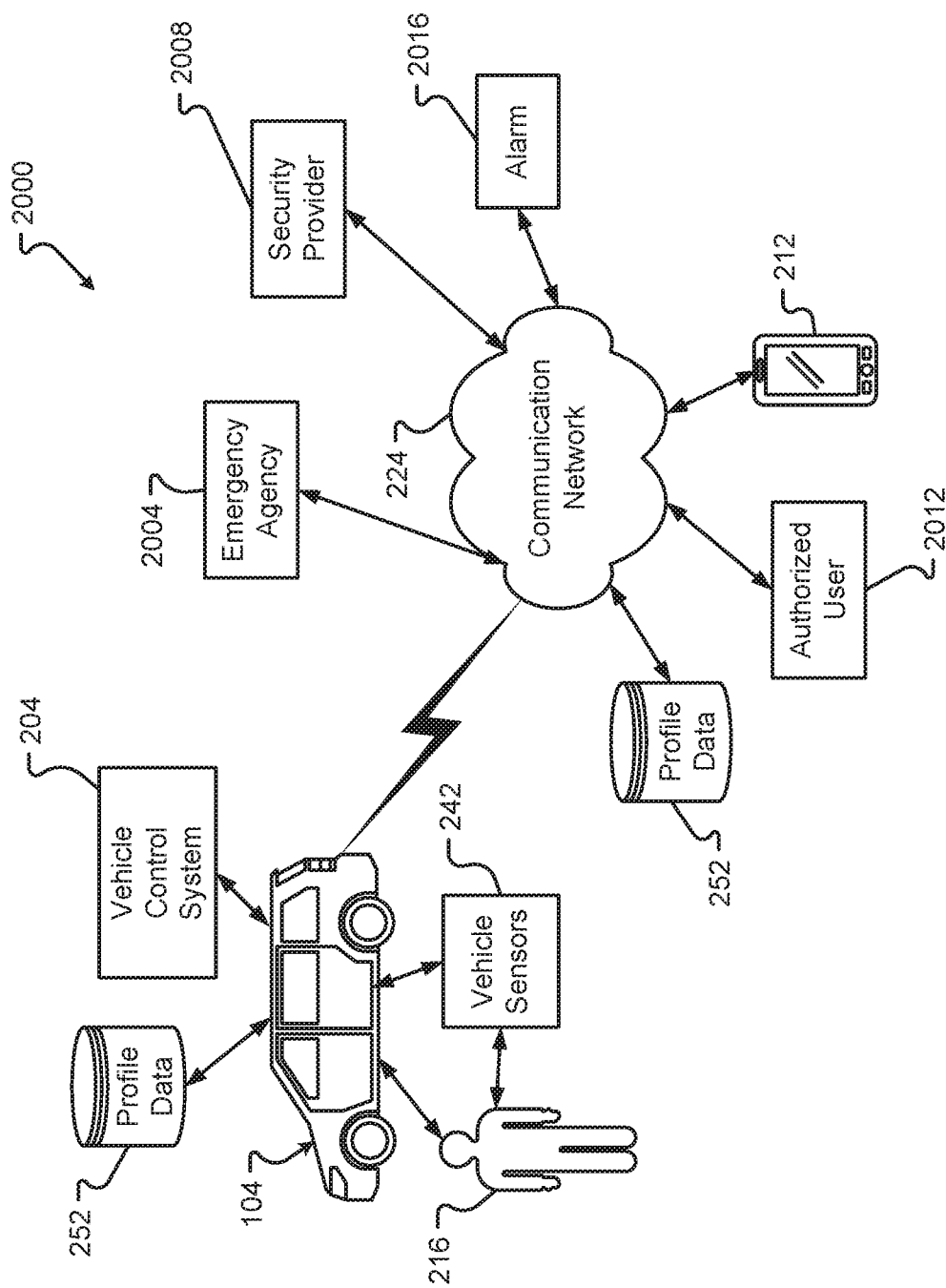
FIG. 20 depicts an embodiment of a vehicle intruder alert detection and indication system.

FIG. 20 depicts an embodiment of a vehicle intruder alert detection and indication system 2000. Vehicle 104 is shown in communication with elements as disclosed above, i.e. vehicle sensors 242, profile data 252, communication network 224 and vehicle control system 204. A user 216 is shown near vehicle 104. The user 216 may be an authorized user or an unauthorized user. An authorized user is typically so identified in profile data 252.

The user 216 is detected by one or more vehicle sensors 242 comprising external sensors and internal sensors. The detection may be of a user 216 near the vehicle 104 and/or of a user 216 inside the vehicle 104. A user that is either near a vehicle 104 or inside a vehicle 104, or both, is referred to as "in contact" with the vehicle 104. Upon detecting a user 216 near or inside of the vehicle 104, profile data 252 is accessed and assessed to determine if the user 216 is an authorized user or an unauthorized user. In the event the user 216 is determined to be an unauthorized user 216, the vehicle control system 204 takes action via communication network 224. The action may comprise providing notice to one or more emergency agencies 2004 such as police, to a security provider 2008 such as a monitoring service that notifies other parties such as the vehicle owner, and one or more authorized users 2012 to include by way of device or user interface 212. Alternatively or additionally, the vehicle control system 204 may disable the vehicle and/or provide an alarm 2016, to include a visual alarm alert (e.g. flashing of headlights) and audio alarm alert (e.g. honking of horn).

Emergency agency 2004 is broadly defined as any entity that provides an emergency response function, comprising police, ambulance, EMTs, firefighters, etc. The security provider 2008 may be a monitoring service that notifies other parties such as the vehicle owner in the event of anomalous states or events associated with the vehicle 104, such as vehicle damage, and unauthorized entry to vehicle 104. Security provider 2008 may comprise any private entity that provides security services to any of user and/or occupants of vehicle and to vehicle itself, such as a security monitoring company, corporate security personnel, etc.

Figure 21:
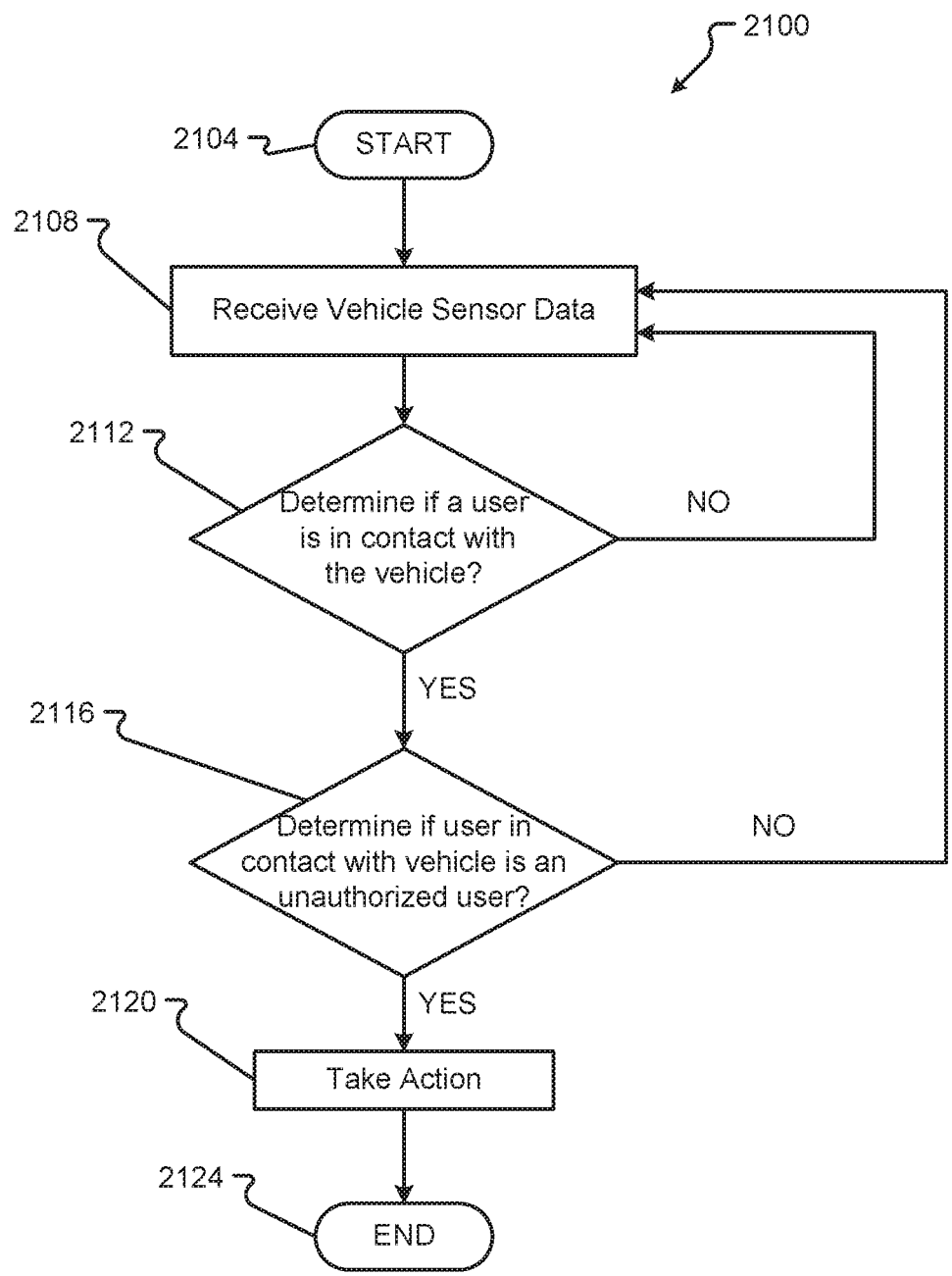
FIG. 21 is a flow diagram of a method for detecting and indicating a vehicle intruder.

An embodiment of a method 2100 for detecting and indicating a vehicle intruder is shown in FIG. 21. While a general order for the steps of the method 2100 is shown in FIG. 21, the method 2100 can include more or fewer steps or can arrange the order of the steps differently than those shown in FIG. 21. Generally, the method 2100 starts with a start operation 2104 and ends with an end operation 2124. The method 2100 can be executed as a set of computer-executable instructions executed by a computer system and encoded or stored on a computer readable medium. Hereinafter, the method 2100 shall be explained with reference to the systems, components, modules, software, data structures, user interfaces, etc. described in conjunction with FIGS. 1-20.

A user 216 may approach vehicle 104 and further may enter vehicle 104. The approaching user 216 may be an authorized user or an unauthorized user. The unauthorized user may alternatively be referred to as an "intruder." A user 216 unidentified or yet determined as to authorized or unauthorized be referred to as a "potential intruder." Vehicle 104 comprises an interior space 108 and is surrounded by a second zone 112 defined by line 120 (see, e.g. FIG. 1). Second zone 112 is defined by one or more vehicle sensors 242.

At step 2108, one or more vehicle sensors 242 sense a user 216 (or any potential intruder, to include, for example, another vehicle, a shopping cart, an instrument of vandalism such as a rock) that enters second zone 112 and/or interior space 108. The vehicle sensors 242 may operate in a continuous or discontinuous mode, may operate at a set or selectable sampling rate, and may be selectable by a user or a remote entity such as a third-party security provider.

One or more vehicle sensors 242 may first detect a potential intruder by way of exterior sensors (see e.g. FIG. 7B). For example, a motion sensor may detect movement near the vehicle 104 and/or an infrared sensor may detect a heat source near the vehicle 104. The definition of "near the vehicle" may be defined by a selectable threshold value. For example, a distance of one foot surrounding the vehicle (i.e. line 120 of FIG. 1) may be defined as a threshold distance. The threshold distance may comprise a plurality of thresholds, i.e. a first threshold and a second threshold wherein different actions are taken. A particular sensor may work in concert with another sensor to provide guidance and/or activate the other sensor. For example, an infrared sensor may detect a heat source and, by way of the vehicle control system 204, task a radar sensor to range to the infrared sensed location of interest.

In another example, an interior sensor (see e.g. FIG. 7A) may sense a potential intruder in the vehicle 104 by an oxygen sensor. That is, an oxygen sensor may sense a spike or rapid rise in oxygen levels in the vehicle 104, which may indicate a person has entered the vehicle 104. Similarly, an acoustic sensor, mounted either on the vehicle 104 as an exterior sensor or mounted inside the vehicle 104 as an interior sensor may detect a window break, perhaps as effected by an instrument of vandalism (e.g. a rock). Further, the one or more sensors 242 may sense a person sitting within the vehicle 104. That is, sensors 242 in a seat may determine or sense that some new amount of weight has been registered. The amount of weight may fall within predetermined parameters (e.g., over a threshold, in a specific range, etc.) to trigger registration or output to the vehicle control system 204.

Upon receiving the vehicle sensor data, the vehicle control system 204 may also perform signal processing of signals received from one or more vehicle sensors 242. Such signal processing may include fused or blended estimation of a measured parameter from a single sensor, such as multiple measurements of a range state parameter from the vehicle 104 to a potential intruder. In a simple case, the vehicle control system 204 may solely receive measurements of range from a single radar sensor, and simple output a running average of the range, e.g. average all measurements over the last 1 sec to provide an average range and angle datum. Optionally, the vehicle control system 204 may perform estimation, blending, or fusion of a measured state parameter from multiple sensors such as multiple radar sensors or a combination of a ladar/lidar range sensor and a radar sensor. Signal processing of such sensor signal measurements may comprise stochastic signal processing, adaptive signal processing, and/or other signal processing techniques known to those skilled in the art.

At step 2112, the vehicle control system 204 accepts vehicle sensor data and determines if a potential intruder is in contact with the vehicle 104. Recall that a potential intruder i.e. user 216 that is either near a vehicle 104 or inside a vehicle 104, or both, is referred to as "in contact" with the vehicle 104. If no contact is detected, the process returns to step 2108 wherein vehicle sensors 242 continue to operate and sensor data is received. A potential intruder is determined to be in contact with the vehicle 104 by way of the vehicle control system 204. That is, the vehicle control system 204 accepts sensor inputs, assesses those sensor inputs, and determines such contact. For example, exterior vehicle sensors 242 such as an electromagnetic sensor may detect a change in the magnetic field on or surrounding the vehicle 104 such that the vehicle control system 204, assessing the electromagnetic sensor data as valid and beyond a selectable threshold, outputs or determines that an entity has made contact with the vehicle 104. For example, that an entity, such as a person, has physically contacted the door handle of the vehicle 104.

Similarly, an interior vehicle weight sensor 242 may detect a rise in weight beyond a selectable threshold has been imparted to the driver's seat. The weight sensor then outputs the measured or sensed weight to the vehicle control system 204 which provides that a potential intruder is in the vehicle 104. Also, the vehicle control system 204 may also associate the potential intruder is in a certain zone 512 or area 508 of the vehicle, i.e the driver's seat. Stated another way, the vehicle sensors 242 output signals to the vehicle control system 204 that an event has been measured or sensed. These data may then in turn be sent to the vehicle control system processor 304 to determine the zone 512 and area 508 where the event occurred.

At step 2116, the vehicle control system 204 determines if the potential intruder user 216 in contact with the vehicle 104 is an authorized user 216. Generally, such an assessment is made by comparing the data received from the one or vehicle sensors 242 against profile data 252. Generally, data that is determined to be consistent with that of an authorized user as characterized in the profile data 252 results in the potential intruder being deemed an authorized user, and those whose data is determined to be inconsistent with that of any authorized users as characterized in the profile data 252 are deemed unauthorized users. If the potential intruder is determined to not be an unauthorized user (i.e. either no determination is made or a determination is made that the potential intruder is an authorized user), the process returns to step 2108 wherein vehicle sensors 242 continue to operate and sensor data is received.

In comparing the received vehicle sensor data 242 of a potential intruder against data maintained in the profile data 252, the vehicle control system 204 also may record the location of the potential intruder. That is, the vehicle control system 204 may determine that the potential intruder is in a certain zone 512 or area 508 based on the signals sent by the vehicle sensors 242. For example, the sensors 242 may send signals to the vehicle control system 204 that an event has occurred. This information may be sent to the vehicle control system processor 304 to determine the zone 512 and area 508 where the event occurred. Further, the vehicle control system 204 may then identify the person.

For example, the one or more vehicle sensors 242 may comprise one or more cameras which image the potential intruder user 216. In such a facial recognition system, the vehicle control system 204 then compares the image(s) received and compares the image against those of authorized users as provided in the profile data 252. If the sensed image is not a sufficient match with those identified as authorized users in the profile data 252, the potential intruder is deemed an unauthorized user. Note that this particular scenario is applicable to images obtained by one or more image sensors mounted externally and/or internally to the vehicle 104. Note that authorized users 216 of a vehicle 104 comprise drivers, passengers and vehicle mechanics In another example, the vehicle control system 204, upon querying the profile data 252, may determine that there exists only one authorized user of the vehicle (e.g. the vehicle owner) and that one authorized user has not granted permission to any other users.

In another example, the one or more vehicle sensors 242 may comprise sensors that provide biometric data. That is, the vehicle control system 204 may determine that the user is unauthorized based on not recognizing certain biometric features.

The vehicle control system 204 can receive the information from the sensors 242 and use that information to search the database 1200 that may be stored within the system data 208. The sensor data may be compared to ID characteristics 1212 to determine if the person has already been identified. The vehicle control system 204 may also send the characteristic data from the sensors to the communication network 224 to a server 228 to compare the sensor data to stored data 232 that may be stored in a cloud system. The person's features can be compared to stored features 1212 to determine if the person in the vehicle 104 can be identified. In this way, these new settings may be ported to other vehicles for the user. Further, the settings in storage system 232 may be retrieved, if local storage does not include the settings in storage system 208.

The vehicle control system 204 may also store data, e.g. in stored data 232, regarding the potential intruder. Such data may be particularly valuable if the potential user is determined to be an unauthorized user and that unauthorized user performs some bad acts with respect to vehicle 104, such as thievery, vandalism and car jacking.

The degree of consistency required between the data received from the one or more vehicle sensors 242 and that contained in the profile data 252 is selectable. For example, if a car driver weight sensor was primarily used to determine if the potential intruder was authorized, the vehicle control system 204 may allow a range of weight within ten (10) pounds of the set of authorized users. Also, upon positive identification of an authorized user, the vehicle control system 204 may update the profile data 252. In the immediately-preceding example, if the weight sensor has recorded the particular authorized user's weight as 187 lb, 3 pounds below the 190 lb value stored in the profile data 252, that authorized user's weight is updated to 187 lb. in the profile data 252.

In step 2120, the vehicle control system 204 takes action in the event an unauthorized user 216 is determined to be in contact with the vehicle 104. The action may comprise providing notice to one or more emergency agencies 2004 such as police, to a security provider 2008 such as a monitoring service that notifies other parties such as the vehicle owner, and one or more authorized users 2012 to include by way of device or user interface 212. The notice or message may be a text message, phone call, email, etc. to the user associated with the vehicle to alert the user of the intrusion.

Alternatively or additionally, the vehicle control system 204 may disable the vehicle (e.g. not allowing the vehicle 104 to start) and/or provide an alarm 2016, to include a visual alarm alert (e.g. flashing of headlights, hazard lights, daytime running lights (DRLs), and/or interior lights) and audio alarm alert (e.g. honking of horn). Further, the step 2124 may include automatically locking an authorized user out of the vehicle 104, for example in the event the user 216 is delinquent in payments or has excessive parking tickets, or if a crime is on-going (e.g. a suspect actively in pursuit of a car to carjack) the authorized user could be automatically locked in the vehicle 104. Also, if vehicle control system 204 determines that an unauthorized user has entered the vehicle 104 and attempting the carjack the vehicle 104, the vehicle control system 204 may disable the vehicle 104 and contact emergency agency 2004 and/or security provider 2008. The method 2100 ends at step 2124.

A vehicle may provide methods and systems for vehicle damage detection, identification and communication. Specifically, a method to detect damage to a vehicle, identify the extent and location of the damage, and communicate the damage event is provided. In the event of damage to a vehicle, the system may take a number of actions. In one embodiment, the actions comprise notifying authorized users of the vehicle, a maintenance provider, an insurance provider and/or an emergency agency, disabling the vehicle, and emitting a visual or audio alarm.

A vehicle may detect that damage has occurred to the vehicle. This detection may be based on sensors associated with the vehicle and/or with a mobile device. In one example, a valet may cause damage to a vehicle while parking it in a lot. In response, the vehicle may take action by sending a message (e.g., text message, phone call, email, etc.) to the user associated with the vehicle to alert the user of the damage. In another example, the vehicle may indicate damage via an altered lighting scheme (e.g., flashing DRLs, hazard lights, interior lighting color and/or behavior, etc.), an alarm (e.g., audible and/or visual), terminated functions, and the like.

Figure 22:
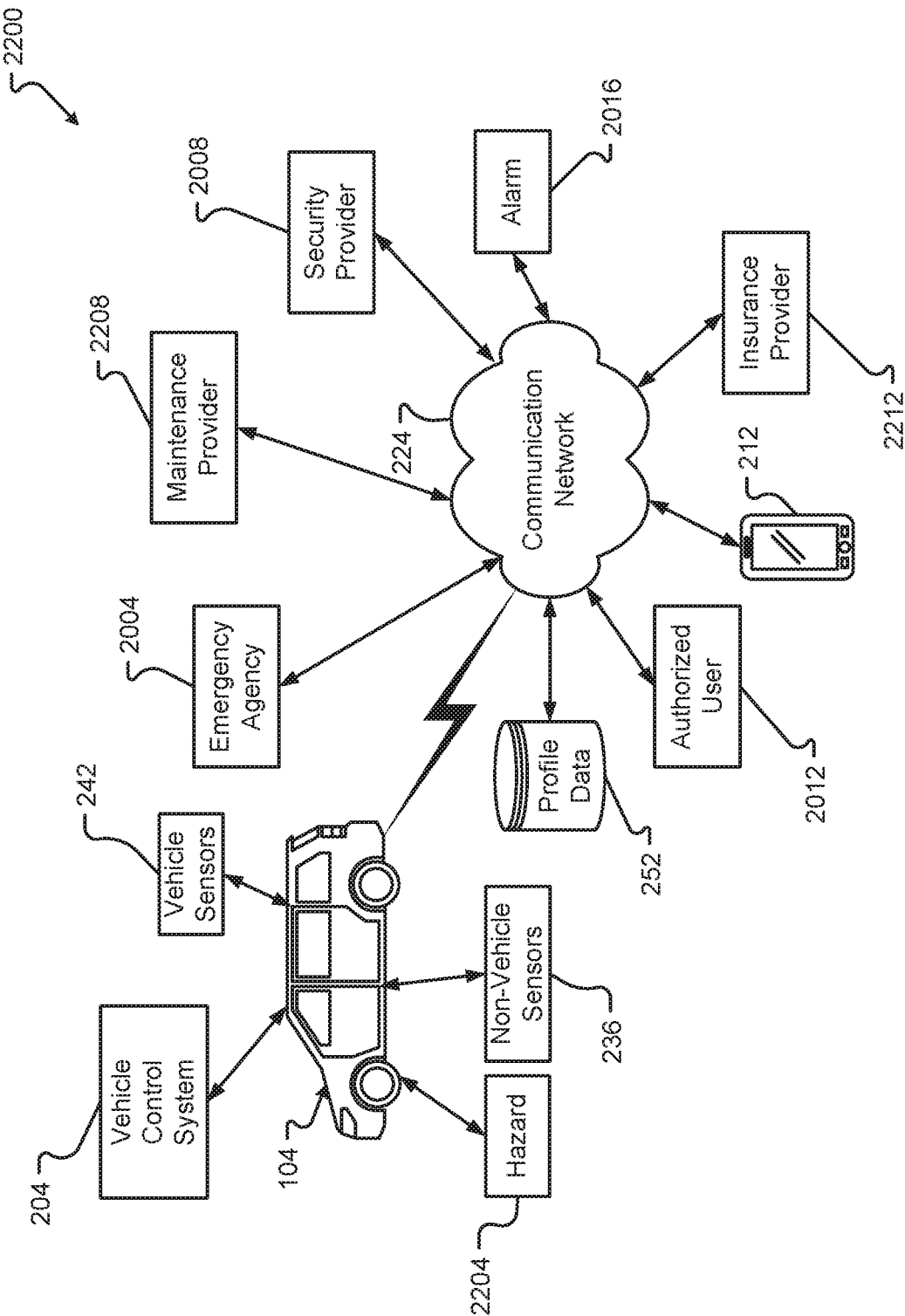
FIG. 22 depicts an embodiment of a vehicle damage detection and identification system.

FIG. 22 depicts an embodiment of a vehicle damage detection and identification system 2200. Vehicle 104 is shown in communication with elements as disclosed above, i.e. vehicle sensors 242, non-vehicle sensors 236, communication network 224 and vehicle control system 204. A hazard 2204 is depicted in communication with the vehicle 104. The hazard 2204 may be, for example, a pothole, another vehicle, a vandal, or other entity that may cause damage to vehicle 104 to include natural hazards like hail. The hazard 2204 may be fixed or moveable. Damage to vehicle 104 is detected by vehicle sensors 242.

One or more of vehicle sensors 242 detect or sense damage to vehicle 242 as associated with a particular location of vehicle 104 associated with one or more areas 508. See FIGS. 5A-C. Upon detection of vehicle damage, the vehicle control system 204 may train vehicle sensors 242 to the surrounding area of vehicle damage, and/or record and train as possible non-vehicle sensors 236 to the surrounding area. Such on-site sensing of the potential cause of the vehicle damage benefits in several ways, to include liability determination and insurance claims. Hazard 2204 may be detected by one or more vehicle sensors 242 comprising external vehicle sensors 242 and non-vehicle sensors 236. Upon detection or sensing of vehicle damage, the vehicle control system 204 may take any of several actions. The action may comprise providing notice to one or more emergency agencies 2004 such as police, to a security provider 2008 such as a monitoring service that notifies other parties such as the vehicle owner, and one or more authorized users 2012 to include by way of device or user interface 212. Alternatively or additionally, the vehicle control system 204 may disable the vehicle and/or provide an alarm 2016, to include a visual alarm alert (e.g. flashing of headlights) and audio alarm alert (e.g. honking of horn), contact a maintenance provider 2208 so as to order repair parts, and contact an insurance provider 2212 to being the claim adjustment process. Also, the vehicle control system 204 may record vehicle damage data and/or hazard data on profile data 252 associated with the user 216 of vehicle 104.

Figure 23:
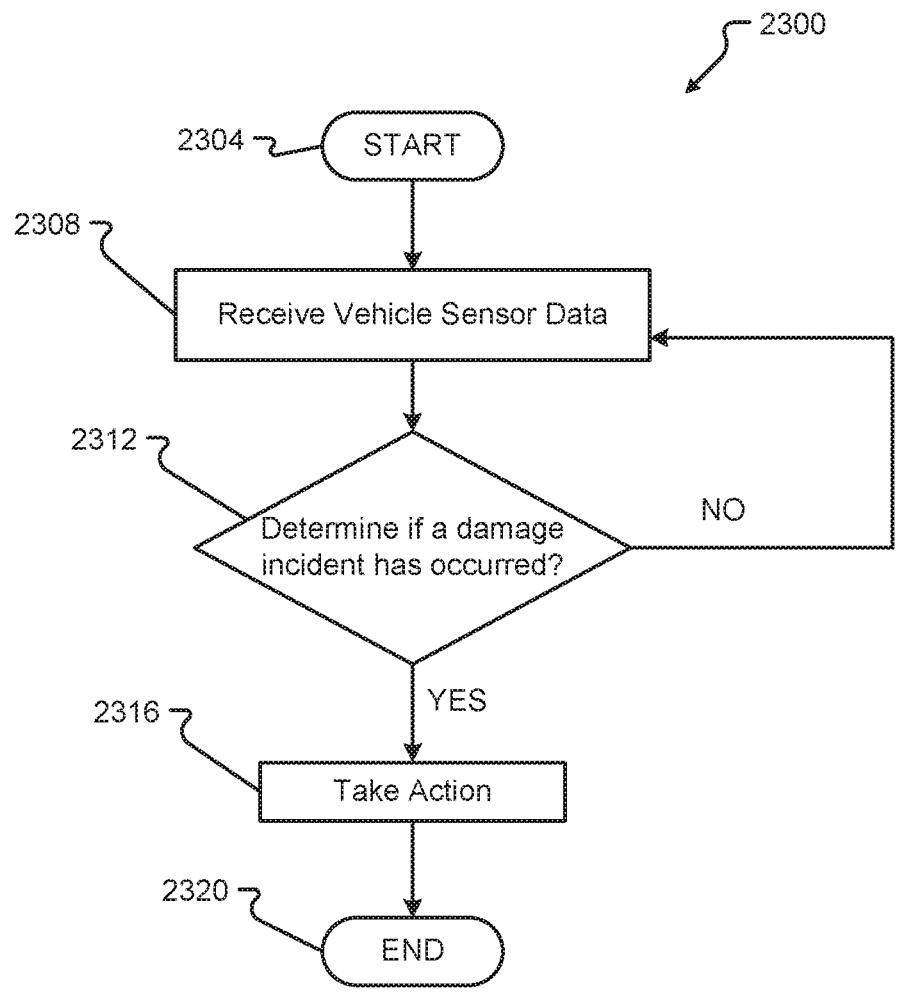
FIG. 23 is a flow diagram of a method for detecting and identifying vehicle damage.

An embodiment of a method 2300 for detecting and identifying vehicle damage is shown in FIG. 23. While a general order for the steps of the method 2300 is shown in FIG. 23, the method 2300 can include more or fewer steps or can arrange the order of the steps differently than those shown in FIG. 23. Generally, the method 2300 starts with a start operation 2304 and ends with an end operation 2320. The method 2300 can be executed as a set of computer-executable instructions executed by a computer system and encoded or stored on a computer readable medium. Hereinafter, the method 2300 shall be explained with reference to the systems, components, modules, software, data structures, user interfaces, etc. described in conjunction with FIGS. 1-22.

At step 2308, one or more vehicle sensors 242 sense damage to vehicle 104. Damage is broadly defined as any unexpected change in condition or state of any portion of vehicle 104, to include the physical exterior surface (i.e. "skin" of the vehicle") and all portions within the physical exterior, i.e. the interior space 108. The vehicle sensors 242 may operate in a continuous or discontinuous mode, may operate at a set or selectable sampling rate, and may be selectable by a user or a remote entity such as a third-party security provider.

The one or more vehicle sensors 242 employed to sense or detect body damage comprise vehicle external sensors such as external safety group sensors 716E. That is, the one or more vehicle sensors 242 may comprise force sensors 768, mechanical motion sensors 772, orientation sensors 776, vehicle body sensors 782, vibration sensors, electromagnetic field sensors, and acoustic sensors. The one or more vehicle sensors 242 are configured to detect damage to vehicle 104 and/or identify its location. It one embodiment, the one or more vehicle sensors 242 may provide a measure of the degree of damage to vehicle 104.

In one example, hazard 2204 may be another vehicle which impacts vehicle 104. Force sensors 768 sense and measure the impact, or G-force, imparted to vehicle 104 and output a signal identifying a force exceeded a selectable threshold. Further, the approximate location of the damage is known based on the location of the force sensor 768. That is, if the force sensor 768 provides a 3-dimensional vector measurement of force, the location of the hazard impact may be determined given other known geometries (i.e. the vehicle geometries). Mechanical motion sensors 772 such as accelerometers may similarly measure and sense the impact from a hazard 2204. Orientation sensors 776, such as accelerometers, gyroscopes, magnetic sensors may also detect a change in orientation of the vehicle, either momentary or permanent, that indicates impact of vehicle 104 with hazard 2204.

The vehicle body sensors 782 may be configured to measure characteristics associated with the body (e.g., body panels, components, chassis, windows, etc.) of a vehicle 104. For example, a vehicle body sensor 782 may be located in the rear bumper area of vehicle 104. Upon contact by a hazard 2204 such as another vehicle above a selectable threshold the vehicle body sensor 782 provides an output signal. For example, the vehicle body sensor 782 might be calibrated to provide a signal if a force at or above five (5) pounds is measured, or if an acceleration above 1 foot/sec is measured. The location of the vehicle body sensor 782 provides an indication of the location of the damage to vehicle 104. The value measured provides an indication of the degree of damage to vehicle 104.

The external safety group sensors 716E may be located in an interior space 108 or an exterior of the vehicle 104.

The one or more vehicle sensors 242 may also identify the location and/or degree of damage to vehicle 104. That is, the sensor arrangement 500 can include one or more areas 508 within the vehicle. An area can be a larger part of the environment inside or outside of the vehicle 104. Thus, area one 508A may include the area within the trunk space or engine space of the vehicle 104 and/or the front passenger compartment. Area two 508B may include a portion of the interior space 108 (e.g., a passenger compartment, etc.) of the vehicle 104. The area N, 508N, may include the trunk space or rear compartment area, when included within the vehicle 104. The interior space 108 may also be divided into other areas. Thus, one area may be associated with the front passenger's and driver's seats, a second area may be associated with the middle passengers' seats, and a third area may be associated with a rear passenger's seat. Each area 508 may include one or more vehicle sensors 242 that are positioned or operate to provide environmental information about that area 508.

Each area 508 may be further separated into one or more zones 512 within the area 508. For example, area 1 508A may be separated into zone A 512A, and zone B 512B. Each zone 512 may be associated with a particular portion of the interior occupied by a passenger. For example, zone A 512A may be associated with a driver. Zone B 512B, may be associated with a front passenger. Each zone 512 may include one or more sensors that are positioned or configured to collect information about the environment or ecosystem associated with that zone or person. As such, one or more vehicle sensors 242 may associate a sensed signal, e.g. a force sensor may register an 11 pound impact to the driver's side window while a vibration sensor registers a corresponding spike in vibration, with a particular identified area of the vehicle via the labeling scheme discussed, i.e. associated with zone 512A (driver).

Associated device sensors 720 can include any sensors that are associated with a device 212, 248 in the vehicle 104. As previously stated, typical devices 212, 248 may include smart phones, tablets, laptops, mobile computers, and the like. It is anticipated that the various sensors associated with these devices 212, 248 can be employed by the vehicle control system 204. For example, a typical smart phone can include, an image sensor, an IR sensor, audio sensor, gyroscope, accelerometer, wireless network sensor, fingerprint reader, and more. These associated device sensors 720 may be used by the vehicle control system 204 to detect and/or identify damage to vehicle 104.

Optionally, the exterior safety sensors 716E may be configured to collect data relating to one or more conditions, objects, vehicle components, and other events that are external to the vehicle 104. For instance, the force sensors 768 in the external safety group 716E may detect and/or record force information associated with the outside of a vehicle 104. For instance, if an object strikes the exterior of the vehicle 104, the force sensors 768 from the exterior safety group 716E may determine a magnitude, location, and/or time associated with the strike.

At step 2312, the vehicle control system 204 accepts vehicle sensor 242 data and determines if a damage incident has occurred to vehicle 104. If no damage has occurred, the process returns to step 2308 wherein vehicle sensors 242 continue to operate and sensor data is received. Vehicle control system 204 determines a damage incident has occurred by assessing the received signals or measurements from the one or more vehicle sensors 242. That is, the vehicle control system 204 accepts sensor inputs, assesses those sensor inputs, and determines if the measurement is indicative of damage to the vehicle 104. For example, a vehicle body sensor 782 may be located in the roof of vehicle 104. Upon contact by a hazard 2204, such as half-inch sized hail, above a selectable threshold the vehicle body sensor 782 provides an output signal. For example, the vehicle body sensor 782 might be calibrated to provide a signal if a force at or above five (3) pounds is measured, or if an acceleration above 0.5 foot/sec is measured, or a displacement of more than one-quarter inch is detected. The location of the vehicle body sensor 782 provides an indication of the location of the damage to vehicle 104. The value measured provides an indication of the degree of damage to vehicle 104. The vehicle sensor 242 would also provide a location of the damage, with respect to a certain zone 512 or area 508 of the vehicle, i.e the vehicle roof. Stated another way, the vehicle sensors 242 output signals to the vehicle control system 204 that an event (vehicle damage) has been measured or sensed. These data may then in turn be sent to the vehicle control system processor 304 to determine the zone 512 and area 508 where the event occurred.

Upon receiving the vehicle sensor data, the vehicle control system 204 may also perform signal processing of signals received from one or more vehicle sensors 242. Such signal processing may include fused or blended estimation of a measured parameter from a single sensor, such as multiple measurements of a range state parameter from the vehicle 104 to a potential intruder. In a simple case, the vehicle control system 204 may solely receive measurements of range from a single force sensor, and simple output a running average of the range, e.g. average all measurements over the last 1 sec to provide an average force value. Optionally, the vehicle control system 204 may perform estimation, blending, or fusion of a measured state parameter from multiple sensors such as multiple force sensors. Signal processing of such sensor signal measurements may comprise stochastic signal processing, adaptive signal processing, and/or other signal processing techniques known to those skilled in the art.

At step 2316, upon detection or sensing of vehicle damage, the vehicle control system 204 may take any of several actions. The action may comprise providing notice to one or more emergency agencies 2004 such as police, to a security provider 2008 such as a monitoring service that notifies other parties such as the vehicle owner, and one or more authorized users 2012 to include by way of device or user interface 212. Alternatively or additionally, the vehicle control system 204 may disable the vehicle and/or provide an alarm 2016, to include a visual alarm alert (e.g. flashing of headlights) and audio alarm alert (e.g. honking of horn), contact a maintenance provider 2208 so as to order repair parts, and contact an insurance provider 2212 to being the claim adjustment process. Also, the vehicle control system 204 may record vehicle damage data and/or hazard data on profile data 252 associated with the user 216 of vehicle 104.

Upon detection of vehicle damage, the vehicle control system 204 may further train vehicle sensors 242 to the surrounding area of vehicle damage, and/or record and train as possible non-vehicle sensors 236 to the surrounding area. Such on-site sensing of the potential cause of the vehicle damage benefits in several ways, to include liability determination and insurance claims. Hazard 2204 may be detected by one or more vehicle sensors 242 comprising external sensors and non-vehicle sensors 236.

One or more vehicle sensors 242 may first detect a potential hazard by way of exterior sensors (see e.g. FIGS. 7B and 22). For example, a motion sensor may detect movement near the vehicle 104 and/or an infrared sensor may detect a heat source near the vehicle 104. The definition of "near the vehicle" may be defined by a selectable threshold value. For example, a distance of ten feet surrounding the vehicle (i.e. line 120 of FIG. 1) may be defined as a threshold distance. The threshold distance may comprise a plurality of thresholds, i.e. a first threshold and a second threshold wherein different actions are taken. A particular sensor may work in concert with another sensor to provide guidance and/or activiate the other sensor. For example, an acoustic sensor may detect that the driver's side window has been shattered and, by way of the vehicle control system 204, task an image sensor to image the area near the driver's side door (to, for example, image the source of the shattered window, such as a vandal).

Hazard is broadly defined as any entity that is cause for damage to vehicle 104. The hazard 2204 may be, for example, a pothole, another vehicle, a vandal, or other entity that may cause damage to vehicle 104 to include natural hazards like hail. Non-vehicle sensors 236, such as real-time weather monitoring, real-time monitoring of traffic conditions or surveillance data such as provided by aerial drones, may be accessed and received by vehicle control system 204 to guide one or more vehicle sensors 242 to a targeted measurement. For example, an aerial drone may provide information that vehicle break-ins have recently occurred near the vehicle 104 and provide and location of such break-ins, thereby triggering the vehicle control system 204 to train or guide an image sensor toward the location of the near-by break-in. In such a manner, a proactive approach to sensing (and optionally recording) a hazard is provided before a damage incident ensues.

The vehicle control system 204 can receive the information from the sensors 242 and use that information to search the database 1200 that may be stored within the system data 208. The sensor data may be compared to maintenance data of vehicle 104 to enable a determination of repair parameters associated with the damage. For example, identification of damage to the rear quarter panel for vehicle 104 allows vehicle maintenance data to be accessed to determine the part number of the rear quarter panel that would be needed as a replacement part. Furthermore, the vehicle control system 204 may then provide such data to a maintenance provider 2208 to provide a price/schedule quote to user 216 to effect the repair. Also, the vehicle control system 204 may also provide such data to an insurance provider 2212 to initiate claim procedures. The user 216 may then interact with one or both of maintenance provider 2208 and insurance provider 2212 via user interface 212 to approve the repair and/or agree to insurance claim resolution. Further, the identified damage and terms thereof may be recorded to profile data 252.

The vehicle control system 204 may also store data regarding the damage. Such data may be particularly valuable if the damage is determined to be the result of an uncooperative entity, such as a vandal, thief, or hit-and-run driver.

Alternatively or additionally, the vehicle control system 204 may disable the vehicle (e.g. not allowing the vehicle 104 to start) and/or provide an alarm 2016, to include a visual alarm alert (e.g. flashing of headlights, hazard lights, daytime running lights (DRLs), and/or interior lights) and audio alarm alert (e.g. honking of horn). Also, the vehicle control system 204 may record vehicle damage data and/or hazard data on profile data 252 associated with the user 216 of vehicle 104. The method 2300 ends at step 2320.

Optionally, in one embodiment the circumstances of damage to a vehicle are recorded, for example on stored data 232, to provide for more instantaneous, more accurate and more comprehensive damage investigation, failure analysis, and criminal guilt and/or civil liability investigation. For example, in the event of a vehicle damage incident due to a hit-and-run driver, comprehensive definition of the circumstances prior, during and sometimes after the incident are recorded, and may be communicated to authorities (e.g. police, insurance provider). For example, such accident data may comprise vehicle type, speed, imagery associated with the hit-and-run offender, site data to include immediate surroundings (which might, for example, provide witnesses to the event).

A vehicle may provide methods and systems for vehicle maintenance and warranty compliance detection and communication. Specifically, a method to monitor the compliance of a user with vehicle maintenance and operating requirements and vehicle warranty terms is provided. In the event a user is not in compliance with a vehicle maintenance item, vehicle operation condition or warranty term, the system may take a number of actions. In one embodiment, the actions comprise notifying a maintenance provider, an insurance provider and a warranty provider. The system may also maintain a historical user compliance database to enable identification and documentation of user compliance for one or more vehicles.

For example, a vehicle may determine if regular maintenance visits are made in accordance with recommended practices. The vehicle may determine whether an unreasonable action (e.g., reckless driving, texting while driving, etc.) caused damage to the vehicle. This determination may be used by vehicle manufacturers, insurance companies, warranty companies, and the like to enforce and police current warranty/maintenance contract provisions.

Furthermore, the determinations made in the aforementioned embodiments may be stored and associated with a vehicle and/or a user. For instance, if a user routinely fails to make maintenance visits, and causes damage to vehicles, the user may be restricted from certain rental agreements, insurance benefits, etc. The information may be stored to a central repository to track user behavior for insurance risks and predictions of risk. In other words, the information may be used to form a "user-based" Carfax® (or Driverfax) information system. However, instead of facts related to a specific vehicle, the user-based system may include facts related to specific user or driver. Details may include "driver has been arrested for driving under the influence," "driver was cited for texting while driving," "driver has been warned for driving without fastened restraint," "driver has been involved in four car accidents," "driver has been addicted to drugs," and the like.

Non-vehicle sensors, such as GPS, may recognize potentially dangerous scenarios and modify a vehicle's functions accordingly. For example, GPS recognizes that the car has been parked in front of a bar for too long and requires a breathalyzer to start the car. In another example, GPS and weather conditions from the internet lock the maximum speed below 50 mph. Also, GPS and weather conditions may automatically change the tire pressure to maximize road gripping potential.

Figure 24:
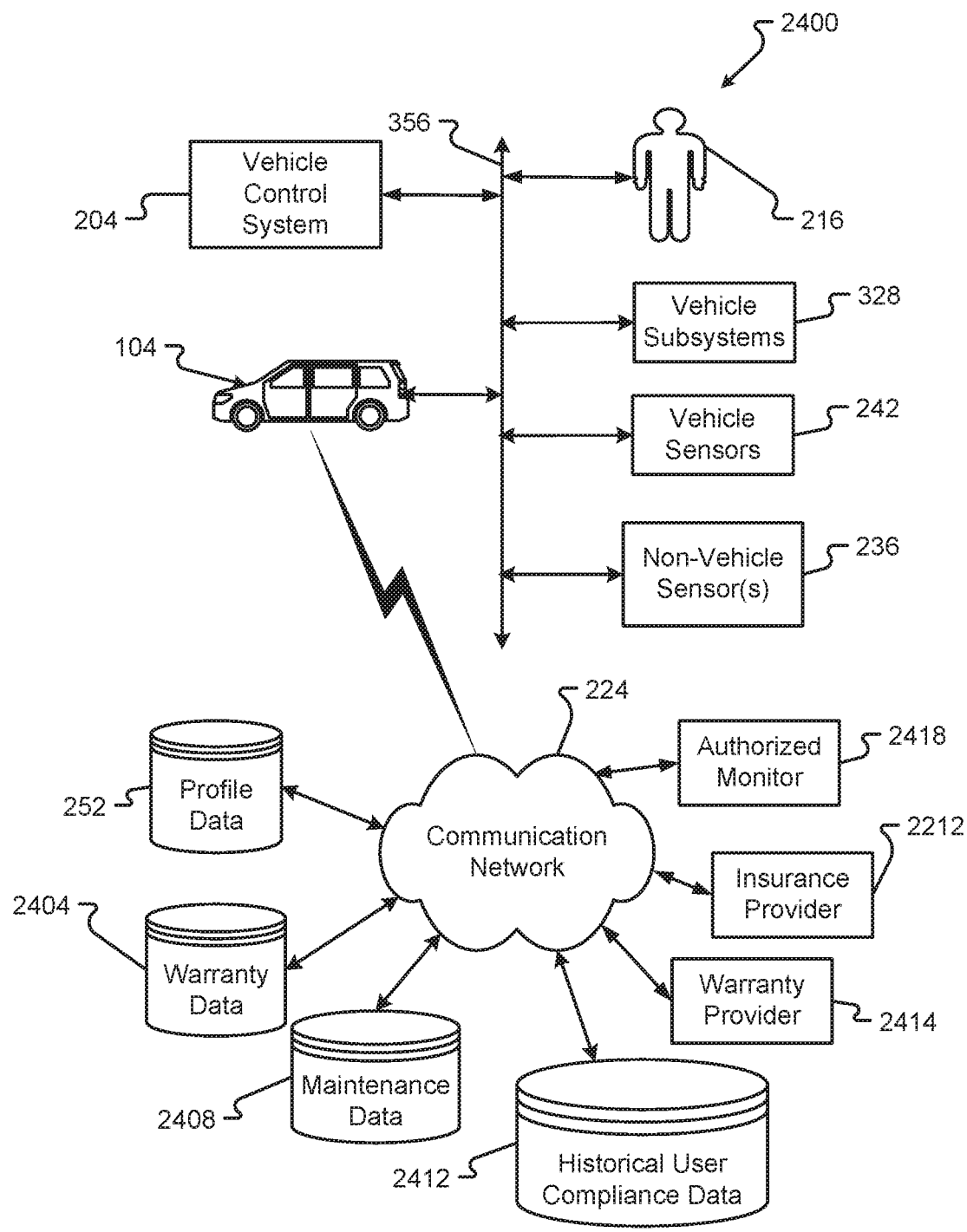
FIG. 24 is a block diagram of an embodiment of a vehicle maintenance and warranty compliance detection environment.

FIG. 24 depicts a block diagram of an embodiment of a vehicle maintenance and warranty compliance detection environment (herein also termed "compliance system") 2400. The compliance system 2400 may comprise warranty data 2404, maintenance data 2408, historical user compliance data 2412, vehicle control system 204, profile data 252, user 216, an insurance provider module 2212, a warranty provider module 2414, vehicle subsystems 328, vehicle sensors 242 and non-vehicle sensors 236. Vehicle control system 204, user 216, vehicle subsystems 328, vehicle sensors 242 and non-vehicle sensors 236 may communicate over a network or bus 356. This communication bus 356 may be bidirectional and perform data communications using any known or future-developed standard or protocol.

An example of the communication bus 356 may be as described in conjunction with FIG. 4. Other components communicate via communication network 224. As one example of the later communication, the warranty provider module 2414 and/or the insurance provider 2212, aside from communicating with each other via communication network 224, may communicate with vehicle sensors 242, and/or non-vehicle sensors via 236 via the vehicle 104.

Hereinafter, the compliance system 2400 shall be explained with reference to the systems, components, modules, software, data structures, user interfaces, etc. described in conjunction with FIGS. 1-23.

One or more of vehicle sensors 242 detect or sense the status and operation of vehicle subsystems 328 as associated with a particular user 216. Vehicle systems 328 can include any of the mechanical, electrical, electromechanical, computer, or other systems associated with the function of the vehicle 104. For example, vehicle systems 328 can include one or more of, but is not limited to, the steering system, the braking system, the engine and engine control systems, the electrical system, the suspension, the drive train, the cruise control system, the radio, the heating, ventilation, air conditioning (HVAC) system, the windows and/or doors, etc. These systems are well known in the art and will not be described further.

Warranty data 2408 contains data associated with a particular user 216 and mapped to a particular vehicle 104 regarding, for example, the level of compliance agreed upon between warranty provider 2414 and user 216 for that particular vehicle 104. Warranty is defined as a guarantee or promise that if the user (e.g. car driver, the "obligee") meets certain requirements, the other party (the "obligor") will provide something of value. For example, the warranty data 2408 may contain terms and conditions of the original vehicle manufacturer as to replacement or repair of defective vehicle components. Terms and conditions may include a restriction as to owner (i.e. a particular item may only be covered if the vehicle is owned by the original purchaser), vehicle mileage, or not exceeded a maximum RPM and/or speed. The promise by the obligator may be free repair or replacement or 50% discount on the same.

Maintenance data 2408 includes data defining required and recommended maintenance items for a particular vehicle and compliance with same. For example, the maintenance data 2408 may identify that a timing belt inspection is required every 10,000 miles. Continuing this example, the warranty data 2408 may define that an owner who misses any required repair will void all aspects of its warranty Maintenance data 2408 may include different levels of requirements, i.e. an oil change may be recommended every 5,000 miles but required every 10,000 miles. Upon completion of a particular maintenance item, the maintenance data 2408 is updated to document the completion, e.g. the date when the item was completed and the service provider performing the maintenance item. Such an update to maintenance data 2408 may be automatically provided via the communication bus 356 to warranty provider 2414 and may also update the historical user compliance data 2412.

The historical user compliance data 2412 maintains data associated with a particular user 216 as to their compliance with maintenance data items and/or warranty data items. For example, the dates of tune-ups and identification of entity who performed the tune-up are stored. The historical user compliance data 2412 may categorize data according to specific vehicle 104.

Profile data 252 is as described above but may also comprise data describing user 216 conformance with vehicle operation performance and conduct. For example, a particular user 216 may be under a driving restriction to not drive at night due to eye sight problems. Deviations from this restriction (i.e. dates, times, location) are recorded in profile data 252.

Insurance Provider 2212 is as described above. Insurance provider 2212 may communicate with profile data 252 to investigate user 216 conformance with user's stated policy data, e.g. amount of driving done per year. That is, a user 216 may attest that he drives 5,000 miles per year yet the profile data 252 records driving over 10,000 miles per year. Such a data discrepancy would enable insurance provider 2414 to query user 216 as to the discrepancy, perhaps resulting in an insurance premium adjustment.

Warranty provider 2414 may communicate with historical user compliance data 2412 to investigate user 216 conformance with warranty terms and conditions. For example, a car manufacturer may warrant that if the car owner maintains a car to the required maintenance standards defined by the car manufacturer, the car manufacturer will replace certain car parts if they fail within a certain amount of time. A common such warranty is to the car powertrain, wherein if the car owner regularly maintains the car as defined by performing all regular maintenance (e.g. oil change every 10,000 miles, etc.) and a component of the powertrain (engine, transmission, drivetrain) needs repair or replacement within 100,000 miles, the car manufacturer will repair or replace the component free of charge. A car is said to be "out of warranty" when any requirement of the warranty has not been met, e.g. the car is beyond 100,000 miles.

In another example, user 216 may own two cars, each with different types of warranties. The first car, while out of warranty (that is devoid of any warranty requirements) due to high mileage from the original manufacturer, is under warranty from another party, i.e. warranty provider 2414. Specifically, the user 216 has entered a contract for a warranty for the brake system. Warranty provider 2414 requires the car owner 216 to obtain annual brake inspections and to never allow the brake pads to drop below 10% remaining wear. If these conditions are met, the warranty provider 2414 will repair the brakes for a flat fee. If either condition is not met, the brake pads will repaired but at a higher price.

Authorized monitor 2418 may comprise a legal or police authority enforcing terms placed on a user 216. For example, the user 216 may be under supervision after a DUI conviction that mandates alcohol blood level monitoring. A vehicle sensors 242, such as a blood alcohol meter mounted on the steering wheel or enabled by sampling interior vehicle air, may provide a measure of user 216 alcohol level. These data may be provided to authorized monitor 2418.

Any of insurance provider 2212, warranty provider 2414 and authorized monitor 2418 may make queries of other elements of compliance system 2400 via communication bus 356. For example, a warranty provider 2414 may send a signal to a vehicle 104 by way of communication network 224 to determine a warranty compliance status, i.e. whether a particular user 216 is in compliance with a particular term of a warranty. In response to receiving the signal as passed via communication bus 356, the vehicle control system 204 performs a query of the warranty data 2404 and/or historical user compliance data 2412 to determine the status sought. Once the warranty status check is performed, the information may be sent via the vehicle control system 204 to the warranty provider 2414.

The data stored in any of profile data 252, warranty data 2404, maintenance data 2408 and/or historical user compliance data 2412 may be structured and configured with data structure of the type previously discussed, e.g. FIGS. 12A-D. For example, the health status 1278 may include any type of information related to a state of the systems to include the warranty compliance data and maintenance data discussed. For instance, an operational condition, manufacturing date, update status, revision information, time in operation, fault status, state of damage detected, inaccurate data reporting, and other types of component/system health status data may be obtained and stored in portion 1278.

One or more warnings may be stored in portion 1286. The warnings data 1286 may include warning generated by the vehicle 104 (e.g. "oil change required within next 500 miles"), systems of the vehicle 104 (e.g. "brake pads now at 80% wear"), manufacturer of the vehicle, federal agency, third party, and/or a user associated with the vehicle. For example, several components of the vehicle may provide health status information (e.g., stored in portion 1278) that, when considered together, may suggest that the vehicle 104 has suffered some type of damage and/or failure. Recognition of this damage and/or failure may be stored in the warnings data portion 1286. The data in portion 1286 may be communicated to one or more parties (e.g., a manufacturer, maintenance facility, user, insurance provider 2212, warranty provider 2414, etc.). In another example, a manufacturer may issue a recall notification for a specific vehicle 104, system of a vehicle 104, and/or a component of a vehicle 104. It is anticipated that the recall notification may be stored in the warning data field 1286. Continuing this example, the recall notification may then be communicated to the user of the vehicle 104 notifying the user of the recall issued by the manufacturer.

Vehicle subsystems 328 can include any of the mechanical, electrical, electromechanical, computer, or other systems associated with the function of the vehicle 100. For example, vehicle systems 328 can include one or more of, but is not limited to, the steering system, the braking system, the engine and engine control systems, the electrical system, the suspension, the drive train, the cruise control system, the radio, the heating, ventilation, air conditioning (HVAC) system, the windows and/or doors, etc. as known to those skilled in the art. Vehicle subsystems 328 may provide a status signal via communication bus 356 to user 216 indicating that a required maintenance item is recommended (e.g. the vehicle 104 is 500 miles from a required oil change) and/or provide an out-of-maintenance indicator to historical user compliance data 2412 and/or warranty provider 2414 indicating that a required maintenance item was not met (e.g. brakes pads have worn down beyond a selectable threshold).

Vehicle sensors 242 may include one or more sensors for providing information to the vehicle control system 204 that determine or provide information about the vehicle subsystems 328 of the vehicle 104 operated by user 216. For example, a stress or strain gauge sensor attached to a portion of the vehicle frame of vehicle 104 may sense an amount of stress or strain, respectively, on vehicle frame. If the sensed stress or strain is outside of a selectable range, a warning signal may be sent to the user 216.

Non-vehicle sensor 236 can be any type of sensor that is not currently associated with the vehicle 104 yet useful in enabling or facilitating operations or functions of a vehicle maintenance and warranty compliance detection environment. For example, non-vehicle sensor 236 can be sensors that aid in monitoring endeavors of the authorized monitor 2418 with respect to the user 216. For example, a particular user 216 may be under license suspension for illegal street racing. An authorized monitor, e.g. a probation officer, may be able to monitor movements of vehicle 104 through a GPS tracker attached to vehicle 104 so to be noticed if the vehicle 104 approaches known street-racing sites. Further, the non-vehicle sensor(s) 236 can be other types of sensors which provide information about the distant environment 116 or other information about the vehicle 104 or the environment 100. These non-vehicle sensors 236 may be operated by third parties but provide information to the vehicle control system 204. Examples of information provided by the sensors 236 and that may be used by the vehicle control system 204 may include weather tracking data, traffic data, user health tracking data, vehicle maintenance data, or other types of data, which may provide environmental or other data to the vehicle control system 204.

The vehicle sensors 242 and non-vehicle sensors 236 may operate in a continuous or discontinuous mode, may operate at a set or selectable sampling rate, and may be selectable by a user or a remote entity such as a third-party security provider.

Figure 25:
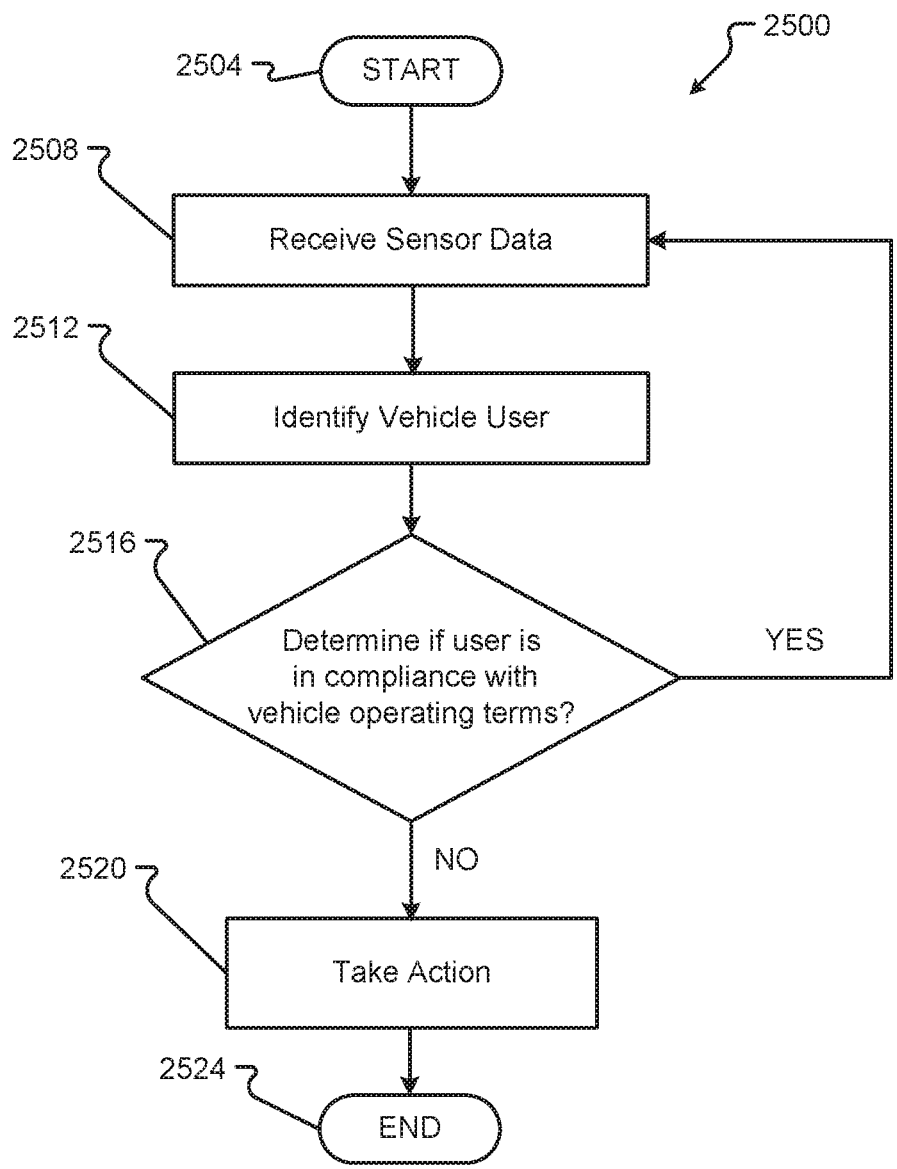
FIG. 25 is a flow diagram of a method for a vehicle maintenance and warranty compliance detection.

An embodiment of a method 2500 for vehicle maintenance and warranty compliance detection is shown in FIG. 25.

While a general order for the steps of the method 2500 is shown in FIG. 25, the method 2500 can include more or fewer steps or can arrange the order of the steps differently than those shown in FIG. 25. Generally, the method 2500 starts with a start operation 2504 and ends with an end operation 2524. The method 2500 can be executed as a set of computer-executable instructions executed by a computer system and encoded or stored on a computer readable medium. Hereinafter, the method 2500 shall be explained with reference to the systems, components, modules, software, data structures, user interfaces, etc. described in conjunction with FIGS. 1-24.

At step 2508, one or more vehicle sensors 242 sense a state or condition of one or more vehicle subsystems 328 and/or conditions of user 216. For example, an oil change monitor sensor may measure mileage of vehicle 104 since last oil change, and provide an alert or notice as a selectable oil change threshold is approached. That is, the oil change monitor sensor may be set to monitor oil changes every 5,000 miles and provide a signal when 4,500 miles has been reached.

At step 2512, the identity of user 216 is determined. Generally, such an identification is made by comparing the data received from the one or vehicle sensors 242 against profile data 252. The identification of a user 216 by way of vehicle sensors 242 has been previously described and will not be repeated here. Once the identity of the user 216 is determined, profile data 252 is accessed to determine user-specific parameters such as warranty terms and conditions, insurance terms and conditions, and any authorized monitors with associated terms and conditions. For example, a particular user 216 may have an insurance policy with a particular insurance provider 2414 which restricts vehicle operation to non-highway driving, a warranty with warranty provider 2414 that requires oil changes every 5,000 miles, and an authorized monitor (e.g. probation officer) that requires user 216 to abstain from consuming alcohol and visiting a bar.

At step 2516, a determination as to whether the user 216 is in compliance with vehicle operating terms is made. For example, continuing the above scenario regarding required oil changes every 5,000 miles, if one or more vehicle sensors 242 determine that a required oil change has been missed by user 216, a signal indicating such is sent to vehicle control system 204. The vehicle control system 204 then queries warranty data 2404 to determine the terms of warranty that user 216 has with warranty provider 2414. If vehicle control system 204 determines that indeed user 216 has missed a required oil change as required by warranty, a determination is made that user 216 is out of compliance with the warranty with warranty provider 2414. If instead vehicle control system 204 determines that user 216 is not out of compliance with the terms of warranty of warranty provider 2414, then the method returns to receive sensor data of step 2508. For example, an oil change monitor sensor may measure mileage of vehicle 104 since last oil change, and provide an alert or notice as a selectable oil change threshold is approached. That is, the oil change monitor sensor may be set to monitor oil changes every 5,000 miles and provide a signal when 4,500 miles has been reached.

At step 2520, the vehicle control system 204 takes action in the event a determination is made at step 2516 that user 216 is out of compliance with a vehicle operating term, such as a warranty with warranty provider 2414. Continuing the oil change example, the vehicle control system 204 may take several actions, to include providing notice to user 216 comprising via user interface 212, updating historical user compliance data 2412 and/or maintenance data to document the non-compliance event, and noticing the warranty provider 2414. The notice or message to warranty provider 2414 and/or user 216 may be a text message, phone call, email, etc. to the user associated with the vehicle to alert the user of the intrusion.

Alternatively or additionally, the vehicle control system 204 may disable the vehicle (e.g. not allowing the vehicle 104 to start) and/or provide an alarm 2016, to include a visual alarm alert (e.g. flashing of headlights, hazard lights, daytime running lights (DRLs), and/or interior lights) and audio alarm alert (e.g. honking of horn) for certain types or categories of non-compliance. For example, a user 216 determined to be drunk may result in the vehicle 104 being disabled and/or automatically locking an authorized user out of the vehicle 104. The method 2100 ends at step 2524.

The vehicle may also provide methods and systems for the automatic communication of damage and health of users in detected vehicle incidents. Specifically, a method to monitor the health of occupants and detect and identify any occupants experiencing a medical anomaly may be provided. In the event a medical anomaly is detected within a vehicle, the system may take a number of actions. In one embodiment, the actions comprise notifying health care providers and emergency personnel or police, communicating accident data, and emitting a visual or audio alarm.

More specifically, for example, a vehicle may automatically assess the health of vehicle occupants in the event of an accident or incident (road rage, shooting, loud noises internal and/or external to the vehicle, etc.). Further, the vehicle may determine number of people involved, vital signs, images from within the vehicle (e.g., via cameras), blackbox type data (e.g., speed at impact, g-forces subjected to vehicle and occupants, time of day, time since impact, time/length of impact, etc.), and communicate data to EMS, Police, Insurance co., mobile phones and other linked devices. Automatic crash reporting for police and insurance reports may be provided; as such, no recreation of the crash required or interviewing of witnesses. Instead, time-stamped GPS data and black-box recordings of the cars involved will paint the whole picture. Furthermore, automatic damage/health assessment in the case of a car crash may be provided; not just location, but the automatic transmission of data to the EMS and police; e.g. number of people in the car, vitals, images from dashboard camera, blackbox data such as speed at impact, etc.

Figure 26:
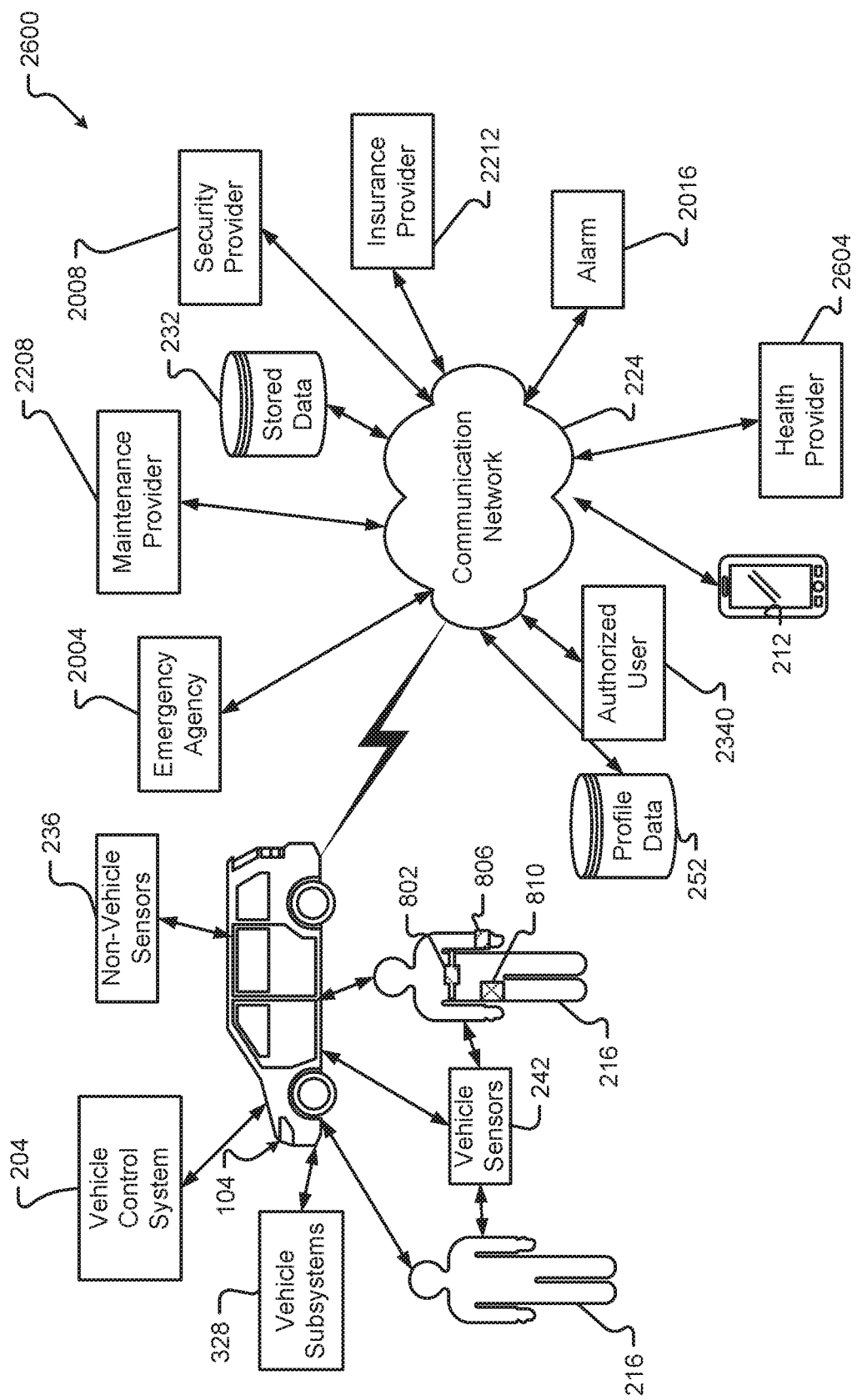
FIG. 26 depicts an embodiment of a system for the automatic communication of damage and health in detected vehicle incidents.

FIG. 26 depicts an embodiment of a system for the automatic communication of damage and health of users in detected vehicle incidents (herein also termed "user health system") 2600. Vehicle 104 is shown in communication with several elements, i.e. vehicle sensors 242, non-vehicle sensors 236, communication network 224, vehicle control system 204 and users 216, one of which is equipped with wearable devices 802, 806, 810. The user health system 2600 may comprise profile data 252, a health provider module 2604, emergency agency module 2004, maintenance provider 2208, alarm 2016, authorized user 2340 and device or user interface 212 and stored data 232. The aforementioned components may communicate over a communication network 224. As one example of the communication, one or more of wearable devices 802, 806, 810 of a particular user 216 may detect a health anomaly regarding user 216 and communicate via communication network 224 to emergency agency 2004 that EMS is required to aid user 216.

Hereinafter, the compliance system 2600 shall be explained with reference to the systems, components, modules, software, data structures, user interfaces, etc. described in conjunction with FIGS. 1-25.

One or more of vehicle sensors 242 detect or sense the status and operation of vehicle 104 comprising vehicle subsystems 328. Vehicle systems 328 can include any of the mechanical, electrical, electromechanical, computer, or other systems associated with the function of the vehicle 104. For example, vehicle systems 328 can include one or more of, but is not limited to, the steering system, the braking system, the engine and engine control systems, the electrical system, the suspension, the drive train, the cruise control system, the radio, the heating, ventilation, air conditioning (HVAC) system, the windows and/or doors, etc. These systems are well known in the art and will not be described further.

Non-vehicle sensor 236 can be any type of sensor that is not currently associated with the vehicle 104 yet useful in enabling or facilitating operations or functions of a user health system 2600. For example, non-vehicle sensor 236 can be sensors that record weather condition, road condition, and/or circumstances present during a designated vehicle 104 event. For example, in the event user 216 is involved in a traffic accident, the vehicle control system 204 may be tasked to record and/or take action of the event. The take action may include recording the road conditions as provided by, for example, a weather service provider. The road conditions may comprise humidity, precipitation present, temperature, visibility and special or unusual conditions such as deer roadway crossings reported in the vicinity. Further, the non-vehicle sensor(s) 236 can be other types of sensors which provide information about the distant environment 116 or other information about the vehicle 104 or the environment 100. These non-vehicle sensors 236 may be operated by third parties but provide information to the vehicle control system 204. Examples of information provided by the sensors 236 and that may be used by the vehicle control system 204 may include weather tracking data, traffic data, user health tracking data, vehicle maintenance data, or other types of data, which may provide environmental or other data to the vehicle control system 204.

One or more of vehicle sensors 242 detect or sense damage to vehicle 242 as associated with a particular location of vehicle 104 associated with one or more areas 508. See FIGS. 5A-C. Upon detection of vehicle damage, the vehicle control system 204 may train vehicle sensors 242 to the surrounding area of vehicle damage, and/or record and train as possible non-vehicle sensors 236 to the surrounding area. Such on-site sensing of the potential cause of the vehicle damage benefits in several ways, to include liability determination and insurance claims. Upon detection or sensing of vehicle damage, the vehicle control system 204 may take any of several actions. The action may comprise providing notice to one or more emergency agencies 2004 such as police, to a security provider 2008 such as a monitoring service that notifies other parties such as the vehicle owner, health provider 2604, and/or one or more authorized users 2012 to include by way of device or user interface 212. Alternatively or additionally, the vehicle control system 204 may disable the vehicle and/or provide an alarm 2016, to include a visual alarm alert (e.g. flashing of headlights) and audio alarm alert (e.g. honking of horn), contact a maintenance provider 2208 so as to order repair parts, and contact an insurance provider 2212 to being the claim adjustment process. Also, the vehicle control system 204 may record vehicle damage data and/or hazard data on profile data 252 associated with the user 216 of vehicle 104.

Health status or state data of a particular user 216 may be measured by several means, comprising vehicle sensors 242 and wearable devices 802, 806, 810. Wearable device 802, 806, 810 may include heart rate monitors, blood pressure monitors, glucose monitors, pedometers, movement sensors, wearable computers, and the like. Examples of wearable computers may be worn by a user 216 and configured to measure user activity, determine energy spent based on the measured activity, track user sleep habits, determine user oxygen levels, monitor heart rate, provide alarm functions, and more. It is anticipated that the wearable devices 802, 806, 810 can communicate with the user/device interaction subsystem 817 via wireless communications channels or direct connection (e.g., where the device docks, or connects, with a USB port or similar interface of the vehicle 104). The wearable sensors may communicate with vehicle control system 204 and/or sensor module 814 (See FIG. 8B) which may be configured to receive and/or interpret input provided by one or more sensors in the vehicle 104. In some cases, the sensors may be associated with one or more user devices (e.g., wearable devices 802, 806, 810, smart phones 212, mobile computing devices 212, 248, and the like). Optionally, the sensors may be associated with the vehicle 104, as described in conjunction with FIGS. 6A-7B.

Other sensors may be included and positioned in the interior space 108 of the vehicle 104. Generally, these interior sensors obtain data about the health of the one or more users 216 (e.g. driver and/or passenger(s)), data about the safety of the driver and/or passenger(s), and/or data about the comfort of the driver and/or passenger(s). The health data sensors can include sensors in the steering wheel that can measure various health telemetry for the person (e.g., heart rate, temperature, blood pressure, blood presence, blood composition, etc.). Sensors in the seats may also provide for health telemetry (e.g., presence of liquid, weight, weight shifts, etc) Infrared sensors could detect a person's temperature; optical sensors can determine a person's position and whether the person has become unconscious. Safety sensors can measure whether the person is acting safely. Optical sensors can determine a person's position and focus. Sensors in the seats may detect if a person is leaning forward or may be injured by a seat belt in a collision. Such sensors may aid emergency responders in determining the health of potentially injured users 216 in the event of an accident. For example, if a sensor definitively determines that a particular occupant has received fatal injuries, emergency personnel may then focus solely on remaining occupants who may be injured or in need of rescue.

Vehicle sensors 242 may comprise one or more of optical, or image, sensors 622A-B (e.g., cameras, etc.), motion sensors 624A-B (e.g., utilizing RF, IR, and/or other sound/image sensing, etc.), steering wheel user sensors 642 (e.g., heart rate, temperature, blood pressure, sweat, health, etc.), seat sensors 677 (e.g., weight, load cell, moisture, electrical, force transducer, etc.), safety restraint sensors 679 (e.g., seatbelt, airbag, load cell, force transducer, etc.), interior sound receivers 692A-B, environmental sensors 694 (e.g., temperature, humidity, air, oxygen, etc.), and the like. The image sensors 622A-B may be used alone or in combination to identify objects, users 216, and/or other features, inside the vehicle 104. Such images may assist emergency responders in understanding circumstances of a vehicle accident regarding users 216. For example, a determination may be made that a particular user 216 has a leg caught under a damaged seat that is compacting the leg, thus not allowing the user 216 to egress the vehicle 104.

The vehicle 104 may include one or more motion sensors 624A-B. These motion sensors 624A-B may detect motion and/or movement of objects inside the vehicle 104. Optionally, the motion sensors 624A-B may be used alone or in combination to detect movement. Interior sound receivers 692A-B may include, but are not limited to, microphones and other types of acoustic-to-electric transducers or sensors. Optionally, the interior sound receivers 692A-B may be configured to receive and convert sound waves into an equivalent analog or digital signal. The interior sound receivers 692A-B may serve to determine one or more locations associated with various sounds in the vehicle 104. Such motion and sound sensors may allow emergency responders to triage those involved in a vehicle accident by identifying those, for example, fatally injured from those not fatally injured.

Vehicle sensors 242 may comprise sensors to measure heart rate to sense arrhythmias, to detect heart attacks or seizures which may prompt the taking of corrective actions for example stopping the car, and sensors that link to health provider 2604 (to include a medical professional so authorized by user 216) to enable assessment of health condition and well-being. One or more vehicle sensors 242 may be linked with external entities that enable more sophisticated interpretation and/or diagnosis of health condition given sensor readings of user health state.

Vehicle sensors 242 may also serve a monitoring function in addition to the afore-mentioned functions in the event of a vehicle accident. That is, during routine driving operations the vehicle sensors 242 may monitor and alert, as necessary, in the event a user 216 experiences a health anomaly. For example, health telemetry and other data may be collected via the steering wheel user sensors 642. Optionally, the steering wheel user sensors 642 may collect heart rate, temperature, blood pressure, and the like, associated with a user 216 via at least one contact disposed on or about the steering wheel 640. Similarly, biometric sensors 756 may be employed to identify and/or record characteristics associated with a user 216. Biometric sensors 756 can include at least one of image sensors, IR sensors, fingerprint readers, weight sensors, load cells, force transducers, heart rate monitors, blood pressure monitors, and the like as provided herein.

Health data of a particular user 216 may be stored by way of the data structures 1200 described above with respect to FIGS. 12A-D. That is, the sensors 242 within the vehicle 104 may be able to either obtain or track health data in portion 1228. Health data 1228 may include any type of physical characteristic associated with the user. For example, a heart rate, a blood pressure, pulse rate, body temperature, respiratory rate, associated vital signs or other types of heath data may be obtained and stored in portion 1228.

The user may have this health data tracked over a period of time to allow for statistical analysis of the user's health while operating the vehicle 104. In this way, if some function of the user's health deviates from a norm (e.g., a baseline or calibrated measurement, average measurements taken over time, and the like), the vehicle 104 may be able to determine there is a problem with the person and react to that data.

Profile data 252 is as described above but may also comprise health data as to a particular user 216. For example, data indicating the user is diabetic, a condition particularly important to EMS personnel in the event of a health emergency, or history of arrhythmias and any medication current prescribed to address the condition.

Maintenance provider 2208 is the entity user 216 has designated as having primary responsibility for maintenance of vehicle 104. However, the maintenance provider 2208 could be more than one entity. The maintenance provider 2208 may or may not be associated with the original equipment manufacturer. The security provider 2008 may be a monitoring service that notifies other parties such as the vehicle owner in the event of anomalous states or events associated with the vehicle 104, such as vehicle damage, and unauthorized entry to vehicle 104. Insurance provider 2212 is the designated insurance carrier for vehicle 104. Health provider 2604 comprises medical professionals designated authorized by user 216, to include primary care physician, preferred hospital, specialist medical professions (e.g. cardiac specialist).

The vehicle sensors 242 and non-vehicle sensors 236 may operate in a continuous or discontinuous mode, may operate at a set or selectable sampling rate, and may be selectable by a user or a remote entity such as a third-party security provider.

Stored data 232 may serve to store data associated with a vehicle accident or incident, to include user 216 health data. Such stored data 232 may be considered the equivalent of "black boxes" associated with aircraft.

Figure 27:
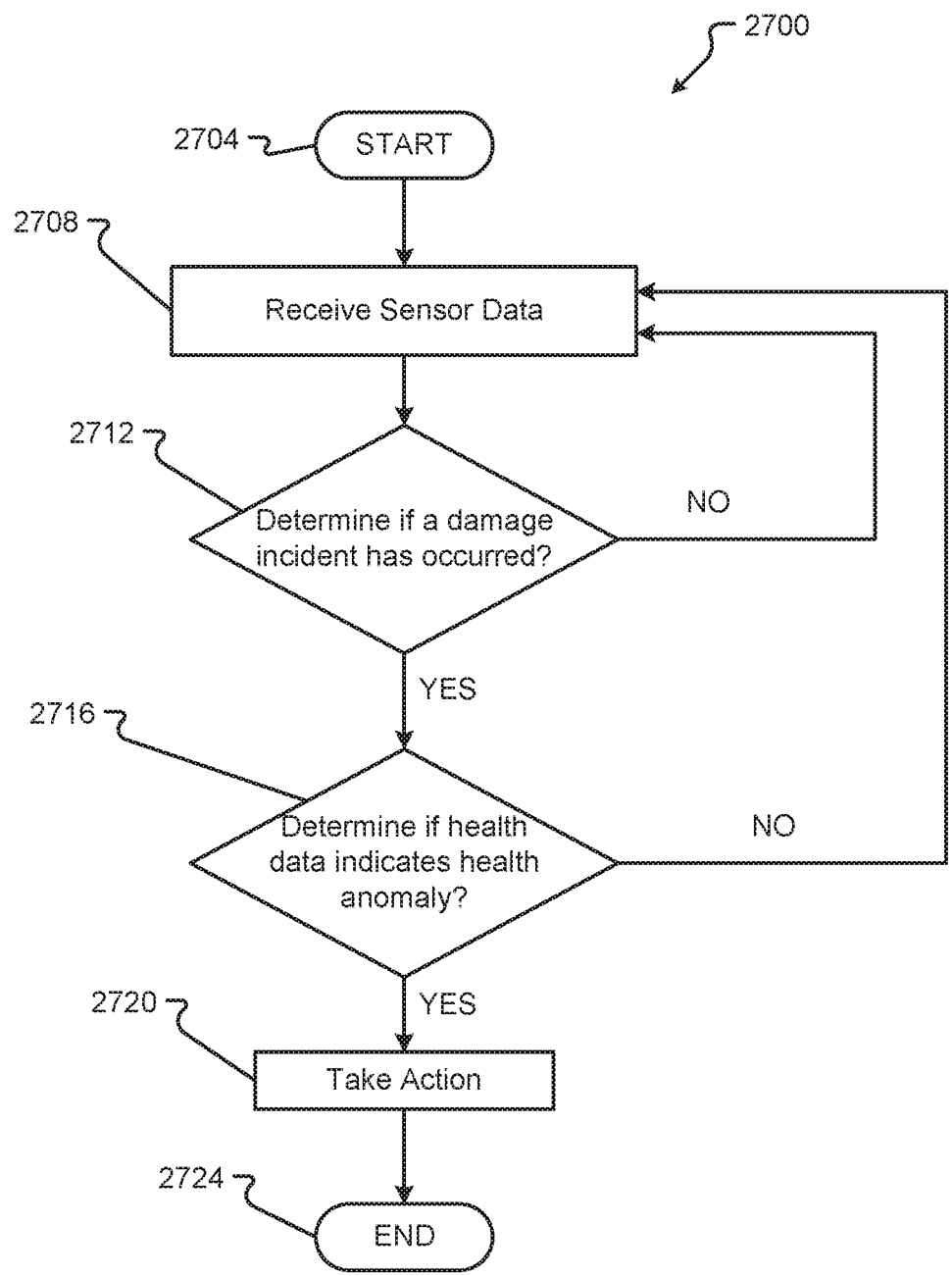
FIG. 27 is a flow diagram of a method for the automatic communication of damage and health in detected vehicle incidents.

An embodiment of a method 2700 for the automatic communication of damage and health in detected vehicle incidents is shown in FIG. 27.

While a general order for the steps of the method 2700 is shown in FIG. 27, the method 2700 can include more or fewer steps or can arrange the order of the steps differently than those shown in FIG. 27. Generally, the method 2700 starts with a start operation 2704 and ends with an end operation 2724. The method 2700 can be executed as a set of computer-executable instructions executed by a computer system and encoded or stored on a computer readable medium. Hereinafter, the method 2700 shall be explained with reference to the systems, components, modules, software, data structures, user interfaces, etc. described in conjunction with FIGS. 1-26.

At step 2708, one or more vehicle sensors 242 sense damage to vehicle 104. Damage is broadly defined as any unexpected change in condition or state of any portion of vehicle 104, to include the physical exterior surface (i.e. "skin" of the vehicle") and all portions within the physical exterior, i.e. the interior space 108. The vehicle sensors 242 may operate in a continuous or discontinuous mode, may operate at a set or selectable sampling rate, and may be selectable by a user or a remote entity such as a third-party security provider 2008.

The one or more vehicle sensors 242 employed to sense or detect body damage comprise vehicle external sensors such as external safety group sensors 716E. That is, the one or more vehicle sensors 242 may comprise force sensors 768, mechanical motion sensors 772, orientation sensors 776, vehicle body sensors 782, vibration sensors, electromagnetic field sensors, and acoustic sensors. The one or more vehicle sensors 242 are configured to detect damage to vehicle 104 and/or identify its location. It one embodiment, the one or more vehicle sensors 242 may provide a measure of the degree of damage to vehicle 104.

In one example, hazard may be another vehicle which impacts vehicle 104. Force sensors 768 sense and measure the impact, or G-force, imparted to vehicle 104 and output a signal identifying a force exceeded a selectable threshold. Further, the approximate location of the damage is known based on the location of the force sensor 768. That is, if the force sensor 768 provides a 3-dimensional vector measurement of force, the location of the hazard impact may be determined given other known geometries (i.e. the vehicle geometries). Mechanical motion sensors 772 such as accelerometers may similarly measure and sense the impact from a hazard. Orientation sensors 776, such as accelerometers, gyroscopes, magnetic sensors may also detect a change in orientation of the vehicle, either momentary or permanent, that indicates impact of vehicle 104 with hazard.

In one example, hazard may be another vehicle which impacts vehicle 104. Force sensors 768 sense and measure the impact, or G-force, imparted to vehicle 104 and output a signal identifying a force exceeded a selectable threshold. Further, the approximate location of the damage is known based on the location of the force sensor 768. That is, if the force sensor 768 provides a 3-dimensional vector measurement of force, the location of the hazard impact may be determined given other known geometries (i.e. the vehicle geometries). Mechanical motion sensors 772 such as accelerometers may similarly measure and sense the impact from a hazard. Orientation sensors 776, such as accelerometers, gyroscopes, magnetic sensors may also detect a change in orientation of the vehicle, either momentary or permanent, that indicates impact of vehicle 104 with a hazard. Such identification and quantification of the source or cause of a vehicle accident directly assists several ways, comprising in accident investigation, liability determination, and emergency response procedures. Indeed, automatic crash reporting for police and insurance reports may thus be enabled. As such, no recreation of the crash is required or interviewing of witnesses. Instead, time-stamped GPS data and black-box recordings (via e.g. stored data 232) of the cars involved accurately document the accident or incident.

The vehicle body sensors 782 may be configured to measure characteristics associated with the body (e.g., body panels, components, chassis, windows, etc.) of a vehicle 104. For example, a vehicle body sensor 782 may be located in the rear bumper area of vehicle 104. Upon contact by a hazard such as another vehicle above a selectable threshold the vehicle body sensor 782 provides an output signal. For example, the vehicle body sensor 782 might be calibrated to provide a signal if a force at or above five (5) pounds is measured, or if an acceleration above 1 foot/sec is measured. The location of the vehicle body sensor 782 provides an indication of the location of the damage to vehicle 104. The value measured provides an indication of the degree of damage to vehicle 104.

The one or more vehicle sensors 242 may also identify the location and/or degree of damage to vehicle 104. That is, the sensor arrangement 500 can include one or more areas 508 within the vehicle. Each zone may include one or more sensors that are positioned or configured to collect information about the environment or ecosystem associated with that zone or person. As such, one or more vehicle sensors 242 may associate a sensed signal, e.g. a force sensor may register an 11 pound impact to the driver's side window while a vibration sensor registers a corresponding spike in vibration, with a particular identified area of the vehicle via the labeling scheme discussed, i.e. associated with zone 512A (driver).

Associated device sensors 720 can include any sensors that are associated with a device 212, 248 in the vehicle 104. As previously stated, typical devices 212, 248 may include smart phones, tablets, laptops, mobile computers, and the like. It is anticipated that the various sensors associated with these devices 212, 248 can be employed by the vehicle control system 204. For example, a typical smart phone can include an image sensor, an IR sensor, audio sensor, gyroscope, accelerometer, wireless network sensor, fingerprint reader, and more. These associated device sensors 720 may be used by the vehicle control system 204 to detect and/or identify damage to vehicle 104.

At step 2712, the vehicle control system 204 accepts vehicle sensor 242 data and determines if a damage incident has occurred to vehicle 104. If no damage has occurred, the process returns to step 2708 wherein vehicle sensors 242 continue to operate and sensor data is received. Vehicle control system 204 determines a damage incident has occurred by assessing the received signals or measurements from the one or more vehicle sensors 242. That is, the vehicle control system 204 accepts sensor inputs, assesses those sensor inputs, and determines if the measurement is indicative of damage to the vehicle 104. For example, a vehicle body sensor 782 may be located in the roof of vehicle 104. Upon contact by a hazard 2204, such as half-inch sized hail, above a selectable threshold the vehicle body sensor 782 provides an output signal. For example, the vehicle body sensor 782 might be calibrated to provide a signal if a force at or above five (5) pounds is measured, or if an acceleration above 0.5 foot/sec is measured, or a displacement of more than one-quarter inch is detected. The location of the vehicle body sensor 782 provides an indication of the location of the damage to vehicle 104. The value measured provides an indication of the degree of damage to vehicle 104. The vehicle sensor 242 would also provide a location of the damage, with respect to a certain zone 512 or area 508 of the vehicle, i.e the vehicle roof. Stated another way, the vehicle sensors 242 output signals to the vehicle control system 204 that an event (vehicle damage) has been measured or sensed. These data may then in turn be sent to the vehicle control system processor 304 to determine the zone 512 and area 508 where the event occurred.

Upon receiving the vehicle sensor data, the vehicle control system 204 may also perform signal processing of signals received from one or more vehicle sensors 242. Such signal processing may include fused or blended estimation of a measured parameter from a single sensor, such as multiple measurements of a range state parameter from the vehicle 104 to a potential intruder. In a simple case, the vehicle control system 204 may solely receive measurements of range from a single force sensor, and simple output a running average of the range, e.g. average all measurements over the last 1 sec to provide an average force value. Optionally, the vehicle control system 204 may perform estimation, blending, or fusion of a measured state parameter from multiple sensors such as multiple force sensors. Signal processing of such sensor signal measurements may comprise stochastic signal processing, adaptive signal processing, and/or other signal processing techniques known to those skilled in the art.

At step 2716, upon detection or sensing of vehicle damage, the vehicle control system 204 determines if the health state of any of the one or more occupant users 216 of vehicle 104 indicates a health anomaly, comprising if any occupants are injured or otherwise in need of medical or other attention. If no users 216 indicate a health anomaly e.g. are in need of medical or other attention, the process returns to step 2708 wherein vehicle sensors 242 continue to operate and sensor data is received. The vehicle control system 204 may compare the received health data from sensors comprising sensors 242 and wearable devices 802, 806, 810 to identify any anomalies, e.g. data out of selectable ranges (e.g. a diastolic blood pressure reading above 100 or a systolic blood pressure above 140) or a detected condition (e.g. heart arrhythmia). Alternatively or additionally, a statistically significant comparison may include determining if there are any parameters that could be deemed anomalous. For example, measured health parameters regarding heart function may be monitored and, if above a selectable threshold value, identified as anomalous and therefore in need of medical attention.

At step 2720, upon determining that one or more users or occupants of vehicle 104 have a health anomaly, e.g. one or more occupants or users 216 of vehicle 104 is injured or otherwise in need of medical attention, the vehicle control system 204 may take any of several actions. The actions may comprise providing notice to one or more emergency agencies 2004 such as police, and to health provider 2604 to obtain for example medical history of an injured party and/or facilitate communications between on-scene EMS personnel and a user's particular medical provider, to a security provider 2008 such as a monitoring service that notifies other parties such as the vehicle owner, and one or more authorized users 2012 to include by way of device or user interface 212.

Continuing the above user under medication for arrhythmia, step 2720 may comprise querying the user profile data 252 to determine user history of heart rate and/or arrhythmia, preferred hospital, primary care physician, emergency contact information, and specialist physician (e.g. cardiologist). As such, the take action step of 2720 may comprise communicating, via communication network 224, to one or more entities identified in data structure 1200 and providing specific health history data (e.g. medication taken), current health status (e.g. vital signs). Such data exchange enables data exchange of critical care data between, for example, on-scene personnel and health provider 2604. Such data exchange is timely and accurate and increases efficacy of medical care to the user 216. Among other things, the user identified hospital may be contacted in advance to prepare for user's arrival, the cardiac specialist may be paged to immediately meet the user at the designated hospital, and user's emergency contacts may be reached.

The take action step of 2720 may comprise information exchange via communication network 224 between emergency agency 2400 and health provider 2604 to increase effectiveness of treatment of a user having a medical emergency or health anomaly. Such information exchange may comprise health diagnostics. For example, the historical health data (e.g. date/time of last arrhythmia medication, date/time/character of last arrhythmias), the on-scene vital sign data (taken by, for example, on-scene personnel, by wearable devices 802, 806, 810, by vehicle sensors 242, etc) may be used by health provider 2604 to diagnose the medical event/anomaly of user 216 and direct emergency personnel or others on-scene, to include user 216, as to recommended actions.

Further, in one embodiment the circumstances of a damage incident are recorded, for example on stored data 232, to provide for more instantaneous, more accurate and more comprehensive accident investigation, failure analysis, and criminal guilt and/or civil liability investigation. For example, in the event of a vehicle damage incident, comprehensive definition of the circumstances prior, during and sometimes after the incident are recorded, and may be communicated to authorities (e.g. police, insurance provider, regulatory entity, authorized users). For example, such accident data may comprise vehicle speed, braking timing and performance to include ABS performance and timing, user operations to include if user was texting while driving, weather conditions, road conditions (to include a sensor that provides coefficient of friction of the roadway surface), user health conditions to include eye gaze vector (e.g. was driver distracted by wildlife at the sign of the road and not looking at stopped traffic immediately in front), operating conditions of other involved vehicles (e.g. through vehicle-mounted camera and/or radar mounted on vehicle established speed of car in front as 20 mph above speed limit resulting in spin-out on turn and unexpected stopping in roadway).

Alternatively or additionally, the vehicle control system 204 may disable the vehicle and/or provide an alarm 2016, to include a visual alarm alert (e.g. flashing of headlights) and audio alarm alert (e.g. honking of horn), contact a maintenance provider 2208 so as to order repair parts, and contact an insurance provider 2212 to being the claim adjustment process. The action of vehicle control system 204 may comprise any measure to provide for the safety of the user(s), such as stopping the vehicle, beginning to autonomounsly drive the vehicle, driving the vehicle to a new location, such as a hospital, waking the driver with an alarm or other noise, or performing some other function that may help maintain the health or safety of the user(s). Also, the vehicle control system 204 may record vehicle damage data and/or hazard data on profile data 252 associated with the user 216 of vehicle 104 to shared data 232. The method 2700 ends at step 2724.

In one embodiment, the system 2600 and/or method 2700 may function as a user health monitoring system irrespective of any damage incident. That is, generally, the method 2700 may receive sensor data at step 2708 comprising user 216 health data (e.g. that of 1228 discussed previously, see e.g. FIG. 12A) such as body temperature, blood pressure, pulse rate, respiratory rate, and other vital signs, and compare that received data at step 2716 to determine if a health anomaly exists for any occupant. The comparison may be through comparison of user 216 health data with user profile information 1238 as stored in profile data 252. For example, a heart rate exceeding a threshold value, as stored in profile information 1238, may determine that the user has a health anomaly. Furthermore, the profile data 252 may also provide that the user is taking a certain level and/or type of prescription medication for arrhythmia and when it was last taken.

The vehicle may also provide methods and systems for vehicle diagnostic detection and communication. Specifically, a method to monitor the health of vehicle systems and subsystems and diagnose detected anomalies is provided. In the event an anomaly or unhealthy state is detected within a vehicle, subsystem or component, the system may take a number of actions. In one embodiment, the actions comprise notifying a maintenance provider, a regulatory monitor, and original equipment manufacturer. The system may also maintain a vehicle fleet-wide performance database to enable identification and analysis of systemic fleet-wide data.

A vehicle may provide automatic diagnostic updates about car's "health" to the dealer or maintenance shop. This may result in the dealer accessing the car's computer remotely to do further diagnostics to a specific car. If done on a large scale, the car manufacturer could actually collect large sets of data to assess a particular vehicle make and/or model and even determine potential design flaws. Data can result in automatic alerts sent to the driver and may also result in the automatic ordering of parts required to repair the car.

In some embodiments, the vehicle diagnostics may be sent to an application running on a user's device (e.g., smart-phone, tablet, computer, etc.). Among other things, the user may determine action items pertaining to the car's diagnostics be interacting with the application.

The application may determine what is wrong with a car or what needs upkeep (changing oil, engine shampoo, low levels of windshield wiper fluid, etc), which interfaces with the car's WI (In-Vehicle Infotainment system), and replicate on a phone app, and be connected to a home automation ecosystem. The application can determine what one can do at home (e.g., one bought a bottle of windshield fluid 2 weeks ago, so a home automation system may remind to refill it upon returning home). In some embodiments, the application may provide a universal notification system, i.e. the car senses when it needs something, e.g. oil change, windshield washer fluid, wiper blades, and notifies the driver as needed. This can be done by the car generating a shopping list. The user can define what items/actions he/she wants to address. Some users may want to change their oil, while other may only feel comfortable changing out wiper blades. Notifications are timed to only arrive during safe driving situations; e.g. while at a red light or during a long, straight stretch of road.

Figure 28:
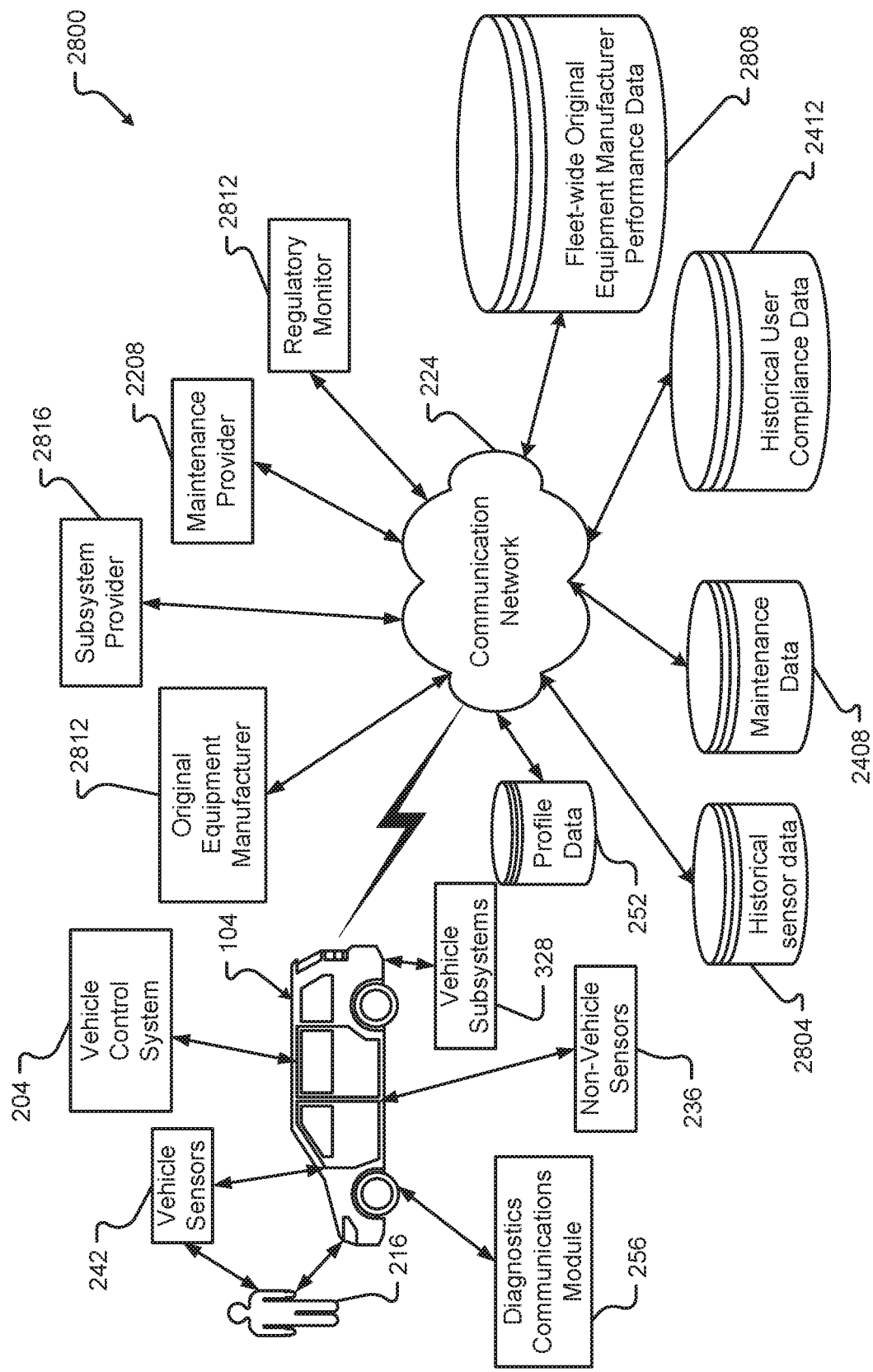
FIG. 28 depicts an embodiment of a vehicle diagnostic detection and communication system.
Figure 29:
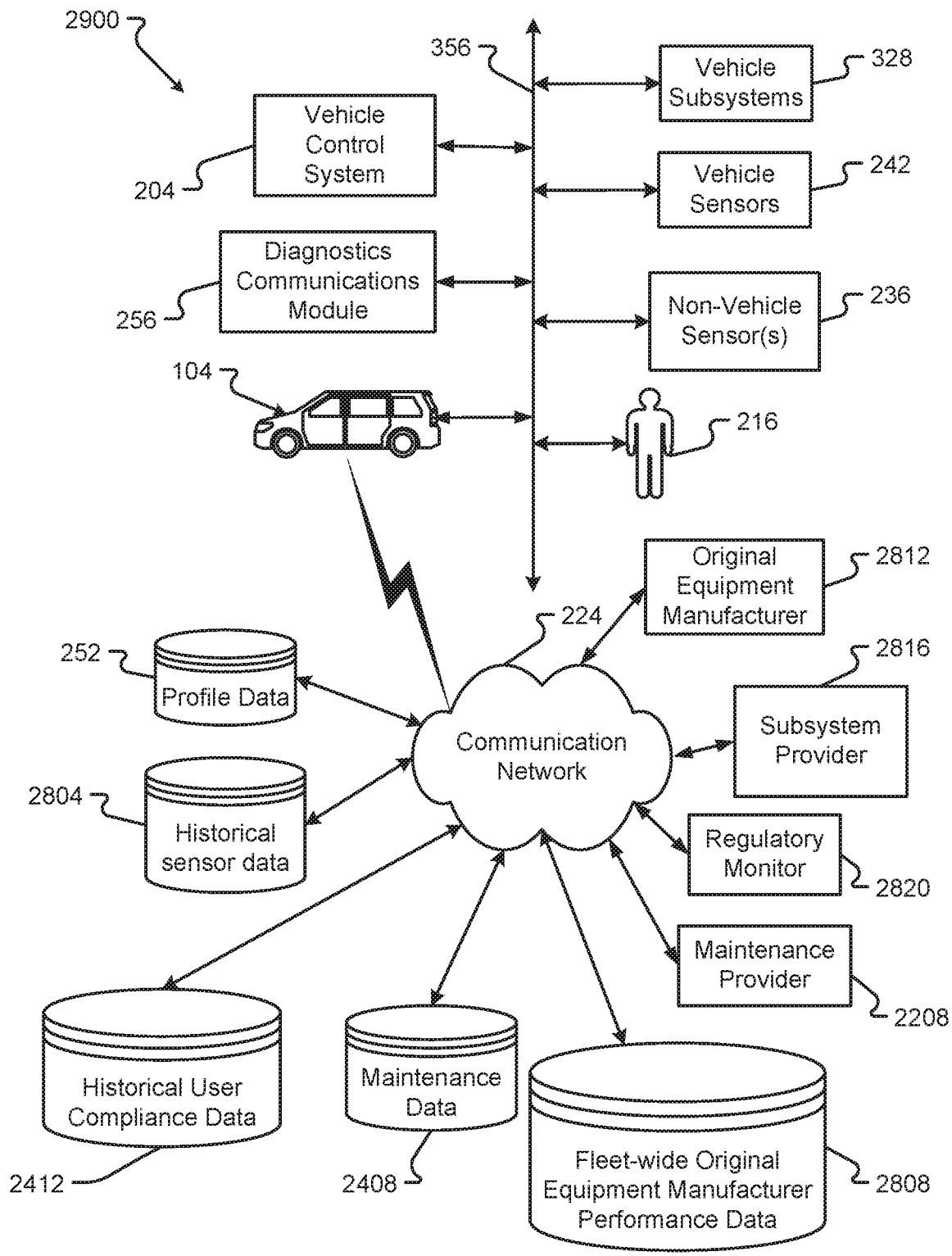
FIG. 29. is a block diagram of an embodiment of a vehicle diagnostic detection and communication environment.

FIG. 28 depicts an embodiment of a vehicle diagnostic detection and communication system 2800 (herein also termed "vehicle diagnostic system") and FIG. 29 depicts a block diagram of an embodiment of a vehicle diagnostic system 2900. Diagnostic is broadly defined as the process or techniques associated with determining the nature and cause of a phenomenon, for example determining why an engine is knocking or a car pulls to the left during braking. The vehicle diagnostic system 2800, 2900 may comprise historical sensor data 2804, historical user compliance data 2412, maintenance data 2408, fleet-wide original equipment manufacturer performance data 2808, vehicle control system 204, profile data 252, user 216, diagnostics communications module 256, an original equipment manufacturer module 2812, subsystem provider module 2816, a maintenance provider module 2208, a regulatory monitor module 2820, vehicle subsystems 328, vehicle sensors 242 and non-vehicle sensors 236.

Vehicle control system 204, user 216, vehicle subsystems 328, diagnostics communications module 256 vehicle sensors 242 and non-vehicle sensors 236 may communicate over a network or bus 356. This communication bus 356 may be bidirectional and perform data communications using any known or future-developed standard or protocol. An example of the communication bus 356 may be as described in conjunction with FIG. 4. Other components communicate via communication network 224. As one example of the later communication, the regulatory monitor 2820 and/or the insurance provider 2212, aside from communicating with each other via communication network 224, may communicate with vehicle sensors 242, and/or non-vehicle sensors via 236 via the vehicle 104. Hereinafter, the vehicle diagnostic system 2800, 2900 shall be explained with reference to the systems, components, modules, software, data structures, user interfaces, etc. described in conjunction with FIGS. 1-27.

One or more of vehicle sensors 242 detect or sense the status and operation of vehicle subsystems 328 as associated with a particular user 216. Vehicle systems 328 can include any of the mechanical, electrical, electromechanical, computer, or other systems associated with the function of the vehicle 104. For example, vehicle systems 328 can include one or more of, but is not limited to, the steering system, the braking system, the engine and engine control systems, the electrical system, the suspension, the drive train, the cruise control system, the radio, the heating, ventilation, air conditioning (HVAC) system, the windows and/or doors, etc as known to those skilled in the art. Vehicle subsystems 328 may provide a status signal via communication bus 356 to user 216 indicating that a required maintenance item is recommended (e.g. the vehicle 104 is 500 miles from a required oil change) and/or provide an out-of-maintenance indicator to historical user compliance data 2412 and/or maintenance provider 2208 indicating that a required maintenance item was not met (e.g. brakes pads have worn down beyond a selectable threshold).

Non-vehicle sensor 236 can be any type of sensor that is not currently associated with the vehicle 104 yet useful in enabling or facilitating operations or functions of a vehicle diagnostic system 2800, 2900. For example, non-vehicle sensor 236 can be sensors that record weather condition, road condition, and/or circumstances present during a designated vehicle 104 event. For example, the in the event a vehicle's anti-lock brake subsystem is engaged, the vehicle control system 204 may be tasked to record and/or take action of the event. The take action may include recording the road conditions as provided by, for example, a weather service provider. The road conditions may comprise humidity, precipitation present, temperature, visibility and special or unusual conditions such as deer roadway crossings reported in the vicinity. Further, the non-vehicle sensor(s) 236 can be other types of sensors which provide information about the distant environment 116 or other information about the vehicle 104 or the environment 100. These non-vehicle sensors 236 may be operated by third parties but provide information to the vehicle control system 204. Examples of information provided by the sensors 236 and that may be used by the vehicle control system 204 may include weather tracking data, traffic data, user health tracking data, vehicle maintenance data, or other types of data, which may provide environmental or other data to the vehicle control system 204.

Profile data 252 is as described above but may also comprise data describing user 216 vehicle operations, e.g. excessive speed driving, activating breaks while engaging accelerator pedal (i.e. "riding the brakes").

The historical user compliance data 2412 maintains data associated with a particular user 216 as to their compliance with maintenance data items. For example, the dates of tune-ups and identification of entity (i.e. the maintenance provider 2208) who performed the tune-up are stored. The historical user compliance data 2412 may categorize data according to specific vehicle 104.

Historical sensor data 2804 records performance characteristics of vehicle sensors 242. For example, records of calibrations performed (to include calibration data itself, date of calibration, party performing the calibration), date of installation, dates and types of maintenance performed, and records of any anomalous behaviors such as reading spikes (i.e. "wild points"). Such historical sensor data 2804 is beneficial in several ways, to include in signal processing algorithms when setting relative weighting of a particular sensor and/or modeling its sensor measurement characteristics (to include noise and accuracy profiles) and in determining the precision, accuracy, reliability of the sensor.

Maintenance data 2408 includes data defining required and recommended maintenance items for a particular vehicle and compliance with same. For example, the maintenance data 2408 may identify that a timing belt inspection is required every 10,000 miles. Maintenance data 2408 may include different levels of requirements, i.e. an oil change may be recommended every 5,000 miles but required every 10,000 miles. Upon completion of a particular maintenance item, the maintenance data 2408 is updated to document the completion, e.g. the date when the item was completed and the service provider performing the maintenance item. Such an update to maintenance data 2408 may be automatically provided via the communication bus 356 to original equipment manufacturer 2812, subsystem provider 2816 and regulatory monitor 2820 and may also update the historical user compliance data 2412.

Fleet-wide original equipment manufacturer performance data 2808 is a central database that compiles and maintains data regarding an entire fleet of similar vehicles and/or similar subsystems. For example, if vehicle 104 was a 2006 Honda Pilot, its data would be stored in fleet-wide original equipment manufacturer performance data 2808 with all similar models of the first generation Honda Pilot, i.e. from 2003-2008. In this way, fleet-wide trends may be analyzed yet also drill-downs to more specific ranges (e.g. all 2006 Honda Pilots with 4-wheel drive).

The data stored in any of profile data 252, historical sensor data 2804, maintenance data 2408, historical user compliance data 2412 and/or fleet-wide original equipment manufacturer performance data 2808 may be structured and configured with data structure of the type previously discussed, e.g. FIGS. 12A-D. For example, the health status 1278 may include any type of information related to a state of the systems to include the warranty compliance data and maintenance data discussed. For instance, an operational condition, manufacturing date, update status, revision information, time in operation, fault status, state of damage detected, inaccurate data reporting, and other types of component/system health status data may be obtained and stored in portion 1278.

One or more warnings may be stored in portion 1286. The warnings data 1286 may include warning generated by the vehicle 104 (e.g. "oil change required within next 500 miles"), systems of the vehicle 104 (e.g. "brake pads now at 80% wear"), manufacturer of the vehicle, federal agency, third party, and/or a user associated with the vehicle. For example, several components of the vehicle may provide health status information (e.g., stored in portion 1278) that, when considered together, may suggest that the vehicle 104 has suffered some type of damage and/or failure. Recognition of this damage and/or failure may be stored in the warnings data portion 1286. The data in portion 1286 may be communicated to one or more parties (e.g., a manufacturer, maintenance facility, user, insurance provider 2212, warranty provider 2414, etc.). In another example, a manufacturer may issue a recall notification for a specific vehicle 104, system of a vehicle 104, and/or a component of a vehicle 104. It is anticipated that the recall notification may be stored in the warning data field 1286. Continuing this example, the recall notification may then be communicated to the user of the vehicle 104 notifying the user of the recall issued by the manufacturer.

The diagnostic communications module 256 may be configured to receive and transmit diagnostic signals and information associated with the vehicle 104 and/or vehicle subsystems 328. Examples of diagnostics signals and information may include, but is in no way limited to, vehicle system warnings, sensor data, vehicle component status, service information, component health, maintenance alerts, recall notifications, predictive analysis, and the like. Embodiments of the diagnostic communications module 256 may handle warning/error signals in a predetermined manner. The signals, for instance, can be presented to one or more of a third party (e.g. the original equipment manufacturer 2812, subsystem provider 2816, regulatory monitor 2820), occupant, vehicle control system 204, and a service provider (e.g., maintenance provider 2208). The diagnostics communications module 256 may determine the specific vehicle subsyetm 328 that is out of specification and/or maintenance requirement, if not a component part within the vehicle subsyatem 256. For example, the diagnostics communications module 256 may determine that the braking system is out of compliance (i.e. is "unhealthy") and also pinpoint the problem to a particular wheel. In one embodiment, such a determination is communicated to the maintenance provider 2208 to enable a cost/schedule quote for repair and/or enable parts required for repair to be immediately ordered.

The diagnostic communications module 256 may be utilized by a third party (i.e., a party other than the user 216, etc.) in communicating vehicle diagnostic information. For instance, original equipment manufacturer 2812 may send a signal to a vehicle 104 to determine a status associated with one or more components associated with the vehicle 104. In response to receiving the signal, the diagnostic communications module 256 may communicate with the vehicle control system 204 to initiate a diagnostic status check. Once the diagnostic status check is performed, the information may be sent via the diagnostic communications module 256 to the manufacturer. This example may be especially useful in determining whether a component recall should be issued based on the status check responses returned from a certain number of vehicles.

A particular vehicle subsystem 328 may be associated with a particular subsystem provider 2816. For example, the engine control system may be provided by a manufacturer other than the original equipment manufacturer 2812. The original equipment manufacturer 2812 is the entity that originally produced the vehicle 104, commonly a large multi-national corporation e.g. Ford, Honda, etc Maintenance provider 2208 is the entity user 216 has designated as having primary responsibility for maintenance of vehicle 104. However, the maintenance provider 2208 could be more than one entity. The maintenance provider 2208 may or may not be associated with the original equipment manufacturer 2812.

Regulatory monitor 2820 is an authorized entity that is empowered to regulate and/or monitor the performance of vehicle 104. For example, the regulatory monitor 2820 could be the National Highway Traffic Safety Administration (NHTSA). Regulatory monitor 2820 has an interest in, for example, trend data regarding performance and/or safety of fleet-wide aspects of vehicle 104 as provided by original equipment manufacturer 2812.

Any of user 216, original equipment manufacturer 2812, subsystem provider 2816 and regulatory monitor 2820 may make queries of other elements of vehicle diagnostic system 2800, 2900 via communication bus 356. For example, an original equipment manufacturer 2812 may send a signal to a vehicle 104 by way of communication network 224 to determine if the user has complied with an urgent safety recall required, for example, a change in an ignition switch. In response to receiving the signal as passed via communication bus 356, the vehicle control system 204 performs a query to determine if the ignition switch in question has indeed been replaced. Such a query may comprise accessing the maintenance data 2408, historical user compliance data 2412 and/or maintenance provider 2208 to determine the status sought. Once the compliance or health check is performed, the information may be sent via the vehicle control system 204 to the original equipment manufacturer 2812.

The vehicle sensors 242 and non-vehicle sensors 236 may operate in a continuous or discontinuous mode, may operate at a set or selectable sampling rate, and may be selectable by a user or a remote entity such as a third-party security provider.

Figure 30:
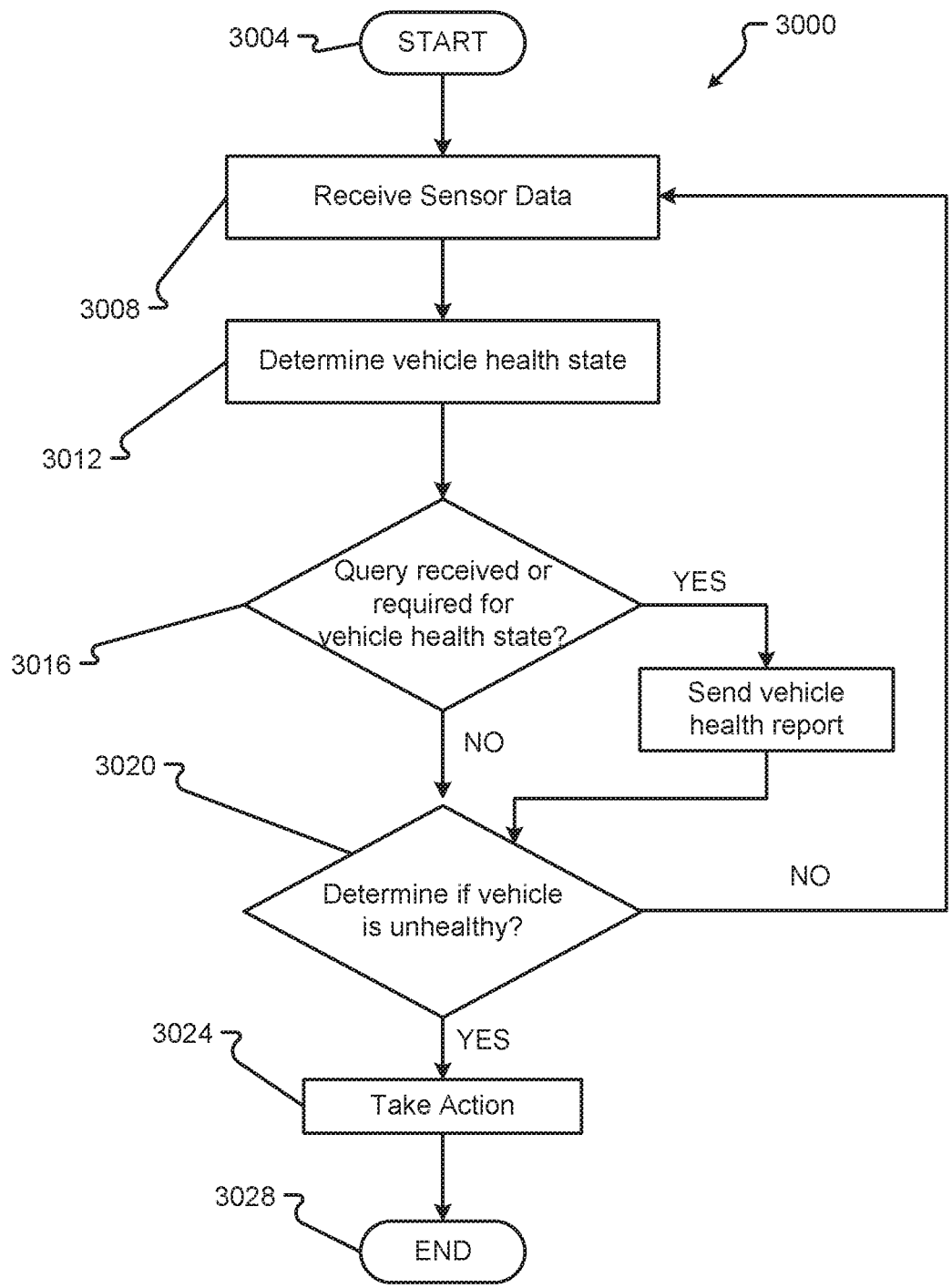
FIG. 30 is a flow diagram of a method for a vehicle diagnostic detection and communication system.

An embodiment of a method 3000 for vehicle diagnostic detection and communication is shown in FIG. 30. While a general order for the steps of the method 3000 is shown in FIG. 30, the method 3000 can include more or fewer steps or can arrange the order of the steps differently than those shown in FIG. 30. Generally, the method 3000 starts with a start operation 3004 and ends with an end operation 3028. The method 3000 can be executed as a set of computer-executable instructions executed by a computer system and encoded or stored on a computer readable medium. Hereinafter, the method 3000 shall be explained with reference to the systems, components, modules, software, data structures, user interfaces, etc. described in conjunction with FIGS. 1-29.

At step 3008, one or more vehicle sensors 242 sense a state or condition of one or more vehicle subsystems 328. For example, an oil change monitor sensor may measure mileage of vehicle 104 since last oil change, and provide an alert or notice as a selectable oil change threshold is approached. That is, the oil change monitor sensor may be set to monitor oil changes every 5,000 miles and provide a signal when 4,500 miles has been reached. Such oil change health status data, for example, may be stored as health status 1278 as part of the oil component 1274 of vehicle system engine 1270 (see e.g. FIG. 12C). Alternatively or additionally, the diagnostics communications module 256 may sense a vehicle 104 warning.

In another example, regulatory monitor 2820, e.g. the NHTSA, may be performing an investigation into suspected problems involving the Anti-lock Braking System (ABS) of a particular vehicle type. As such, NHTSA has mandated that all vehicles of a particular type record conditions of and performance of the ABS system whenever it is used. Such data may be stored in fleet-wide original equipment manufacturer performance data 2808 with associated vehicle 1282 identified (i.e. the vehicle make/model targeted by NHTSA), vehicle system 1270 identified (i.e. braking system) and component ID 1274 (i.e. ABS). Additional data may also be stored, such as roadway conditions (e.g. coefficient of friction of roadway), weather (e.g. outside temperature, humidity), user performance (e.g. length of time ABS was engaged) and user traits (e.g. age, need for prescription eyewear, traffic incident history).

At step 3012, the vehicle control system 204 accepts vehicle sensor 242 data and/or data from diagnostics communications module 256 and determines the health state of the vehicle 104. Such a health state comprises a numerical value and/or may provide a within specification/requirement or out of specification/requirement designation. For example, a vehicle sensor 242 may solely provide a reading that the two brake pads on the front left wheel disc brakes are at ⅛ inch and ¼ inch thickness. The vehicle control system 204 and/or diagnostics communications module 256 may then accept that reading and query the maintenance data 2408 and/or original equipment manufacturer 2812 (or subsystem provider 2816 if that entity provided the braking subsystem) to determine if the brakes are in specification/requirement. Upon determining that brake pads must be replaced when at ⅛ inch or below, vehicle control system 204 and/or diagnostics communications module 256 determines that the "health" state of the front left brake system is "unhealthy." Alternatively or additionally, the vehicle sensor 242 itself may provides an "out of spec" signal whenever a brake pad falls below ⅛ inch in thickness.

Upon receiving the vehicle sensor data, the vehicle control system 204 may also perform signal processing of signals received from one or more vehicle sensors 242. Such signal processing may include fused or blended estimation of a measured parameter from a single sensor, such as multiple measurements of a oil pressure readings. In a simple case, the vehicle control system 204 may solely receive measurements of oil pressure from a single pressure sensor, and simply output a running average of the pressure, e.g. average all measurements over the last 1 sec to provide an average pressure value. Optionally, the vehicle control system 204 may perform estimation, blending, or fusion of a measured state parameter from multiple sensors such as multiple force sensors. Signal processing of such sensor signal measurements may comprise stochastic signal processing, adaptive signal processing, and/or other signal processing techniques known to those skilled in the art.

At step 3016, a determination is made as to whether a query has been received (e.g. by a maintenance provider 2208, diagnostics communications module 256, user 216) or a set periodic determination is required as to the health state of vehicle 104. For example, the user 216 may have enrolled in a service with a maintenance provider 2816 and/or original equipment manufacturer 2812 (sometimes termed "manufacturer support service") which continually transmits the operational "health" status of her vehicle 104, so as to effectively provide continuous monitoring of the health of vehicle 104. If no such query is required or has been received, the method returns to step 3008 to receive sensor data. If a determination that a query is required or has been received, the method continues to step 3020.

Continuing the ABS example involving regulatory monitor 2208 NHTSA, the data stored in fleet-wide original equipment manufacturer performance data 2808 may be made available to NHTSA in several ways. For example, vehicle control system 204 could notice NHTSA by email that new data has been entered in fleet-wide original equipment manufacturer performance data 2808.

At step 3020, the vehicle control system 204 and/or diagnostics communications module 256 determines if the vehicle 104 is healthy. The health of the vehicle 104 may be determined or reported based on selectable parameters, as selected by those comprising user 216, original equipment manufacturer 2812, subsystem provider 2816 and regulatory monitor 2820. For example, a user 216 may select that if any one of a set of subsystems indicates an out of specification reading, the health of the vehicle 104 is to be deemed "unhealthy." In contrast, regulatory monitor 2820, for example as part of a broad safety investigation into the performance of antilock braking systems, may select that only if a component of the ABS system is out of specification is the vehicle 104 to be deemed unhealthy.

At step 3024, the vehicle control system 204 takes action in the event a determination is made at step 3020 that the vehicle 104 and/or a particular subsystem 328 is unhealthy. Continuing the ABS example, in the event that a determination is made that the ABS is out of specification, the vehicle control system 204 may take several actions, to include providing notice to user 216 comprising via user interface 212, updating fleet-wide original equipment manufacturer performance data 2808 and/or maintenance data 2408 to document the unhealthy status, and further noticing the regulatory monitor 2820, original equipment manufacturer 2812 and/or maintenance provider 2208. The notice or message to regulatory monitor 2820, original equipment manufacturer 2812, maintenance provider 2208 and/or user 216 may be a text message, phone call, email, etc.

Alternatively or additionally, the vehicle control system 204 may disable the vehicle (e.g. not allowing the vehicle 104 to start) and/or provide an alarm 2016, to include a visual alarm alert (e.g. flashing of headlights, hazard lights, daytime running lights (DRLs), and/or interior lights) and audio alarm alert (e.g. honking of horn) for certain selectable levels of unhealthy state. Such an alarm may be provided in the event the brake lines have been severed (e.g. by a vandal) thereby rendering the vehicle 104 unsafe to operate. The method 2100 ends at step 2524.

A vehicle may provide methods and systems for vehicle diagnostic detection and identification through vehicle sensitive skin. Specifically, a method to monitor the exterior surface of skin of a vehicle to enable detection and identification of damage to the vehicle exterior surface. In one embodiment, a change in skin condition provides monitoring of vehicle performance and identifies vehicle operating abnormalities. In the event vehicle skin damage is detected, the system may take a number of actions. In one embodiment, the actions comprise notifying authorized users of the vehicle, a maintenance and diagnostics service provider, a security provider, and emitting a visual or audio alarm.

More specifically, a vehicle may incorporate a sensitive automobile "skin" to detect when and where a vehicle receives minor damage; e.g. a scratch or a dent. This sensitive vehicle skin may assist with fault analysis and may provide a vehicle skin monitoring function. Among other things, the vehicle may include a series of sensors that can determine mechanical and/or electrical characteristics of physical and/or electrical components. In one example, a vehicle may establish a skin condition baseline. The baseline (or calibration) may be used to compare a current condition to the baseline condition to detect possible damage and/or other inconsistencies. An example of skin condition may include electrical resistivity, or radio frequency (RF) signal, across one or more sections of a vehicle panel, component, assembly, etc.

Figure 31:
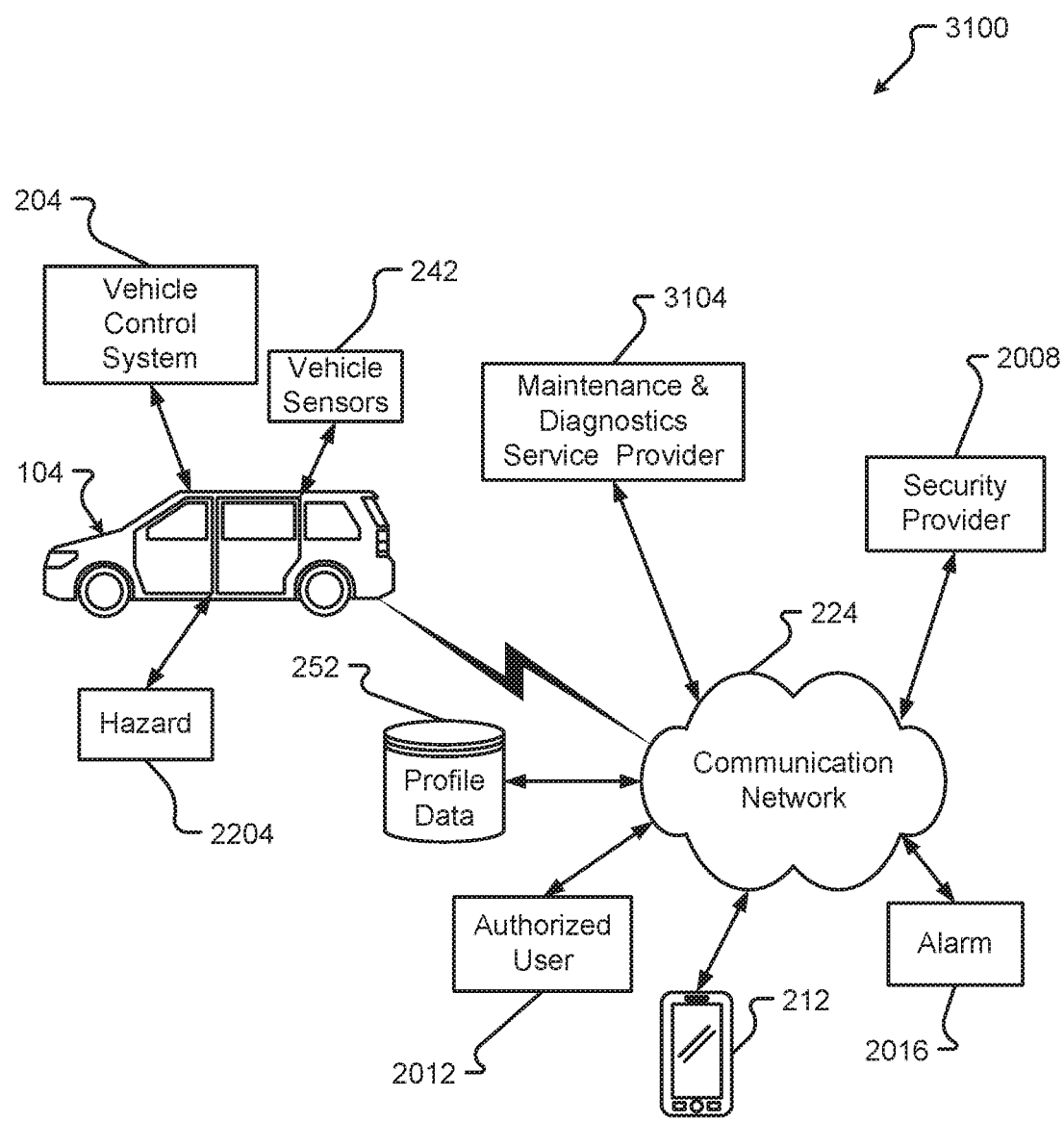
FIG. 31 depicts an embodiment of a vehicle diagnostic detection through sensitive vehicle skin system.

FIG. 31 depicts an embodiment of a vehicle diagnostic detection through sensitive vehicle skin system 3100. Vehicle 104 is shown in communication with elements as disclosed above, i.e. vehicle sensors 242, communication network 224 and vehicle control system 204. A hazard 2204 is depicted in communication with the vehicle 104. The hazard 2204 may be, for example, another vehicle, a shopping cart, a vandal, or other entity that may cause damage to vehicle 104 to include natural hazards like hail. The hazard 2204 may be fixed or moveable. Damage to vehicle 104 is detected by vehicle sensors 242.

One or more of vehicle sensors 242 detect or sense a change to a baseline skin condition to vehicle 242 as associated with a particular location of vehicle 104 associated with one or more areas 508. See FIGS. 5A-C. The vehicle sensors comprise one or more vehicle body sensors 782. The vehicle body sensors 782 may be configured to measure characteristics associated with the body (e.g., body panels, components, chassis, windows, etc.) of a vehicle 104. For example, two vehicle body sensors 782, including a first body sensor and a second body sensor, may be located at some distance apart. Continuing this example, the first body sensor may be configured to send an electrical signal across the body of the vehicle 104 to the second body sensor, or vice versa. Upon receiving the electrical signal from the first body sensor, the second body sensor may record a detected current, voltage, resistance, and/or combinations thereof associated with the received electrical signal. Values (e.g., current, voltage, resistance, etc.) for the sent and received electrical signal may be stored in a memory. These values can be compared to determine whether subsequent electrical signals sent and received between vehicle body sensors 782 deviate from the stored values. When the subsequent signal values deviate from the stored values, the difference may serve to indicate damage and/or loss of a body component.

Additionally or alternatively, the deviation may indicate a problem with the vehicle body sensors 782. The vehicle body sensors 782 may communicate with each other, a vehicle control system 204, and/or systems of the vehicle system 200 via a communications channel 356. Although described using electrical signals, it should be appreciated that alternative embodiments of the vehicle body sensors 782 may use sound waves and/or light to perform a similar function.

In another example, the one or more vehicle body sensors 782 may measure deviation of the vehicle skin from a baseline measurement, e.g. electrical resistance, magnetic field, and frequency response. Here, vehicle "skin" broadly refers to the exterior surface of a vehicle 104, which traditionally is of a metal or metal alloy such as aluminum. However, vehicle skin also includes any type of material used in vehicle body exteriors to include fiberglass and composite materials. Also, frequency response means determination of the natural vibration modes of a physical system (e.g. a vehicle door panel, a vehicle fender, an entire vehicle outside skin). The body sensors 782 may be installed on an interior or exterior surface of the vehicle ski, or embedded within the skin. For example, the body sensor may be a wire running through the inside of a composite body apnel such as a vehicle door.

The vehicle body sensors 782 measure deviation of the vehicle skin from a baseline measurement typically obtained through a calibration process. For example, an electrical resistance sensor, after installation at the site of vehicle production, records a baseline measurement of the electrical resistance of a particular designated vehicle area, perhaps a rear quarter panel made of a uniform type of metal alloy. The range of the electrical resistance sensor is then calibrated to prevent nuisance recordings yet provide adequate sensitivity to changes in electrical resistance. Further, a threshold value is selected that, when exceeded, will trigger a signal output from the electrical resistance sensor. Alternatively, the electrical resistance sensor may routinely sense electrical resistance and output same to the vehicle control system 242 which performs its own threshold-exceed determination.

In another example, the vehicle body sensor 782 may provide an electromagnetic pulse of energy to a designated portion (to include all or a substantial portion) of the vehicle 104 to establish a baseline frequency response. Such a frequency response calibration is then compared against by subsequent frequency response data collections to identify any deviations deemed significant. A significant deviation may be a change in frequency components (e.g. magnitude, phase) beyond a selectable threshold.

The afore-mentioned deviations sensed by one or more vehicle sensors 242 may indicate skin damage to the vehicle 242. Additionally or alternatively, the deviations may indicate a developing or existing abnormality with the vehicle 104. For example, a change in the frequency response may indicate a change in the vibration characteristics of the vehicle 104, perhaps due to a slipping timing belt or a suspension problem. By first sensing an abnormality, then identifying the location and/or conditions of the abnormality (e.g. during high-speed operations, during engine idle, during high-radius turns) the sensed condition provides assistance in diagnosing the budding or existing problem with the vehicle 104.

Upon detection of a change in skin condition the vehicle control system 204 may train vehicle sensors 242 to the surrounding area of skin condition deviation or change, and/or record and train as possible non-vehicle sensors 236 to the surrounding area. Such on-site sensing of the potential cause of the skin condition deviation may be beneficial in several ways, to include liability determination and insurance claims. Hazard 2204 may be detected by one or more vehicle sensors 242 comprising external vehicle sensors 242. Upon detection or sensing of a deviation in the skin state or condition of the vehicle 104, the vehicle control system 204 may take any of several actions. The action may comprise providing notice to a security provider 2008 such as a monitoring service that notifies other parties such as the vehicle owner, a maintenance and diagnostics service provider 3104 and one or more authorized users 2012 to include by way of device or user interface 212. Alternatively or additionally, the vehicle control system 204 may disable the vehicle and/or provide an alarm 2016, to include a visual alarm alert (e.g. flashing of headlights) and audio alarm alert (e.g. honking of horn), and contact a maintenance and diagnostics service provider 3104 so as to order repair parts and/or enable diagnostics to be performed. Also, the vehicle control system 204 may record vehicle damage data and/or hazard data on profile data 252 associated with the user 216 of vehicle 104.

Figure 32:
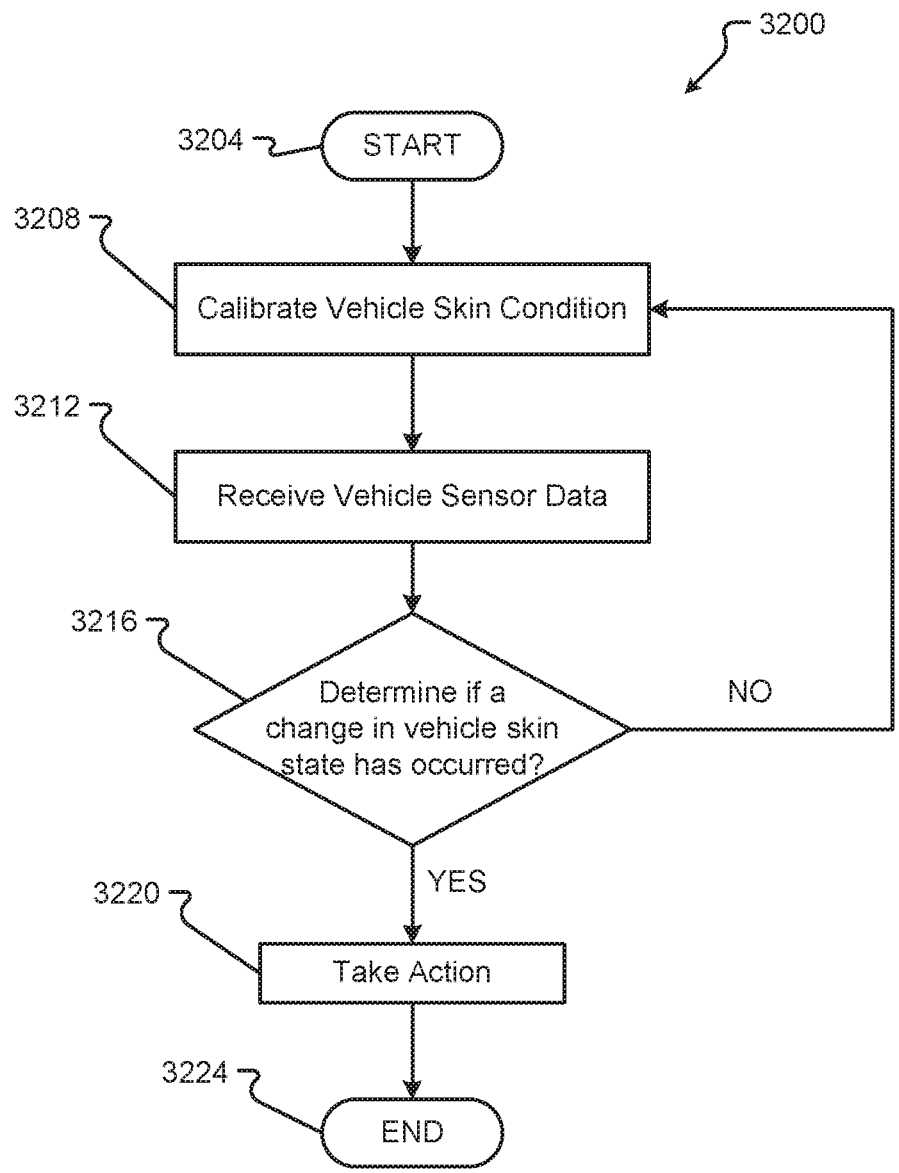
FIG. 32 is a flow diagram of a method for vehicle diagnostic detection through sensitive vehicle skin.

FIG. 32 is a flow diagram of a method for vehicle diagnostic detection through sensitive vehicle skin. While a general order for the steps of the method 3200 is shown in FIG. 32, the method 3200 can include more or fewer steps or can arrange the order of the steps differently than those shown in FIG. 32. Generally, the method 3200 starts with a start operation 3204 and ends with an end operation 3224. The method 3200 can be executed as a set of computer-executable instructions executed by a computer system and encoded or stored on a computer readable medium. Hereinafter, the method 3200 shall be explained with reference to the systems, components, modules, software, data structures, user interfaces, etc. described in conjunction with FIGS. 1-31.

At step 3208, the one or more vehicle sensors 242, comprising the vehicle body sensors 782, used to monitor vehicle skin status or state are calibrated. Calibration is broadly defined as the process of comparing sensor measurements against a known truth to establish the accuracy and/or gain schedule of a sensor device. In this disclosure the term calibration also refers to a baseline or nominal measurement condition, such as a baseline or calibrated vehicle electrical conductivity value. The one or more vehicle sensors 242 may be calibrated individually or collectively, and at regular intervals or intermittent intervals. As discussed above, the calibration may enable the removal of nuisance or "wild point" measurements from a given sensor.

At step 3212, the one or more vehicle sensors 242 sense vehicle skin state or status and/or deviations and are received by the vehicle control system 204. For example, an electrical conductivity sensor may periodically measure or sense a conductivity of a portion of the vehicle 104 and, on an event-driven basis, provide an output in the event of a deviation from a baseline value. The vehicle sensors 242 may operate in a continuous or discontinuous mode, may operate at a set or selectable sampling rate, and may be selectable by a user or a remote entity such as a third-party security provider.

The one or more vehicle sensors 242 employed to sense or detect changes in vehicle skin state comprise vehicle external sensors such as external safety group sensors 716E. That is, the one or more vehicle sensors 242 may comprise force sensors 768, mechanical motion sensors 772, orientation sensors 776, vehicle body sensors 782, vibration sensors, electromagnetic field sensors, and acoustic sensors. The one or more vehicle sensors 242 are configured to detect damage to vehicle 104, comprising the vehicle skin, and/or identify its location. It one embodiment, the one or more vehicle sensors 242 may provide a measure of the degree of damage to the skin of vehicle 104. Futhermore, the one or more vehicle sensors 242 employed to sense or detect changes in vehicle skin state may be configured to engage and/or interconnect with vehicle body sensors 782 configured to measure characteristics associated with the body (e.g., body panels, components, chassis, windows, etc.) other than the vehicle skin state of a vehicle 104.

The one or more vehicle sensors 242 employed to sense or detect changes in vehicle skin state may be located in an interior space 108 or an exterior of the vehicle 104 and not mounted or disposed directly on or in the vehicle skin location of interest. For example, a camera could be mounted on the rear-view mirror so as to face the hood of vehicle 104 and detect changes in the skin condition of the vehicle hood. The one or more vehicle sensors 242 may also identify the location and/or degree of skin damage to vehicle 104.

Associated device sensors 720 can include any sensors that are associated with a device 212, 248 in the vehicle 104. As previously stated, typical devices 212, 248 may include smart phones, tablets, laptops, mobile computers, and the like. It is anticipated that the various sensors associated with these devices 212, 248 can be employed by the vehicle control system 204. For example, a typical smart phone can include, an image sensor, an IR sensor, audio sensor, gyroscope, accelerometer, wireless network sensor, fingerprint reader, and more. These associated device sensors 720 may be used by the vehicle control system 204 to detect and/or identify damage and/or changes to vehicle skin state.

Optionally, the exterior safety sensors 716E may be configured to collect data relating to one or more conditions, objects, vehicle components, and other events that are external to the vehicle 104. For instance, the force sensors 768 in the external safety group 716E may detect and/or record force information associated with the outside of a vehicle 104 given an anomaly detected in the skin of the hood of the vehicle 104. For example, if an object (e.g. shopping cart) strikes the driver's side door of the vehicle 104, the force sensors 768 from the exterior safety group 716E may determine a magnitude, location, and/or time associated with the strike in addition to a measurement by the one or more vehicle sensors 242 employed to sense or detect changes in vehicle skin state.

At step 3216, a determination is made as to whether a change or deviation in vehicle skin state has occurred. If no such change or detection has occurred, the process returns to step 3208 wherein vehicle sensors 242 continue to operate and sensor data is received. Vehicle control system 204 determines a change in vehicle skin condition has occurred by assessing the received signals or measurements from the one or more vehicle sensors 242, such as the vehicle body sensors 782. That is, the vehicle control system 204 accepts sensor inputs, assesses those sensor inputs, and determines if the measurement is indicative of a selectable level of change in skin condition to the vehicle 104. For example, a vehicle body sensor 782 capable of measuring vibration may be located in the door panel of a vehicle 104. Also located in the door panel is an actuator capable of imparting vibrations to the door panel so that, in coordination with the vibration sensor, a vibratory frequency analysis may be periodically performed. A change in the frequency analysis indicates a change to the physical properties of the door panel, such as prompted by a change (a scratch, a "ding" or other damage) to the door panel skin. Similarly, a vehicle body sensors 782 might be an electrical conductivity sensor configured to detect changes in electrical conductivity. The level of sensitivity, or a threshold value in which a skin anomaly of change is declared, is selectable.

Upon determination that a change in state or condition of vehicle skin has occurred, the zone of vehicle 104 wherein the skin change has occurred is recorded. The location of the vehicle body sensor 782 provides an indication of the location of the vehicle skin condition change (which may translate to damage to the vehicle skin). The value measured (i.e. the amount of change or absolute value) provides an indication of the degree of potential damage to vehicle 104. Stated another way, the vehicle sensors 242 output signals to the vehicle control system 204 that an event (a change in a nominal value of skin state or a value of skin state above a selectable threshold) has been measured or sensed. These data may then in turn be sent to the vehicle control system processor 304 to determine the zone 512 and area 508 where the event occurred.

Upon receiving the vehicle sensor data, the vehicle control system 204 may also perform signal processing of signals received from one or more vehicle sensors 242. Such signal processing may include fused or blended estimation of a measured parameter from a single sensor, such as multiple measurements of a range state parameter from the vehicle 104 to a potential intruder. In a simple case, the vehicle control system 204 may solely receive measurements of electrical conductivity from a single sensor, and simpley output a running average of the conductivity, e.g. average all measurements over the last 1 sec to provide an average value. Optionally, the vehicle control system 204 may perform estimation, blending, or fusion of a measured state parameter from multiple sensors such as multiple conductivity sensors. Signal processing of such sensor signal measurements may comprise stochastic signal processing, adaptive signal processing, and/or other signal processing techniques known to those skilled in the art.

At step 3220, upon detection or sensing of a change in vehicle skin state, the vehicle control system 204 may take any of several actions. The action may comprise providing notice to a security provider 2008 such as a monitoring service that notifies other parties such as the vehicle owner, and one or more authorized users 2012 to include by way of device or user interface 212. Alternatively or additionally, the vehicle control system 204 may disable the vehicle and/or provide an alarm 2016, to include a visual alarm alert (e.g. flashing of headlights) and audio alarm alert (e.g. honking of horn), and contact a maintenance and diagnostics provider 2208 so as to facilitate diagnostics of any sensed anomaly of the vehicle and/or order repair parts (if for example, vehicle damage is indicated). Also, the vehicle control system 204 may record vehicle damage data and/or hazard data on profile data 252 associated with the user 216 of vehicle 104.

Upon detection of a change to the vehicle skin state, the vehicle control system 204 may further train vehicle sensors 242 to the surrounding area of the vehicle 104, and/or record and train as possible non-vehicle sensors 236 to the surrounding area. Such on-site sensing of the potential cause of the vehicle damage benefits in several ways, to include liability determination and insurance claims. Hazard 2204 may be detected by one or more vehicle sensors 242 comprising external sensors and non-vehicle sensors 236. For example, a change to a door panel's skin state may indicate damage caused by an errant driver "hazard;" a vehicle sensor 242 such as a camera could be alerted to image the area to allow identification of the errant driver in the event the driver does not provide his contact information.

The vehicle control system 204 can receive the information from the sensors 242 of a skin state change and use that information to search the database 1200 that may be stored within the system data 208. The sensor data may be compared to maintenance data and/or performance data of vehicle 104 to enable a determination of repair parameters associated with the damage. For example, the skin state deviations may indicate a developing or existing abnormality with the vehicle 104. For example, a change in the frequency response may indicate a change in the vibration characteristics of the vehicle 104, perhaps due to a slipping timing belt or a suspension problem. By first sensing an abnormality, then identifying the location and/or conditions of the abnormality (e.g. during high-speed operations, during engine idle, during high-radius turns) the sensed condition provides assistance in diagnosing the budding or existing problem with the vehicle 104. Such data may be sent to the maintenance and diagnostics service provider.The vehicle control system 204 may also store data regarding the change in skin state.

Alternatively or additionally, the vehicle control system 204 may disable the vehicle (e.g. not allowing the vehicle 104 to start) and/or provide an alarm 2016, to include a visual alarm alert (e.g. flashing of headlights, hazard lights, daytime running lights (DRLs), and/or interior lights) and audio alarm alert (e.g. honking of horn).Also, the vehicle control system 204 may record vehicle damage data and/or hazard data on profile data 252 associated with the user 216 of vehicle 104. The method 3200 ends at step 32240.

The vehicle may provide methods and systems for vehicle diagnostics and roadside assistance. Specifically, a method to monitor the health of vehicle systems and subsystems and diagnose detected anomalies may be provided. In the event a vehicle anomaly is detected or a vehicle user otherwise requests assistance, the system may take a number of actions. In one embodiment, the actions comprise noticing a maintenance provider, emergency personnel and emitting a visual or audio alarm.

A vehicle may assist drivers who require help due to flat tire or other automobile malfunction or automobile failure. The assistance may comprise calling for help or a tow-truck, identifying nearby maintenance shops available to provide immediate assistance (e.g. will tow the car or do the repair), or performing diagnosis if not perform the repair remotely.

Figure 33:
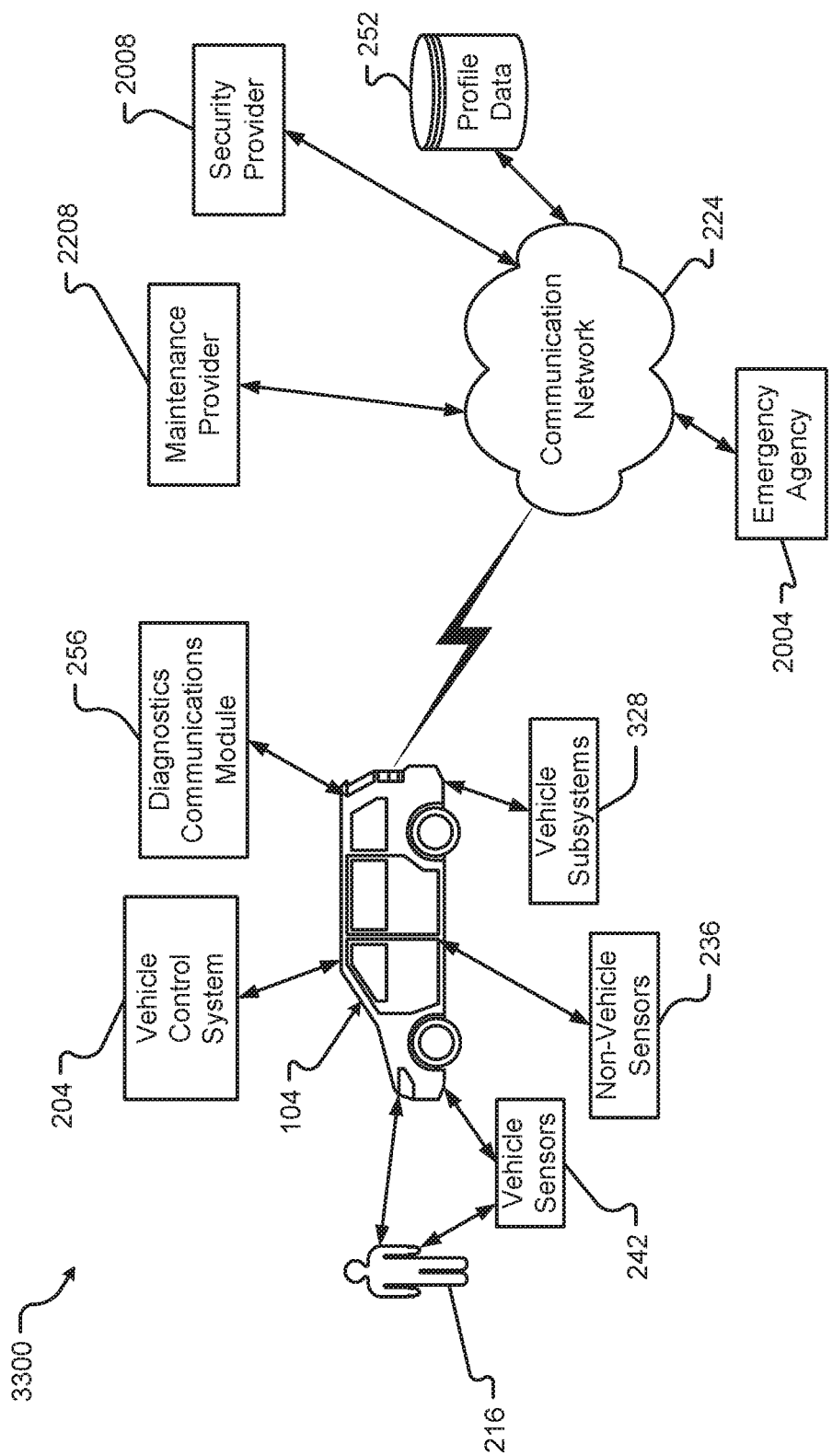
FIG. 33 depicts an embodiment of a vehicle diagnostics and roadside assistance system.

FIG. 33 depicts an embodiment of a vehicle diagnostics and roadside assistance system (herein also termed "roadside assistance system") 3300. The roadside assistance system 3300 may comprise vehicle control system 204, profile data 252, user 216, diagnostics communications module 256, maintenance provider module 2208, security provider module 2820, emergency agency module 2004, vehicle subsystems 328, vehicle sensors 242 and non-vehicle sensors 236.

Emergency 2004 is broadly defined as any entity that provides an emergency response function, comprising police, ambulance, EMTs, firefighters, etc. Security provider 2008 may be a monitoring service that notifies other parties such as the vehicle owner in the event of anomalous states or events associated with the vehicle 104, such as vehicle damage, and unauthorized entry to vehicle 104. Security provider 2008 may comprise any private entity that provides security services to any of user and/or occupants of vehicle and to vehicle itself, such as a security monitoring company, corporate security personnel, etc.

Vehicle control system 204, user 216, vehicle subsystems 328, diagnostics communications module 256, vehicle sensors 242 and non-vehicle sensors 236 may communicate over a network or bus 356. This communication bus 356 may be bidirectional and perform data communications using any known or future-developed standard or protocol. An example of the communication bus 356 may be as described in conjunction with FIG. 4. Other components communicate via communication network 224. As one example of the later communication, the security provider 2008 and/or emergency agency 2004, aside from communicating with each other via communication network 224, may communicate with diagnostics communications module 256, vehicle control system 204, vehicle sensors 242, and/or non-vehicle sensors via 236 via the vehicle 104. Hereinafter, the roadside assistance system 3300 shall be explained with reference to the systems, components, modules, software, data structures, user interfaces, etc. described in conjunction with FIGS. 1-32.

One or more of vehicle sensors 242 may detect or sense the status and operation of vehicle subsystems 328 as associated with a particular user 216. Vehicle systems 328 can include any of the mechanical, electrical, electromechanical, computer, or other systems associated with the function of the vehicle 104. For example, vehicle systems 328 can include one or more of, but is not limited to, the steering system, the braking system, the engine and engine control systems, the electrical system, the suspension, the drive train, the cruise control system, the radio, the heating, ventilation, air conditioning (HVAC) system, the windows and/or doors, etc as known to those skilled in the art. Vehicle subsystems 328 may provide a status signal via communication bus 356 to user 216 indicating that a required maintenance item is recommended (e.g. the vehicle 104 is 500 miles from a required oil change) and/or provide an out-of-maintenance indicator to historical user compliance data 2412 and/or maintenance provider 2208 indicating that a required maintenance item was not met (e.g. brakes pads have worn down beyond a selectable threshold).

Vehicle sensors 242 may comprise sensors to measure heart rate to sense arrhythmias, to detect heart attacks or seizures which may prompt the taking of corrective actions for example stopping the car, and sensors that link to health provider 2604 (to include a medical professional so authorized by user 216) to enable assessment of health condition and well-being. One or more vehicle sensors 242 may be linked with external entities that enable more sophisticated interpretation and/or diagnosis of health condition given sensor readings of user health state.

Vehicle sensors 242 may also serve a user health monitoring function. That is, during routine driving operations the vehicle sensors 242 may monitor and alert, as necessary, in the event a user 216 experiences a health anomaly. For example, health telemetry and other data may be collected via the steering wheel user sensors 642. Optionally, the steering wheel user sensors 642 may collect heart rate, temperature, blood pressure, and the like, associated with a user 216 via at least one contact disposed on or about the steering wheel 640. Similarly, biometric sensors 756 may be employed to identify and/or record characteristics associated with a user 216. Biometric sensors 756 can include at least one of image sensors, IR sensors, fingerprint readers, weight sensors, load cells, force transducers, heart rate monitors, blood pressure monitors, and the like as provided herein.

Health data of a particular user 216 may be stored by way of the data structures 1200 described above with respect to FIGS. 12A-D. That is, the sensors 242 within the vehicle 104 may be able to either obtain or track health data in portion 1228. Health data 1228 may include any type of physical characteristic associated with the user. For example, a heart rate, a blood pressure, pulse rate, body temperature, respiratory rate, associated vital signs or other types of heath data may be obtained and stored in portion 1228.

Non-vehicle sensor 236 can be any type of sensor that is not currently associated with the vehicle 104 yet useful in enabling or facilitating operations or functions of a vehicle diagnostic system 2800, 2900. For example, non-vehicle sensor 236 can be sensors that record weather condition, road condition, and/or circumstances present during a designated vehicle 104 event. These non-vehicle sensors 236 may be operated by third parties but provide information to the vehicle control system 204. Examples of information provided by the sensors 236 and that may be used by the vehicle control system 204 may include weather tracking data, traffic data, user health tracking data, vehicle maintenance data, or other types of data, which may provide environmental or other data to the vehicle control system 204.

Profile data 252 is as described above but may also comprise data describing user 216 preferences regarding vehicle warnings and/or preferred vendors. For example, the user may prefer to only be warned of vehicle conditions that pose an immediate or near-immediate threat to safety (e.g. brakes pads below a threshold level) and not be informed of items not posing an immediate threat (e.g. windshield washer fluid low in weather conditions that are clear without precipitation). Similarly, the user may have present maintenance providers 2208 preferred for major maintenance (e.g. the affiliate of the vehicle OEM) and another maintenance provider for routine items (e.g. inflation of tires to a preferred pressure).

The diagnostic communications module 256 may be configured to receive and transmit diagnostic signals and information associated with the vehicle 104 and/or vehicle subsystems 328. Examples of diagnostics signals and information may include, but is in no way limited to, vehicle system warnings, sensor data, vehicle component status, service information, component health, maintenance alerts, recall notifications, predictive analysis, and the like. Embodiments of the diagnostic communications module 256 may handle warning/error signals in a predetermined manner. The signals, for instance, can be presented to one or more of a third party (e.g. the 2208, security provider 2008), occupant, vehicle control system 204, and a emergency agency 2004. The diagnostics communications module 256 may determine the specific vehicle subsystem 328 that is out of specification and/or maintenance requirement, if not a component part within the vehicle subsystem 256. For example, the diagnostics communications module 256 may determine that the braking system is out of compliance (i.e. is "unhealthy") and also pinpoint the problem to a particular wheel. In one embodiment, such a determination is communicated to the maintenance provider 2208 to enable a cost/schedule quote for repair and/or enable parts required for repair to be immediately ordered.

The vehicle sensors 242 and non-vehicle sensors 236 may operate in a continuous or discontinuous mode, may operate at a set or selectable sampling rate, and may be selectable by a user or a remote entity such as a third-party security provider.

Figure 34:
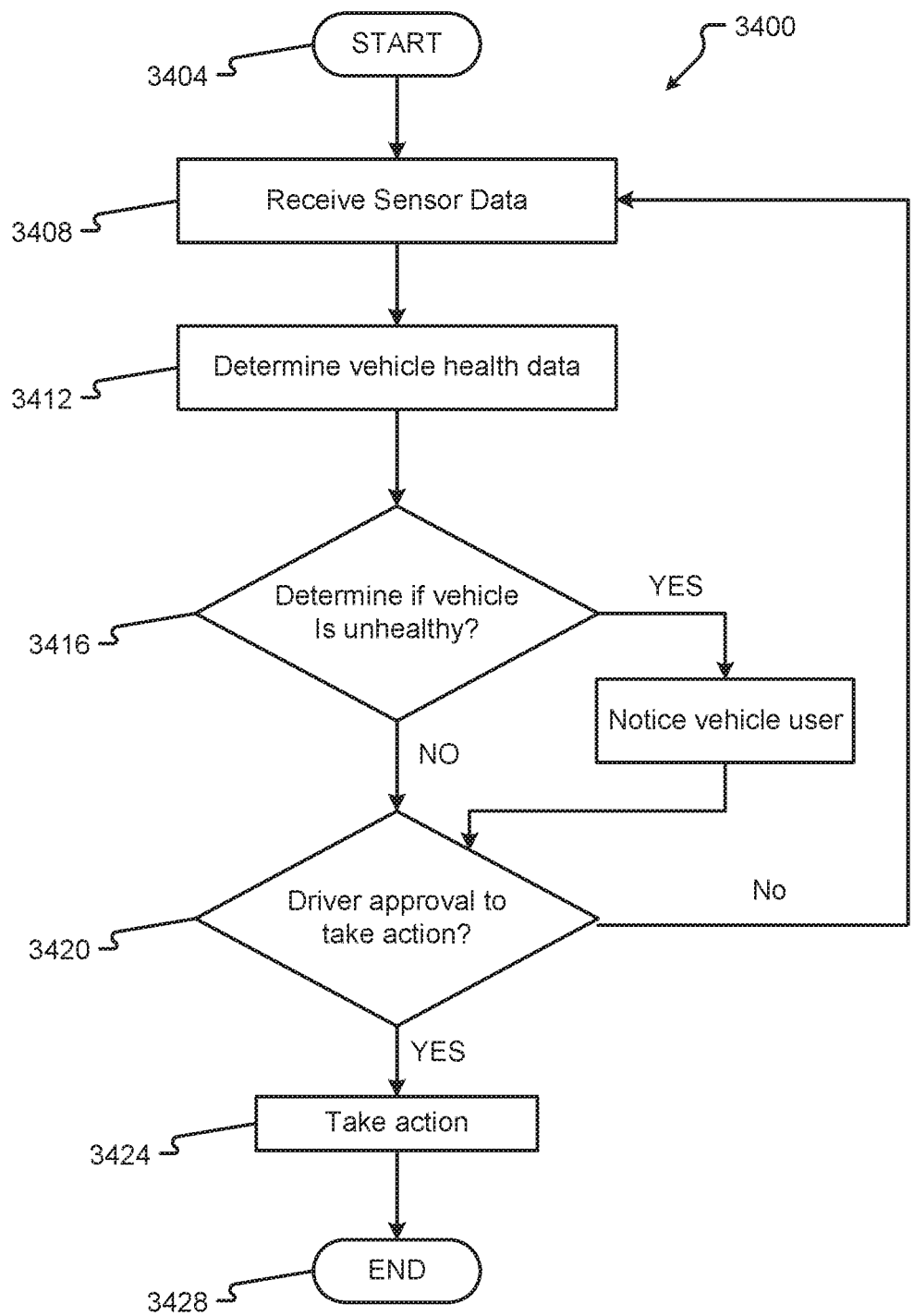
FIG. 34 is a flow diagram of a method for vehicle diagnostics and roadside assistance.

An embodiment of a method 3400 for a vehicle diagnostics and roadside assistance system is shown in FIG. 34. While a general order for the steps of the method 3400 is shown in FIG. 34, the method 3400 can include more or fewer steps or can arrange the order of the steps differently than those shown in FIG. 34. Generally, the method 3400 starts with a start operation 3404 and ends with an end operation 3428. The method 3400 can be executed as a set of computer-executable instructions executed by a computer system and encoded or stored on a computer readable medium. Hereinafter, the method 3400 shall be explained with reference to the systems, components, modules, software, data structures, user interfaces, etc. described in conjunction with FIGS. 1-33.

At step 3408, one or more vehicle sensors 242 sense a state or condition of one or more vehicle subsystems 328. For example, an oil change monitor sensor may measure mileage of vehicle 104 since last oil change, and provide an alert or notice as a selectable oil change threshold is approached. That is, the oil change monitor sensor may be set to monitor oil changes every 5,000 miles and provide a signal when 4,500 miles has been reached. Such oil change health status data, for example, may be stored as health status 1278 as part of the oil component 1274 of vehicle system engine 1270 (see e.g. FIG. 12C). Alternatively or additionally, the diagnostics communications module 256 may sense a vehicle 104 warning.

At step 3012, the vehicle control system 204 accepts vehicle sensor 242 data and/or data from diagnostics communications module 256 and determines the health state of the vehicle 104. Such a health state comprises a numerical value and/or may provide a within specification/requirement or out of specification/requirement designation. For example, a vehicle sensor 242 may solely provide a reading that the left rear tire is below a specified threshold tire pressure. The threshold tire pressure may be selected by the user 216 (e.g. at 42 PSI for a harder ride but better gas mileage), maintenance provider 2208 (at 35 PSI for a softer ride) or original equipment manufacturer (at 38 PSI). The vehicle control system 204 and/or diagnostics communications module 256 may then accept the tire pressure reading and optionally query the maintenance data 2408 and/or original equipment manufacturer 2812 to determine if the brakes are in specification/requirement. Upon determining that the left rear tire is indeed below a minimal safe tire pressure (e.g. 25 PSI), vehicle control system 204 and/or diagnostics communications module 256 determines that the "health" state of the left rear tire is "unhealthy." Alternatively or additionally, the vehicle sensor 242 itself may provide an "out of spec" signal whenever a tire pressure falls below a selectable value, e.g. maintenance provider 2208 value of 35 PSI.

Upon receiving the vehicle sensor data, the vehicle control system 204 may also perform signal processing of signals received from one or more vehicle sensors 242. Such signal processing may include fused or blended estimation of a measured parameter from a single sensor, such as multiple measurements of an oil pressure readings. In a simple case, the vehicle control system 204 may solely receive measurements of oil pressure from a single pressure sensor, and simply output a running average of the pressure, e.g. average all measurements over the last 1 sec to provide an average pressure value. Optionally, the vehicle control system 204 may perform estimation, blending, or fusion of a measured state parameter from multiple sensors such as multiple force sensors. Signal processing of such sensor signal measurements may comprise stochastic signal processing, adaptive signal processing, and/or other signal processing techniques known to those skilled in the art.

At step 3416, the vehicle control system 204 and/or diagnostics communications module 256 determines if the vehicle 104 is healthy. The health of the vehicle 104 may be determined or reported based on selectable parameters, as selected by those comprising user 216, original equipment manufacturer 2812, subsystem provider 2816 and regulatory monitor 2820. For example, a maintenance provider 2208 may select that if any one of a set of subsystems indicates an out of specification reading, the health of the vehicle 104 is to be determined to be "unhealthy." If the vehicle 106 is deemed unhealthy, then the user 104 is noticed through any of several means comprising display 212 and dashboard indicator warning. If the vehicle is not determined to be unhealthy, the method 3400 moves to step 3420.

At step 3420, the driver or user 104 is queried as to whether assistance is sought. That is, the user 104 is queried as to what, if any, action he would like performed. If the user 216 indicates that no action is sought, the method returns to step 3408 and sensor data is received. If the user 216 requests action, the method moves to step 3424.

At step 3424, the vehicle control system 204 takes action in the event a determination is made at step 3020 that the vehicle 104 and/or a particular subsystem 328 is unhealthy and the user 216 requests action be taken. Continuing the low pressure tire example, the vehicle control system 204 may take several actions (all at the option and selectable by the user), to include notifying maintenance provider 2208 of the unhealthy status and identified unhealthy part or condition. The notice or message may be a text message, phone call, email, etc.

Alternatively or additionally, the vehicle control system 204 may disable the vehicle (e.g. not allowing the vehicle 104 to start) and/or provide an alarm 2016, to include a visual alarm alert (e.g. flashing of headlights, hazard lights, daytime running lights (DRLs), and/or interior lights) and audio alarm alert (e.g. honking of horn) for certain selectable levels of unhealthy state. The method 2100 ends at step 3424.

In one embodiment, the system 3300 and/or method 3400 may function as a driver assistance and targeted interactive information system irrespective of any vehicle health issue. That is, generally, the method 3400 may receive a query from user 216 asking what the recommended tire pressure is, given the user 216 has pulled into a gas station and is servicing his tires. User 216 so queries maintenance provider 2208 via communications network 224. The maintenance provider 2208 receives the user query, combines the query with vehicle type data e.g. 1282 which identifies nominal recommended tire pressure, adjusts as necessary given locale weather conditions (as obtained, e.g. from GPS-enabled weather status data provided by non-vehicle sensors 236), and replies to user that the recommended tire pressure, given the vehicle type and local weather conditions is 36 PSI.

The exemplary systems and methods of this disclosure have been described in relation to configurable vehicle consoles and associated devices. However, to avoid unnecessarily obscuring the present disclosure, the preceding description omits a number of known structures and devices. This omission is not to be construed as a limitation of the scopes of the claims. Specific details are set forth to provide an understanding of the present disclosure. It should however be appreciated that the present disclosure may be practiced in a variety of ways beyond the specific detail set forth herein.

Furthermore, while the exemplary aspects, embodiments, options, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a Personal Computer (PC), laptop, netbook, smart phone, Personal Digital Assistant (PDA), tablet, etc., or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system. For example, the various components can be located in a switch such as a PBX and media server, gateway, in one or more communications devices, at one or more users' premises, or some combination thereof. Similarly, one or more functional portions of the system could be distributed between a telecommunications device(s) and an associated computing device.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

It should be appreciated that the various processing modules (e.g., processors, vehicle systems, vehicle subsystems, modules, etc.), for example, can perform, monitor, and/or control critical and non-critical tasks, functions, and operations, such as interaction with and/or monitoring and/or control of critical and non-critical on board sensors and vehicle operations (e.g., engine, transmission, throttle, brake power assist/brake lock-up, electronic suspension, traction and stability control, parallel parking assistance, occupant protection systems, power steering assistance, self-diagnostics, event data recorders, steer-by-wire and/or brake-by-wire operations, vehicle-to-vehicle interactions, vehicle-to-infrastructure interactions, partial and/or full automation, telematics, navigation/SPS, multimedia systems, audio systems, rear seat entertainment systems, game consoles, tuners (SDR), heads-up display, night vision, lane departure warning, adaptive cruise control, adaptive headlights, collision warning, blind spot sensors, park/reverse assistance, tire pressure monitoring, traffic signal recognition, vehicle tracking (e.g., LoJack™), dashboard/instrument cluster, lights, seats, climate control, voice recognition, remote keyless entry, security alarm systems, and wiper/window control). Processing modules can be enclosed in an advanced EMI-shielded enclosure containing multiple expansion modules. Processing modules can have a "black box" or flight data recorder technology, containing an event (or driving history) recorder (containing operational information collected from vehicle on board sensors and provided by nearby or roadside signal transmitters), a crash survivable memory unit, an integrated controller and circuitry board, and network interfaces.

Critical system controller(s) can control, monitor, and/or operate critical systems. Critical systems may include one or more of (depending on the particular vehicle) monitoring, controlling, operating the ECU, TCU, door settings, window settings, blind spot monitor, monitoring, controlling, operating the safety equipment (e.g., airbag deployment control unit, collision sensor, nearby object sensing system, seat belt control unit, sensors for setting the seat belt, etc.), monitoring and/or controlling certain critical sensors such as the power source controller and energy output sensor, engine temperature, oil pressure sensing, hydraulic pressure sensors, sensors for headlight and other lights (e.g., emergency light, brake light, parking light, fog light, interior or passenger compartment light, and/or tail light state (on or off)), vehicle control system sensors, wireless network sensor (e.g., Wi-Fi and/or Bluetooth sensors, etc.), cellular data sensor, and/or steering/torque sensor, controlling the operation of the engine (e.g., ignition, etc.), head light control unit, power steering, display panel, switch state control unit, power control unit, and/or brake control unit, and/or issuing alerts to a user and/or remote monitoring entity of potential problems with a vehicle operation.

Non-critical system controller(s) can control, monitor, and/or operate non-critical systems. Non-critical systems may include one or more of (depending on the particular vehicle) monitoring, controlling, operating a non-critical system, emissions control, seating system controller and sensor, infotainment/entertainment system, monitoring certain non-critical sensors such as ambient (outdoor) weather readings (e.g., temperature, precipitation, wind speed, and the like), odometer reading sensor, trip mileage reading sensor, road condition sensors (e.g., wet, icy, etc.), radar transmitter/receiver output, brake wear sensor, oxygen sensor, ambient lighting sensor, vision system sensor, ranging sensor, parking sensor, heating, venting, and air conditioning (HVAC) system and sensor, water sensor, air-fuel ratio meter, hall effect sensor, microphone, radio frequency (RF) sensor, and/or infrared (IR) sensor.

It is an aspect of the present disclosure that one or more of the non-critical components and/or systems provided herein may become critical components and/or systems, and/or vice versa, depending on a context associated with the vehicle.

Optionally, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

This application is also related to PCT Patent Application Nos. PCT/US14/34092, filed on Apr. 15, 2014, entitled, "Building Profiles Associated with Vehicle Users"; PCT/US14/34099, filed on Apr. 15, 2014, entitled "Access and Portability of User Profiles Stored as Templates"; PCT/US14/34087, filed on Apr. 15, 2014, entitled "User Interface and Virtual Personality Presentation Based on User Profile"; PCT/US14/34088, filed on Apr. 15, 2014, entitled "Creating Targeted Advertising Profiles Based on User Behavior"; PCT/US14/34232, filed on Apr. 15, 2014, entitled "Behavior Modification via Altered Map Routes Based on User Profile Information"; PCT/US14/34098, filed on Apr. 15, 2014, entitled "Vehicle Location-Based Home Automation Triggers"; PCT/US14/34108, filed on Apr. 15, 2014, entitled "Vehicle Initiated Communications with Third Parties via Virtual Personalities"; PCT/US14/34101, filed on Apr. 15, 2014, entitled "Vehicle Intruder Alert Detection and Indication"; PCT/US14/34103, filed on Apr. 15, 2014, entitled "Driver Facts Behavior Information Storage System"; PCT/US14/34114, filed on Apr. 15, 2014, entitled "Synchronization Between Vehicle and User Device Calendar"; PCT/US14/34125, filed on Apr. 15, 2014, entitled "User Gesture Control of Vehicle Features"; PCT/US14/34254, filed on Apr. 15, 2014, entitled "Central Network for the Automated Control of Vehicular Traffic"; PCT/US14/34194, filed on Apr. 15, 2014, entitled "Vehicle-Based Multimode Discovery"; U.S. application Ser. No. 13/843,011, filed on Mar. 15, 2013, entitled "Vehicle Occupant Health Data Gathering and Monitoring"; PCT/US2012/065421, filed on Nov. 16, 2012, entitled "Feature Recognition for Configuring a Vehicle Console and Associated Devices"; and U.S. patent application Ser. No. 13/679,443, filed on Nov. 16, 2012, entitled "Method and System for Maintaining and Reporting Vehicle Occupant Information". The entire disclosures of the applications listed above are hereby incorporated by reference, in their entirety, for all that they teach and for all purposes.

What is claimed is:

1. A method for managing vehicle intrusions by a vehicle control system, the method comprising:

detecting, at a motion sensor communicably coupled to a vehicle, movement within a first threshold distance of the vehicle;

in response to detecting movement within the first threshold distance of the vehicle at the motion sensor, activating one or more electromagnetic sensors communicably coupled to the vehicle;

detecting, at the one or more electromagnetic sensors, that an entity has made contact with the vehicle;

in response to detecting that an entity has made contact with the vehicle at the one or more electromagnetic sensors, activating an image sensor mounted externally to the vehicle;

capturing an image at the image sensor mounted externally to the vehicle;

comparing the image to one or more images of authorized users of the vehicle stored within a profile database; and in response to determining that the image does not match the one or more images of authorized users of the vehicle, providing a notice of unauthorized use of the vehicle to a device associated with an authorized user of the vehicle.

2. The method of claim 1, further comprising providing a notice of unauthorized use of the vehicle to an emergency responder in response to determining that the image does not match the one or more images of authorized users of the vehicle.

3. The method of claim 1, further comprising detecting a heat source within the first threshold distance of the vehicle at an infrared sensor communicably coupled to the vehicle and activating the one or more electromagnetic sensors communicably coupled to the vehicle in response to detecting the movement and the heat source within the first threshold distance of the vehicle.

4. The method of claim 1, further comprising:
in response to detecting movement within the first threshold distance of the vehicle, activating an infrared sensor communicably coupled to the vehicle; and
detecting, at the infrared sensor communicably coupled to the vehicle, a heat source within a second threshold distance of the vehicle, wherein the second threshold distance of the vehicle is less than the first threshold distance of the vehicle, and wherein the one or more electromagnetic sensors are activated in response to detecting both the movement within the first threshold distance of the vehicle and the heat source within the second threshold distance of the vehicle.

5. The method of claim 1, wherein detecting that an entity has made contact with the vehicle and the one or more electromagnetic sensors further comprises detecting that the entity has physically contacted a door handle of the vehicle.

6. The method of claim 1, further comprising disabling the vehicle in response to determining that the image does not match the one or more images of authorized users of the vehicle.

7. The method of claim 1, further comprising activating a visual alarm on the vehicle in response to determining that the image does not match the one or more images of authorized users of the vehicle.

8. The method of claim 1, further comprising activating an audio alarm on the vehicle in response to determining that the image does not match the one or more images of authorized users of the vehicle.

9. The method of claim 1, wherein the notice of unauthorized use of the vehicle is a phone call or text message.

10. The method of claim 1, further comprising providing a notice of unauthorized use of the vehicle to a monitoring service in response to determining that the image does not match the one or more images of authorized users of the vehicle.

11. A method for managing vehicle intrusions by a vehicle control system, the method comprising:
detecting, at a motion sensor communicably coupled to a vehicle, movement within a threshold distance of the vehicle;
in response to detecting movement within the threshold distance of the vehicle at the motion sensor, activating an image sensor mounted externally to the vehicle;
capturing an image at the image sensor mounted externally to the vehicle;

comparing the image to one or more images of authorized users of the vehicle stored within a profile database; and in response to determining that the image does not match the one or more images of authorized users of the vehicle, providing a notice of unauthorized use of the vehicle to a device associated with an authorized user of the vehicle.

12. A system for managing vehicle intrusions, the system comprising:
a motion sensor communicably coupled to a vehicle;
one or more electromagnetic sensors communicably coupled to the vehicle;
an image sensor mounted externally to the vehicle; and
a vehicle control system installed in the vehicle and configured to:
detect, at the motion sensor, movement within a first threshold distance of the vehicle;
in response to detecting movement within the first threshold distance of the vehicle at the motion sensor, activate the one or more electromagnetic sensors communicably coupled to the vehicle;
detect, at the one or more electromagnetic sensors, that an entity has made contact with the vehicle;
in response to detecting that an entity has made contact with the vehicle at the one or more electromagnetic sensors, activate the image sensor mounted externally to the vehicle;
capture an image at the image sensor mounted externally to the vehicle;
compare the image to one or more images of authorized users of the vehicle stored within a profile database; and
in response to determining that the image does not match the one or more images of authorized users of the vehicle, provide a notice of unauthorized use of the vehicle to a device associated with an authorized user of the vehicle.

13. The system of claim 12, wherein the vehicle control system is further configured to provide a notice of unauthorized use of the vehicle to an emergency responder in response to determining that the image does not match the one or more images of authorized users of the vehicle.

14. The system of claim 12, further comprising an infrared sensor communicably coupled to the vehicle and wherein the vehicle control system is further configured to detect a heat source within the first threshold distance of the vehicle at the infrared sensor and activate the one or more electromagnetic sensors communicably coupled to the vehicle in response to detecting the movement and the heat source within the first threshold distance of the vehicle.

15. The system of claim 12, wherein the vehicle control system is configured to detect that an entity has made contact with the vehicle and the one or more electromagnetic sensors by detecting that the entity has physically contacted a door handle of the vehicle.

16. The system of claim 12, wherein the vehicle control system is further configured to disable the vehicle in response to determining that the image does not match the one or more images of authorized users of the vehicle.

17. The system of claim 12, wherein the vehicle control system is further configured to activate a visual alarm on the vehicle in response to determining that the image does not match the one or more images of authorized users of the vehicle.

18. The system of claim 12, wherein the vehicle control system is further configured to activate an audio alarm on the vehicle in response to determining that the image does not match the one or more images of authorized users of the vehicle.

19. The system of claim 12, wherein the notice of unauthorized use of the vehicle is a phone call or text message.

20. The system of claim 12, wherein the vehicle control system is further configured to provide a notice of unauthorized use of the vehicle to a monitoring service in response to determining that the image does not match the one or more images of authorized users of the vehicle.

* * * * *